United States Patent
Gardinier et al.

(10) Patent No.: US 12,421,242 B2
(45) Date of Patent: Sep. 23, 2025

(54) SUBSTITUTED TETRAHYDROPYRROLO-PYRIDINONE COMPOUNDS AND THEIR USE IN TREATING MEDICAL CONDITIONS

(71) Applicant: Karuna Therapeutics, Inc., Princeton, NJ (US)

(72) Inventors: Kevin Matthew Gardinier, Arlington, MA (US); James Edmund Audia, Chicago, IL (US); James Monn, Indianapolis, IN (US); Jason Myers, Indianapolis, IN (US); Nadia M. Ahmad, Saffron Walden (GB); Emanuela Gancia, Saffron Walden (GB); Niall Wagstaff, Saffron Walden (GB); David G. Evans, Saffron Walden (GB); Fabien Jean Ghislain Roussel, Saffron Walden (GB); Elizabeth Anne Skidmore, Saffron Walden (GB)

(73) Assignee: Karuna Therapeutics, Inc., Princeton, NJ (US)

( * ) Notice: Subject to any disclaimer, the term of this patent is extended or adjusted under 35 U.S.C. 154(b) by 0 days.

(21) Appl. No.: 18/740,233

(22) Filed: Jun. 11, 2024

(65) Prior Publication Data
US 2024/0336619 A1 Oct. 10, 2024

Related U.S. Application Data

(63) Continuation of application No. PCT/US2023/084185, filed on Dec. 15, 2023.

(60) Provisional application No. 63/433,156, filed on Dec. 16, 2022.

(51) Int. Cl.
| | |
|---|---|
| *C07D 487/04* | (2006.01) |
| *A61K 31/437* | (2006.01) |
| *A61K 31/444* | (2006.01) |
| *C07D 519/00* | (2006.01) |

(52) U.S. Cl.
CPC .......... *C07D 487/04* (2013.01); *A61K 31/437* (2013.01); *A61K 31/444* (2013.01); *C07D 519/00* (2013.01)

(58) Field of Classification Search
CPC .. C07D 487/04; C07D 519/00; A61K 31/437; A61K 31/444
USPC ........................................................ 544/105
See application file for complete search history.

(56) References Cited

U.S. PATENT DOCUMENTS

| | | | |
|---|---|---|---|
| 10,604,519 B2 | 3/2020 | Zhang et al. | |
| 2011/0020423 A1 | 1/2011 | Elenko et al. | |
| 2019/0314354 A1 | 10/2019 | Chase et al. | |
| 2020/0182850 A1 | 6/2020 | Kimura et al. | |
| 2021/0145804 A1 | 5/2021 | Brannan et al. | |

FOREIGN PATENT DOCUMENTS

| | | |
|---|---|---|
| WO | WO-2004029051 A1 | 4/2004 |
| WO | WO-2009108499 A1 | 9/2009 |
| WO | WO-2015027204 A1 | 2/2015 |
| WO | WO-2015032286 A1 | 3/2015 |
| WO | WO-2016106331 A1 | 6/2016 |
| WO | WO-2017201132 A2 | 11/2017 |
| WO | WO-2018002760 A1 | 1/2018 |
| WO | WO-2018066718 A1 | 4/2018 |
| WO | WO-2018118736 A1 | 6/2018 |
| WO | WO-2018234953 A1 | 12/2018 |
| WO | WO-2022226078 A1 | 10/2022 |
| WO | WO-2023196952 A2 | 10/2023 |
| WO | WO-2024130064 A1 | 6/2024 |
| WO | WO-2024130065 A1 | 6/2024 |
| WO | WO-2024130066 A1 | 6/2024 |
| WO | WO-2024130068 A1 | 6/2024 |

OTHER PUBLICATIONS

Deng, X. et al., "Synthesis and preliminary evaluation of 18F-labeled 1-(6,7-dimethyl-4-(methylamino)-1,3-dihydro-2H-pyrrolo[3,4-c]pyridin-2-yl)-2-(trans-2-(6-fluoropyridin-3-yl)cyclopropyl)ethan-1-one for imaging muscarinic acetylcholine receptor subtype 4," Tetrahedron Letters, 2020, vol. 61, 152060.
CAS Registry No. 2383899-95-2; STN Entry date Nov. 27, 2019; 6H-Pyrrolo[3,4-b]pyridine-6-carboxylic acid, 1,2,5,7-tetrahydro-2-oxo-, 1, 1-dimethylethyl ester.
CAS Registry No. 1416373-74-4; STN Entry date Jan. 10, 2013; 2H-Pyrrolo[3,4-b]pyridin-2-one, 1,5,6,7-tetrahydro-.
CAS Registry No. 1989671-41-1; STN Entry date Sep. 8, 2016; 2H-Pyrrolo[3,4-b]pyridin-2-one, 1,5,6,7-tetrahydro-, hydrochloride (1:1).
CAS Registry No. 2613382-91-3; STN Entry date Mar. 18, 2021; 2H-Pyrrolo[3,4-b]pyridin-2-one, 1,5,6,7-tetrahydro-, hydrochloride (1:2).
CAS Registry No. 2090989-59-4; STN Entry date Apr. 17, 2017; 2H-Pyrrolo[3,4-b]pyridin-2-one, 3-bromo-1,5,6,7-tetrahydro-.
CAS Registry No. 2386002-95-3; STN Entry Date Dec. 1, 2019; 1,2-dimethylethyl 5,7-dihydro-4-(methylamino)-2-(trifluoromethyl)-6H-pyrrolo[3,4-d]pyrimidine-6-carboxylate.
CAS Registry No. 2384921-65-5; STN Entry Date Nov. 28, 2019; 1,1-dimethylethyl 2-chloro-5,7-dihydro-4-(methylamino)-6H-pyrrolo[3,4-d]pyrimidine-6-carboxylate.

(Continued)

*Primary Examiner* — Kahsay Habte

(74) *Attorney, Agent, or Firm* — Honigman LLP; Andrew Chipouras; Jonathan P. O'Brien

(57) ABSTRACT

The invention provides substituted tetrahydropyrrolo-pyridinone compounds, pharmaceutical compositions, and their use in treating muscarinic acetylcholine receptor mediated disorders.

50 Claims, No Drawings

(56) References Cited

OTHER PUBLICATIONS

CAS Registry No. 1896462-97-7; STN Entry Date Apr. 24, 2016; 2-chloro-6,7-dihydro-4-methoxy-5H-pyrrolo[3,4-d]pyrimidine.
CAS Registry No. 1555492-80-2; STN Entry Date Feb. 25, 2014; 6,7-dihydro-4-methoxy-2.5-dimethyl-5H-pyrrolo[3,4-d]pyrimidine.
CAS Registry No. 1780613-88-8; STN Entry Date Jun. 15, 2015; N-cyclopropyl-6,7-dihydro-2-methyl-5H-pyrrolo[3,4-d]pyrimidin-4-amine.
CAS Registry No. 1891290-33-7; STN Entry Date Apr. 17, 2016; 4-chloro-6,7-dihydro-2-methoxy-5H-pyrrolo[3,4-d]pyrimidine.
CAS Registry No. 1393585-22-2; STN Entry Date Sep. 5, 2012; 1,1-dimethylethyl 4-chloro-5,7-dihydro-2(trifluoromethyl)-6H-pyrrolo[3,4-d]pyrimidine-6-carboxylate.
International Search Report and Written Opinion of the International Searching Authority, for International Application No. PCT/US2023/084185, dated Feb. 29, 2024, 13 pages.

SUBSTITUTED TETRAHYDROPYRROLO-PYRIDINONE COMPOUNDS AND THEIR USE IN TREATING MEDICAL CONDITIONS

CROSS-REFERENCE TO RELATED APPLICATIONS

This application is a continuation of International (PCT) patent application Ser. No. PCT/US2023/084185, filed Dec. 15, 2023, which claims the benefit of and priority to U.S. Provisional patent application Ser. No. 63/433,156, filed Dec. 16, 2022; the contents of each of which are hereby incorporated by reference in their entirety.

FIELD OF THE INVENTION

The invention provides substituted tetrahydropyrrolo-pyridinone compounds, pharmaceutical compositions, and their use in treating muscarinic acetylcholine receptor mediated disorders.

BACKGROUND

Muscarinic acetylcholine receptor mediated disorders such as major depressive disorder (MDD), bipolar disorder (BPD), and schizophrenia are psychiatric disorders that continue to be a significant public health problem. Antidepressant drugs, mood stabilizers, and antipsychotics currently available to patients can alleviate certain symptoms of mood disorders in some patients but are only partially effective for a significant number of patients, with many patients being refractory to treatment using currently available drugs. Patients with major depressive disorder often present with at least two weeks of pervasive low mood, low, self-esteem, and loss of interest or pleasure in normally enjoyable activities, Patients with bipolar disorder often present with periods of depression and periods of abnormally elevated mood that last from days to weeks each. Patients with schizophrenia often present with active social avoidance, passive social withdrawal, emotional withdrawal, and anxiety. Supportive therapies are used in some contexts to help alleviate the symptoms of muscarinic acetylcholine receptor mediated disorders; however, supportive therapies do not directly treat the disorder and are not a good long-term solution to the patients' medical needs.

Compounds that modulate the muscarinic acetylcholine receptor can be used to treat diseases associated with muscarinic acetylcholine receptor activity, such as major depressive disorder, bipolar disorder, and schizophrenia. The muscarinic acetylcholine receptor is an acetylcholine receptor that forms G protein-coupled receptor complexes in the cell membrane of certain neurons and other cells. U.S. Pat. No. 10,604,519 describes certain compounds as being active towards the M4 muscarinic acetylcholine receptor. However, new compounds with good drug-like properties are needed to treat muscarinic acetylcholine receptor mediated disorders.

The present invention addresses the foregoing need and provides other related advantages.

SUMMARY

The invention provides substituted tetrahydropyrrolo-pyridinone compounds, pharmaceutical compositions, and their use in treating muscarinic acetylcholine receptor mediated disorders. In particular, one aspect of the invention provides a collection of substituted tetrahydropyrrolo-pyridinone compounds, such as a compound represented by Formula I:

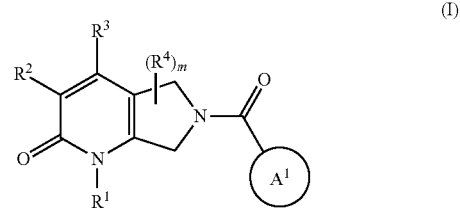

or a pharmaceutically acceptable salt thereof, where the variables are as defined in the detailed description. Further description of additional collections of substituted tetrahydropyrrolo-pyridinone compounds are described in the detailed description. The compounds may be part of a pharmaceutical composition comprising a pharmaceutically acceptable carrier.

Another aspect of the invention provides a method of treating a muscarinic acetylcholine receptor mediated disorder. The method comprises administering to a subject in need thereof a therapeutically effective amount of a compound described herein, such as a compound of Formula I, to treat muscarinic acetylcholine receptor mediated disorder, as further described in the detailed description.

Another aspect of the invention provides a method of activating a muscarinic acetylcholine receptor. The method comprises contacting a muscarinic acetylcholine receptor with an effective amount of a compound described herein, such as a compound of Formula I, to activate the muscarinic acetylcholine receptor, as further described in the detailed description.

DETAILED DESCRIPTION

The invention provides substituted tetrahydropyrrolo-pyridinone compounds, pharmaceutical compositions, and their use in treating muscarinic acetylcholine receptor mediated disorders. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

Compounds of the present invention include those described generally herein, and are further illustrated by the classes, subclasses, and species disclosed herein. As used herein, the following definitions shall apply unless otherwise indicated. These definitions apply regardless of whether a term is used by itself or in combination with other terms, unless otherwise indicated. Hence, the definition of "alkyl" applies to "alkyl" as well as the "alkyl" portions of "—O-alkyl" etc. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "cycloaliphatic"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e., carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e., carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally, or alternatively, any substitutable nitrogen of a bridged bicyclic group is optionally substituted. Exemplary bicyclic rings include:

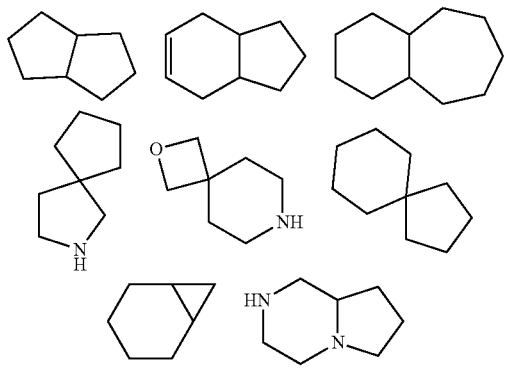

Exemplary Bridged Bicyclics Include:

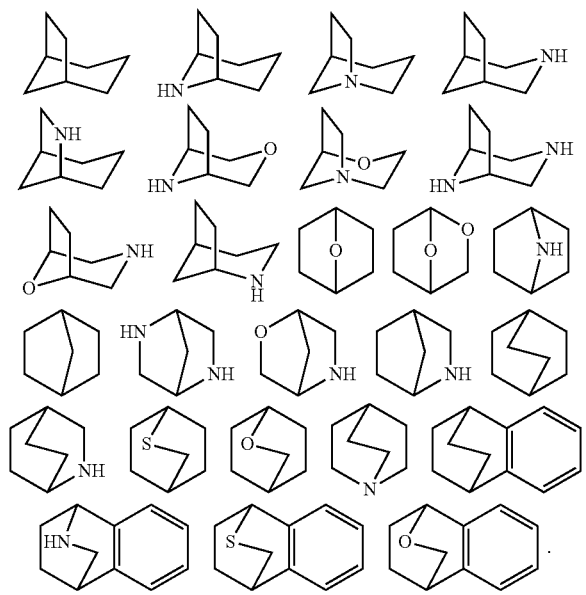

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "—(C$_0$ alkylene)-" refers to a bond. Accordingly, the term "—(C$_{0-3}$ alkylene)-" encompasses a bond (i.e., C$_0$) and a —(C$_{1-3}$ alkylene)- group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. The term "phenylene" refers to a multivalent phenyl group having the appropriate number of open valences to account for groups attached to it.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

The term "heteroarylene" refers to a multivalent heteroaryl group having the appropriate number of open valences to account for groups attached to it. For example, "heteroarylene" is a bivalent heteroaryl group when it has two groups attached to it; "heteroarylene" is a trivalent heteroaryl group when it has three groups attached to it.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted. The term "oxo-heterocyclyl" refers to a heterocyclyl substituted by one or more oxo group. The term "heterocyclylene" refers to a multivalent heterocyclyl group having the appropriate number of open valences to account for groups attached to it. For example, "heterocyclylene" is a bivalent heterocyclyl group when it has two groups attached to it; "heterocyclylene" is a trivalent heterocyclyl group when it has three groups attached to it. The term "oxo-heterocyclylene" refers to a multivalent oxo-heterocyclyl group having the appropriate number of open valences to account for groups attached to it.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; $-(CH_2)_{0-4}R°$; $-(CH_2)_{0-4}OR°$; $-O(CH_2)_{0-4}R°$, $-O-(CH_2)_{0-4}C(O)OR°$; $-(CH_2)_{0-4}CH(OR°)_2$; $-(CH_2)_{0-4}SR°$; $-(CH_2)_{0-4}Ph$, which may be substituted with R°; $-(CH_2)_{0-4}O(CH_2)_{0-1}Ph$ which may be substituted with R°; $-CH=CHPh$, which may be substituted with R°; $-(CH_2)_{0-4}O(CH_2)_{0-1}$-pyridyl which may be substituted with R°; $-NO_2$; $-CN$; $-N_3$; $-(CH_2)_{0-4}N(R°)_2$; $-(CH_2)_{0-4}N(R°)C(O)R°$; $-N(R°)C(S)R°$; $-(CH_2)_{0-4}N(R°)C(O)NR°_2$; $-N(R°)C(S)NR°_2$; $-(CH_2)_{0-4}N(R°)C(O)OR°$; $-N(R°)N(R°)C(O)R°$; $-N(R°)N(R°)C(O)NR°_2$; $-N(R°)N(R°)C(O)OR°$; $-(CH_2)_{0-4}C(O)R°$; $-C(S)R°$; $-(CH_2)_{0-4}C(O)OR°$; $-(CH_2)_{0-4}C(O)SR°$; $-(CH_2)_{0-4}C(O)OSiR°_3$; $-(CH_2)_{0-4}OC(O)R°$; $-OC(O)(CH_2)_{0-4}SR-$, $SC(S)SR°$; $-(CH_2)_{0-4}SC(O)R°$; $-(CH_2)_{0-4}C(O)NR°_2$; $-C(S)NR°_2$; $-C(S)SR°$; $-SC(S)SR°$, $-(CH_2)_{0-4}OC(O)NR°_2$; $-C(O)N(OR°)R°$; $-C(O)C(O)R°$; $-C(O)CH_2C(O)R°$; $-C(NOR°)R°$; $-(CH_2)_{0-4}SSR°$; $-(CH_2)_{0-4}S(O)_2R°$; $-(CH_2)_{0-4}S(O)_2OR°$; $-(CH_2)_{0-4}OS(O)_2R°$; $-S(O)_2NR°_2$; $-S(O)(NR°)R°$; $-S(O)_2N=C(NR°_2)_2$; $-(CH_2)_{0-4}S(O)R°$; $-N(R°)S(O)_2NR°_2$; $-N(R°)S(O)_2R°$; $-N(OR°)R°$; $-C(NH)NR°_2$; $-P(O)_2R°$; $-P(O)R°_2$; $-OP(O)R°_2$; $-OP(O)(OR°)_2$; $SiR°_3$; $-(C_{1-4}$ straight or branched alkylene$)O-N(R°)_2$; or $-(C_{1-4}$ straight or branched alkylene$)C(O)O-N(R°)_2$.

Each R° is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of R° selected from $=O$ and $=S$; or each R° is optionally substituted with a monovalent substituent independently selected from halogen, $-(CH_2)_{0-2}R^{\bullet}$, -(haloR$^{\bullet}$), $-(CH_2)_{0-2}OH$, $-(CH_2)_{0-2}OR^{\bullet}$, $-(CH_2)_{0-2}CH(OR^{\bullet})_2$; $-O(haloR^{\bullet})$, $-CN$, $-N_3$, $-(CH_2)_{0-2}C(O)R^{\bullet}$, $-(CH_2)_{0-2}C(O)OH$, $-(CH_2)_{0-2}C(O)OR^{\bullet}$, $-(CH_2)_{0-2}SR^{\bullet}$, $-(CH_2)_{0-2}SH$, $-(CH_2)_{0-2}NH_2$, $-(CH_2)_{0-2}NHR^{\bullet}$, $-(CH_2)_{0-2}NR^{\bullet}_2$, $-NO_2$, $-SiR^{\bullet}_3$, $-OSiR^{\bullet}_3$, $-C(O)SR^{\bullet}$, $-(C_{1-4}$ straight or branched alkylene$)C(O)OR^{\bullet}$, or $-SSR^{\bullet}$.

Each R$^{\bullet}$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each R$^{\bullet}$ is unsubstituted or where preceded by halo is substituted only with one or more halogens; or wherein an optional substituent on a saturated carbon is a divalent substituent independently selected from $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, or a divalent substituent bound to vicinal substitutable carbons of an "optionally substituted" group is $-O(CR^*_2)_{2-3}O-$, wherein each independent occurrence of R* is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When R* is $C_{1-6}$ aliphatic, R* is optionally substituted with halogen, $-R^{\bullet}$, -(haloR$^{\bullet}$), $-OH$, $-OR^{\bullet}$, $-O(haloR^{\bullet})$, $-CN$, $-C(O)OH$, $-C(O)OR^{\bullet}$, $-NH_2$, $-NHR^{\bullet}$, $-NR^{\bullet}_2$, or $-NO_2$, wherein each R$^{\bullet}$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each R$^{\bullet}$ is unsubstituted or where preceded by halo is substituted only with one or more halogens.

An optional substituent on a substitutable nitrogen is independently $-R^{\dagger}$, $-NR^{\dagger}_2$, $-C(O)R^{\dagger}$, $-C(O)OR^{\dagger}$, $-C(O)C(O)R^{\dagger}$, $-C(O)CH_2C(O)R^{\dagger}$, $-S(O)_2R^{\dagger}$, $-S(O)_2NR^{\dagger}_2$, $-C(S)NR^{\dagger}_2$, $-C(NH)NR^{\dagger}_2$, or $-N(R^{\dagger})S(O)_2R^{\dagger}$; wherein each R$^{\dagger}$ is independently hydrogen, $C_{1-6}$ aliphatic, unsubstituted $-OPh$, or an unsubstituted 5-6-membered saturated, partially unsaturated, or aryl ring having 0-4 heteroatoms independently selected from nitrogen, oxygen, or sulfur, or, two independent occurrences of R$^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when R$^{\dagger}$ is $C_{1-6}$ aliphatic, R$^{\dagger}$ is optionally substituted with halogen, $-R^{\bullet}$, -(haloR$^{\bullet}$), $-OH$, $-OR^{\bullet}$, $-O(haloR^{\bullet})$, $-CN$, $-C(O)OH$, $-C(O)OR^{\bullet}$, $-NH_2$, $-NHR^{\bullet}$, $-NR^{\bullet}_2$, or $-NO_2$, wherein each R$^{\bullet}$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each R$^{\bullet}$ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. The invention includes compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as an atropisomer (e.g., substituted biaryls), all forms of such atropisomer are considered part of this invention.

Chemical names, common names, and chemical structures may be used interchangeably to describe the same structure. If a chemical compound is referred to using both a chemical structure and a chemical name, and an ambiguity exists between the structure and the name, the structure predominates. It should also be noted that any carbon as well as heteroatom with unsatisfied valences in the text, schemes, examples and tables herein is assumed to have the sufficient number of hydrogen atom(s) to satisfy the valences.

The terms "a" and "an" as used herein mean "one or more" and include the plural unless the context is inappropriate.

The term "alkyl" refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_3$-$C_6$ cycloalkyl," derived from a cycloalkane. Exemplary cycloalkyl groups include cyclohexyl, cyclopentyl, cyclobutyl, and cyclopropyl. The term "cycloalkylene" refers to a bivalent cycloalkyl group.

The term "haloalkyl" refers to an alkyl group that is substituted with at least one halogen. Exemplary haloalkyl groups include —CH$_2$F, —CHF$_2$, —CF$_3$, —CH$_2$CF$_3$, —CF$_2$CF$_3$, and the like. The term "haloalkylene" refers to a bivalent haloalkyl group.

The term "hydroxyalkyl" refers to an alkyl group that is substituted with at least one hydroxyl. Exemplary hydroxyalkyl groups include —CH$_2$CH$_2$OH, —C(H)(OH)CH$_3$, —CH$_2$C(H)(OH)CH$_2$CH$_2$OH, and the like.

The terms "alkenyl" and "alkynyl" are art-recognized and refer to unsaturated aliphatic groups analogous in length and possible substitution to the alkyls described above, but that contain at least one double or triple bond respectively.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. The term "haloalkoxyl" refers to an alkoxyl group that is substituted with at least one halogen. Exemplary haloalkoxyl groups include —OCH$_2$F, —OCHF$_2$, —OCF$_3$, —OCH$_2$CF$_3$, —OCF$_2$CF$_3$, and the like.

The term "oxo" is art-recognized and refers to a "=O" substituent. For example, a cyclopentane substituted with an oxo group is cyclopentanone.

The symbol " $\sim\!\sim\!\sim$ " indicates a point of attachment.

When any substituent or variable occurs more than one time in any constituent or the compound of the invention, its definition on each occurrence is independent of its definition at every other occurrence, unless otherwise indicated.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

As used herein, the terms "subject" and "patient" are used interchangeable and refer to organisms to be treated by the methods of the present invention. Such organisms preferably include, but are not limited to, mammals (e.g., murines, simians, equines, bovines, porcines, canines, felines, and the like), and most preferably includes humans.

The term "$EC_{50}$" is art-recognized and refers to the concentration of a compound that is required to achieve 50% of the maximal response.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified.

I. Substituted Tetrahydropyrrolo-Pyridinone Compounds

One aspect of the invention provides substituted tetrahydropyrrolo-pyridinone compounds. The compounds may be used in the pharmaceutical compositions and therapeutic methods described herein. Exemplary compounds are described in the following sections, along with exemplary procedures for making the compounds.

One aspect of the invention provides a compound represented by Formula I:

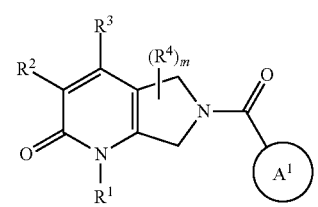

or a pharmaceutically acceptable salt thereof; wherein:

$R^1$ is $C_{1-6}$ alkyl, $C_{1-6}$ haloalkyl, $C_{3-6}$ cycloalkyl, —($C_{1-6}$ alkylene)-($C_{3-6}$ cycloalkyl), or hydrogen;

$R^2$ is halo, $C_{1-4}$ alkyl, $C_{1-4}$ haloalkyl, or hydrogen;

$R^3$ is $C_{1-4}$ alkyl, $C_{1-4}$ haloalkyl, $C_{1-4}$ alkoxyl, —S—($C_{1-4}$ alkyl), or halo;

$R^4$ represents independently for each occurrence $C_{1-4}$ alkyl, $C_{1-4}$ haloalkyl, or halo;

$R^5$ represents independently for each occurrence $C_{1-6}$ alkyl, halo, $C_{1-6}$ haloalkyl, $C_{3-6}$ cycloalkyl, hydroxyl, $C_{1-6}$ alkoxyl, —($C_{1-6}$ alkylene)-($C_{1-6}$ alkoxyl), —($C_{1-6}$ alkylene)-($C_{3-6}$ cycloalkyl), —($C_{1-6}$ haloalkylene)-($C_{3-6}$ cycloalkyl), or —($C_{1-6}$ alkylene)-($C_{3-6}$ halocycloalkyl); or two occurrences of $R^5$ are taken together with their intervening atoms to form a 4-7 membered ring containing 1 or 2 heteroatoms independently selected from oxygen, nitrogen, and sulfur;

$R^6$ is (i) —($C_{0-4}$ alkylene)-(3-7 membered saturated or unsaturated heterocyclyl containing 1, 2, or 3 heteroatoms independently selected from nitrogen, oxygen, and sulfur), (ii) —($C_{0-4}$ alkylene)-(5-6 membered heteroaryl containing 1, 2, or 3 heteroatoms independently selected from nitrogen, oxygen, and sulfur), or (iii) —($C_{0-4}$ alkylene)-phenyl, wherein the heterocyclyl, heteroaryl, and phenyl are substituted with 0, 1, 2, or 3 occurrences of $R^7$;

$R^7$ represents independently for each occurrence $C_{1-6}$ alkyl, halo, $C_{1-6}$ haloalkyl, $C_{3-6}$ cycloalkyl, hydroxyl, or $C_{1-6}$ alkoxyl;

A¹ is a 5-6 membered monocyclic heteroaryl containing 1, 2, or 3 heteroatoms independently selected from nitrogen, oxygen, and sulfur, an 8-10 membered bicyclic heteroaryl containing 1, 2, or 3 heteroatoms independently selected from nitrogen, oxygen, and sulfur, or phenyl, wherein the heteroaryl and phenyl are substituted with n occurrences of $R^5$ and t occurrences of $R^6$;

m is 0, 1, 2, or 3;

n is 0, 1, or 2; and t is 0 or 1.

The definitions of variables in Formula I above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula I.

As defined generally above, $R^1$ is $C_{1-6}$ alkyl, $C_{1-6}$ haloalkyl, $C_{3-6}$ cycloalkyl, —($C_{1-6}$ alkylene)-($C_{3-6}$ cycloalkyl), or hydrogen. In certain embodiments, $R^1$ is $C_{1-6}$ alkyl, $C_{1-6}$ haloalkyl, $C_{3-6}$ cycloalkyl, or —($C_{1-6}$ alkylene)-($C_{3-6}$ cycloalkyl). In certain embodiments, $R^1$ is $C_{1-6}$ haloalkyl, $C_{3-6}$ cycloalkyl, —($C_{1-6}$ alkylene)-($C_{3-6}$ cycloalkyl), or hydrogen. In certain embodiments, $R^1$ is $C_{1-6}$ alkyl, $C_{3-6}$ cycloalkyl, —($C_{1-6}$ alkylene)-($C_{3-6}$ cycloalkyl), or hydrogen. In certain embodiments, $R^1$ is $C_{1-6}$ alkyl, $C_{1-6}$ haloalkyl, —($C_{1-6}$ alkylene)-($C_{3-6}$ cycloalkyl), or hydrogen. In certain embodiments, $R^1$ is $C_{1-6}$ alkyl, $C_{1-6}$ haloalkyl, $C_{3-6}$ cycloalkyl, or hydrogen.

In certain embodiments, $R^1$ is $C_{3-6}$ cycloalkyl, —($C_{1-6}$ alkylene)-($C_{3-6}$ cycloalkyl), or hydrogen. In certain embodiments, $R^1$ is $C_{1-6}$ haloalkyl, —($C_{1-6}$ alkylene)-($C_{3-6}$ cycloalkyl), or hydrogen. In certain embodiments, $R^1$ $C_{1-6}$ haloalkyl, $C_{3-6}$ cycloalkyl, or hydrogen. In certain embodiments, $R^1$ is $C_{1-6}$ haloalkyl, $C_{3-6}$ cycloalkyl, or —($C_{1-6}$ alkylene)-($C_{3-6}$ cycloalkyl). In certain embodiments, $R^1$ is $C_{1-6}$ alkyl, —($C_{1-6}$ alkylene)-($C_{3-6}$ cycloalkyl), or hydrogen. In certain embodiments, $R^1$ is $C_{1-6}$ alkyl, $C_{3-6}$ cycloalkyl, or hydrogen. In certain embodiments, $R^1$ is $C_{1-6}$ alkyl, $C_{3-6}$ cycloalkyl, or —($C_{1-6}$ alkylene)-($C_{3-6}$ cycloalkyl). In certain embodiments, $R^1$ is $C_{1-6}$ alkyl, $C_{1-6}$ haloalkyl, or hydrogen. In certain embodiments, $R^1$ is $C_{1-6}$ alkyl, $C_{1-6}$ haloalkyl, or —($C_{1-6}$ alkylene)-($C_{3-6}$ cycloalkyl). In certain embodiments, $R^1$ is $C_{1-6}$ alkyl, $C_{1-6}$ haloalkyl, or $C_{3-6}$ cycloalkyl.

In certain embodiments, $R^1$ is $C_{1-6}$ alkyl. In certain embodiments, $R^1$ is $C_{1-4}$ alkyl. In certain embodiments, $R^1$ is $C_{1-3}$ alkyl. In certain embodiments, $R^1$ is $C_{2-6}$ alkyl. In certain embodiments, $R^1$ is $C_{3-6}$ alkyl. In certain embodiments, $R^1$ is methyl, ethyl, or propyl. In certain embodiments, $R^1$ is methyl. In certain embodiments, $R^1$ is ethyl.

In certain embodiments, $R^1$ is $C_{1-6}$ haloalkyl. In certain embodiments, $R^1$ is $C_{1-4}$ haloalkyl. In certain embodiments, $R^1$ is $C_{1-3}$ haloalkyl. In certain embodiments, $R^1$ is $C_{2-6}$ haloalkyl. In certain embodiments, $R^1$ is $C_{3-6}$ haloalkyl. In certain embodiments, $R^1$ is $C_{1-6}$ haloalkyl, wherein the halogen is F. In certain embodiments, $R^1$ is $C_{1-4}$ haloalkyl, wherein the halogen is F. In certain embodiments, $R^1$ is $C_{1-3}$ haloalkyl, wherein the halogen is F. In certain embodiments, $R^1$ is $C_{2-6}$ haloalkyl, wherein the halogen is F. In certain embodiments, $R^1$ is $C_{3-6}$ haloalkyl, wherein the halogen is F.

In certain embodiments, $R^1$ is $CF_3$. In some embodiments, $R^1$ is $CHF_2$. In some embodiments, $R^1$ is —$CH_2CF_3$. In some embodiments, $R^1$ is —$CH_2CHF_2$.

In certain embodiments, $R^1$ is $C_{3-6}$ cycloalkyl. In certain embodiments, $R^1$ is $C_{4-6}$ cycloalkyl. In certain embodiments, $R^1$ is $C_{5-6}$ cycloalkyl. In certain embodiments, $R^1$ is cyclopropyl.

In certain embodiments, $R^1$ is —($C_{1-6}$ alkylene)-($C_{3-6}$ cycloalkyl). In certain embodiments, $R^1$ is —($C_{1-4}$ alkylene)-($C_{3-6}$ cycloalkyl). In certain embodiments, $R^1$ is —($C_{2-6}$ alkylene)-($C_{3-6}$ cycloalkyl). In certain embodiments, $R^1$ is —($C_{1-4}$ alkylene)-($C_{5-6}$ cycloalkyl). In certain embodiments, $R^1$ is —($C_{1-3}$ alkylene)-($C_{4-6}$ cycloalkyl). In certain embodiments, $R^1$ is —($C_{1-2}$ alkylene)-($C_{3-5}$ cycloalkyl). In certain embodiments, $R^1$ is —$CH_2$-cyclopropyl.

In certain embodiments, $R^1$ is hydrogen.

In certain embodiments, $R^1$ is selected from those depicted in Table 1.

As defined generally above, $R^2$ is halo, $C_{1-4}$ alkyl, $C_{1-4}$ haloalkyl, or hydrogen. In certain embodiments, $R^2$ is halo, $C_{1-4}$ alkyl, or $C_{1-4}$ haloalkyl. In certain embodiments, $R^2$ is $C_{1-4}$ alkyl, $C_{1-4}$ haloalkyl, or hydrogen. In certain embodiments, $R^2$ is halo, $C_{1-4}$ haloalkyl, or hydrogen. In certain embodiments, $R^2$ is halo, $C_{1-4}$ alkyl, or hydrogen. In certain embodiments, $R^2$ is $C_{1-4}$ haloalkyl or hydrogen. In certain embodiments, $R^2$ is $C_{1-4}$ alkyl or hydrogen. In certain embodiments, $R^2$ is $C_{1-4}$ alkyl or $C_{1-4}$ haloalkyl. In certain embodiments, $R^2$ is halo or hydrogen. In certain embodiments, $R^2$ is halo or $C_{1-4}$ haloalkyl. In certain embodiments, $R^2$ is halo or $C_{1-4}$ alkyl.

In certain embodiments, $R^2$ is halo. In certain embodiments, $R^2$ is selected from F, Cl, and Br. In certain embodiments, $R^2$ is selected from F and Cl. In certain embodiments, $R^2$ is F. In certain embodiments, $R^2$ is Cl.

In certain embodiments, $R^2$ is $C_{1-4}$ alkyl. In certain embodiments, $R^2$ is $C_{1-3}$ alkyl. In certain embodiments, $R^2$ is $C_{2-4}$ alkyl. In certain embodiments, $R^2$ is $C_{3-4}$ alkyl. In certain embodiments, $R^2$ is methyl, ethyl, or propyl. In certain embodiments, $R^2$ is methyl. In certain embodiments, $R^2$ is ethyl.

In certain embodiments, $R^2$ is $C_{1-4}$ haloalkyl. In certain embodiments, $R^2$ is $C_{1-3}$ haloalkyl. In certain embodiments, $R^2$ is $C_{2-4}$ haloalkyl. In certain embodiments, $R^2$ is $C_{3-4}$ haloalkyl. In certain embodiments, $R^2$ is $C_{1-4}$ haloalkyl, wherein the halogen is F. In certain embodiments, $R^2$ is $C_{1-4}$ haloalkyl, wherein the halogen is selected F. In certain embodiments, $R^2$ is $C_{1-3}$ haloalkyl, wherein the halogen is F. In certain embodiments, $R^2$ is $C_{2-4}$ haloalkyl, wherein the halogen is F. In certain embodiments, $R^2$ is $C_{3-4}$ haloalkyl, wherein the halogen is F.

In certain embodiments, $R^2$ is $CF_3$. In some embodiments, $R^2$ is $CHF_2$. In some embodiments, $R^2$ is —$CH_2CF_3$. In some embodiments, $R^2$ is —$CH_2CHF_2$. In certain embodiments, $R^2$ is hydrogen.

In certain embodiments, $R^2$ is selected from those depicted in Table 1.

As defined generally above, $R^3$ is $C_{1-4}$ alkyl, $C_{1-4}$ haloalkyl, $C_{1-4}$ alkoxyl, —S—($C_{1-4}$ alkyl), or halo. In certain embodiments, $R^3$ is $C_{1-4}$ haloalkyl, $C_{1-4}$ alkoxyl, —S—($C_{1-4}$ alkyl), or halo. In certain embodiments, $R^3$ is $C_{1-4}$ alkyl, $C_{1-4}$ alkoxyl, —S—($C_{1-4}$ alkyl), or halo. In certain embodiments, $R^3$ is $C_{1-4}$ alkyl, $C_{1-4}$ haloalkyl, —S—($C_{1-4}$ alkyl), or halo. In certain embodiments, $R^3$ is $C_{1-4}$ alkyl, $C_{1-4}$ haloalkyl, $C_{1-4}$ alkoxyl, or halo. In certain embodiments, $R^3$ is $C_{1-4}$ alkyl, $C_{1-4}$ haloalkyl, $C_{1-4}$ alkoxyl, or —S—($C_{1-4}$ alkyl).

In certain embodiments, $R^3$ is $C_{1-4}$ alkoxyl, —S—($C_{1-4}$ alkyl), or halo. In certain embodiments, $R^3$ is $C_{1-4}$ haloalkyl, —S—($C_{1-4}$ alkyl), or halo. In certain embodiments, $R^3$ is $C_{1-4}$ haloalkyl, $C_{1-4}$ alkoxyl, or halo. In certain embodiments, $R^3$ is $C_{1-4}$ haloalkyl, $C_{1-4}$ alkoxyl, or —S—($C_{1-4}$ alkyl). In certain embodiments, $R^3$ is $C_{1-4}$ alkyl, —S—($C_{1-4}$ alkyl), or halo. In certain embodiments, $R^3$ is $C_{1-4}$ alkyl, $C_{1-4}$ alkoxyl, or halo. In certain embodiments, $R^3$ is $C_{1-4}$ alkyl, $C_{1-4}$ alkoxyl, or —S—($C_{1-4}$ alkyl). In certain embodiments, $R^3$ is $C_{1-4}$ alkyl, $C_{1-4}$ haloalkyl, or halo. In certain embodiments, $R^3$ is $C_{1-4}$ alkyl, $C_{1-4}$ haloalkyl, or —S—($C_{1-4}$ alkyl). In certain embodiments, $R^3$ is $C_{1-4}$ alkyl, $C_{1-4}$ haloalkyl, or $C_{1-4}$ alkoxyl.

In certain embodiments, $R^3$ is $C_{1-4}$ alkyl. In certain embodiments, $R^3$ is $C_{1-3}$ alkyl. In certain embodiments, $R^3$ is $C_{2-4}$ alkyl. In certain embodiments, $R^3$ is $C_{3-4}$ alkyl. In certain embodiments, $R^3$ is methyl, ethyl, or propyl. In certain embodiments, $R^3$ is methyl. In certain embodiments, $R^3$ is ethyl.

In certain embodiments, $R^3$ is $C_{1-4}$ haloalkyl. In certain embodiments, $R^\circ$ is $C_{1-3}$ haloalkyl. In certain embodiments, $R^3$ is $C_{2-4}$ haloalkyl. In certain embodiments, $R^3$ is $C_{3-4}$ haloalkyl. In certain embodiments, $R^3$ is $C_{1-4}$ haloalkyl, wherein the halogen is F. In certain embodiments, $R^3$ is $C_{1-4}$ haloalkyl, wherein the halogen is selected F. In certain embodiments, $R^3$ is $C_{1-3}$ haloalkyl, wherein the halogen is F. In certain embodiments, $R^3$ is $C_{2-4}$ haloalkyl, wherein the halogen is F. In certain embodiments, $R^3$ is $C_{3-4}$ haloalkyl, wherein the halogen is F.

In certain embodiments, $R^3$ is $CF_3$. In some embodiments, $R^3$ is $CHF_2$. In some embodiments, $R^3$ is —$CH_2CF_3$. In some embodiments, $R^3$ is —$CH_2CHF_2$.

In certain embodiments, $R^3$ is $C_{1-4}$ alkoxyl. In certain embodiments, $R^3$ is $C_{1-3}$ alkoxyl. In certain embodiments, $R^3$ is $C_{2-4}$ alkoxyl. In certain embodiments, $R^3$ is $C_{3-4}$ alkoxyl. In certain embodiments, $R^3$ is —$OCH_3$, —$OCH_2CH_3$, —$OCH(CH_3)_2$, or —$OC(CH_3)_3$. In certain embodiments, $R^3$ is —$OCH_3$. In certain embodiments, $R^3$ is —$OCH_2CH_3$. In certain embodiments $R^3$ is —$OCH(CH_3)_2$. In certain embodiments, $R^3$ is —$OC(CH_3)_3$. In certain embodiments, $R^3$ is —$OCHF_2$.

In certain embodiments, $R^3$ is —S—($C_{1-4}$ alkyl). In certain embodiments, $R^3$ is —S—($C_{1-3}$ alkyl). In certain embodiments, $R^3$ is —S—($C_{2-4}$ alkyl). In certain embodiments, $R^3$ is —S—($C_{3-4}$ alkyl). In certain embodiments, $R^3$ is —$SCH_3$, —$SCH_2CH_3$, —$SCH(CH_3)_2$, or —$SC(CH_3)_3$.

In certain embodiments, $R^3$ is halo. In certain embodiments, $R^3$ is selected from $C_1$, and Br. In certain embodiments, $R^3$ is selected from F and Cl. In certain embodiments, $R^3$ is F. In certain embodiments, $R^3$ is Cl.

In certain embodiments, $R^3$ is selected from those depicted in Table 1.

As defined generally above, $R^4$ represents independently for each occurrence $C_{1-4}$ alkyl, $C_{1-4}$ haloalkyl, or halo. In certain embodiments, $R^4$ represents independently for each occurrence $C_{1-4}$ haloalkyl, or halo. In certain embodiments, $R^4$ represents independently for each occurrence $C_{1-4}$ alkyl or halo. In certain embodiments, $R^4$ represents independently for each occurrence $C_{1-4}$ alkyl, or $C_{1-4}$ haloalkyl.

In certain embodiments, $R^4$ represents independently for each occurrence $C_{1-4}$ alkyl. In certain embodiments, $R^4$ represents independently for each occurrence $C_{1-3}$ alkyl. In certain embodiments, $R^4$ represents independently for each occurrence $C_{2-4}$ alkyl. In certain embodiments, $R^4$ represents independently for each occurrence $C_{3-4}$ alkyl. In certain embodiments, $R^4$ represents independently for each occurrence methyl, ethyl, or propyl. In certain embodiments, $R^4$ is methyl.

In certain embodiments, $R^4$ represents independently for each occurrence $C_{1-4}$ haloalkyl. In certain embodiments, $R^4$ represents independently for each occurrence $C_{1-3}$ haloalkyl. In certain embodiments, $R^4$ represents independently for each occurrence $C_{2-4}$ haloalkyl. In certain embodiments, $R^4$ represents independently for each occurrence $C_{3-4}$ haloalkyl.

In certain embodiments, $R^4$ is $C_{1-4}$ haloalkyl, wherein the halogen is F. In certain embodiments, $R^4$ is $C_{1-3}$ haloalkyl, wherein the halogen is F. In certain embodiments, $R^4$ is $C_{2-4}$ haloalkyl, wherein the halogen is F. In certain embodiments, $R^4$ is $C_{3-4}$ haloalkyl, wherein the halogen is F. In certain embodiments, $R^4$ represents independently for each occurrence halo. In certain embodiments, $R^4$ represents independently for each occurrence Cl or F.

In certain embodiments, $R^4$ is $C_{1-4}$ alkyl, $C_{1-4}$ haloalkyl, or halo. In certain embodiments, $R^4$ is $C_{1-4}$ haloalkyl or halo. In certain embodiments, $R^4$ is $C_{1-4}$ alkyl or halo. In certain embodiments, $R^4$ is $C_{1-4}$ alkyl or $C_{1-4}$ haloalkyl.

In certain embodiments, $R^4$ is $CF_3$. In some embodiments, $R^4$ is $CHF_2$. In some embodiments, $R^4$ is —$CH_2CF_3$. In some embodiments, $R^4$ is —$CH_2CHF_2$.

In certain embodiments, $R^4$ is halo. In certain embodiments, $R^4$ is selected from F and Cl. In certain embodiments, $R^4$ is F. In certain embodiments, $R^4$ is $C_1$.

In certain embodiments, $R^4$ is selected from those depicted in Table 1.

As defined generally above, $R^5$ represents independently for each occurrence $C_{1-6}$ alkyl, halo, $C_{1-6}$ haloalkyl, $C_{3-6}$ cycloalkyl, hydroxyl, $C_{1-6}$ alkoxyl, —($C_{1-6}$ alkylene)-($C_{1-6}$ alkoxyl), —($C_{1-6}$ alkylene)-($C_{3-6}$ cycloalkyl), —($C_{1-6}$ haloalkylene)-($C_{3-6}$ cycloalkyl), or —($C_{1-6}$ alkylene)-($C_{3-6}$ halocycloalkyl); or two occurrences of $R^5$ are taken together with their intervening atoms to form a 4-7 membered ring containing 1 or 2 heteroatoms independently selected from oxygen, nitrogen, and sulfur. In certain embodiments, $R^5$ represents independently for each occurrence $C_{1-6}$ alkyl, halo, $C_{1-6}$ haloalkyl, $C_{3-6}$ cycloalkyl, hydroxyl, $C_{1-6}$ alkoxyl, —($C_{1-6}$ alkylene)-($C_{1-6}$ alkoxyl), —($C_{1-6}$ alkylene)-($C_{3-6}$ cycloalkyl), or —($C_{1-6}$ alkylene)-($C_{3-6}$ halocycloalkyl); or two occurrences of $R^5$ are taken together with their intervening atoms to form a 4-7 membered ring containing 1 or 2 heteroatoms independently selected from oxygen, nitrogen, and sulfur. In certain embodiments, $R^5$ represents independently for each occurrence halo, $C_{1-6}$ haloalkyl, $C_{3-6}$ cycloalkyl, hydroxyl, $C_{1-6}$ alkoxyl, —($C_{1-6}$ alkylene)-($C_{1-6}$ alkoxyl), —($C_{1-6}$ alkylene)-($C_{3-6}$ cycloalkyl), or —($C_{1-6}$ alkylene)-($C_{3-6}$ halocycloalkyl); or two occurrences of $R^5$ are taken together with their intervening atoms to form a 4-7 membered ring containing 1 or 2 heteroatoms independently selected from oxygen, nitrogen, and sulfur.

In certain embodiments, $R^5$ represents independently for each occurrence $C_{1-6}$ alkyl, $C_{1-6}$ haloalkyl, $C_{3-6}$ cycloalkyl, hydroxyl, $C_{1-6}$ alkoxyl, —($C_{1-6}$ alkylene)-($C_{1-6}$ alkoxyl), —($C_{1-6}$ alkylene)-($C_{3-6}$ cycloalkyl), or —($C_{1-6}$ alkylene)-($C_{3-6}$ halocycloalkyl); or two occurrences of $R^5$ are taken together with their intervening atoms to form a 4-7 membered ring containing 1 or 2 heteroatoms independently selected from oxygen, nitrogen, and sulfur. In certain embodiments, $R^5$ represents independently for each occurrence $C_{1-6}$ alkyl, halo, $C_{3-6}$ cycloalkyl, hydroxyl, $C_{1-6}$ alkoxyl, —($C_{1-6}$ alkylene)-($C_{1-6}$ alkoxyl), —($C_{1-6}$ alkylene)-($C_{3-6}$ cycloalkyl), or —($C_{1-6}$ alkylene)-($C_{3-6}$ halocycloalkyl); or two occurrences of $R^5$ are taken together with their intervening atoms to form a 4-7 membered ring containing 1 or 2 heteroatoms independently selected from oxygen, nitrogen, and sulfur. In certain embodiments, $R^5$ represents independently for each occurrence $C_{1-6}$ alkyl, halo, $C_{1-6}$ haloalkyl, hydroxyl, $C_{1-6}$ alkoxyl, —($C_{1-6}$ alkylene)-($C_{1-6}$ alkoxyl), —($C_{1-6}$ alkylene)-($C_{3-6}$ cycloalkyl), or —($C_{1-6}$ alkylene)-($C_{3-6}$ halocycloalkyl); or two occurrences of $R^5$ are taken together with their intervening atoms to form a 4-7 membered ring containing 1 or 2 heteroatoms independently selected from oxygen, nitrogen, and sulfur.

In certain embodiments, $R^5$ represents independently for each occurrence $C_{1-6}$ alkyl, halo, $C_{1-6}$ haloalkyl, $C_{3-6}$ cycloalkyl, $C_{1-6}$ alkoxyl, —($C_{1-6}$ alkylene)-($C_{1-6}$ alkoxyl), —($C_{1-6}$ alkylene)-($C_{3-6}$ cycloalkyl), or —($C_{1-6}$ alkylene)-($C_{3-6}$ halocycloalkyl); or two occurrences of $R^5$ are taken together with their intervening atoms to form a 4-7 membered ring containing 1 or 2 heteroatoms independently selected from oxygen, nitrogen, and sulfur. In certain embodiments, $R^5$ represents independently for each occurrence $C_{1-6}$ alkyl, halo, $C_{1-6}$ haloalkyl, $C_{3-6}$ cycloalkyl, hydroxyl, —($C_{1-6}$ alkylene)-($C_{1-6}$ alkoxyl), —($C_{1-6}$ alkylene)-($C_{3-6}$ cycloalkyl), or —($C_{1-6}$ alkylene)-($C_{3-6}$ halocycloalkyl); or two occurrences of $R^5$ are taken together with their intervening atoms to form a 4-7 membered ring containing 1 or 2 heteroatoms independently selected from oxygen, nitrogen, and sulfur. In certain embodiments, $R^5$ represents independently for each occurrence $C_{1-6}$ alkyl, halo, $C_{1-6}$ haloalkyl, $C_{3-6}$ cycloalkyl, hydroxyl, $C_{1-6}$ alkoxyl, —($C_{1-6}$ alkylene)-($C_{3-6}$ cycloalkyl), or —($C_{1-6}$ alkylene)-($C_{3-6}$ halocycloalkyl); or two occurrences of $R^5$ are taken together with their intervening atoms to form a 4-7 membered ring containing 1 or 2 heteroatoms independently selected from oxygen, nitrogen, and sulfur.

In certain embodiments, $R^5$ represents independently for each occurrence $C_{1-6}$ alkyl, halo, $C_{1-6}$ haloalkyl, $C_{3-6}$ cycloalkyl, hydroxyl, $C_{1-6}$ alkoxyl, —($C_{1-6}$ alkylene)-($C_{1-6}$ alkoxyl), or —($C_{1-6}$ alkylene)-($C_{3-6}$ halocycloalkyl); or two occurrences of $R^5$ are taken together with their intervening atoms to form a 4-7 membered ring containing 1 or 2 heteroatoms independently selected from oxygen, nitrogen, and sulfur.

In certain embodiments, $R^5$ represents independently for each occurrence $C_{1-6}$ alkyl, halo, $C_{1-6}$ haloalkyl, $C_{3-6}$ cycloalkyl, hydroxyl, $C_{1-6}$ alkoxyl, —($C_{1-6}$ alkylene)-($C_{1-6}$ alkoxyl), or —($C_{1-6}$ alkylene)-($C_{3-6}$ cycloalkyl); or two occurrences of $R^5$ are taken together with their intervening atoms to form a 4-7 membered ring containing 1 or 2 heteroatoms independently selected from oxygen, nitrogen, and sulfur. In certain embodiments, $R^5$ represents independently for each occurrence $C_{1-6}$ alkyl, halo, $C_{1-6}$ haloalkyl, $C_{3-6}$ cycloalkyl, hydroxyl, $C_{1-6}$ alkoxyl, —($C_{1-6}$ alkylene)-($C_{1-6}$ alkoxyl), —($C_{1-6}$ alkylene)-($C_{3-6}$ cycloalkyl), or —($C_{1-6}$ alkylene)-($C_{3-6}$ halocycloalkyl). In certain embodiments, $R^5$ represents independently for each occurrence —($C_{1-6}$ alkylene)-($C_{1-6}$ alkoxyl), —($C_{1-6}$ alkylene)-($C_{3-6}$ cycloalkyl), or —($C_{1-6}$ alkylene)-($C_{3-6}$ halocycloalkyl); or two occurrences of $R^5$ are taken together with their intervening atoms to form a 4-7 membered ring containing 1 or 2 heteroatoms independently selected from oxygen, nitrogen, and sulfur.

In certain embodiments, $R^5$ represents independently for each occurrence $C_{1-6}$ alkyl, halo, $C_{1-6}$ haloalkyl, $C_{3-6}$ cycloalkyl, or —($C_{1-6}$ alkylene)-($C_{3-6}$ cycloalkyl).

In certain embodiments, $R^5$ represents independently for each occurrence $C_{1-6}$ alkyl. In certain embodiments, $R^5$ represents independently for each occurrence $C_{1-4}$ alkyl. In certain embodiments, $R^5$ represents independently for each occurrence $C_{1-3}$ alkyl. In certain embodiments, $R^5$ represents independently for each occurrence $C_{2-6}$ alkyl. In certain embodiments, $R^5$ represents independently for each occurrence $C_{3-6}$ alkyl. In certain embodiments, $R^5$ represents independently for each occurrence methyl, ethyl, or propyl.

In certain embodiments, $R^5$ represents independently for each occurrence halo. In certain embodiments, $R^5$ represents independently for each occurrence F or Cl. In certain embodiments, $R^5$ represents independently for each occurrence F or Cl.

In certain embodiments, $R^5$ represents independently for each occurrence $C_{1-6}$ haloalkyl. In certain embodiments, $R^5$ represents independently for each occurrence $C_{1-4}$ haloalkyl. In certain embodiments, $R^5$ represents independently for each occurrence $C_{1-3}$ haloalkyl. In certain embodiments, $R^5$ represents independently for each occurrence $C_{2-6}$ haloalkyl. In certain embodiments, $R^5$ represents independently for each occurrence $C_{3-6}$ haloalkyl.

In certain embodiments, $R^5$ represents independently for each occurrence $C_{1-6}$ haloalkyl, wherein the halogen is F. In certain embodiments, $R^5$ represents independently for each occurrence $C_{1-4}$ haloalkyl, wherein the halogen represents independently for each occurrence selected F. In certain embodiments, $R^5$ represents independently for each occurrence $C_{1-3}$ haloalkyl, wherein the halogen is F. In certain embodiments, $R^5$ represents independently for each occurrence $C_{2-6}$ haloalkyl, wherein the halogen is F. In certain embodiments, $R^5$ represents independently for each occurrence $C_{3-6}$ haloalkyl, wherein the halogen is F.

In certain embodiments, $R^5$ represents independently for each occurrence —$CF_3$, —$CHF_2$, —$CH_2CF_3$, or —$CH_2CHF_2$. In certain embodiments, $R^5$ is —$CF_3$. In certain embodiments, $R^5$ is —$CHF_2$.

In certain embodiments, $R^5$ represents independently for each occurrence $C_{3-6}$ cycloalkyl. In certain embodiments, $R^5$ represents independently for each occurrence $C_{4-6}$ cycloalkyl. In certain embodiments, $R^5$ represents independently for each occurrence $C_{5-6}$ cycloalkyl.

In certain embodiments, $R^5$ represents independently for each occurrence $C_3$ cycloalkyl. In certain embodiments, $R^5$ represents independently for each occurrence $C_4$ cycloalkyl. In certain embodiments, $R^5$ represents independently for each occurrence $C_5$ cycloalkyl. In certain embodiments, $R^5$ represents independently for each occurrence $C_6$ cycloalkyl.

In certain embodiments, $R^5$ represents independently for each occurrence cyclopropyl or cyclopentyl.

In certain embodiments, $R^5$ represents independently for each occurrence $C_{1-6}$ alkoxyl. In certain embodiments, $R^5$ represents independently for each occurrence $C_{1-3}$ alkoxyl. In certain embodiments, $R^5$ represents independently for each occurrence $C_{2-6}$ alkoxyl. In certain embodiments, $R^5$ represents independently for each occurrence $C_{4-6}$ alkoxyl. In certain embodiments, $R^5$ represents independently for each occurrence —$OCH_3$, —$OCH_2CH_3$, —$OCH_2CH_2CH_3$, —$OCH_2CH_2CH_2CH_3$, —$O(CH_2)_4CH_3$, —$OCH(CH_3)_2$, —$OCH_2CH(CH_3)_2$, —$OCH_2CH_2CH(CH_3)_2$, —$O(CH_2)_3CH(CH_3)_2$, —$OC(CH_3)_3$, —$OCH_2C(CH_3)_3$, or —$OCH_2CH_2C(CH_3)_3$. In certain embodiments, $R^5$ represents independently for each occurrence —$OCH_3$ or —$OCH_2CH_3$.

In certain embodiments, $R^5$ represents independently for each occurrence —($C_{1-6}$ alkylene)-($C_{3-6}$ cycloalkyl). In certain embodiments, $R^5$ represents independently for each occurrence —($C_{1-4}$ alkylene)-($C_{3-6}$ cycloalkyl). In certain embodiments, $R^5$ represents independently for each occurrence —($C_{2-6}$ alkylene)-($C_{3-6}$ cycloalkyl). In certain embodiments, $R^5$ represents independently for each occurrence —($C_{1-4}$ alkylene)-($C_{5-6}$ cycloalkyl). In certain embodiments, $R^5$ represents independently for each occurrence —($C_{1-3}$ alkylene)-($C_{4-6}$ cycloalkyl). In certain embodiments, $R^5$ represents independently for each occurrence —($C_{1-2}$ alkylene)-($C_{3-5}$ cycloalkyl).

In certain embodiments, $R^5$ represents independently for each occurrence —($C_{1-6}$ alkylene)-($C_{1-6}$ alkoxyl). In certain embodiments, $R^5$ represents independently for each occurrence —($C_{1-4}$ alkylene)-($C_{3-6}$ alkoxyl). In certain embodiments, $R^5$ represents independently for each occurrence —($C_{2-6}$ alkylene)-($C_{3-6}$ alkoxyl). In certain embodiments, $R^5$ represents independently for each occurrence —($C_{1-4}$ alkylene)-($C_{5-6}$ alkoxyl). In certain embodiments, $R^5$ represents independently for each occurrence —($C_{1-3}$ alkylene)-($C_{4-6}$ alkoxyl). In certain embodiments, $R^5$ represents independently for each occurrence —($C_{1-2}$ alkylene)-($C_{3-5}$ alkoxyl).

In certain embodiments, $R^5$ represents independently for each occurrence —($C_{1-6}$ alkylene)-($C_{3-6}$ halocycloalkyl). In certain embodiments, $R^5$ represents independently for each occurrence —($C_{1-4}$ alkylene)-($C_{3-6}$ halocycloalkyl). In certain embodiments, $R^5$ represents independently for each occurrence —($C_{2-6}$ alkylene)-($C_{3-6}$ halocycloalkyl). In certain embodiments, $R^5$ represents independently for each occurrence —($C_{1-4}$ alkylene)-($C_{5-6}$ halocycloalkyl). In certain embodiments, $R^5$ represents independently for each occurrence —($C_1$-3 alkylene)-($C_{4-6}$ halocycloalkyl). In certain embodiments, $R^5$ represents independently for each occurrence —($C_{1-2}$ alkylene)-($C_{3-5}$ halocycloalkyl).

In certain embodiments, $R^5$ is $C_{1-6}$ alkyl. In certain embodiments, $R^5$ is $C_{1-4}$ alkyl. In certain embodiments, $R^5$ is $C_{1-3}$ alkyl. In certain embodiments, $R^5$ is $C_{2-6}$ alkyl. In certain embodiments, $R^5$ is $C_{3-6}$ alkyl. In certain embodiments, $R^5$ is methyl, ethyl, or propyl.

In certain embodiments, $R^5$ is halo. In certain embodiments, $R^5$ is selected from F and Cl. In certain embodiments, $R^5$ is F. In certain embodiments, $R^5$ is $C_1$.

In certain embodiments, $R^5$ is $C_{1-6}$ haloalkyl. In certain embodiments, $R^5$ is $C_{1-4}$ haloalkyl. In certain embodiments, $R^5$ is $C_{1-3}$ haloalkyl. In certain embodiments, $R^5$ is $C_{2-6}$ haloalkyl. In certain embodiments, $R^5$ is $C_{3-6}$ haloalkyl.

In certain embodiments, $R^5$ is $C_{1-6}$ haloalkyl, wherein the halogen is F. In certain embodiments, $R^5$ is $C_{1-4}$ haloalkyl, wherein the halogen is selected F. In certain embodiments, $R^5$ is $C_{1-3}$ haloalkyl, wherein the halogen is F. In certain embodiments, $R^5$ is $C_{2-6}$ haloalkyl, wherein the halogen is F. In certain embodiments, $R^5$ is $C_{3-6}$ haloalkyl, wherein the halogen is F.

In certain embodiments, $R^5$ is —$CF_3$. In some embodiments, $R^5$ is —$CHF_2$. In some embodiments, $R^5$ is —$CH_2CF_3$. In some embodiments, $R^5$ is —$CH_2CHF_2$.

In certain embodiments, $R^5$ is $C_{3-6}$ cycloalkyl. In certain embodiments, $R^5$ is $C_{4-6}$ cycloalkyl. In certain embodiments, $R^5$ is $C_{5-6}$ cycloalkyl. In certain embodiments, $R^5$ is $C_3$ cycloalkyl. In certain embodiments, $R^5$ is $C_4$ cycloalkyl. In certain embodiments, $R^5$ is $C_5$ cycloalkyl. In certain embodiments, $R^5$ is $C_6$ cycloalkyl. In certain embodiments, $R^5$ is selected from cyclopropyl and cyclopentyl. In certain embodiments, $R^5$ is cyclopropyl.

In certain embodiments, $R^5$ is hydroxyl.

In certain embodiments, $R^5$ is $C_{1-6}$ alkoxyl. In certain embodiments, $R^5$ is $C_{1-3}$ alkoxyl. In certain embodiments, $R^5$ is $C_{2-6}$ alkoxyl. In certain embodiments, $R^5$ is $C_{4-6}$ alkoxyl. In certain embodiments, $R^5$ is —$OCH_3$, —$OCH_2CH_3$, —$OCH_2CH_2CH_3$, —$OCH_2CH_2CH_2CH_3$, —$O(CH_2)_4CH_3$, —$OCH(CH_3)_2$, —$OCH_2CH(CH_3)_2$, —$OCH_2CH_2CH(CH_3)_2$, —$O(CH_2)_3CH(CH_3)_2$, —$OC(CH_3)_3$, —$OCH_2C(CH_3)_3$, or —$OCH_2C(CH_3)_3$. In certain embodiments, $R^5$ is —$OCH_3$ or —$OCH_2CH_3$.

In certain embodiments, $R^5$ is —($C_{1-6}$ alkylene)-($C_{3-6}$ cycloalkyl). In certain embodiments, $R^5$ is —($C_{1-4}$ alkylene)-($C_{3-6}$ cycloalkyl). In certain embodiments, $R^5$ is —($C_{2-6}$ alkylene)-($C_{3-6}$ cycloalkyl). In certain embodiments, $R^5$ is —($C_{1-4}$ alkylene)-($C_{5-6}$ cycloalkyl). In certain embodiments, $R^5$ is —($C_{1-3}$ alkylene)-($C_{4-6}$ cycloalkyl). In certain embodiments, $R^5$ is —($C_{1-2}$ alkylene)-($C_{3-5}$ cycloalkyl).

In certain embodiments, $R^5$ is —($C_{1-6}$ alkylene)-($C_{1-6}$ alkoxyl). In certain embodiments, $R^5$ is —($C_{1-4}$ alkylene)-($C_{3-6}$ alkoxyl). In certain embodiments, $R^5$ is —($C_{2-6}$ alkylene)-($C_{3-6}$ alkoxyl). In certain embodiments, $R^5$ is —($C_{1-4}$ alkylene)-($C_{5-6}$ alkoxyl). In certain embodiments, $R^5$ is —($C_{1-3}$ alkylene)-($C_{4-6}$ alkoxyl). In certain embodiments, $R^5$ is —($C_{1-2}$ alkylene)-($C_{3-5}$ alkoxyl).

In certain embodiments, $R^5$ is —($C_{1-6}$ alkylene)-($C_{3-6}$ halocycloalkyl). In certain embodiments, $R^5$ is —($C_{1-4}$ alkylene)-($C_{3-6}$ halocycloalkyl). In certain embodiments, $R^5$ is —($C_{2-6}$ alkylene)-($C_{3-6}$ halocycloalkyl). In certain embodiments, $R^5$ is —($C_{1-4}$ alkylene)-($C_{5-6}$ halocycloalkyl). In certain embodiments, $R^5$ is —($C_{1-3}$ alkylene)-($C_{4-6}$ halocycloalkyl). In certain embodiments, $R^5$ is —($C_{1-2}$ alkylene)-($C_{3-5}$ halocycloalkyl).

In certain embodiments, two occurrences of $R^5$ are taken together with their intervening atoms to form a 4-7 membered ring containing 1 or 2 heteroatoms independently selected from oxygen, nitrogen, and sulfur. In certain embodiments, two occurrences of $R^5$ are taken together with their intervening atoms to form a 4-6 membered ring containing 1 or 2 heteroatoms independently selected from oxygen, nitrogen, and sulfur. In certain embodiments, two occurrences of $R^5$ are taken together with their intervening atoms to form a 4-7 membered ring containing 1 heteroatom independently selected from oxygen, nitrogen, and sulfur. In certain embodiments, two occurrences of $R^5$ are taken together with their intervening atoms to form a 4-7 membered ring containing 2 heteroatoms independently selected from oxygen, nitrogen, and sulfur. In certain embodiments, two occurrences of $R^5$ are taken together with their intervening atoms to form a 5-6 membered ring containing 2 heteroatoms independently selected from oxygen, nitrogen, and sulfur.

In certain embodiments, $R^5$ is selected from those depicted in Table 1.

As defined generally above, $R^6$ is (i) —($C_{0-4}$ alkylene)-(3-7 membered saturated or unsaturated heterocyclyl containing 1, 2, or 3 heteroatoms independently selected from nitrogen, oxygen, and sulfur), (ii) —($C_{0-4}$ alkylene)-(5-6 membered heteroaryl containing 1, 2, or 3 heteroatoms independently selected from nitrogen, oxygen, and sulfur), or (iii) —($C_{0-4}$ alkylene)-phenyl, wherein the heterocyclyl, heteroaryl, and phenyl are substituted with 0, 1, 2, or 3 occurrences of $R^7$.

In certain embodiments, $R^6$ is (i) —($C_{0-4}$ alkylene)-(3-7 membered saturated or unsaturated heterocyclyl containing 1, 2, or 3 heteroatoms independently selected from nitrogen, oxygen, and sulfur), (ii) —($C_{0-4}$ alkylene)-(5-6 membered heteroaryl containing 1, 2, or 3 heteroatoms independently selected from nitrogen, oxygen, and sulfur), or (iii) —($C_{0-4}$ alkylene)-phenyl, wherein the heterocyclyl, heteroaryl, and phenyl are substituted with 1, 2, or 3 occurrences of $R^7$.

In certain embodiments, $R^6$ is —($C_{0-4}$ alkylene)-(5-6 membered heteroaryl containing 1, 2, or 3 heteroatoms independently selected from nitrogen, oxygen, and sulfur), or —($C_{0-4}$ alkylene)-phenyl, wherein the heteroaryl and phenyl are substituted with 0, 1, 2, or 3 occurrences of $R^7$.

In certain embodiments, $R^6$ is —($C_{0-4}$ alkylene)-(3-7 membered saturated or unsaturated heterocyclyl containing 1, 2, or 3 heteroatoms independently selected from nitrogen, oxygen, and sulfur), or —($C_{0-4}$ alkylene)-phenyl, wherein the heterocyclyl and phenyl are substituted with 0, 1, 2, or 3 occurrences of $R^7$. In certain embodiments, $R^6$ is —($C_{0-4}$ alkylene)-(3-7 membered saturated or unsaturated heterocyclyl containing 1, 2, or 3 heteroatoms independently selected from nitrogen, oxygen, and sulfur), or —($C_{0-4}$ alkylene)-(5-6 membered heteroaryl containing 1, 2, or 3 heteroatoms independently selected from nitrogen, oxygen, and sulfur). In certain embodiments, $R^6$ is —($C_{0-4}$ alkylene)-(3-7 membered saturated or unsaturated heterocyclyl containing 1, 2, or 3 heteroatoms independently selected from nitrogen, oxygen, and sulfur), wherein the heterocyclyl is substituted with 0, 1, 2, or 3 occurrences of $R^7$.

In certain embodiments, $R^6$ is —($C_{0-4}$ alkylene)-(3-7 membered saturated or unsaturated heterocyclyl containing 1, 2, or 3 heteroatoms independently selected from nitrogen, oxygen, and sulfur), wherein the heterocyclyl is substituted with 0, 1, 2, or 3 occurrences of $R^7$. In certain embodiments, $R^6$ is —($C_{1-4}$ alkylene)-(3-7 membered saturated or unsaturated heterocyclyl containing 1, 2, or 3 heteroatoms independently selected from nitrogen, oxygen, and sulfur), wherein the heterocyclyl is substituted with 0, 1, 2, or 3 occurrences of $R^7$. In certain embodiments, $R^6$ is —($C_{2-4}$ alkylene)-(3-7 membered saturated or unsaturated heterocyclyl containing 1, 2, or 3 heteroatoms independently selected from nitrogen, oxygen, and sulfur), wherein the heterocyclyl is substituted with 0, 1, 2, or 3 occurrences of $R^7$. In certain embodiments, $R^6$ is —($C_{0-4}$ alkylene)-(3-6 membered saturated or unsaturated heterocyclyl containing 1, 2, or 3 heteroatoms independently selected from nitrogen, oxygen, and sulfur), wherein the heterocyclyl is substituted with 0, 1, 2, or 3 occurrences of $R^7$. In certain embodiments, $R^6$ is —($C_{0-4}$ alkylene)-(3-5 membered saturated or unsaturated heterocyclyl containing 1, 2, or 3 heteroatoms independently selected from nitrogen, oxygen, and sulfur), wherein the heterocyclyl is substituted with 0, 1, 2, or 3 occurrences of $R^7$. In certain embodiments, $R^6$ is —($C_{1-3}$ alkylene)-(3-6 membered saturated or unsaturated heterocyclyl containing 1, 2, or 3 heteroatoms independently selected from nitrogen, oxygen, and sulfur), wherein the heterocyclyl is substituted with 0, 1, 2, or 3 occurrences of $R^7$.

In certain embodiments, $R^6$ is —$CH_2$-(3-7 membered saturated or unsaturated heterocyclyl containing 1, 2, or 3 heteroatoms independently selected from nitrogen, oxygen, and sulfur), wherein the heterocyclyl is substituted with 0, 1, 2, or 3 occurrences of $R^7$. In certain embodiments, $R^6$ is —$CH_2CH_2$-(3-7 membered saturated or unsaturated heterocyclyl containing 1, 2, or 3 heteroatoms independently selected from nitrogen, oxygen, and sulfur), wherein the heterocyclyl is substituted with 0, 1, 2, or 3 occurrences of $R^7$. In certain embodiments, $R^6$ is —$CH_2$-(4-6 membered saturated or unsaturated heterocyclyl containing 1 or heteroatoms independently selected from nitrogen, oxygen, and sulfur), wherein the heterocyclyl is substituted with 0, 1, 2, or 3 occurrences of $R^7$. In certain embodiments, $R^6$ is —$CH_2CH_2$-(4-6 membered saturated or unsaturated heterocyclyl containing 1 or 2 heteroatoms independently selected from nitrogen, oxygen, and sulfur), wherein the heterocyclyl is substituted with 0, 1, 2, or 3 occurrences of $R^7$.

In certain embodiments, $R^6$ is —($C_{0-4}$ alkylene)-(5-6 membered heteroaryl containing 1, 2, or 3 heteroatoms independently selected from nitrogen, oxygen, and sulfur), wherein the heteroaryl is substituted with 0, 1, 2, or 3 occurrences of $R^7$. In certain embodiments, $R^6$ is —($C_{1-4}$ alkylene)-(5-6 membered heteroaryl containing 1, 2, or 3 heteroatoms independently selected from nitrogen, oxygen, and sulfur), wherein the heteroaryl is substituted with 0, 1, 2, or 3 occurrences of $R^7$. In certain embodiments, $R^6$ is —($C_{2-4}$ alkylene)-(5-6 membered heteroaryl containing 1, 2, or 3 heteroatoms independently selected from nitrogen, oxygen, and sulfur), wherein the heteroaryl is substituted with 0, 1, 2, or 3 occurrences of $R^7$. In certain embodiments, $R^6$ is —($C_{0-4}$ alkylene)-(5 membered heteroaryl containing 1, 2, or 3 heteroatoms independently selected from nitrogen, oxygen, and sulfur), wherein the heteroaryl is substituted with 0, 1, 2, or 3 occurrences of $R^7$. In certain embodiments, $R^6$ is —($C_{0-4}$ alkylene)-(6 membered heteroaryl containing 1, 2, or 3 heteroatoms independently selected from nitrogen, oxygen, and sulfur) wherein the heteroaryl is substituted with 0, 1, 2, or 3 occurrences of $R^7$. In certain embodiments, $R^6$ is —($C_{0-2}$ alkylene)-(5-6 membered heteroaryl containing 1, 2, or 3 heteroatoms independently selected from nitrogen, oxygen, and sulfur), wherein the heteroaryl is substituted with 0, 1, 2, or 3 occurrences of $R^7$.

In certain embodiments, $R^6$ is —$CH_2$-(5-6 membered heteroaryl containing 1, 2, or 3 heteroatoms independently selected from nitrogen, oxygen, and sulfur), wherein the heteroaryl is substituted with 0, 1, 2, or 3 occurrences of $R^7$. In certain embodiments, $R^6$ is —$CH_2CH_2$-(5-6 membered heteroaryl containing 1, 2, or 3 heteroatoms independently selected from nitrogen, oxygen, and sulfur), wherein the heteroaryl is substituted with 0, 1, 2, or 3 occurrences of $R^7$.

In certain embodiments, $R^6$ is —$CH_2$-(phenyl), wherein the phenyl is substituted with 0, 1, 2, or 3 occurrences of $R^7$. In certain embodiments, $R^6$ is —$CH_2CH_2$-(phenyl), wherein the phenyl is substituted with 0, 1, 2, or 3 occurrences of $R^7$. In certain embodiments, $R^6$ is —$CH_2$-(phenyl), wherein the phenyl is substituted with 1, 2, or 3 occurrences of $R^7$. In certain embodiments, $R^6$ is —$CH_2CH_2$-(phenyl), wherein the phenyl is substituted with 1, 2, or 3 occurrences of $R^7$.

In certain embodiments, $R^6$ is —($C_{0-4}$ alkylene)-phenyl, wherein the phenyl is substituted with 0, 1, 2, or 3 occurrences of $R^7$. In certain embodiments, $R^6$ is —($C_{1-4}$ alkylene)-phenyl, wherein the phenyl is substituted with 0, 1, 2, or 3 occurrences of $R^7$. In certain embodiments, $R^6$ is —($C_{2-4}$ alkylene)-phenyl, wherein the phenyl is substituted with 0, 1, 2, or 3 occurrences of $R^7$. In certain embodiments, $R^6$ is —($C_{0-2}$ alkylene)-phenyl, wherein the phenyl is substituted with 0, 1, 2, or 3 occurrences of $R^7$. In certain embodiments, $R^6$ is —($C_{0-4}$ alkylene)-phenyl, wherein the phenyl is substituted with 1, 2, or 3 occurrences of $R^7$. In certain embodiments, $R^6$ is —($C_{1-4}$ alkylene)-phenyl, wherein the phenyl is substituted with 1, 2, or 3 occurrences of $R^7$. In certain embodiments, $R^6$ is —$CH_2$-(phenyl), wherein the phenyl is substituted with 0, 1, 2, or 3 occurrences of $R^7$. In certain embodiments, $R^6$ is —$CH_2CH_2$-(phenyl), wherein the phenyl is substituted with 0, 1, 2, or 3 occurrences of $R^7$.

In certain embodiments, $R^6$ is selected from those depicted in Table 1.

As defined generally above, $R^7$ represents independently for each occurrence $C_{1-6}$ alkyl, halo, $C_{1-6}$ haloalkyl, $C_{3-6}$ cycloalkyl, hydroxyl, or $C_{1-6}$ alkoxyl. In certain embodiments, $R^7$ represents independently for each occurrence $C_{1-6}$ alkyl, halo, $C_{1-6}$ haloalkyl, $C_{3-6}$ cycloalkyl, hydroxyl, or $C_{1-6}$ alkoxyl. In certain embodiments, $R^7$ represents independently for each occurrence halo, $C_{1-6}$ haloalkyl, $C_{3-6}$ cycloalkyl, hydroxyl, or $C_{1-6}$ alkoxyl. In certain embodiments, $R^7$ represents independently for each occurrence $C_{1-6}$ alkyl, $C_{1-6}$ haloalkyl, $C_{3-6}$ cycloalkyl, hydroxyl, or $C_{1-6}$ alkoxyl. In certain embodiments, $R^7$ represents independently for each occurrence $C_{1-6}$ alkyl, halo, $C_{3-6}$ cycloalkyl, hydroxyl, or $C_{1-6}$ alkoxyl. In certain embodiments, $R^7$ represents independently for each occurrence $C_{1-6}$ alkyl, halo, $C_{1-6}$ haloalkyl, hydroxyl, or $C_{1-6}$ alkoxyl. In certain embodiments, $R^7$ represents independently for each occurrence $C_{1-6}$ alkyl, halo, $C_{1-6}$ haloalkyl, $C_{3-6}$ cycloalkyl, or $C_{1-6}$ alkoxyl. In certain embodiments, $R^7$ represents independently for each occurrence $C_{1-6}$ alkyl, halo, $C_{1-6}$ haloalkyl, $C_{3-6}$ cycloalkyl, or hydroxyl.

In certain embodiments, $R^7$ represents independently for each occurrence $C_{1-6}$ haloalkyl, $C_{3-6}$ cycloalkyl, hydroxyl, or $C_{1-6}$ alkoxyl. In certain embodiments, $R^7$ represents independently for each occurrence halo, $C_{3-6}$ cycloalkyl, hydroxyl, or $C_{1-6}$ alkoxyl. In certain embodiments, $R^7$ represents independently for each occurrence halo, $C_{1-6}$ haloalkyl, hydroxyl, or $C_{1-6}$ alkoxyl. In certain embodiments, $R^7$ represents independently for each occurrence halo, $C_{1-6}$ haloalkyl, $C_{3-6}$ cycloalkyl, or $C_{1-6}$ alkoxyl. In certain embodiments, $R^7$ represents independently for each occurrence halo, $C_{1-6}$ haloalkyl, $C_{3-6}$ cycloalkyl, or hydroxyl. In certain embodiments, $R^7$ represents independently for each occurrence $C_{1-6}$ alkyl, $C_{3-6}$ cycloalkyl, hydroxyl, or $C_{1-6}$ alkoxyl. In certain embodiments, $R^7$ represents independently for each occurrence $C_{1-6}$ alkyl, $C_{1-6}$ haloalkyl, hydroxyl, or $C_{1-6}$ alkoxyl. In certain embodiments, $R^7$ represents independently for each occurrence $C_{1-6}$ alkyl, $C_{1-6}$ haloalkyl, $C_{3-6}$ cycloalkyl, or $C_{1-6}$ alkoxyl. In certain embodiments, $R^7$ represents independently for each occurrence $C_{1-6}$ alkyl, $C_{1-6}$ haloalkyl, $C_{3-6}$ cycloalkyl, or hydroxyl. In certain embodiments, $R^7$ represents independently for each occurrence $C_{1-6}$ alkyl, $C_{1-6}$ haloalkyl, $C_{3-6}$ cycloalkyl, or hydroxyl. In certain embodiments, $R^7$ represents independently for each occurrence $C_{1-6}$ alkyl, halo, hydroxyl, or $C_{1-6}$ alkoxyl. In certain embodiments, $R^7$ represents independently for each occurrence $C_{1-6}$ alkyl, halo, $C_{3-6}$ cycloalkyl, or $C_{1-6}$ alkoxyl. In certain embodiments, $R^7$ represents independently for each occurrence $C_{1-6}$ alkyl, halo, $C_{3-6}$ cycloalkyl, or hydroxyl. In certain embodiments, $R^7$ represents independently for each occurrence $C_{1-6}$ alkyl, halo, $C_{1-6}$ haloalkyl, or $C_{1-6}$ alkoxyl. In certain embodiments, $R^7$ represents independently for each occurrence $C_{1-6}$ alkyl, halo, $C_{1-6}$ haloalkyl, or hydroxyl. In certain embodiments, $R^7$ represents independently for each occurrence $C_{1-6}$ alkyl, halo, $C_{1-6}$ haloalkyl, or $C_{3-6}$ cycloalkyl.

In certain embodiments, $R^7$ represents independently for each occurrence $C_{1-6}$ alkyl. In certain embodiments, $R^7$ represents independently for each occurrence $C_{1-4}$ alkyl. In certain embodiments, $R^7$ represents independently for each occurrence $C_{1-3}$ alkyl. In certain embodiments, $R^7$ represents independently for each occurrence $C_{2-6}$ alkyl. In certain embodiments, $R^7$ represents independently for each occurrence $C_{3-6}$ alkyl. In certain embodiments, $R^7$ represents independently for each occurrence methyl, ethyl, or propyl.

In certain embodiments, $R^7$ represents independently for each occurrence $C_{1-6}$ haloalkyl. In certain embodiments, $R^7$ represents independently for each occurrence $C_{1-4}$ haloalkyl. In certain embodiments, $R^7$ represents independently for each occurrence $C_{1-3}$ haloalkyl. In certain embodiments, $R^7$ represents independently for each occurrence $C_{2-6}$ haloalkyl. In certain embodiments, $R^7$ represents independently for each occurrence $C_{3-6}$ haloalkyl.

In certain embodiments, $R^7$ represents independently for each occurrence $C_{1-6}$ haloalkyl, wherein the halogen is F. In certain embodiments, $R^7$ represents independently for each occurrence $C_{1-4}$ haloalkyl, wherein the halogen is F. In certain embodiments, $R^7$ represents independently for each occurrence $C_{1-3}$ haloalkyl, wherein the halogen is F. In certain embodiments, $R^7$ represents independently for each occurrence $C_{2-6}$ haloalkyl, wherein the halogen is F. In certain embodiments, $R^7$ represents independently for each occurrence $C_{3-6}$ haloalkyl, wherein the halogen is F. In certain embodiments, $R^7$ represents independently for each occurrence —$CF_3$, —$CHF_2$, —$CH_2CF_3$, or —$CH_2CHF_2$.

In certain embodiments, $R^7$ represents independently for each occurrence $C_{3-6}$ cycloalkyl. In certain embodiments, $R^7$ represents independently for each occurrence $C_{4-6}$ cycloalkyl. In certain embodiments, $R^7$ represents independently for each occurrence $C_{5-6}$ cycloalkyl. In certain embodiments, $R^7$ represents independently for each occurrence cyclopropyl or cyclopentyl.

In certain embodiments, $R^7$ represents independently for each occurrence $C_{1-6}$ alkoxyl. In certain embodiments, $R^7$ represents independently for each occurrence $C_{1-3}$ alkoxyl. In certain embodiments, $R^7$ represents independently for each occurrence $C_{2-6}$ alkoxyl. In certain embodiments, $R^7$ represents independently for each occurrence $C_{4-6}$ alkoxyl.

In certain embodiments, $R^7$ represents independently for each occurrence —$OCH_3$, —$OCH_2CH_3$, —$OCH_2CH_2CH_3$, —$OCH_2CH_2CH_2CH_3$, —$O(CH_2)_4CH_3$, —$OCH(CH_3)_2$, —$OCH_2CH(CH_3)_2$, —$OCH_2CH_2CH(CH_3)_2$, —$O(CH_2)_3CH(CH_3)_2$, —$OC(CH_3)_3$, —$OCH_2C(CH_3)_3$, or —$OCH_2CH_2C(CH_3)_3$. In certain embodiments, $R^7$ represents independently for each occurrence —$OCH_3$ or —$OCH_2CH_3$.

In certain embodiments, $R^7$ is $C_{1-6}$ alkyl. In certain embodiments, $R^7$ is $C_{1-4}$ alkyl. In certain embodiments, $R^7$ is $C_{1-3}$ alkyl. In certain embodiments, $R^7$ is $C_{2-6}$ alkyl. In certain embodiments, $R^7$ is $C_{3-6}$ alkyl. In certain embodiments, $R^7$ is methyl, ethyl, or propyl.

In certain embodiments, $R^7$ is halo. In certain embodiments, $R^7$ is Cl or F. In certain embodiments, $R^7$ is F. In certain embodiments, $R^7$ is Cl.

In certain embodiments, $R^7$ is $C_{1-6}$ haloalkyl. In certain embodiments, $R^7$ is $C_{1-4}$ haloalkyl. In certain embodiments, $R^7$ is $C_{1-3}$ haloalkyl. In certain embodiments, $R^7$ is $C_{2-6}$ haloalkyl. In certain embodiments, $R^7$ is $C_{3-6}$ haloalkyl.

In certain embodiments, $R^7$ is $C_{1-6}$ haloalkyl, wherein the halogen is F. In certain embodiments, $R^7$ is $C_{1-4}$ haloalkyl, wherein the halogen is selected F. In certain embodiments, $R^7$ is $C_{1-3}$ haloalkyl, wherein the halogen is F. In certain embodiments, $R^7$ is $C_{2-6}$ haloalkyl, wherein the halogen is F. In certain embodiments, $R^7$ is $C_{3-6}$ haloalkyl, wherein the halogen is F.

In certain embodiments, $R^7$ is —$CF_3$. In some embodiments, $R^7$ is —$CHF_2$. In some embodiments, $R^7$ is —$CH_2CF_3$. In some embodiments, $R^7$ is —$CH_2CHF_2$. In certain embodiments, $R^7$ is $C_{3-6}$ cycloalkyl. In certain embodiments, $R^7$ is $C_{4-6}$ cycloalkyl. In certain embodiments, $R^7$ is $C_{5-6}$ cycloalkyl. In certain embodiments, $R^7$ is cyclopropyl, cyclobutyl, or cyclopentyl. In certain embodiments, $R^7$ is cyclopropyl. In certain embodiments, $R^7$ is hydroxyl.

In certain embodiments, $R^7$ is $C_{1-6}$ alkoxyl. In certain embodiments, $R^7$ is $C_{1-3}$ alkoxyl. In certain embodiments, $R^7$ is $C_{2-6}$ alkoxyl. In certain embodiments, $R^7$ is $C_{4-6}$ alkoxyl. In certain embodiments, $R^7$ is —$OCH_3$, —$OCH_2CH_3$, —$OCH_2CH_2CH_3$, —$OCH_2CH_2CH_2CH_3$, —$O(CH_2)_4CH_3$, —$OCH(CH_3)_2$, —$OCH_2CH(CH_3)_2$, —$OCH_2CH_2CH(CH_3)_2$, —$O(CH_2)_3CH(CH_3)_2$, —$OC(CH_3)_3$, —$OCH_2C(CH_3)_3$, or —$OCH_2CH_2C(CH_3)_3$. In certain embodiments, $R^7$ is —$OCH_3$ or —$OCH_2CH_3$.

In certain embodiments, $R^7$ is selected from those depicted in Table 1.

As defined generally above, $A^1$ is a 5-6 membered monocyclic heteroaryl containing 1, 2, or 3 heteroatoms independently selected from nitrogen, oxygen, and sulfur, an 8-10 membered bicyclic heteroaryl containing 1, 2, or 3 heteroatoms independently selected from nitrogen, oxygen, and sulfur, or phenyl, wherein the heteroaryl and phenyl are substituted with n occurrences of $R^5$ and t occurrences of $R^6$.

In certain embodiments, $A^1$ is an 8-10 membered bicyclic heteroaryl containing 1, 2, or 3 heteroatoms independently selected from nitrogen, oxygen, and sulfur, or phenyl, wherein the heteroaryl and phenyl are substituted with n occurrences of $R^5$ and t occurrences of $R^6$.

In certain embodiments, $A^1$ is a 5-6 membered monocyclic heteroaryl containing 1, 2, or 3 heteroatoms independently selected from nitrogen, oxygen, and sulfur, or phenyl, wherein the heteroaryl and phenyl are substituted with n occurrences of $R^5$ and t occurrences of $R^6$. In certain embodiments, $A^1$ is a 5-6 membered monocyclic heteroaryl containing 1, 2, or 3 heteroatoms independently selected from nitrogen, oxygen, and sulfur, or an 8-10 membered bicyclic heteroaryl containing 1, 2, or 3 heteroatoms independently selected from nitrogen, oxygen, and sulfur, or wherein the heteroaryl is substituted with n occurrences of $R^5$ and t occurrences of $R^6$.

In certain embodiments, $A^1$ is a 5-6 membered monocyclic heteroaryl containing 1, 2, or 3 heteroatoms independently selected from nitrogen, oxygen, and sulfur, wherein the heteroaryl is substituted with n occurrences of $R^5$ and t occurrences of $R^6$. In certain embodiments, $A^1$ is a 8-10 membered bicyclic heteroaryl containing 1, 2, or 3 heteroatoms independently selected from nitrogen, oxygen, and sulfur, wherein the heteroaryl is substituted with n occurrences of $R^5$ and t occurrences of $R^6$. In certain embodiments, $A^1$ is phenyl, wherein the phenyl is substituted with n occurrences of $R^5$ and t occurrences of $R^6$. In certain embodiments, $A^1$ is a 5 membered monocyclic heteroaryl containing 1 or 2 heteroatoms independently selected from nitrogen and oxygen, wherein the heteroaryl is substituted with n occurrences of $R^5$ and t occurrences of $R^6$.

In certain embodiments, $A^1$ is pyrazolyl, imidazolyl, oxazolyl, isoxazolyl, thiazolyl, pyrrolyl, thiophenyl, or pyridinyl, each of which is substituted with n occurrences of $R^5$ and t occurrences of $R^6$. In certain embodiments, $A^1$ is pyrazolyl, imidazolyl, oxazolyl, or isoxazolyl, each of which is substituted with n occurrences of $R^5$ and t occurrences of $R^6$. In certain embodiments, $A^1$ is pyrazolyl substituted with n occurrences of $R^5$ and t occurrences of $R^6$.

In certain embodiments, $A^1$ is selected from those depicted in Table 1.

As defined generally above, m is 0, 1, 2, or 3. In certain embodiments, m is 1, 2, or 3. In certain embodiments, m is 0, 2, or 3. In certain embodiments, m is 0, 1, or 3. In certain embodiments, m is 0, 1, or 2. In certain embodiments, m is 2 or 3. In certain embodiments, m is 0 or 1. In certain embodiments, m is 0 or 3. In certain embodiments, m is 0 or 2. In certain embodiments, m is 1 or 2. In certain embodiments, m is 1 or 3. In certain embodiments, m is 0. In certain embodiments, m is 1. In certain embodiments, m is 2. In certain embodiments, m is 3.

As defined generally above, n is 0, 1, or 2. In certain embodiments, n is 1 or 2. In certain embodiments, n is 0 or 2. In certain embodiments, n is 0 or 1. In certain embodiments, n is 0. In certain embodiments, n is 1. In certain embodiments, n is 2.

As defined generally above, t is 0 or 1. In certain embodiments, t is 0. In certain embodiments, t is 1.

In certain embodiments, t is 1, and n is 0.

The description above describes multiple embodiments relating to compounds of Formula I. The patent application specifically contemplates all combinations of the embodiments.

In certain embodiments, the compound of Formula I is further defined by Formula Ia or a pharmaceutically acceptable salt thereof, wherein the indicated variables are as defined in the description of Formula I above:

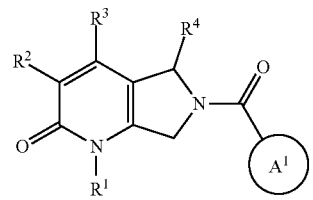

Ia

In certain embodiments, the compound of Formula I is further defined by Formula Ib, Ic, Id, or Ie or a pharmaceutically acceptable salt thereof, wherein the indicated variables are as defined in the description of Formula I above:

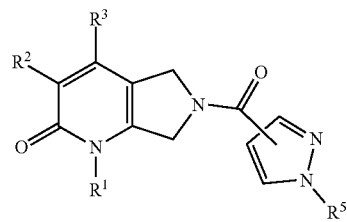

Ib

Ic

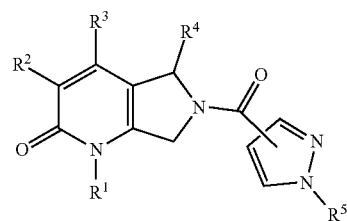

Id

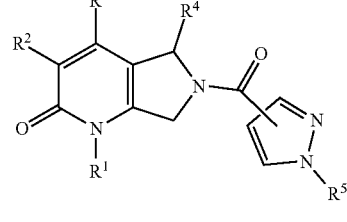

Ie

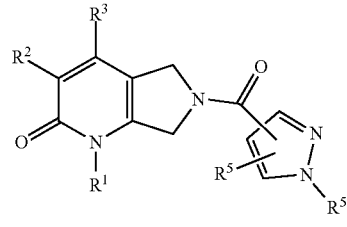

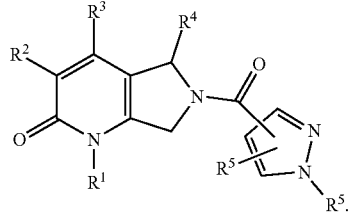

In certain embodiments, the compound of Formula I is further defined by Formula If or Ig or a pharmaceutically acceptable salt thereof, wherein the indicated variables are as defined in the description of Formula I above:

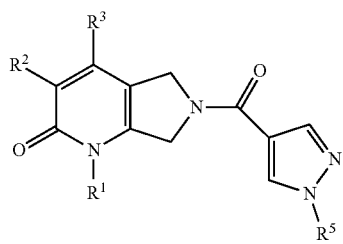

If

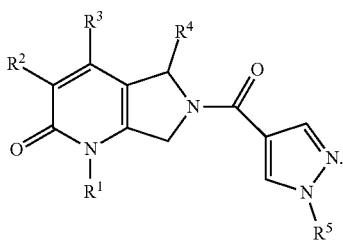

Ig

In certain embodiments, the compound of Formula I is further defined by Formula Ih, Ii, Ij, Ik, Il, and Im or a pharmaceutically acceptable salt thereof, wherein the indicated variables are as defined in the description of Formula I above:

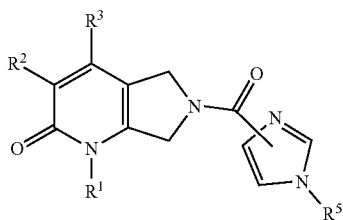

Ih

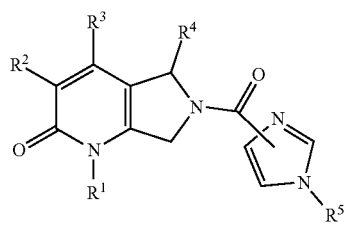

Ii

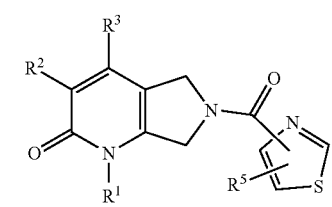

Ij

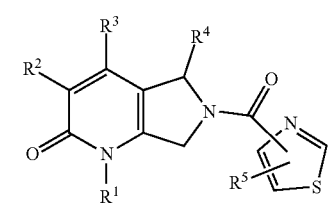

Ik

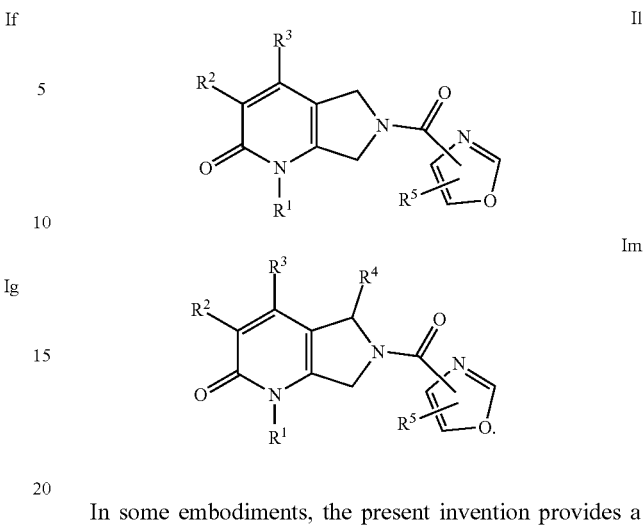

In some embodiments, the present invention provides a compound of Formula I, wherein each of the variables is as defined above and described in embodiments herein, both singly and in combination.

The description above describes multiple embodiments relating to compounds of Formula I. The patent application specifically contemplates all combinations of the embodiments.

Exemplary Specific Compounds

In certain embodiments, the compound is a compound in Table 1 or a pharmaceutically acceptable salt thereof. In certain embodiments, the compound is a compound in Table 1.

TABLE 1

Exemplary Compounds

| Compound No. | Structure |
|---|---|
| I-1 | 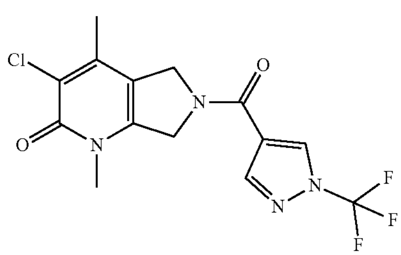 [SMILES: Cc1c2c(n(C)c(=O)c1Cl)CN(C(=O)c1cnn(C(F)(F)F)c1)C2] |
| I-2 | 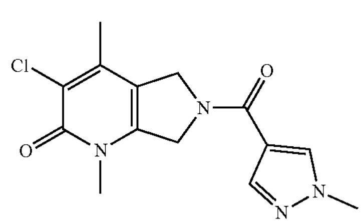 [SMILES: Cc1c2c(n(C)c(=O)c1Cl)CN(C(=O)c1cnn(C)c1)C2] |

TABLE 1-continued

Exemplary Compounds

| Compound No. | Structure |
|---|---|
| I-3 | |
| I-4 | |
| I-5 | |
| I-6 | |
| I-7 | |
| I-8 | 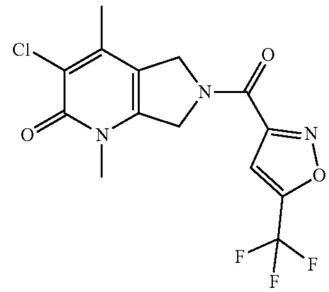 [SMILES: Cc1c2c(n(C)c(=O)c1Cl)CN(C(=O)c1cc(C(F)(F)F)on1)C2] |
| I-9 | 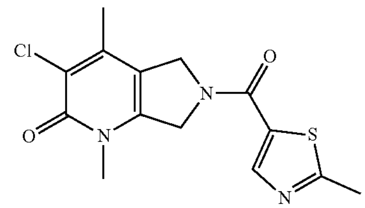 [SMILES: Cc1ncc(C(=O)N2Cc3c(C)c(Cl)c(=O)n(C)c3C2)s1] |
| I-10 | 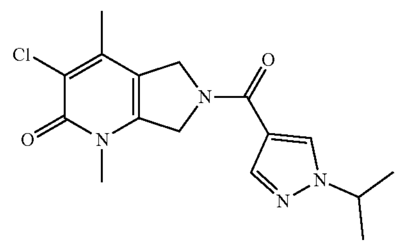 [SMILES: Cc1c2c(n(C)c(=O)c1Cl)CN(C(=O)c1cnn(C(C)C)c1)C2] |
| I-11 | 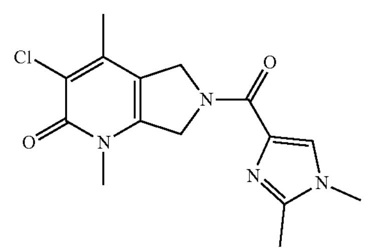 [SMILES: Cc1c2c(n(C)c(=O)c1Cl)CN(C(=O)c1cn(C)c(C)n1)C2] |
| I-12 | 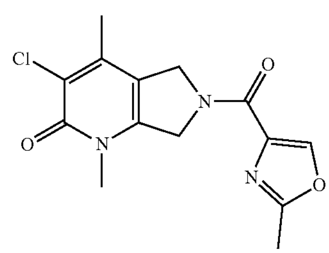 [SMILES: Cc1nc(C(=O)N2Cc3c(C)c(Cl)c(=O)n(C)c3C2)co1] |
| I-13 | 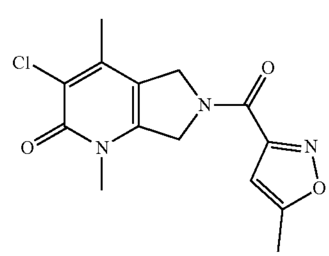 [SMILES: Cc1cc(C(=O)N2Cc3c(C)c(Cl)c(=O)n(C)c3C2)no1] |

TABLE 1-continued

Exemplary Compounds

| Compound No. | Structure |
|---|---|
| I-14 | (chloro-methyl-pyrrolopyridinone carbonyl-1-isopropyl-imidazole) |
| I-15 | (chloro-methyl-pyrrolopyridinone carbonyl-1-trifluoromethyl-imidazole) |
| I-16 | (chloro-methyl-pyrrolopyridinone carbonyl-1-trifluoromethyl-pyrazole) |
| I-17 | (chloro-methyl-pyrrolopyridinone carbonyl-1-difluoromethyl-pyrazole) |
| I-18 | (chloro-methyl-pyrrolopyridinone carbonyl-1,2-dimethyl-imidazole) |
| I-19 | (chloro-methyl-pyrrolopyridinone carbonyl-1-isobutyl-imidazole) |
| I-20 | (chloro-methyl-pyrrolopyridinone carbonyl-5-methyl-thiazole) |
| I-21 | (chloro-methyl-pyrrolopyridinone carbonyl-2-cyclopropyl-thiazole) |
| I-22 | (chloro-methyl-pyrrolopyridinone carbonyl-4-methyl-oxazole) |
| I-23 | (chloro-methyl-pyrrolopyridinone carbonyl-1-benzyl-pyrazole) |
| I-24 | (chloro-methyl-pyrrolopyridinone carbonyl-tetrahydroimidazo[1,2-a]pyridine) |

TABLE 1-continued

Exemplary Compounds

| Compound No. | Structure |
|---|---|
| I-25 | 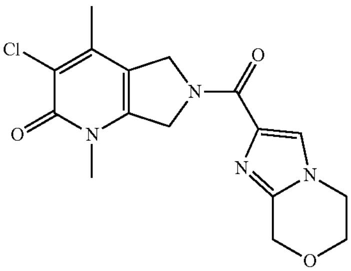 [SMILES: Cc1c2c(n(C)c(=O)c1Cl)CN(C(=O)c1cn3c(n1)COCC3)C2] |
| I-26 | 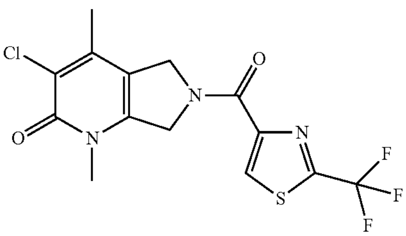 [SMILES: Cc1c2c(n(C)c(=O)c1Cl)CN(C(=O)c1csc(C(F)(F)F)n1)C2] |
| I-27 | 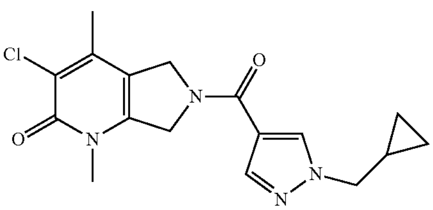 [SMILES: Cc1c2c(n(C)c(=O)c1Cl)CN(C(=O)c1cnn(CC3CC3)c1)C2] |
| I-28 | 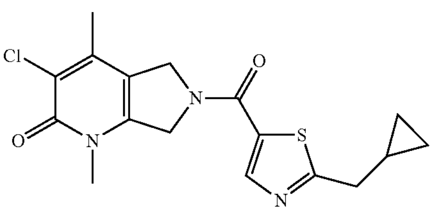 [SMILES: Cc1c2c(n(C)c(=O)c1Cl)CN(C(=O)c1cnc(CC3CC3)s1)C2] |
| I-29 | 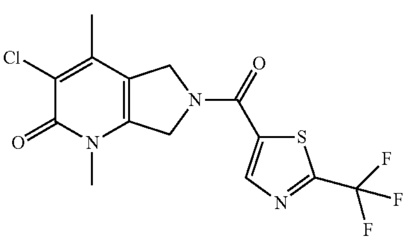 [SMILES: Cc1c2c(n(C)c(=O)c1Cl)CN(C(=O)c1cnc(C(F)(F)F)s1)C2] |
| I-30 | 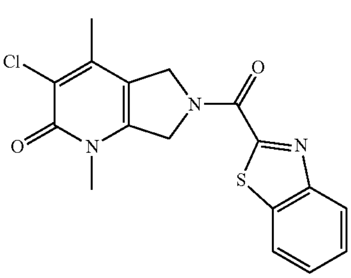 [SMILES: Cc1c2c(n(C)c(=O)c1Cl)CN(C(=O)c1nc3ccccc3s1)C2] |
| I-31 | |
| I-32 | |
| I-33 | |
| I-34 | |
| I-35 | |
| I-36 | |

TABLE 1-continued

Exemplary Compounds

| Compound No. | Structure |
|---|---|
| I-37 | 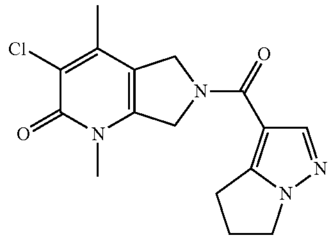 [SMILES: Cc1c2c(n(C)c(=O)c1Cl)CN(C(=O)c1cnn3c1CCC3)C2] |
| I-38 | 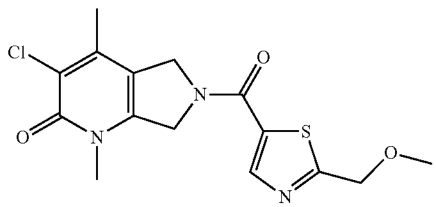 [SMILES: COCc1ncc(C(=O)N2Cc3c(C)c(Cl)c(=O)n(C)c3C2)s1] |
| I-39 | 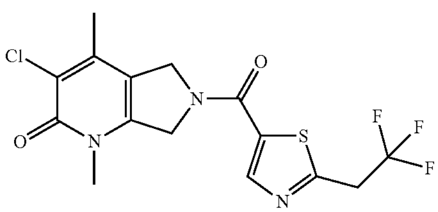 [SMILES: Cc1c2c(n(C)c(=O)c1Cl)CN(C(=O)c1cnc(CC(F)(F)F)s1)C2] |
| I-40 | 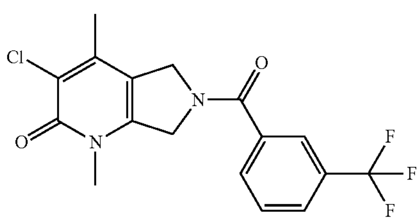 [SMILES: Cc1c2c(n(C)c(=O)c1Cl)CN(C(=O)c1cccc(C(F)(F)F)c1)C2] |
| I-41 | 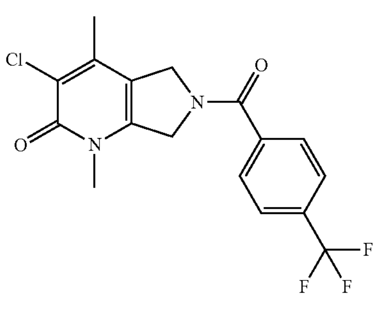 |
| I-42 | 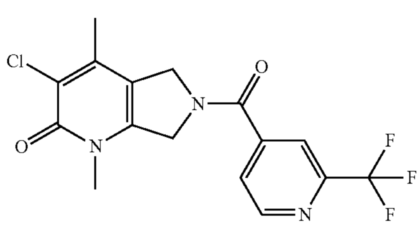 [SMILES: Cc1c2c(n(C)c(=O)c1Cl)CN(C(=O)c1ccnc(C(F)(F)F)c1)C2] |
| I-43 | |
| I-44 | |
| I-45 | |
| I-46 | |
| I-47 | |

TABLE 1-continued
Exemplary Compounds
| Compound No. | Structure |
|---|---|
| I-48 | 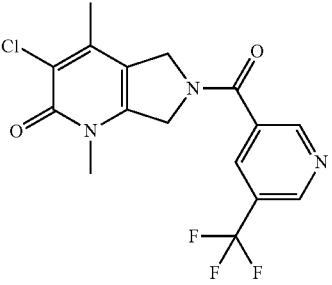 [SMILES: Cc1c2c(n(C)c(=O)c1Cl)CN(C(=O)c1cncc(C(F)(F)F)c1)C2] |
| I-49 | 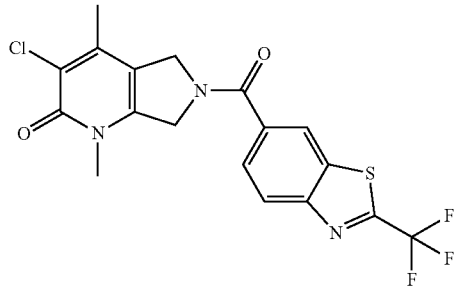 [SMILES: Cc1c2c(n(C)c(=O)c1Cl)CN(C(=O)c1ccc3nc(C(F)(F)F)sc3c1)C2] |
| I-50 | 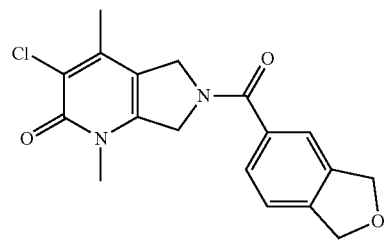 [SMILES: Cc1c2c(n(C)c(=O)c1Cl)CN(C(=O)c1ccc3c(c1)COC3)C2] |
| I-51 | 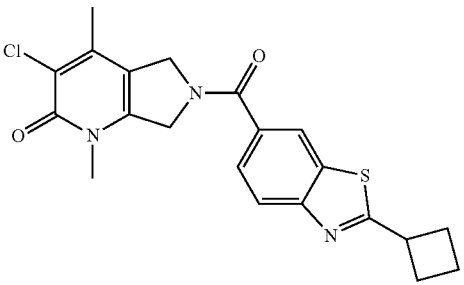 [SMILES: Cc1c2c(n(C)c(=O)c1Cl)CN(C(=O)c1ccc3nc(C4CCC4)sc3c1)C2] |
| I-52 | 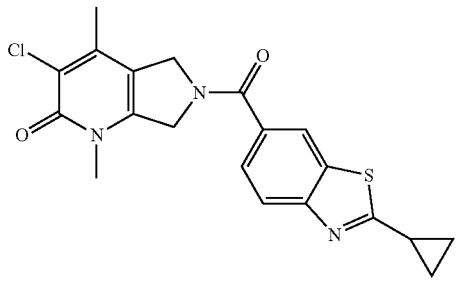 [SMILES: Cc1c2c(n(C)c(=O)c1Cl)CN(C(=O)c1ccc3nc(C4CC4)sc3c1)C2] |
| I-53 | 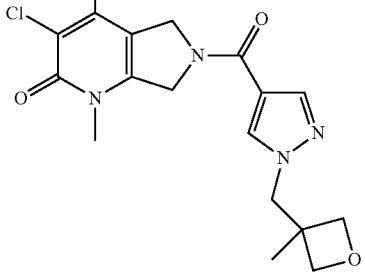 |
| I-54 | 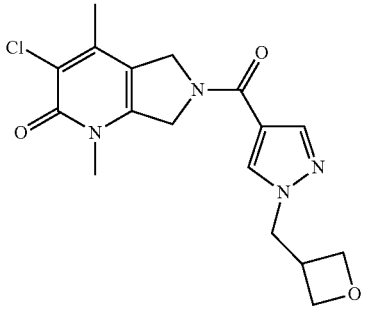 [SMILES: Cc1c2c(n(C)c(=O)c1Cl)CN(C(=O)c1cnn(CC3COC3)c1)C2] |
| I-55 | 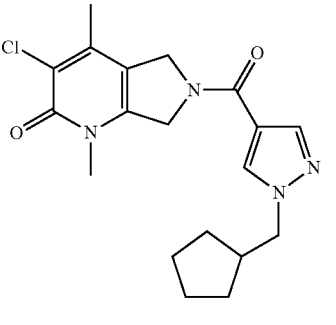 [SMILES: Cc1c2c(n(C)c(=O)c1Cl)CN(C(=O)c1cnn(CC3CCCC3)c1)C2] |
| I-56 | 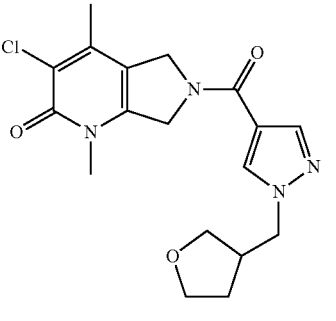 [SMILES: Cc1c2c(n(C)c(=O)c1Cl)CN(C(=O)c1cnn(CC3CCOC3)c1)C2] |

TABLE 1-continued

Exemplary Compounds

| Compound No. | Structure |
|---|---|
| I-57 | |
| I-58 | |
| I-59 | |
| I-60 | |
| I-61 | |
| I-62 | 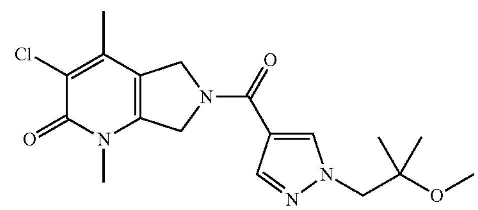 [SMILES: COC(C)(C)Cn1cc(C(=O)N2Cc3c(C)c(Cl)c(=O)n(C)c3C2)cn1] |
| I-63 | 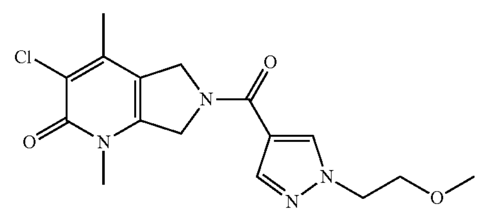 [SMILES: COCCn1cc(C(=O)N2Cc3c(C)c(Cl)c(=O)n(C)c3C2)cn1] |
| I-64 | 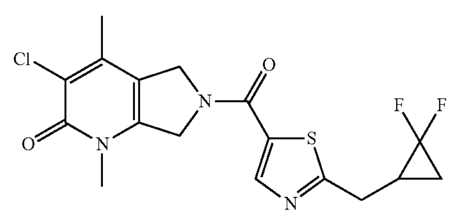 [SMILES: Cc1c2c(n(C)c(=O)c1Cl)CN(C(=O)c1cnc(CC3CC3(F)F)s1)C2] |
| I-65 | 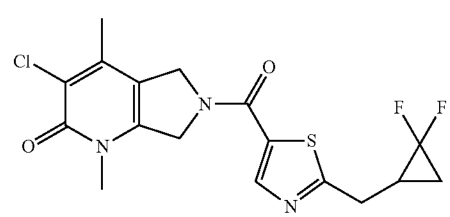 [SMILES: Cc1c2c(n(C)c(=O)c1Cl)CN(C(=O)c1cnc(CC3CC3(F)F)s1)C2] |
| I-66 | 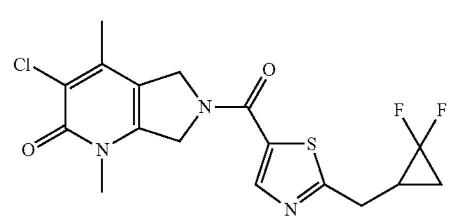 [SMILES: Cc1c2c(n(C)c(=O)c1Cl)CN(C(=O)c1cnc(CC3CC3(F)F)s1)C2] |
| I-67 | 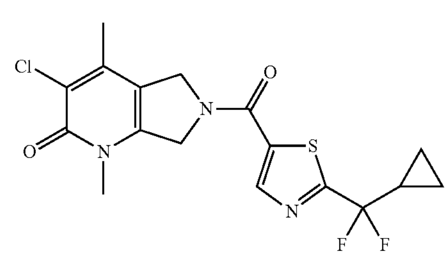 [SMILES: Cc1c2c(n(C)c(=O)c1Cl)CN(C(=O)c1cnc(C(F)(F)C3CC3)s1)C2] |

TABLE 1-continued
Exemplary Compounds
| Compound No. | Structure |
|---|---|
| I-68 | 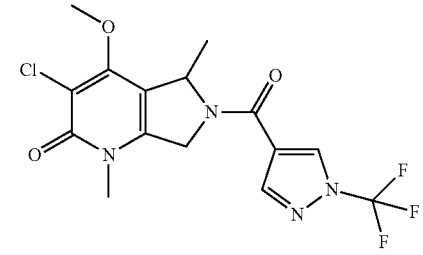 [SMILES: COc1c2c(n(C)c(=O)c1Cl)CN(C(=O)c1cnn(C(F)(F)F)c1)C2C] |
| I-69 | |
| I-70 | |
| I-71 | |
| I-72 | |
| I-73 | 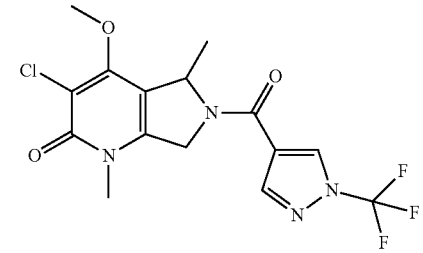 |
| I-74 | 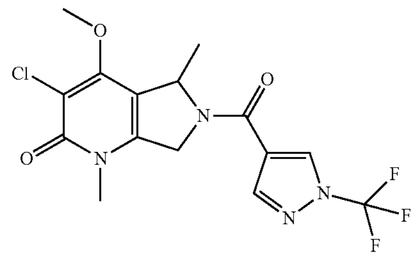 [SMILES: COc1c2c(n(C)c(=O)c1Cl)CN(C(=O)c1cnn(C(F)(F)F)c1)C2C] |
| I-75 | 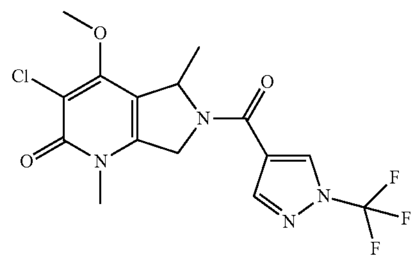 [SMILES: COc1c2c(n(C)c(=O)c1Cl)CN(C(=O)c1cnn(C(F)(F)F)c1)C2C] |
| I-76 | 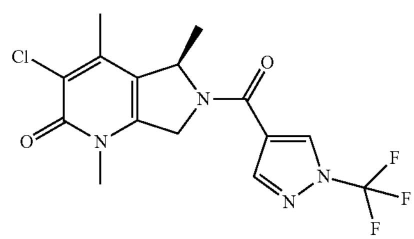 [SMILES: Cc1c2c(n(C)c(=O)c1Cl)CN(C(=O)c1cnn(C(F)(F)F)c1)[C@@H]2C] |
| I-77 | 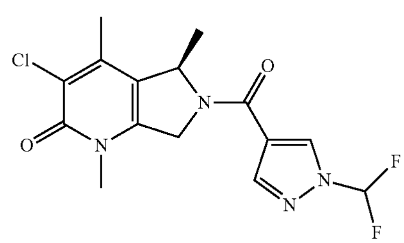 [SMILES: Cc1c2c(n(C)c(=O)c1Cl)CN(C(=O)c1cnn(C(F)F)c1)[C@@H]2C] |
| I-78 | 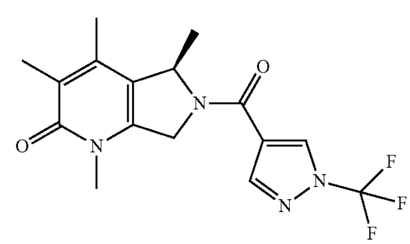 [SMILES: Cc1c2c(n(C)c(=O)c1C)CN(C(=O)c1cnn(C(F)(F)F)c1)[C@@H]2C] |

TABLE 1-continued
Exemplary Compounds
| Compound No. | Structure |
|---|---|
| I-79 | 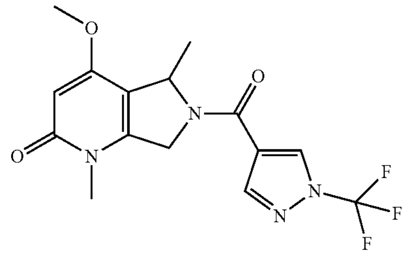 [SMILES: COc1cc(=O)n(C)c2c1C(C)N(C(=O)c1cnn(C(F)(F)F)c1)C2] |
| I-80 | 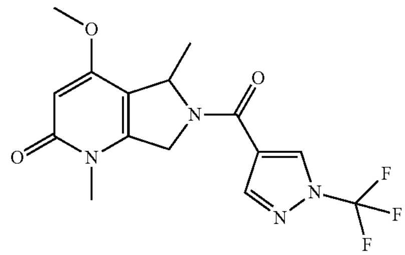 [SMILES: COc1cc(=O)n(C)c2c1C(C)N(C(=O)c1cnn(C(F)(F)F)c1)C2] |
| I-81 | 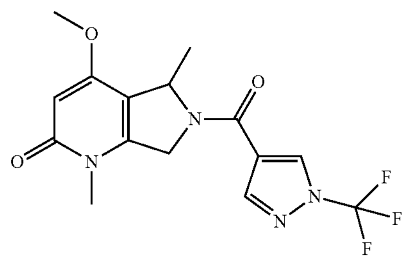 [SMILES: COc1cc(=O)n(C)c2c1C(C)N(C(=O)c1cnn(C(F)(F)F)c1)C2] |
| I-82 | 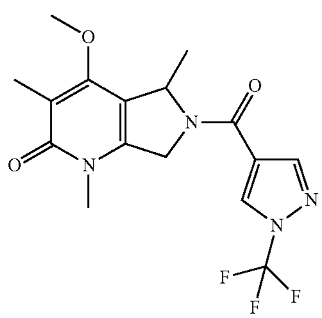 [SMILES: COc1c2c(n(C)c(=O)c1C)CN(C(=O)c1cnn(C(F)(F)F)c1)C2C] |
| I-83 | Stereoisomer 1 |
| I-84 |  Stereoisomer 2 |
| I-85 | |
| I-86 | |
| I-87 | |
| I-88 | |

TABLE 1-continued
Exemplary Compounds
| Compound No. | Structure |
|---|---|
| I-89 | 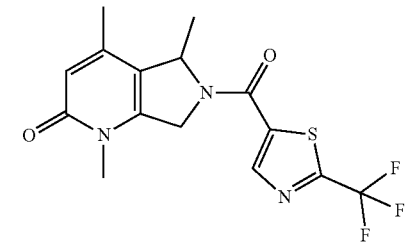 |
| I-90 | 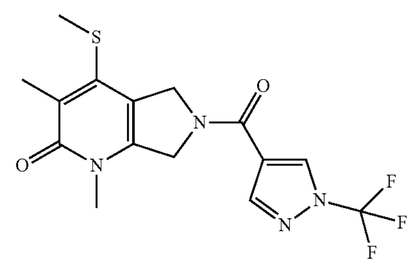 [SMILES: COc1c2c(n(C)c(=O)c1C)CN(C(=O)c1cnn(C(F)(F)F)c1)C2] |
| I-91 | 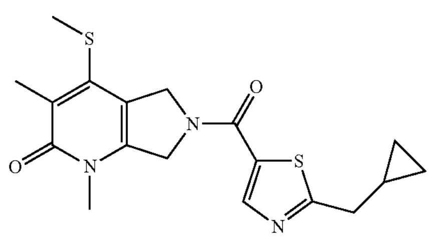 [SMILES: CSc1c2c(n(C)c(=O)c1C)CN(C(=O)c1cnc(CC3CC3)s1)C2] |
| I-92 | 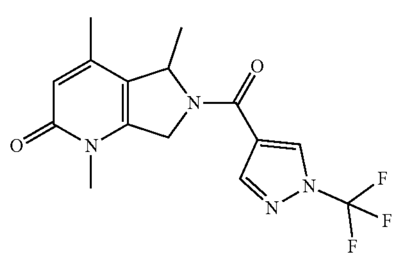 [SMILES: Cc1cc(=O)n(C)c2c1C(C)N(C(=O)c1cnn(C(F)(F)F)c1)C2] |
| I-93 | 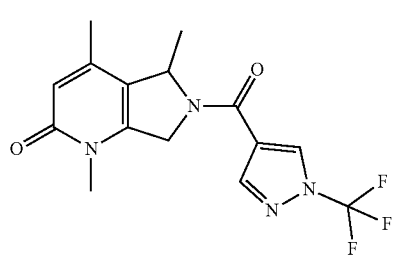 [SMILES: Cc1cc(=O)n(C)c2c1C(C)N(C(=O)c1cnn(C(F)(F)F)c1)C2] |
| I-94 | 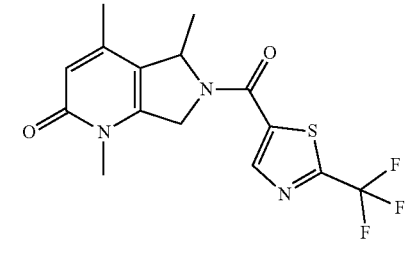 [SMILES: Cc1cc(=O)n(C)c2c1C(C)N(C(=O)c1cnc(C(F)(F)F)s1)C2] |
| I-95 | 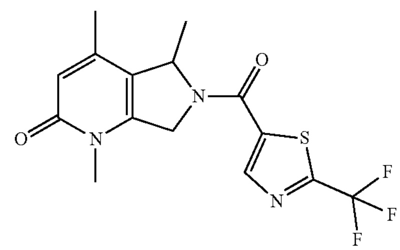 [SMILES: Cc1cc(=O)n(C)c2c1C(C)N(C(=O)c1cnc(C(F)(F)F)s1)C2] |
| I-96 | 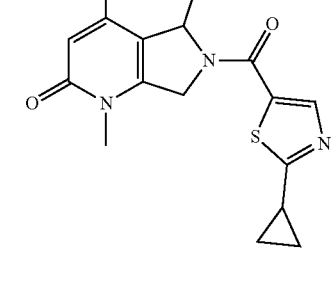 |
| I-97 | 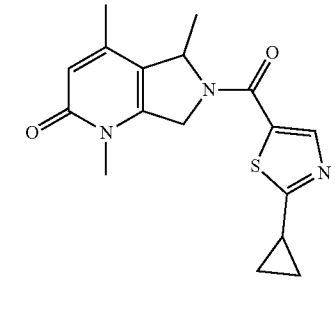 [SMILES: Cc1cc(=O)n(C)c2c1C(C)N(C(=O)c1cnc(C3CC3)s1)C2] |
| I-98 | 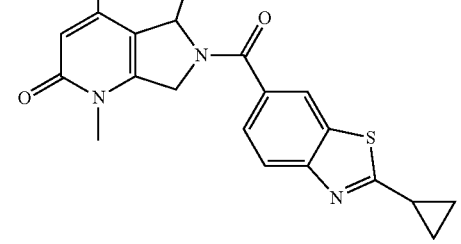 |

TABLE 1-continued

Exemplary Compounds

| Compound No. | Structure |
|---|---|
| I-99 | 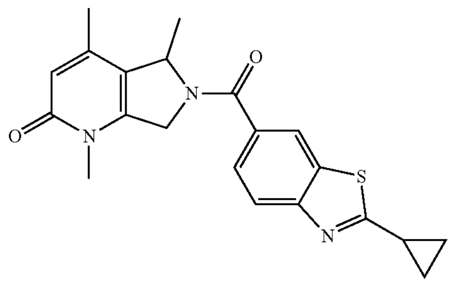 [SMILES: Cc1cc(=O)n(C)c2c1C(C)N(C(=O)c1ccc3nc(C4CC4)sc3c1)C2] |
| I-100 | 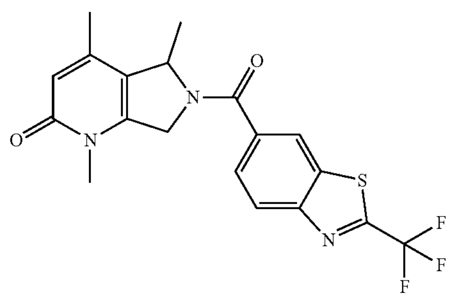 [SMILES: Cc1cc(=O)n(C)c2c1C(C)N(C(=O)c1ccc3nc(C(F)(F)F)sc3c1)C2] |
| I-101 | 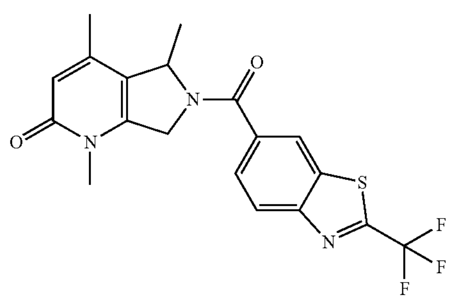 [SMILES: Cc1cc(=O)n(C)c2c1C(C)N(C(=O)c1ccc3nc(C(F)(F)F)sc3c1)C2] |
| I-102 | 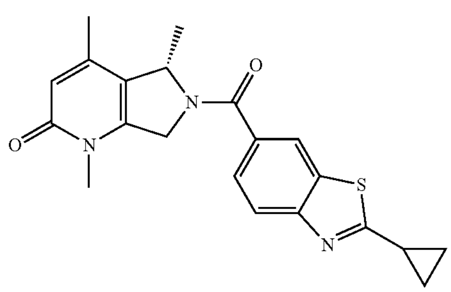 [SMILES: Cc1cc(=O)n(C)c2c1[C@H](C)N(C(=O)c1ccc3nc(C4CC4)sc3c1)C2] |
| I-103 | 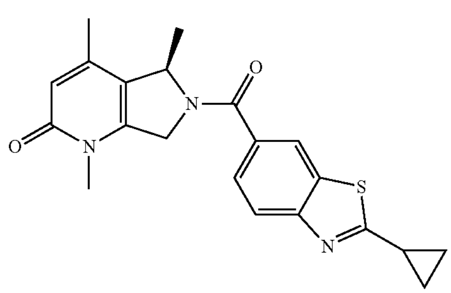 [SMILES: Cc1cc(=O)n(C)c2c1[C@@H](C)N(C(=O)c1ccc3nc(C4CC4)sc3c1)C2] |
| I-104 | 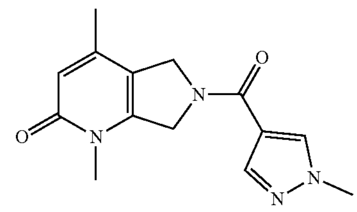 [SMILES: Cc1cc(=O)n(C)c2c1CN(C(=O)c1cnn(C)c1)C2] |
| I-105 | 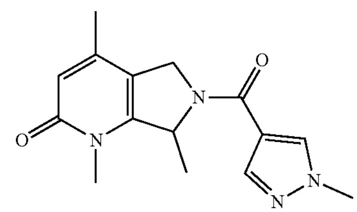 [SMILES: Cc1cc(=O)n(C)c2c1CN(C(=O)c1cnn(C)c1)C2C] |
| I-106 | 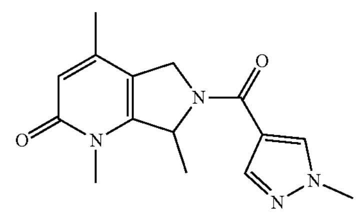 [SMILES: Cc1cc(=O)n(C)c2c1CN(C(=O)c1cnn(C)c1)C2C] |
| I-107 | 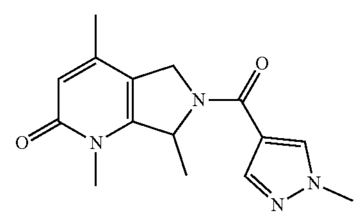 [SMILES: Cc1cc(=O)n(C)c2c1CN(C(=O)c1cnn(C)c1)C2C] |
| I-108 | 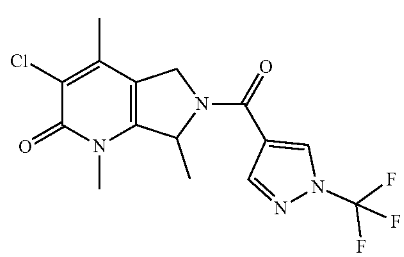 [SMILES: Cc1c2c(n(C)c(=O)c1Cl)C(C)N(C(=O)c1cnn(C(F)(F)F)c1)C2] |
| I-109 | 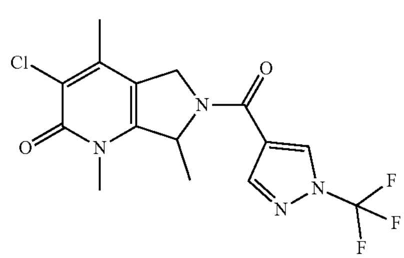 [SMILES: Cc1c2c(n(C)c(=O)c1Cl)C(C)N(C(=O)c1cnn(C(F)(F)F)c1)C2] |

TABLE 1-continued

Exemplary Compounds

| Compound No. | Structure |
|---|---|
| I-110 | 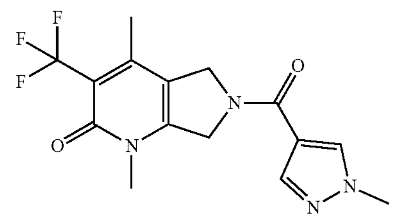 [SMILES: Cc1c2c(n(C)c(=O)c1C(F)(F)F)CN(C(=O)c1cnn(C)c1)C2] |
| I-111 | 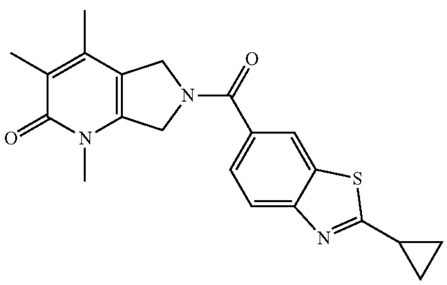 [SMILES: Cc1c2c(n(C)c(=O)c1C)CN(C(=O)c1ccc3nc(C4CC4)sc3c1)C2] |
| I-112 | 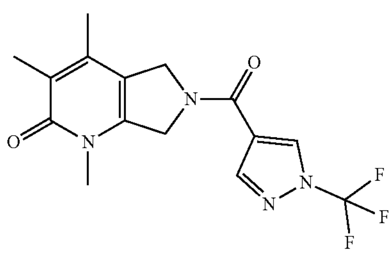 [SMILES: Cc1c2c(n(C)c(=O)c1C)CN(C(=O)c1cnn(C(F)(F)F)c1)C2] |
| I-113 | 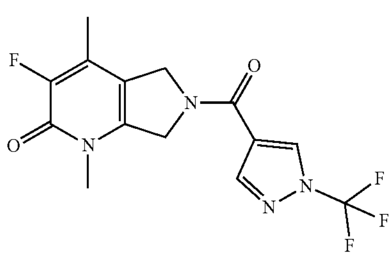 [SMILES: Cc1c2c(n(C)c(=O)c1F)CN(C(=O)c1cnn(C(F)(F)F)c1)C2] |
| I-114 | 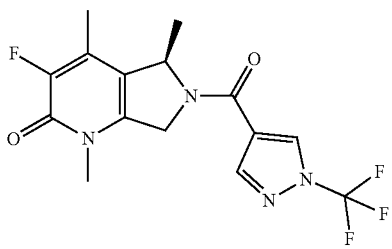 [SMILES: Cc1c2c(n(C)c(=O)c1F)CN(C(=O)c1cnn(C(F)(F)F)c1)[C@@H]2C] |
| I-115 | |

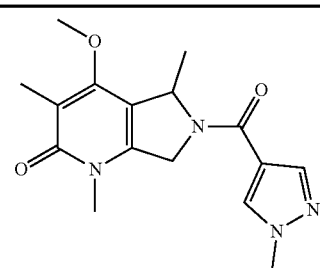

Synthetic Methods

Methods for preparing compounds described herein are illustrated in the following synthetic Scheme. The Scheme is given for the purpose of illustrating the invention, and not intended to limit the scope or spirit of the invention. Starting materials shown in the Scheme can be obtained from commercial sources or can be prepared based on procedures described in the literature.

Scheme 1 illustrates a general method for preparing tetrahydropyrrolo-pyridinones C. Tetrahydro-2H-pyrrolo[3,4-b]pyridin-2-one A is coupled to carboxylic acid B using amide-bond forming conditions (e.g., HATU mediated acid amine coupling) to afford tetrahydropyrrolo-pyridinones C.

SCHEME 1.

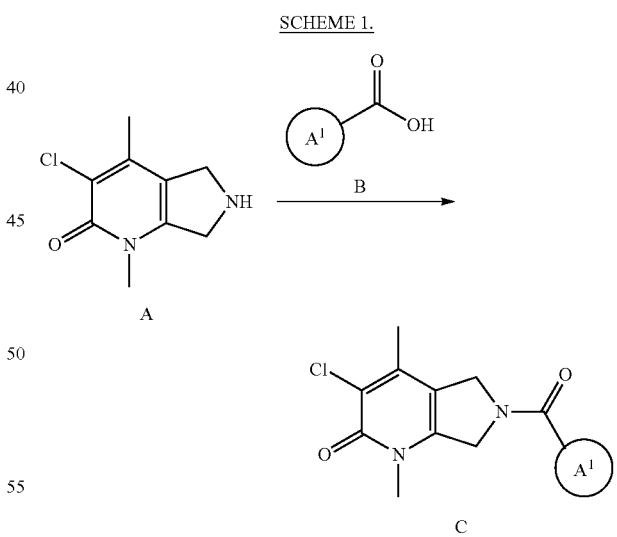

$A^1$ is an optionally substituted 5-6 membered monocyclic heteroaryl, 8-10 membered bicyclic heteroaryl, or phenyl In the Scheme, it is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated (for example, use of protecting groups or alternative reactions). Protecting group chemistry and strategy is well known in the art, for example, as described in detail in "Protecting Groups in Organic Synthesis", T. W. Greene and P. G. M. Wuts, 3$^{rd}$ edition, John Wiley & Sons, 1999, the entire contents of which are hereby incorporated by reference. The modular synthetic route illustrated in Scheme 1 can also be readily modified by one of skill in the art to provide additional compounds by conducting functional group transformations on the intermediate and final compounds. Such functional group transformations are well known in the art, as described in, for example, "Comprehensive Organic Synthesis" (B. M. Trost & I. Fleming, eds., 1991-1992).

Compounds Useful in Synthetic Procedures

Another aspect of the invention provides compounds that are useful in the synthetic procedures. For example, one aspect of the invention provides a compound of Formula II:

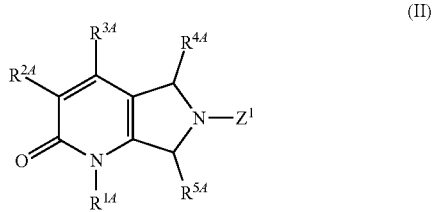

(II)

or a salt thereof; wherein:
$R^{1A}$ is $C_{1-6}$ alkyl, $C_{1-6}$ haloalkyl, $C_{3-6}$ cycloalkyl, —($C_{1-6}$ alkylene)-($C_{3-6}$ cycloalkyl), or hydrogen;
$R^{2A}$ is halo, $C_{1-4}$ alkyl, $C_{1-4}$ haloalkyl, or hydrogen;
$R^{3A}$ is $C_{1-4}$ alkyl, $C_{1-4}$ haloalkyl, $C_{1-4}$ alkoxyl, $C_{1-4}$ haloalkoxyl, —S—($C_{1-4}$ alkyl), or halo;
$R^{4A}$ and $R^{5A}$ are independently hydrogen, $C_{1-4}$ alkyl, $C_{1-4}$ haloalkyl, or halo; and
$Z^1$ is hydrogen or —C(O)$_2$($C_{1-6}$ alkyl).

The definitions of variables in Formula II above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula II.

As defined generally above, $R^{1A}$ is $C_{1-6}$ alkyl, $C_{1-6}$ haloalkyl, $C_{3-6}$ cycloalkyl, —($C_{1-6}$ alkylene)-($C_{3-6}$ cycloalkyl), or hydrogen. In certain embodiments, $R^{1A}$ is hydrogen, methyl, or

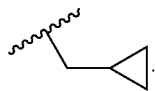

In certain embodiments, $R^{1A}$ is hydrogen. In certain embodiments, $R^{1A}$ is methyl. In certain embodiments, $R^{1A}$ is $C_{1-6}$ alkyl. In certain embodiments, $R^{1A}$ is $C_{1-6}$ haloalkyl. In certain embodiments, $R^{1A}$ is $C_{3-6}$ cycloalkyl. In certain embodiments, $R^{1A}$ is —($C_{1-6}$ alkylene)-($C_{3-6}$ cycloalkyl). In certain embodiments, $R^{1A}$ is selected from the groups depicted in the compounds in Table 1-A below.

As defined generally above, $R^{2A}$ is halo, $C_{1-4}$ alkyl, $C_{1-4}$ haloalkyl, or hydrogen. In certain embodiments, $R^{2A}$ is hydrogen, fluoro, chloro, methyl, or —CF$_3$. In certain embodiments, $R^{2A}$ is hydrogen. In certain embodiments, $R^{2A}$ is fluoro. In certain embodiments, $R^{2A}$ is chloro. In certain embodiments, $R^{2A}$ is methyl. In certain embodiments, $R^{2A}$ is —CF$_3$. In certain embodiments, $R^{2A}$ is halo. In certain embodiments, $R^{2A}$ is $C_{1-4}$ alkyl. In certain embodiments, $R^{2A}$ is $C_{1-4}$ haloalkyl. In certain embodiments, $R^{2A}$ is selected from the groups depicted in the compounds in Table 1-A below.

As defined generally above, $R^{3A}$ is $C_{1-4}$ alkyl, $C_{1-4}$ haloalkyl, $C_{1-4}$ alkoxyl, $C_{1-4}$ haloalkoxyl, —S—($C_{1-4}$ alkyl), or halo. In certain embodiments, $R^{3A}$ is methyl, —OCH$_3$, —OCH$_2$CH$_3$, —OCHF$_2$, or —SCH$_3$. In certain embodiments, $R^{3A}$ is methyl. In certain embodiments, $R^{3A}$ is —OCH$_3$. In certain embodiments, $R^{3A}$ is —OCH$_2$CH$_3$. In certain embodiments, $R^{3A}$ is —OCHF$_2$. In certain embodiments, $R^{3A}$ is —SCH$_3$. In certain embodiments, $R^{3A}$ is $C_{1-4}$ alkyl. In certain embodiments, $R^{3A}$ is $C_{1-4}$ haloalkyl. In certain embodiments, $R^{3A}$ is $C_{1-4}$ alkoxyl. In certain embodiments, $R^{3A}$ is $C_{1-4}$ haloalkoxyl. In certain embodiments, $R^{3A}$ is —S—($C_{1-4}$ alkyl). In certain embodiments, $R^{3A}$ is halo. In certain embodiments, $R^{3A}$ is selected from the groups depicted in the compounds in Table 1-A below.

As defined generally above, $R^{4A}$ and $R^{5A}$ are independently hydrogen, $C_{1-4}$ alkyl, $C_{1-4}$ haloalkyl, or halo. In certain embodiments, $R^{4A}$ is hydrogen or methyl. In certain embodiments, $R^{4A}$ is hydrogen. In certain embodiments, $R^{4A}$ is methyl. In certain embodiments, $R^{4A}$ is $C_{1-4}$ alkyl. In certain embodiments, $R^{4A}$ is $C_{1-4}$ haloalkyl. In certain embodiments, $R^{4A}$ is halo. In certain embodiments, $R^{4A}$ is selected from the groups depicted in the compounds in Table 1-A below. In certain embodiments, $R^{5A}$ is hydrogen or methyl. In certain embodiments, $R^{5A}$ is hydrogen. In certain embodiments, $R^{5A}$ is methyl. In certain embodiments, $R^{5A}$ is $C_{1-4}$ alkyl. In certain embodiments, $R^{5A}$ is $C_{1-4}$ haloalkyl. In certain embodiments, $R^{5A}$ is halo. In certain embodiments, $R^{5A}$ is selected from the groups depicted in the compounds in Table 1-A below.

As defined generally above, $Z^1$ is hydrogen or —C(O)$_2$($C_{1-6}$ alkyl). In certain embodiments, $Z^1$ is hydrogen or tert-butoxycarbonyl. In certain embodiments, $Z^1$ is hydrogen. In certain embodiments, $Z^1$ is tert-butoxycarbonyl. In certain embodiments, $Z^1$ is —C(O)$_2$($C_{1-6}$ alkyl). In certain embodiments, $Z^1$ is selected from the groups depicted in the compounds in Table 1-A below.

The description above describes multiple embodiments relating to compounds of Formula II. The patent application specifically contemplates all combinations of the embodiments.

Another aspect of the invention provides a compound in Table 1-A below.

TABLE 1-A

[Structure with $R^{3A}$, $R^{4A}$, $R^{2A}$, $R^{1A}$, $R^{5A}$, $Z^1$ substituents on a pyrrolo-pyridinone core]

| Compound No. | $R^{1A}$ | $R^{2A}$ | $R^{3A}$ | $R^{4A}$ | $R^{5A}$ | $Z^1$ |
|---|---|---|---|---|---|---|
| II-1 | methyl | Cl | methyl | H | H | H |
| II-2 | H | H | methyl | H | H | H |
| II-3 | 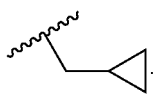 | Cl | methyl | H | H | H |
| II-4 | methyl | Cl | methoxy | methyl | H | H |
| II-5 | methyl | Cl | methyl | methyl | H | H |
| II-6 | methyl | methyl | methyl | methyl | H | H |
| II-7 | methyl | H | methoxy | methyl | H | H |
| II-8 | methyl | methyl | methoxy | methyl | H | H |
| II-9 | methyl | methyl | methoxy | H | H | H |
| II-10 | methyl | methyl | ethoxy | H | H | H |
| II-11 | methyl | methyl | —OCHF$_2$ | H | H | H |
| II-12 | methyl | methyl | —SCH$_3$ | H | H | H |
| II-13 | methyl | H | methyl | methyl | H | H |
| II-14 | methyl | H | methyl | H | H | H |
| II-15 | methyl | H | methyl | H | methyl | H |
| II-16 | methyl | Cl | methyl | H | methyl | H |
| II-17 | methyl | —CF$_3$ | methyl | H | H | H |
| II-18 | methyl | methyl | methyl | H | H | H |
| II-19 | methyl | F | methyl | H | H | H |
| II-20 | methyl | F | methyl | methyl | H | H |

In certain embodiments, $R^{1A}$ is hydrogen, methyl, or

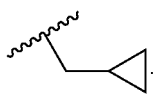

In certain embodiments, $R^{2A}$ is hydrogen, fluoro, chloro, methyl, or —CF$_3$. In certain embodiments, $R^{3A}$ is methyl, —OCH$_3$, —OCH$_2$CH$_3$, —OCHF$_2$, or —SCH$_3$. In certain embodiments, $R^{4A}$ is hydrogen or methyl. In certain embodiments, $R^{5A}$ is hydrogen or methyl. In certain embodiments, $Z^1$ is hydrogen or tert-butoxycarbonyl.

II. Therapeutic Applications

Another aspect of the invention provides a method of treating a muscarinic acetylcholine receptor mediated disorder, wherein the method comprises administering to a subject in need thereof a therapeutically effective amount of a compound described herein, such as a compound of Formula I, to treat the muscarinic acetylcholine receptor mediated disorder. In certain embodiments, the particular compound of Formula I is a compound defined by one of the embodiments described in Section I, above.

Methods described herein may be further defined according to additional features, such as the identity of the muscarinic acetylcholine receptor mediated disorder and/or the subject.

Muscarinic acetylcholine receptor mediated disorders can be treated or prevented by modulating the muscarinic system. Such diseases include those in which direct activation of muscarinic acetylcholine receptors themselves or inhibition of cholinesterase enzymes provides a therapeutic effect. Exemplary muscarinic acetylcholine receptor medicated disorders include schizophrenia, movement disorders, mood disorders, cognitive disorders, attention disorders, addictive disorders, and pain. In certain embodiments, the muscarinic acetylcholine receptor mediated disorder is selected from schizophrenia, movement disorders, mood disorders, cognitive disorders, attention disorders, addictive disorders, and neurologic disorders. In certain embodiments, the muscarinic acetylcholine receptor mediated disorder is a movement disorder, mood disorder, or cognitive disorder. In certain embodiments, the muscarinic acetylcholine receptor mediated disorder is selected from attention disorders and addictive disorders.

In certain embodiments, the muscarinic acetylcholine receptor mediated disorder is schizophrenia or a related disorder. Disorders related to schizophrenia include schizoaffective disorder, psychosis disorders, psychosis associated with Alzheimer's disease, Hereditary Cerebral Hemorrhage with Amyloidosis of the Dutch-Type (HCHWA-D), Creutzfeldt-Jakob disease, prion disorder, psychosis associated with Parkinson's disease, psychotic depression, bipolar disorder, bipolar with psychosis, Huntington's disease, Lewy Body dementia, cerebral amyloid angiopathy, or any other disease with psychotic features.

In certain embodiments, the muscarinic acetylcholine receptor mediated disorder is selected from a schizo-affective disorder, psychosis, delusional disorders, psychosis associated with Alzheimer's disease, Hereditary Cerebral Hemorrhage with Amyloidosis of the Dutch-Type (HCHWA-D), Creutzfeldt-Jakob disease, prion disorder, psychosis associated with Parkinson's disease, psychotic depression, bipolar disorder, bipolar with psychosis, Huntington's disease, cerebral amyloid angiopathy, and Lewy Body dementia. In certain embodiments, the muscarinic acetylcholine receptor mediated disorder is selected from a schizo-affective disorder, psychosis, psychosis associated with Alzheimer's disease, Hereditary Cerebral Hemorrhage with Amyloidosis of the Dutch-Type (HCHWA-D), Creutzfeldt-Jakob disease, prion disorder, psychosis associated with Parkinson's disease, psychotic depression, bipolar disorder, bipolar with psychosis, Huntington's disease, cerebral amyloid angiopathy, and Lewy Body dementia.

In certain embodiments, the muscarinic acetylcholine receptor mediated disorder is a movement disorder. Exemplary movement disorders include Gilles de la Tourette's syndrome, Friederich's ataxia, amyotrophic lateral sclerosis, progressive supranuclear palsy, Huntington's chorea, dyskinesia, restless leg syndrome, and other diseases or disorders whose symptoms include excessive movements, tics, and spasms. In certain embodiments, the muscarinic acetylcholine receptor mediated disorder is selected from Gilles de la Tourette's syndrome, Friederich's ataxia, amyotrophic lateral sclerosis, progressive supranuclear palsy, Huntington's chorea, dyskinesia, and restless leg syndrome.

In certain embodiments, the muscarinic acetylcholine receptor mediated disorder is a mood disorder. Exemplary mood disorders include major depressive disorder, dysthymia, recurrent brief depression, minor depression disorder, bipolar disorder, mania, and anxiety. In certain embodiments, the muscarinic acetylcholine receptor mediated disorder is selected from major depressive disorder, dysthymia, recurrent brief depression, minor depression disorder, bipolar disorder, mania, and anxiety.

In certain embodiments, the muscarinic acetylcholine receptor mediated disorder is a cognitive disorder. Exemplar cognitive disorders are diseases or disorders marked by a cognitive deficit (e.g., having abnormal working memory, problem-solving abilities, etc.), such as Alzheimer's disease, Hereditary Cerebral Hemorrhage with Amyloidosis of the Dutch-Type (HCHWA-D), Creutzfeldt-Jakob disease, prion disorder, Parkinson's Disease, Parkinson's Disease-levodopa-induced dyskinesia, cerebral amyloid angiopathy, dementia (e.g., AIDS-related dementia, vascular dementia, age-related dementia, dementia associated with Lewy bodies, and idiopathic dementia), Pick's disease, tauopathies, synucleinopathies, confusion, mild cognitive impairment, cognitive deficit associated with fatigue, learning disorders, traumatic brain injury, autism, age-related cognitive decline, and Cushing's Disease, a cognitive impairment associated with autoimmune diseases.

In certain embodiments, the muscarinic acetylcholine receptor mediated disorder is selected from Alzheimer's disease, Hereditary Cerebral Hemorrhage with Amyloidosis of the Dutch-Type (HCHWA-D). Creutzfeldt-Jakob disease, prion disorder, Parkinson's Disease, Parkinson's Disease-levodopa-induced dyskinesia cerebral amyloid angiopathy, dementia (e.g., AIDS-related dementia, vascular dementia, age-related dementia, dementia associated with Lewy bodies, and idiopathic dementia), Pick's disease, tauopathies, synucleinopathies, confusion, mild cognitive impairment, cognitive deficit associated with fatigue, learning disorders, traumatic brain injury, autism, age-related cognitive decline, and Cushing's Disease.

In certain embodiments, the muscarinic acetylcholine receptor mediated disorder is an attention disorder. Exemplary attention disorders are diseases or conditions marked by having an abnormal or decreased attention span, such as attention deficit and hyperactivity disorder (ADHD), attention deficit disorder (ADD), Dubowitz Syndrome, FG Syndrome, Down's Syndrome, growth delay due to insulin-like growth factor I (IGF1) deficiency, hepatic encephalopathy syndrome, and Strauss Syndrome.

In certain embodiments, the muscarinic acetylcholine receptor mediated disorder is selected from hyperactivity disorder (ADHD), attention deficit disorder (ADD), Dubowitz Syndrome, FG Syndrome, Down's Syndrome, growth delay due to insulin-like growth factor I (IGF1) deficiency, hepatic encephalopathy syndrome, and Strauss Syndrome In certain embodiments, the muscarinic acetylcholine receptor mediated disorder is an addictive disorder. Exemplary addictive disorders are diseases or conditions marked by addiction or substance dependence as defined by the *Diagnostic & Statistical Manual V* (DSM-5). Such disorders are often characterized by physical dependence, withdrawal, and tolerance to a substance. Such substances include but are not limited to alcohol, cocaine, amphetamines, opioids, benzodiazepines, inhalants, nicotine, barbiturates, cocaine, and *cannabis*. Addictive disorders also encompass behaviors that a patient does compulsively or continually despite clear negative consequences. For instance, ludomania (gambling addiction or compulsive gambling) is recognized by those skilled in the art as being an addictive behavior that often has devastating consequences. In certain embodiments, the addictive behavior may be Internet Gaming Disorder (gaming addiction), as defined in the DSM-5.

In certain embodiments, the muscarinic acetylcholine receptor mediated disorder is addiction to one of the following substances: alcohol, cocaine, amphetamines, opioids, benzodiazepines, inhalants, nicotine, barbiturates, cocaine, or *cannabis*; ludomania; and Internet Gaming Disorder.

In certain embodiments, the muscarinic acetylcholine receptor mediated disorder is a neurologic disorder. Exemplary neurologic disorders are pain, physical suffering, or discomfort caused by illness or injury. Pain is a subjective experience, and the perception of pain is performed as part of the central nervous system (CNS). Usually, noxious (peripheral) stimuli are transmitted to the CNS beforehand, but the pain is not always associated with nociception. A broad variety of clinical pain exists, derived from different underlying pathophysiological mechanisms, and needs different treatment approaches. Several major types of clinical pain have been characterized: acute pain, chronic pain, neuropathic pain, inflammatory pain, and nociceptive pain.

In certain embodiments, the muscarinic acetylcholine receptor mediated disorder is selected from acute pain, chronic pain, neuropathic pain, inflammatory pain, and nociceptive pain. In certain embodiments, the muscarinic acetylcholine receptor mediated disorder is acute pain. In certain embodiments, the muscarinic acetylcholine receptor mediated disorder is chronic pain. In certain embodiments, the muscarinic acetylcholine receptor mediated disorder is neuropathic pain. In certain embodiments, the muscarinic acetylcholine receptor mediated disorder is inflammatory pain. In certain embodiments, the muscarinic acetylcholine receptor mediated disorder is nociceptive pain. In certain embodiments, the muscarinic acetylcholine receptor mediated disorder is inflammatory pain or nociceptive pain.

In certain embodiments, the muscarinic acetylcholine receptor mediated disorder is selected from a schizo-affective disorder, psychosis, psychosis associated with Alzheimer's disease, Hereditary Cerebral Hemorrhage with Amyloidosis of the Dutch-Type (HCHWA-D), Creutzfeldt-Jakob disease, prion disorder, psychosis associated with Parkinson's disease, Parkinson's Disease-levodopa-induced dyskinesia psychotic depression, bipolar disorder, bipolar with psychosis, Huntington's disease, cerebral amyloid angiopathy, Lewy Body dementia, Gilles de la Tourette's syndrome, Friederich's ataxia, amyotrophic lateral sclerosis, progressive supranuclear palsy, Huntington's chorea, dyskinesia, restless leg syndrome, major depressive disorder, dysthymia, recurrent brief depression, minor depression disorder, bipolar disorder, mania, anxiety, Alzheimer's disease, Hereditary Cerebral Hemorrhage with Amyloidosis of the Dutch-Type (HCHWA-D), Creutzfeldt-Jakob disease, prion disorder, Parkinson's Disease, Parkinson's Disease—levodopa-induced dyskinesia, dementia (including, but not limited to, AIDS-related dementia, vascular dementia, age-related dementia, dementia associated with Lewy bodies, and idiopathic dementia), Pick's disease, tauopathies, synucleinopathies, confusion, mild cognitive impairment, cognitive deficit associated with fatigue, learning disorders, traumatic brain injury, autism, age-related cognitive decline, Cushing's Disease, hyperactivity disorder (ADHD), attention deficit disorder (ADD), Dubowitz Syndrome, FG Syndrome, Down's Syndrome, growth delay due to insulin-like growth factor I (IGF1) deficiency, hepatic encephalopathy syndrome, and Strauss Syndrome, and addiction to one of the following substances: alcohol, cocaine, amphetamines, opioids, benzodiazepines, inhalants, nicotine, barbiturates, cocaine, or cannabis, ludomania, Internet Gaming Disorder, acute pain, chronic pain, neuropathic pain, inflammatory pain, and nociceptive pain.

In certain embodiments, the muscarinic acetylcholine receptor mediated disorder is schizophrenia, psychosis, mild cognitive impairment, Alzheimer's Disease, Parkinson's Disease, Parkinson's Disease-levodopa-induced dyskinesia. Huntington's Disease, dyskinesia, cerebral amyloid angiopathy, dementia, Hereditary Cerebral Hemorrhage with Amyloidosis of the Dutch-Type (HCHWA-D), Creutzfeldt-Jakob disease, a prion disorder, amyotrophic lateral sclerosis, progressive supranuclear palsy, autism, addiction, or a sleep disorder.

In certain embodiments, the muscarinic acetylcholine receptor mediated disorder is a schizo-affective disorder, psychosis, a delusional disorder, psychosis associated with Alzheimer's disease, psychosis associated with Parkinson's disease, psychotic depression, bipolar disorder, bipolar with psychosis, Huntington's disease, Lewy Body dementia, Gilles de la Tourette's syndrome, Friederich's ataxia, Huntington's chorea, restless leg syndrome, major depressive disorder, dysthymia, recurrent brief depression, minor depression disorder, mania, anxiety, Alzheimer's disease, Parkinson's Disease, dementia, Pick's disease, tauopathies, synucleinopathies, confusion, cognitive deficit associated with fatigue, a learning disorder, traumatic brain injury, autism, age-related cognitive decline, Cushing's Disease, attention deficit and hyperactivity disorder (ADHD), attention deficit disorder (ADD), Dubowitz Syndrome, FG Syndrome, Down's Syndrome, growth delay due to insulin-like growth factor I (IGF1) deficiency, hepatic encephalopathy syndrome, Strauss Syndrome, or agitation associated with neurodegeneration.

Method of Activating a Muscarinic Acetylcholine Receptor

Another aspect of the invention provides a method of activating a muscarinic acetylcholine receptor. The method comprises contacting a muscarinic acetylcholine receptor with an effective amount of a compound described herein, such as a compound of Formula I, to activate the muscarinic acetylcholine receptor, as further described in the detailed description.

In certain embodiments, the muscarinic acetylcholine receptor is muscarinic acetylcholine receptor M4.

Subjects

In certain embodiments, the subject is a human. In certain embodiments, the subject is an adult human. In certain embodiments, the subject is a pediatric human.

Medical Uses

Another aspect of the invention provides for the use of a compound described herein (such as a compound of Formula I, or other compounds in Section I) in the manufacture of a medicament. In certain embodiments, the medicament is for treating a disorder described herein, such as a muscarinic acetylcholine receptor mediated disorder.

Another aspect of the invention provides for the use of a compound described herein (such as a compound of Formula I, or other compounds in Section I) for treating a medical disorder, such as a medical disorder described herein, such as a muscarinic acetylcholine receptor mediated disorder.

Assay for Evaluating Compound Biological Activity in Rats

Compounds may be tested for ability to impact behavior activity of rats according to the following procedures. Animals: Adult male, Sprague Dawley rats (Envigo, Indianapolis, IN, USA) are housed in a colony maintained at 23° C. with 12 h light/dark cycles (lights on at 0600 hours). All animals weigh 290-330 g at the beginning of the study and are equally divided into 5 groups (n=8 per group) and received one of the treatment conditions listed below. Behavioral Procedures: Studies are conducted in MedAssociates open field chambers (27.3 cm×27.3 cm×20.3 cm, MedAssociates, St. Albans, VT) in which movement is automatically tracked and recorded by 16 beam arrays. The administration pretreatment of the test article is determined to coincide with Tmax at the time of the amphetamine-evoked session with optimal route of administration. All groups are subcutaneously treated with 0.5 mg/kg amphetamine (AMP). The test article is tested in three dose groups with a half-log increase between doses. Risperidone (0.55 mg/kg, 30 minutes, s.c.) may be used as a positive control and is administered to group 5. To determine the role of test article on AMP-evoked hyperlocomotion, rats are placed in the open area and allowed to habituate for 30 min before being s.c. dosed with 0.5 mg/kg AMP. Locomotor data (distance traveled) is recorded as 5-minute bins throughout the 90-minute session. The dose of AMP is chosen based on the selective increase in locomotor behavior relative to stereotypes. The dose of risperidone is chosen that produced reliable effects and served as a positive control. Statistical Analysis: Spontaneous locomotion (prior to AMP administration) is calculated as the total distance traveled during the first 30 minutes of the experimental session. AMP-evoked responses are calculated as the total distance traveled during the last 60 minutes of the experimental session which commenced immediately after AMP administration. Locomotor data may be analyzed by a one-way ANOVA. When there is a significant overall ANOVA, post hoc comparisons may be made by Dunnett's test with statistical significance determined as $p<0.05$.

IV. Combination Therapy

Another aspect of the invention provides for combination therapy. Compounds described herein (such as a compound of Formula I, or other compounds in Section I) or their pharmaceutically acceptable salts may be used in combination with additional therapeutic agents to treat medical disorders, such as a muscarinic acetylcholine receptor mediated disorder.

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

One or more other therapeutic agent may be administered separately from a compound or composition of the invention, as part of a multiple dosage regimen. Alternatively, one or more other therapeutic agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and a compound or composition of the invention are administered as a multiple dosage regimen more than 24 hours apart.

Additional Therapeutics Agents for Treating a Muscarinic Acetylcholine Receptor Mediated Disorder Various pharmaceutically active agents may be selected for use in conjunction with the compounds of the present invention, depending on the disease, disorder, or condition to be treated. Pharmaceutically active agents that may be used in combination with the compositions of the present invention include, without limitation:

(i) acetylcholinesterase inhibitors, such as donepezil hydrochloride (ARICEPT, MEMAC), physostigmine salicylate (ANTILIRIUM), physostigmine sulfate (ESERINE), metrifonate, neostigmine, ganstigmine, pyridostigmine (MESTINON), ambenonium (MYTELASE), demecarium, Debio 9902 (also known as ZT-1; Debiopharm), rivastigmine (EXELON), ladostigil, NP-0361, galantamine hydrobromide (RAZADYNE, RIMINYL, NIVALIN), tacrine (COGNEX), tolserine, velnacrine maleate, memoquin, huperzine A (HUP-A; NeuroHitech), phenserine, edrophonium (ENLON, TENSILON), and INM-176;

(ii) amyloid-β (or fragments thereof), such as AB1.15 conjugated to pan HLA DR-binding epitope (PADRE), ACC-001 (Elan/Wyeth), ACI-01, ACI-24, AN-1792, Afhtope AD-01, CAD106, and V-950;

(iii) antibodies to amyloid-β (or fragments thereof), such as ponezumab, solanezumab, bapineuzumab (also known as AAB-001), AAB-002 (Wyeth/Elan), ACI-01-Ab7, BAN-2401, intravenous Ig (GAMMAGARD), LY2062430 (humanized m266; Lilly), R1450 (Roche), ACU-5A5, huCO91, and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(iv) amyloid-lowering or -inhibiting agents (including those that reduce amyloid production, accumulation and fibrillization) such as dimebon, davunetide, eprodisate, leuprolide, SK-PC-B70 M, celecoxib, lovastatin, anapsos, oxiracetam, pramiracetam, varenicline, nicergoline, colostrinin, bisnorcymserine (also known as BNC), NICS-15 (Humanetics), E-2012 (Eisai), pioglitazone, clioquinol (also known as PBT1), PBT2 (Prana Biotechnology), flurbiprofen (ANSAID, FROBEN) and its R-enantiomer tarenflurbil 34 (FLURIZAN), nitroflurbiprofen, fenoprofen (FENOPRON, NALFON), ibuprofen (ADVIL, MOTRIN, NUROFEN), ibuprofen lysinate, meclofenamic acid, meclofenamate sodium (MECLOMEN), indomethacin (INDOCIN), diclofenac sodium (VOLTAREN), diclofenac potassium, sulindac (CLINORIL), sulindac sulfide, diflunisal (DOLOBID), naproxen (NAPROSYN), naproxen sodium (ANAPROX, ALEVE), ARC031 (Archer Pharmaceuticals), CAD-106 (Cytos), LY450139 (Lilly), insulin-degrading enzyme (also known as insulysin), the *Gingko biloba* extract EGb-761 (ROKAN, TEBONIN), tramiprosate (CEREBRIL, ALZHEMED), eprodisate (FIBRILLEX, KIACTA), compound W [3,5-bis(4-nitrophenoxy)benzoic acid], NGX-96992, neprilysin (also known as neutral endopeptidase (NEP)), scyllo-inositol (also known as scyllitol), atorvastatin (LIPITOR), simvastatin (ZOCOR), KLVFF-(EEX)3, SKF-74652, ibutamoren mesylate, BACE inhibitors such as ASP-1702, SCH-745966, JNJ-715754, AMG-0683, AZ-12304146, BMS-782450, GSK-188909, NB-533, E2609 and TTP-854; gamma secretase modulators such as ELND-007; and RAGE (receptor for advanced glycation end-products) inhibitors, such as TTP488 (Transtech) and TTP4000 (Transtech), and those disclosed in U.S. Pat. No. 7,285,293, including PTI-777;

(v) alpha-adrenergic receptor agonists, such as guanfacine (INTUNIV, TENEX), clonidine (CATAPRES), metaraminol (ARAMINE), methyldopa (ALDOMET, DOPAMET, NOVOMEDOPA), tizanidine (ZANAFLEX), phenylephrine (also known as neosynephrine), methoxamine, cirazoline, guanfacine (INTUNIV), lofexidine, xylazine, modafinil (PROVIGIL), adrafinil, and armodafinil (NUVIGIL);

(vi) beta-adrenergic receptor blocking agents (beta blockers), such as carteolol, esmolol (BREVIBLOC), labetalol (NORMODYNE, TRANDATE), oxprenolol (LARACOR, TRASACOR), pindolol (VISKEN), propanolol (INDERAL), sotalol (BETAPACE, SOTALEX, SOTACOR), timolol (BLOCADREN, TIMOPTIC), acebutolol (SECTRAL, PRENT), nadolol (CORGARD), metoprolol tartrate (LOPRESSOR), metoprolol succinate (TOPROL-XL), atenolol (TENORMIN), butoxamine, and SR 59230A (Sanofi);

(vii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERMSCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BAN- THINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL)

(viii) anticonvulsants, such as carbamazepine (TEGRETOL, CARBATROL), oxcarbazepine (TRILEPTAL), phenytoin sodium (PHENYTEK), fosphenytoin (CEREBYX, PRODILANTIN), divalproex sodium (DEPAKOTE), gabapentin (NEURONTIN), pregabalin (LYRICA), topiramate (TOPAMAX), valproic acid (DEPAKENE), valproate sodium (DEPACON), 1-benzyl-5-bromouracil, progabide, beclamide, zonisamide (TRERIEF, EXCEGRAN), CP-465022, retigabine, talampanel, and primidone (MYSOLINE);

(ix) antipsychotics, such as lurasidone (LATUDA, also known as SM-13496; Dainippon Sumitomo), aripiprazole (ABILIFY), chlorpromazine (THORAZINE), haloperidol (HALDOL), iloperidone (FANAPTA), flupentixol decanoate (DEPIXOL, FLUANXOL), reserpine (SERPLAN), pimozide (ORAP), fluphenazine decanoate, fluphenazine hydrochloride, prochlorperazine (COMPRO), asenapine (SAPHRIS), loxapine (LOXITANE), molindone (MOBAN), perphenazine, thioridazine, thiothixene, trifluoperazine (STELAZINE), ramelteon, clozapine (CLOZARIL), norclozapine (ACP-104), risperidone (RISPERDAL), paliperidone (INVEGA), melperone, olanzapine (ZYPREXA), quetiapine (SEROQUEL), talnetant, amisulpride, ziprasidone (GEODON), blonanserin (LONASEN), and ACP-103 (Acadia Pharmaceuticals);

(x) calcium channel blockers such as lomerizine, ziconotide, nilvadipine (ESCOR, NIVADIL), diperdipine, amlodipine (NORVASC, ISTIN, AMLODIN), felodipine (PLENDIL), nicardipine (CARDENE), nifedipine (ADALAT, PROCARDIA), MEM 1003 and its parent compound nimodipine (NIMOTOP), nisoldipine (SULAR), nitrendipine, lacidipine (LACIPIL, MOTENS), lercanidipine (ZANIDIP), lifarizine, diltiazem (CARDIZEM), verapamil (CALAN, VERELAN), AR-R 18565 (AstraZeneca), and enecadin;

(xi) catechol O-methyltransferase (COMT) inhibitors, such as nitecapone, tolcapone (TASMAR), entacapone (COMTAN), and tropolone;

(xii) central nervous system stimulants, such as atomoxetine, reboxetine, yohimbine, caffeine, phenmetrazine, phendimetrazine, pemoline, fencamfamine (GLUCOENERGAN, REACTIVAN), fenethylline (CAPTAGON), pipradol (MERETRAN), deanol (also known as dimethylaminoethanol), methylphenidate (DAYTRANA), methylphenidate hydrochloride (RITALIN), dexmethylphenidate (FOCALIN), amphetamine (alone or in combination with other CNS stimulants, e.g., ADDERALL (amphetamine aspartate, amphetamine sulfate, dextroamphetamine saccharate, and dextroamphetamine sulfate)), dextroamphetamine sulfate (DEXEDRINE, DEXTROSTAT), methamphetamine (DESOXYN), lisdexamfetamine (VYVANSE), and benzphetamine (DIDREX);

(xiii) corticosteroids, such as prednisone (STERAPRED, DELTASONE), prednisolone (PRELONE), prednisolone acetate (OMNIPRED, PRED MILD, PRED FORTE), prednisolone sodium phosphate (ORAPRED ODT), methylprednisolone (MEDROL); methylprednisolone acetate (DEPOMEDROL), and methylprednisolone sodium succinate (A-METHAPRED, SOLUMEDROL);

(xiv) dopamine receptor agonists, such as apomorphine (APOKYN), bromocriptine (PARLODEL), cabergoline (DOSTINEX), dihydrexidine, dihydroergokryptine, fenoldopam (CORLOPAM), lisuride (DOPERGIN), terguride spergolide (PERMAX), piribedil (TRIVASTAL, TRASTAL), pramipexole (MIRAPEX), quinpirole, ropinirole (REQUIP), rotigotine (NEUPRO), SKF-82958 (Glaxo-SmithKline), cariprazine, pardoprunox and sarizotan; (xv) dopamine receptor antagonists, such as chlorpromazine, fluphenazine, haloperidol, loxapine, risperidone, thioridazine, thiothixene, trifluoperazine, tetrabenazine (NITOMAN, XENAZINE), 7-hydroxyamoxapine, droperidol (INAPSINE, DRIDOL, DROPLETAN), domperidone (MOTILIUM), L-741742, L-745870, raclopride, SB-277011A, SCH-23390, ecopipam, SKF-83566, and metoclopramide (REGLAN);

(xvi) dopamine reuptake inhibitors such as bupropion, safinamide, nomifensine maleate (MERITAL), vanoxerine (also known as GBR-12909) and its decanoate ester DBL-583, and amineptine;

(xvii) gamma-amino-butyric acid (GABA) receptor agonists, such as baclofen (LIORESAL, KEMSTRO), siclofen, pentobarbital (NEMBUTAL), progabide (GABRENE), and clomethiazole;

(xviii) histamine 3 (H3) antagonists such as ciproxifan, tiprolisant, 5-38093, irdabisant, pitolisant, GSK-239512, GSK-207040, JNJ-5207852, JNJ-17216498, HPP-404, SAR-110894, trans-N-ethyl-3-fluoro-3-[3-fluoro-4-(pyrrolidin-1-ylmethyl)phenylcyclobutan-ecarboxamide (PF-3654746 and those disclosed in US Patent Publication Nos US2005-0043354, US2005-0267095, US2005-0256135, US2008-0096955, US2007-1079175, and US2008-0176925; International Patent Publication Nos WO2006/15138431, and WO2007/088,462; and U.S. Pat. No. 7,115,600);

(xix) immunomodulators such as glatiramer acetate (also known as copolymer-1; COPAXONE), MBP-8298 (synthetic myelin basic protein peptide), dimethyl fumarate, fingolimod (also known as FTY720), roquinimex (LINOMIDE), laquinimod (also known as ABR-215062 and SAIK-MS), ABT-874 (human anti-1 L-12 antibody; Abbott), rituximab (RITUXAN), alemtuzumab (CAMPATH), daclizumab (ZENAPAX), and natalizumab (TYSABRI);

(xx) immunosuppressants such as methotrexate (TREXALL, RHEUMATREX), mitoxantrone (NOVANTRONE), mycophenolate mofetil (CELLCEPT), mycophenolate sodium (MYFORTIC), azathioprine (AZASAN, IMURAN), mercaptopurine (PURINETHOL), cyclophosphamide (NEOSAR, CYTOXAN), chlorambucil (LEUKERAN), cladribine (LEUSTATIN, MYLINAX), alpha-fetoprotein, etanercept (ENBREL), and 4-(benzyloxy)-5-[(5-undecy1-2H-pyrrol-2-ylidene)methyl]-1H, 1H-2,2'-bipyrrole (also known as PNU-156804);

(xxi) interferons, including interferon beta-la (AVONEX, REBIF) and interferon beta-lb (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA), benserazide (MADOPAR), a-methyldopa, monofluoromethyldopa, difluoromethyldopa, brocresine, or m-hydroxybenzylhydrazine);

(xxiii) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), LY-233536 and LY-235959 (both Lilly), methadone, (DOLOPHINE), neramexane, perzinfotel, phencyclidine, tianeptine (STABLON), dizocilpine (also known as MK-801), EAB-318 (Wyeth), ibogaine, voacangine, tiletamine, riluzole (RILUTEK), aptiganel (CERESOTAT), gavestinel, and remacimide;

(xxiv) monoamine oxidase (MAO) inhibitors, such as selegiline (EMSAM), selegiline hydrochloride (1-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xxv) muscarinic receptor (particularly M1 subtype) agonists, such as cevimeline, levetiracetam, bethanechol chloride (DUVOID, URECHOLINE), itameline, pilocarpine (SALAGEN), NGX267, arecoline, L-687306 (Merck), L-689660 (Merck), furtrethonium iodide (FURAMON, FURANOL), furtrethonium benzenesulfonate, furtrethonium p-toluenesulfonate, McN-A-343, oxotremorine, sabcomeline, AC-90222 (Acadia Pharmaceuticals), and carbachol (CARBASTAT, MIOSTAT, CARBOPTIC);

(xxvi) neuroprotective drugs such as bosutinib, condoliase, airmoclomol, lamotrigine, perampanel, aniracetam, minaprime, riluzole, N-hydroxy-1,2,4,9-tetrahydro-3H-carbazol-3-imine, desmoteplase, anatibant, astaxanthin, neuropeptide NAP (e.g., AL-108 and AL-208; both Allon Therapeutics), neurostrol, perampenel, ispronicline, bis(4-B-Dglucopyranosyloxybenzyl)-2-B-D-glucopyranosyl-2-isobutyltartrate (also known as dactylorhin B or DHB), formobactin, xaliproden (xAPRILA), lactacystin, dimeboline hydrochloride (DIMEBON), disufenton (CEROVIVE), arundic acid (ONO-2506, PROGLIA, CEREACT), citicoline (also known as cytidine 5'-diphosphocholine), edaravone (RADICUT), AEOL-10113 and AEOL-10150 (both Aeolus Pharmaceuticals), AGY-94806 (also known as SA-450 and Msc-1), granulocyte-colony stimulating factor (also known as AX-200), BAY-38-7271 (also known as KN-387271; Bayer AG), ancrod (VIPRINEX, ARWIN), DP-b99 (D-Pharm Ltd), HF-0220 (17-B-hydroxyepiandrosterone; Newron Pharmaceuticals), HF-0420 (also known as oligotropin), pyridoxal 5'-phosphate (also known as MC-1), microplasmin, S-18986, piclozotan, NP031112, tacrolimus, L-seryl-L-methionyl-L-alanyl-L-lysyl-L-glutamyl-glycyl-L-valine, AC-184897 (Acadia Pharmaceuticals), ADNF-14 (National Institutes of Health), stilbazulenyl nitrone, SUNN8075 (Daiichi Suntory Biomedical Research), and zonampanel;

(xxvii) nicotinic receptor agonists, such as epibatidine, bupropion, CP-601927, varenicline, ABT-089 (Abbott), ABT-594, AZD-0328 (AstraZeneca), EVP-6124, R3487 (also known as MEM3454; Roche/Memory Pharmaceuticals), R4996 (also known as MEM63908; Roche/Memory Pharmaceuticals), TC-4959 and TC-5619 (both Targacept), and RJR-2403;

(xxviii) norepinephrine (noradrenaline) reuptake inhibitors, such as atomoxetine (STRATTERA), doxepin (APONAL, ADAPIN, SINEQUAN), nortriptyline (AVENTYL, PAMELOR, NORTRILEN), amoxapine (ASENDIN, DEMOLOX, MOXIDIL), reboxetine (EDRONAX, VESTRA), viloxazine (VIVALAN), maprotiline (DEPRILEPT, LUDIOMIL, PSYMION), bupropion (WELLBUTRIN), and radaxafine;

(xxix) phosphodiesterase (PDE) inhibitors, including but not limited to, (a) PDE1 inhibitors (e.g., vinpocetine (CAVINTON, CERACTIN, INTELECTOL) and those disclosed in U.S. Pat. No. 6,235,742, (b) PDE2 inhibitors (e.g., erythro-9-(2-hydroxy-3-nonyl)adenine (EHNA), BAY 60-7550, and those described in U.S. Pat. No. 6,174,884), (c) PDE3 inhibitors (e.g., anagrelide, cilostazol, milrinone, olprinone, parogrelil, and pimobendan), (d) PDE4 inhibitors (e.g., apremilast, ibudilastroflumilast, rolipram, Ro 20-1724, ibudilast (KETAS), piclamilast (also known as RP73401), CDP840, cilomilast (ARIFLO), roflumilast, tofimilast, oglemilast (also known as GRC 3886), tetomilast (also known as OPC-6535), lirimifast, theophylline (UNIPHYL, THEOLAIR), arofylline (also known as LAS-31025), doxofylline, RPR-122818, or mesembrine), and (e) PDE5 38 inhibitors (e.g., sildenafil (VIAGRA, REVATIO), tadalafil (CIALIS), vardenafil (LEVITRA, VIVANZA), udenafil, avanafil, dipyridamole (PERSANTINE), E-4010, E-4021, E-8010, zaprinast, iodenafil, mirodenafil, DA-8159, and those disclosed in International Patent Applications WO2002/020521, WO2005/049616, WO2006/120552, WO2006/126081, WO2006/126082, WO2006/126083, and WO2007/122466), (f) PDE7 inhibitors; (g) PDE8 inhibitors; (h) PDE9 inhibitors (e.g., BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), (i) PDE10 inhibitors such as 2-({4-[1-methyl-4-(pyridin-4-yl)-1H-pyrazol-3-yl]phenoxymethyl)quinolin-3(4H)-one and SCH-1518291; and (j) PDE11 inhibitors;

(xxx) quinolines, such as quinine (including its hydrochloride, dihydrochloride, sulfate, bisulfate and gluconate salts), chloroquine, sontoquine, hydroxychloroquine (PLAQUENIL), mefloquine (LARIAM), and amodiaquine (CAMOQUIN, FLAVOQUINE);

(xxxi) B-secretase inhibitors, such as ASP-1702, SCH-745966, JNJ-715754, AMG-0683, AZ-12304146, BMS-782450, GSK-188909, NB-533, LY-2886721, E-2609, HPP-854, (+)-phenserine tartrate (POSIPHEN), LSN-2434074 (also known as LY-2434074), KMI-574, SCH-745966, AcrER (N2-acetyl-D-arginyl-L-arginine), loxistatin (also known as E64d), and CA074 Me;

(xxxii) y-secretase inhibitors and modulators, such as BMS-708163 (Avagacest), WO20060430064 (Merck), DSP8658 (Dainippon), ITI-009, L-685458 (Merck), ELANG, ELAN-Z, 4-chloro-N-[(2S)-3-ethyl-1-hydroxypentan-2-yl]benzenesulfonamide;

(xxxiii) serotonin (5-hydroxytryptamine) 1A (5-HT,A) receptor antagonists, such as spiperone, levo-pindolol, BMY 7378, NAD-299, S-(−)-UH-301, NAN 190, lecozotan;

(xxxiv) serotonin (5-hydroxytryptamine) 2C (5-HT2c) receptor agonists, such as vabicaserin and zicronapine;

(xxxv) serotonin (5-hydroxytryptamine) 4 (5-HT4) receptor agonists, such as PRX-03140 (Epix);

(xxxvi) serotonin (5-hydroxytryptamine) 6 (5-HT) receptor antagonists, such as A-964324, AVI-101, AVN-211, mianserin (TORVOL, BOLVIDON, NORVAL), methiothepin (also known as metitepine), ritanserin, ALX-1161, ALX-1175, MS-245, LY-483518 (also known as SGS518; Lilly), MS-245, Ro 04-6790, Ro 43-68544, Ro 63-0563, Ro 65-7199, Ro 65-7674, SB-399885, SB-214111, SB-258510, SB-271046, SB-357134, SB-699929, SB-271046, SB-742457 (GlaxoSmithKline), Lu AE58054 (Lundbeck A/S), and PRX-07034 (Epix); 50

(xxxvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine, neuralstem and tesofensine;

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline, idebenone, PYM50028 (COGANE; Phytopharm), and AIT-082 (NEOTROFIN);

(xxxix) Glycine transporter-1 inhibitors such as paliflutine, ORG-25935, JNJ-17305600, and ORG-26041;

(xl) AMPA-type glutamate receptor modulators such as perampanel, mibampator, selurampanel, GSK-729327, N-{(3 S,4 S)-4-[4-(5-cyanothiophen-2-yl)phenoxy]tetrahydro-furan-3-yl]propane-2-sulfonamide, and the like.

(xli) Janus kinase inhibitors (JAK) such as, but not limited to, tofacitinib, ruxolitinib, baricitinib, CYT387, GLPG0634, lestaurtinib, pacritinib, and TG101348.

(xlii) Interleukin-1 receptor-associated kinase 4 inhibitors (IRAK4) such as, but not limited to, PF-06650833.

In certain embodiments, the additional therapeutic agent is an orthosteric agonist of the muscarinic acetylcholine receptor.

In certain embodiments, methods described herein further comprise administering to the subject in need thereof a therapeutically effective amount of an orthosteric agonist of the muscarinic acetylcholine receptor. In certain embodiments, the orthosteric agonist of the muscarinic acetylcholine receptor is administered to the subject concurrently with a substituted tetrahydropyrrolo-pyridinone compound described herein, such as a compound of Formula I.

In certain embodiments, the subject is administered a pharmaceutical composition comprising (i) the orthosteric agonist of the muscarinic acetylcholine receptor and (ii) a substituted tetrahydropyrrolo-pyridinone compound described herein, such as a compound of Formula I.

In certain embodiments, the orthosteric agonist of the muscarinic acetylcholine receptor is administered to the subject separately from a substituted tetrahydropyrrolo-pyridinone compound described herein, such as a compound of Formula I. In certain embodiments, the orthosteric agonist of the muscarinic acetylcholine receptor is administered to the subject via a first pharmaceutical composition, and the substituted tetrahydropyrrolo-pyridinone compound described herein, such as a compound of Formula I, is administered to the subject via a second pharmaceutical composition.

In certain embodiments, the amount of (i) orthosteric agonist of the muscarinic acetylcholine receptor and/or (ii) substituted tetrahydropyrrolo-pyridinone compound described herein, such as a compound of Formula I, that is administered to the patient is reduced compared to use of either the (i) orthosteric agonist of the muscarinic acetylcholine receptor or (ii) a substituted tetrahydropyrrolo-pyridinone compound described herein, such as a compound of Formula I, in a monotherapy treatment.

Accordingly, another aspect of the invention provides a method for treating a disorder ameliorated by muscarinic receptor activation in a subject in need thereof, wherein the method comprises administering to the subject a substituted tetrahydropyrrolo-pyridinone compound described herein, such as a compound of Formula I, in combination with an orthosteric agonist of the muscarinic acetylcholine receptor (e.g., xanomeline or a salt thereof) wherein the orthosteric agonist of the muscarinic acetylcholine receptor and the substituted tetrahydropyrrolo-pyridinone compound operate on the same muscarinic acetylcholine receptor subtype. In certain embodiments, the orthosteric agonist of the muscarinic acetylcholine receptor and the substituted tetrahydropyrrolo-pyridinone compound operate on the M1 subtype or M4 subtype of the muscarinic acetylcholine receptor.

The terms "muscarinic orthosteric agonist," "orthosteric muscarinic agonist," and "muscarinic agonist" refers to agents that activate the muscarinic acetylcholine receptor. "Orthosteric" refers to a site of a receptor in which the endogenous ligand binds to produce its effect. That is, muscarinic orthosteric agonists bind to the site of the muscarinic acetylcholine receptor in which endogenous muscarinic ligands bind to produce their effects.

Muscarinic acetylcholine receptors are G-protein coupled receptors with five different receptor subtypes (M1-M5), each of which is found in the CNS with different tissue distributions. The term "muscarinic acetylcholine receptor" refers to G-protein-linked receptors that bind the neurotransmitter acetylcholine. "M1" means subtype one muscarinic acetylcholine receptor. "M2" means subtype two muscarinic acetylcholine receptor. "M3" means subtype three muscarinic acetylcholine receptor. "M4" means subtype four muscarinic acetylcholine receptor. "M5" means subtype five muscarinic acetylcholine receptor.

An agonist of the muscarinic acetylcholine receptor may be selective or prefer binding to only one muscarinic receptor subtype, partially selective or prefer binding to two to four subtypes, or non-selective, preferring to bind to each of the five subtypes. Agonists of the muscarinic acetylcholine receptor can be parasympathomimetic. Their mechanism of action is different depending on which receptor is activated. For instance, the mood stabilizers lithium and valproic acid, used for treating bipolar depression, may affect the muscarinic system, mainly through the M4 subtype receptor. Genetic evidence directly links the muscarinic system and alcohol addiction.

In certain embodiments, the agonist of the muscarinic acetylcholine receptor is an orthosteric agonist of the muscarinic acetylcholine receptor. In certain embodiments, the orthosteric agonist of the muscarinic acetylcholine receptor is a compound in the following table or a pharmaceutically acceptable salt thereof.

| Orthosteric Agonist Compound | Muscarinic Acetylcholine Receptor Subtype | | | | |
|---|---|---|---|---|---|
| | M1 | M2 | M3 | M4 | M5 |
| 77-LH-28-1 | X | | | | |
| A 72055 | X | X | | | |
| AF 125 | X | | | | |
| AF 150(S) | X | | | | |
| aceclidine | | | X | | |
| alvameline | X | | | | |
| arecoline | | | X | | |
| bethanechol | X | X | X | X | X |
| carbachol | X | X | X | X | X |
| cevimeline | X | | X | | |
| CI 1017 | X | | | X | |
| CMI 1145 | | X | | X | |
| CMI 936 | | | | X | |
| FPL 14995 | X | | | | |
| furmethide | | X | | X | |
| HTL-0016878 | | | | X | |
| iperoxo | X | X | X | X | X |
| itrameline | X | | X | | |
| KST 5452 | X | | | | |
| L 670,548 | | | X | | |
| L 687,306 | X | | | | |
| L 689,660 | X | | X | | |
| L 686,986 | X | | | | |
| methacholine | X | X | X | X | X |
| N-desmethylclozapine | X | | | | |
| MCD 386 | X | | | | |
| milameline | X | X | X | X | X |
| NC 111585 | X | | | | |
| nebracetam | X | | | | |
| NGX267 | X | | | | |
| ORG 20091 | X | | | | |
| oxotremorine | X | X | X | X | |
| PD 142505 | X | | | | |
| PD 151832 | X | | | | |
| PDC 008004 | | X | | | |
| pilocarpine | X | X | X | X | |
| RU 35963 | | | X | | |
| sabcomeline | X | | | | |
| SR 46559A | X | | | | |
| talsaclidine | X | | | | |
| tazomeline | X | X | X | X | X |
| thiopilocarpine | X | | | | |
| tremorine | X | X | X | X | X |
| vedaclidine | X | | | X | |
| xanomeline | X | | | X | |
| WAY-131256 | X | X | | | |
| WAY-132983 | X | | | | |
| YM 796 | X | | | | |
| YM 954 | X | | | | |

In certain embodiments, the agonist of the muscarinic acetylcholine receptor is an orthosteric agonist of the muscarinic acetylcholine receptor selected from 77-LH-28-1, A 72055, AF 125, AF 150(S), aceclidine, alvameline, arecoline, bethanechol, carbachol, cevimeline, CI 1017, CMI 1145, CMI 936, FPL 14995, furmethide, HTL-0016878, iperoxo, itrameline, KST 5452, L 670,548, L 687,306, L 689,660, L 686,986, methacholine, N-desmethylclozapine, MCD 386, milameline, NC 111585, nebracetam, NGX267, ORG 20091, oxotremorine, PD 142505, PD 151832, PDC 008004, pilocarpine, RU 35963, sabcomeline, SR 46559A, talsaclidine, tazomeline, thiopilocarpine, tremorine, vedaclidine, xanomeline, WAY-131256, WAY-132983, YM 796, YM 954, or a pharmaceutically acceptable salt thereof.

In certain embodiments, the agonist of the muscarinic acetylcholine receptor is an orthosteric agonist of the muscarinic acetylcholine receptor selected from xanomeline or a pharmaceutically acceptable salt thereof. Xanomeline has activity towards both the M1 and M4 muscarinic acetylcholine receptors.

In certain embodiments, the agonist of the muscarinic acetylcholine receptor is a M1 orthosteric agonist of the muscarinic acetylcholine receptor selected from 77-LH-28-1, A 72055, AF 125, AF 150(S), alvameline, bethanechol, carbachol, cevimeline, CI 1017, FPL 14995, iperoxo, itrameline, KST 5452, L 687,306, L 689,660, L 686,986, methacholine, N-desmethylclozapine, MCD 386, milameline, NC 111585, nebracetam, NGX267, ORG 20091, oxotremorine, PD 142505, PD 151832, pilocarpine, sabcomeline, SR 46559A, talsaclidine, tazomeline, thiopilocarpine, tremorine, vedaclidine, xanomeline, WAY-131256, WAY-132983, YM 796, YM 954, or a pharmaceutically acceptable salt thereof.

In certain embodiments, methods described herein further comprise administering to the subject in need thereof a therapeutically effective amount of an orthosteric antagonist of the muscarinic acetylcholine receptor. In certain embodiments, the orthosteric antagonist of the muscarinic acetylcholine receptor is trospium chloride.

Additional Considerations

The doses and dosage regimen of the active ingredients used in the combination therapy may be determined by an attending clinician. In certain embodiments, the compound described herein (such as a compound of Formula I, or other compounds in Section I) and the additional therapeutic agent(s) are administered in doses commonly employed when such agents are used as monotherapy for treating the disorder. In other embodiments, the compound described herein (such as a compound of Formula I, or other compounds in Section I) and the additional therapeutic agent(s) are administered in doses lower than the doses commonly employed when such agents are used as monotherapy for treating the disorder. In certain embodiments, the compound described herein (such as a compound of Formula I, or other compounds in Section I) and the additional therapeutic agent(s) are present in the same composition, which is suitable for oral administration.

In certain embodiments, the compound described herein (such as a compound of Formula I, or other compounds in Section I) and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of the compound described herein (such as a compound of Formula I, or other compounds in Section I), a pharmaceutically acceptable carrier, vehicle or diluent, and optionally at least one additional therapeutic agent listed above.

III. Pharmaceutical Compositions and Dosing Considerations

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. In certain embodiments, the invention provides a pharmaceutical composition comprising a compound described herein (such as a compound of Formula I, or other compounds in Section I) and a pharmaceutically acceptable carrier.

The phrase "therapeutically effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising a compound described herein in a therapeutically effective amount for the treatment of a medical disorder described herein.

EXAMPLES

The invention now being generally described, will be more readily understood by reference to the following examples, which are included merely for purposes of illustration of certain aspects and embodiments of the present invention, and is not intended to limit the invention.

General Synthetic and Analytical Methods

Analytical data is included within the procedures below, in the illustrations of the general procedures, or in the tables of examples. Unless otherwise stated, all $^1$H NMR data were collected on a Bruker Avance 400 MHz equipped with 5 mm QNP probe or Bruker Avance III 400 MHz, 5 mm BBFO probe or Fourier 300 MHz, 5 mm dual probe instruments and chemical shifts are quoted in parts per million (ppm). LC/MS was performed on Acquity UPLC H-Class (quaternary pump/PDA detector) coupled to QDa Mass Spectrometer or Acquity UPLC (binary pump/PDA detector) coupled to ZQ Mass Spectrometer or Acquity UPLC with Waters DAD coupled to SQD2 Mass Spectrometer. LC/MS data is referenced to LC/MS conditions using the method number provided in Table 2

TABLE 2

LC/MS Analysis Methods

| Method | Conditions |
|---|---|
| A | LC/MS analysis condition: Column: ACQUITY UPLC BEH C18 1.7 μm, 50 × 2.1 mm, maintained at 40° C. Mobile phase: MeCN (0.03% ammonia) in water (0.03% ammonia). Gradient from 8% to 97% within 1.9 min; Flow rate: 0.8 ml/min; Wavelength: 190-400 nm DAD. Acquity UPLC H-Class with PDA detector and QDa Mass Spectrometer. |
| B | LC/MS analysis condition: Column: Acquity UPLC HSS C18 1.8 μm, 100 × 2.1 mm plus guard cartridge, maintained at 40° C. Mobile phase: MeCN (0.1% formic acid) in water (0.1% formic acid). Gradient from 5% to 95% within 6.8 min; Flow rate: 0.4 ml/min; Wavelength: 210-400 nm DAD. Waters DAD + Waters SQD2, single quadrapole UPLC-MS. |
| C | LC/MS analysis condition: Column: ACQUITY UPLC BEH C18 1.7 μm, 100 × 2.1 mm, maintained at 40° C. Mobile phase: MeCN (0.1% formic acid) in water (0.1% formic acid). Gradient from 5% to 95% within 6.8 min; Flow rate: 0.4 ml/min; Wavelength: 200-500 nm DAD. Acquity UPLC with PDA detector and ZQ Mass Spectrometer. |
| D | LC/MS analysis condition: Column: ACQUITY UPLC BEH C18 1.7 μm, 100 × 2.1 mm, maintained at 40° C. Mobile phase: MeCN (0.1% ammonia) in water (0.1% ammonia). Gradient from 5% to 95% within 6.8 min; Flow rate: 0.4 ml/min; Wavelength: 200-500 nm DAD. Acquity UPLC with PDA detector and ZQ Mass Spectrometer. |
| E | LC/MS analysis condition: Column: ACQUITY UPLC BEH Shield RP18 1.7 μm, 100 × 2.1 mm, maintained at 40° C. Mobile phase: MeCN in water (10 mM ammonium hydrogen carbonate). Gradient from 5% to 95% within 6.8 min; Flow rate: 0.4 ml/min; Wavelength: 210-400 nm DAD. Acquity UPLC with Waters DAD and Waters SQD2, single quadrapole UPLC-MS. |
| F | LC/MS analysis condition: Column: Acquity UPLC BEH C18 1.7 μm, 100 × 2.1 mm, maintained at 40° C. Mobile phase: MeCN (0.1% formic acid) in water (0.1% formic acid). Gradient from 5% to 80% within 2.25 min; Flow rate: 1.5 ml/min; Wavelength: 210-400 nm DAD. Acquity UPLC with PDA detector and QDa Mass Spectrometer. |

Purification Methods

For the general procedures, intermediate and final compounds may be purified by any technique or combination of techniques known to one skilled in the art. Some examples that are not limiting include flash chromatography performed on the COMBIFLASH® Companion purification system or the Biotage SP1 purification system, products were purified using an Isolute® SPE Si II cartridge, ('Isolute SPE Si cartridge' refers to a pre-packed polypropylene column containing unbonded activated silica with irregular particles with average size of 50 μm and nominal 60 Å porosity), and a solvent or combination of solvents (heptane, EtOAc, DCM, MeOH, MeCN, water, etc.) that elutes the desired compounds; RP-HPLC purification performed on Waters Mass Directed FractionLynx systems (2767 autosampler, System Fluidics Organiser, 2998 Photodiode array, 2545 pump, 3×515 pump, QDa mass spectrometer), Gilson system (GX281 autosampler, 322 pump, 155 UV/vis detector), Interchim PuriFlash 4125 coupled to a UV DAD (see Table 3 for some non-limiting conditions); SFC purification performed on a Waters Thar Prep100 system (P200 CO2 pump, 2545 modifier pump, 2998 UV/VIS detector, 2767 liquid handler with Stacked Injection Module) or Waters Thar Investigator semi preparative system (Waters Fluid Delivery Module, 2998 UV/VIS detector, Waters Fraction Collection Module) (see Table 3 for some non-limiting conditions); recrystallization from an appropriate solvent (MeOH, EtOH, IPA, EtOAc, toluene, etc.) or combination of solvents (EtOAc/heptane, EtOAc/MeOH, etc.); precipitation from a combination of solvents (DMF/water, DMSO/DCM, EtOAc/heptane, etc.); trituration with an appropriate solvent (EtOAc, DCM, MeCN, MeOH, EtOH, IPA, n-PrOH, etc.); extractions by dissolving a compound in a liquid and washing with an appropriately immiscible liquid (DCM/water, EtOAc/water, DCM/saturated NaHCO$_3$, EtOAc/saturated NaHCO$_3$, DCM/10% aqueous HCl, EtOAc/10% aqueous HCl, etc.); and/or distillation (simple, fractional, Kugelrohr, etc.). Descriptions of these techniques can be found in the following references: Gordon, A. J. and Ford, R. A. "The Chemist's Companion", 1972; Palleros, D. R. "Experimental Organic Chemistry", 2000; Still, W. C., Kahn and M. Mitra, A. J. Org. Chem. 1978, 43(14), 2923-2925; Yan, B. "Analysis and Purification Methods in Combinatorial Chemistry" 2003; Harwood, L. M., Moody, C. J. and Percy, J. M. "Experimental Organic Chemistry: Standard and Microscale, $2^{nd}$ Edition", 1999.

TABLE 3

RP-HPLC and SFC Purification Methods

| Method | Conditions |
|---|---|
| 1 | RP-HPLC purification condition: Column Waters Xbridge Phenyl 10 μm, 19 × 150 mm. Mobile phase: MeOH in water (10 mM NH$_4$HCO$_3$); Flow rate: 20 ml/min; Wavelength: 210-400 nm DAD. Sample injected in DMSO (+optional formic acid and water), 28 min non-linear gradient from 20% to 80% MeOH, centered around a specific focused gradient. |

TABLE 3-continued

RP-HPLC and SFC Purification Methods

| Method | Conditions |
|---|---|
| 2 | Interchim RP-HPLC purification condition: Column PuriFlash C18HP 15 μm, 40 × 215 mm. Mobile phase: MeCN in water (0.1% HCOOH); Flow rate: 32 ml/min; Wavelength: 210-400 nm DAD. Sample injected in DMSO (+optional formic acid and water), 40 min non-linear gradient from 5% to 95% MeCN, centered around a specific focused gradient. |
| 3 | RP-HPLC purification condition: Column Waters Sunfire C18 10 μm, 19 × 150 mm. Mobile phase: MeCN in water (0.1% HCOOH); Flow rate: 20 ml/min; Wavelength: 210-400 nm DAD. Sample injected in DMSO (+optional formic acid and water), 28 min non-linear gradient from 20% to 80% MeCN, centered around a specific focused gradient. |
| 4 | RP-HPLC purification condition: Column Waters Sunfire C18 10 μm, 19 × 150 mm. Mobile phase: MeCN in water (10 mM $NH_4HCO_3$); Flow rate: 20 ml/min; Wavelength: 210-400 nm DAD. Sample injected in DMSO (+optional formic acid and water), 28 min non-linear gradient from 5% to 60% MeCN, centered around a specific focused gradient. |
| 5 | RP-HPLC purification condition: Column Waters Luna Phenyl 10 μm, 21.2 × 150 mm. Mobile phase: MeOH in water (0.1% HCOOH); Flow rate: 20 ml/min; Wavelength: 210-400 nm DAD. Sample injected in DMSO (+optional formic acid and water), 28 min non-linear gradient from 40% to 100% MeOH, centered around a specific focused gradient. |
| 6 | SFC purification condition (chiral): Column YMC Amylose-C 5 μm, 10 × 250 mm. Mobile phase: MeOH (0.1% DEA)/$CO_2$; Flow rate: 15 ml/min; Wavelength: 240 nm DAD. Sample injected in optional MeOH, MeCN or DCM alone or in combination, 6 min non-linear gradient from 45% to 55% MeOH, centered around a specific focused gradient. |
| 7 | SFC purification condition (chiral): Column YMC Amylose-C 5 μm, 20 × 250 mm. Mobile phase: MeOH (0.1% $NH_4OH$)/$CO_2$; Flow rate: 100 ml/min; Wavelength: 300 nm DAD. Sample injected in optional MeOH, MeCN or DCM alone or in combination, 6 min non-linear gradient from 10% to 90% MeOH, centered around a specific focused gradient. |
| 8 | Interchim RP-HPLC purification condition: Column PuriFlash C18HP 15 μm, 40 × 215 mm. Mobile phase: MeCN in water (0.1% $NH_4OH$); Flow rate: 32 ml/min; Wavelength: 210-400 nm DAD. Sample injected in DMSO (+optional formic acid and water), 40 min non-linear gradient from 10% to 95% MeCN, centered around a specific focused gradient. |
| 9 | SFC purification condition (chiral): Column LUX Cellulose-3 5 μm, 21.2 × 250 mm. Mobile phase: IPA (0.1% DEA)/$CO_2$; Flow rate: 100 ml/min; Wavelength: 310 nm DAD. Sample injected in optional MeOH, MeCN or DCM alone or in combination, 6 min non-linear gradient from 20% to 80% IPA, centered around a specific focused gradient. |
| 10 | SFC purification condition (chiral): Column LUX Cellulose-3 5 μm, 10 × 250 mm. Mobile phase: IPA (0.1% DEA)/$CO_2$; Flow rate: 15 ml/min; Wavelength: 240 nm DAD. Sample injected in optional MeOH, MeCN or DCM alone or in combination, 6 min non-linear gradient from 15% to 85% IPA, centered around a specific focused gradient. |
| 11 | SFC purification condition (chiral): Column LUX Cellulose-3 5 μm, 10 × 250 mm. Mobile phase: MeOH (0.1% DEA)/$CO_2$; Flow rate: 15 ml/min; Wavelength: 270 nm DAD. Sample injected in optional MeOH, MeCN or DCM alone or in combination, 6 min non-linear gradient from 15% to 85% IPA, centered around a specific focused gradient. |
| 12 | SFC purification condition (chiral): Column Cellulose-C 5 μm, 20 × 250 mm. Mobile phase: IPA (0.1% DEA)/Heptane; Flow rate: 20 ml/min; Wavelength: 310 nm DAD. Sample injected in optional MeOH, MeCN or DCM alone or in combination, 6 min non-linear gradient from 40% to 60% IPA, centered around a specific focused gradient. |
| 13 | SFC purification condition (chiral): Column LUX Cellulose-3 5 μm, 21.2 × 250 mm. Mobile phase: MeOH (0.1% DEA)/$CO_2$; Flow rate: 100 ml/min; Wavelength: 270 nm DAD. Sample injected in optional MeOH, MeCN or DCM alone or in combination, 6 min non-linear gradient from 25% to 75% MeOH, centered around a specific focused gradient. |

Abbreviations

° C. Degrees Celsius
DAD Diode array detector
DCM Dichloromethane
DEA Diethylamine
DMA N,N-Dimethylacetamide
DMF N,N-Dimethylformamide
DMSO Dimethyl sulfoxide
EtOAc Ethyl acetate
EtOH Ethanol
H Hour(s)
$H_2O$ Water
HATU 1-[Bis(dimethylamino)methylene]-1H-1,2,3-triazolo[4,5-b]pyridinium 3-oxide hexafluorophosphate
HCl Hydrochloride
HCOOH Formic acid
IMS Industrial methylated spirits
IPA Isopropyl alcohol
LC/MS Liquid Chromatography/Mass Spectrometry
LiCl Lithium chloride
m/z Mass-to-charge ratio
MeCN Acetonitrile
MeOH Methanol MgSO₄ Magnesium sulphate
MHz Megahertz
Min Minute(s)
MS Mass Spectrometer
Na₂SO₄ Sodium sulphate
NaHCO₃ Sodium bicarbonate
NaOH Sodium hydroxide
NH₄HCO₃ Ammonium bicarbonate
NH₄OH Ammonium hydroxide
NMR Nuclear Magnetic Resonance
Pd(dppf)Cl₂ [1,1'-Bis(diphenylphosphino)ferrocene]dichloropalladium(II)
Pd(PPh₃)₄ Tetrakis(triphenylphosphine)palladium(0)
PdCl₂(PPh₃)₂ Bis(triphenylphosphine)palladium(II) dichloride
RP-HPLC Reverse Phase-High Performance Liquid Chromatography
R$_t$ Retention time
RT Room temperature
SFC Supercritical Fluid Chromatography
TBME tert-Butyl methyl ether
THF Tetrahydrofuran
UPLC Ultra Performance Liquid Chromatography Example 1—Synthesis of Compound Int-5: 3-chloro-1,4-dimethyl-6-(1-(trifluoromethyl)-1H-pyrazole-4-carbonyl)-1,5,6,7-tetrahydro-2H-pyrrolo[3,4-b]pyridin-2-one The title compound was prepared according to the following procedures.

Preparation of Int-1: But-2-ynoyl Chloride

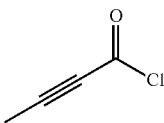

To a solution of 2-butynoic acid (13 g, 155 mmol) in DCM (550 mL) was added DMF (0.6 mL) and oxalyl chloride (14 mL, 162 mmol) via dropwise addition. The reaction stirred at RT for 5 h. The reaction mixture, as a yellow solution was advanced directly to the next step. ¹H NMR (400 MHz, CDCl3) δ 5.30 (s, 3H).

Preparation of Int-2: Tert-Butyl (Z)-3-(methylimino)pyrrolidine-1-carboxylate

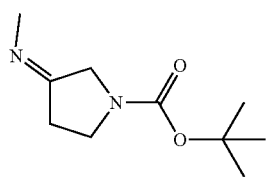

A reaction vessel was charged with N-boc-3-pyrrolidinone (29 g, 155 mmol) and dissolved in 2 M methylamine in THF (130 mL, 260 mmol). The reaction stirred at RT for 15 min and then heated to 60° C. The reaction was stirred at 60° C. for 5 h then the reaction mixture was concentrated in vacuo to afford the title compound as a yellow oil (31 g, quantitative). Material advanced to next step without characterization.

Preparation of Int-3: tert-Butyl 1,4-dimethyl-2-oxo-1,2,5,7-tetrahydro-6H-pyrrolo[3,4-b]pyridine-6-carboxylate

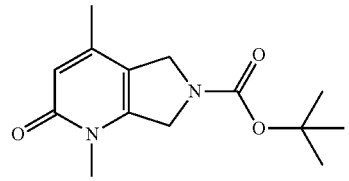 [SMILES: Cc1cc(=O)n(C)c2c1CN(C(=O)OC(C)(C)C)C2]

To a solution of tert-butyl (Z)-3-(methylimino)pyrrolidine-1-carboxylate (31 g, 155 mmol) and triethylamine (65 mL, 464 mmol) in DCM (400 mL) at 0° C. was added a solution of but-2-ynoyl chloride (16 g, 155 mmol) via dropwise addition, over a period of 2 h. The reaction was stirred at 0° C. for 1.5 h. The reaction was allowed to warm to RT and stirred at RT for 48 h. The reaction mixture was next partitioned between DCM and distilled water. The organic layer was separated. The combined organic layer was washed with saturated brine, dried (MgSO₄) and concentrated in vacuo. The residue was purified by flash column chromatography (EtOAc to MeOH, gradient elution) to afford the title compound as a brown solid (13 g, 32%). LC/MS (Table 2, Method A): R$_t$=1.24 min; m/z=265 [M+H]⁺.

Preparation of Int-4: Tert-Butyl 3-chloro-1,4-dimethyl-2-oxo-1,2,5,7-tetrahydro-6H-pyrrolo[3,4-b]pyridine-6-carboxylate

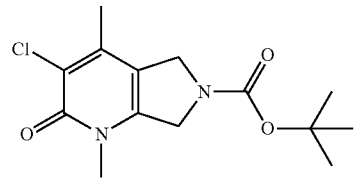 [SMILES: Cc1c2c(n(C)c(=O)c1Cl)CN(C(=O)OC(C)(C)C)C2]

To a solution of tert-butyl 1,4-dimethyl-2-oxo-1,2,5,7-tetrahydro-6H-pyrrolo[3,4-b]pyridine-6-carboxylate (5 g, 19 mmol) in DMF (50 mL) and MeCN (100 mL) under a nitrogen atmosphere was added N-chlorosuccinimide (2.9 g, 22 mmol) and the reaction was heated to 55° C. The reaction stirred at 55° C. under a nitrogen atmosphere for 1.5 h. The reaction mixture was allowed to cool to RT and quenched by pouring into distilled water (1 L). The mixture was stirred for 30 min. The reaction mixture was filtered, washed with distilled water and concentrated in vacuo to afford the title compound as a pale brown solid (2.8 g, 50%). LC/MS (Table 2, Method A): R$_t$=1.20 min; m/z=299 [M+H]⁺.

Preparation of Int-5: 3-Chloro-1,4-dimethyl-1,5,6,7-tetrahydro-2H-pyrrolo[3,4-b]pyridin-2-one Hydrochloride

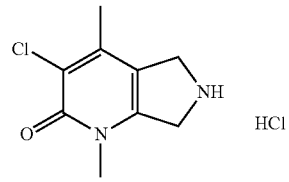

To a solution of tert-butyl 3-chloro-1,4-dimethyl-2-oxo-1,2,5,7-tetrahydro-6H-pyrrolo[3,4-b]pyridine-6-carboxylate (2.8 g, 9.4 mmol) in DCM (40 mL) was added 4 M HCl in 1,4-dioxane (48 mL, 192 mmol). The reaction stirred at RT for 4 h. The reaction mixture was concentrated in vacuo to afford the title compound as a pale brown solid (2.2 g, 97%). LC/MS (Table 2, Method A): $R_t$=0.66 min; m/z=199 [M+H]$^+$.

Example 2—Synthesis of Compound I-1: 3-chloro-1,4-dimethyl-6-(1-(Trifluoromethyl)-1H-pyrazole-4-carbonyl)-1,5,6,7-tetrahydro-2H-pyrrolo[3,4-b]pyridin-2-one

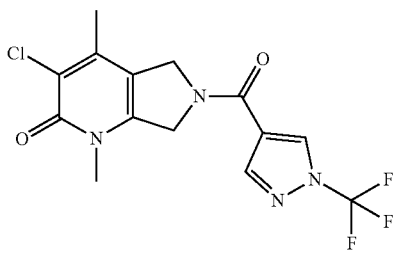 [SMILES: Cc1c2c(n(C)c(=O)c1Cl)CN(C(=O)c1cnn(C(F)(F)F)c1)C2]

To a solution of 3-chloro-1,4-dimethyl-1,5,6,7-tetrahydro-2H-pyrrolo[3,4-b]pyridin-2-one hydrochloride (40 mg, 0.16 mmol) and 1-(trifluoromethyl)pyrazole-4-carboxylic acid (35 mg, 0.19 mmol) in DMF (1.5 mL) was added N,N-diisopropylethylamine (97 mL, 0.56 mmol) and HATU (109 mg, 0.29 mmol). The reaction stirred at RT for 0.5 h. The reaction mixture was next partitioned between EtOAc and aqueous sodium hydrogen carbonate. The organic layer was separated. The combined organic layer was washed with saturated brine, dried (Na$_2$SO$_4$) and concentrated in vacuo. The residue was purified by reverse phase HPLC (Table 3, Method 1) to afford the title compound as an off-white solid (9.1 mg, 16%). $^1$H NMR (400 MHz, DMSO-d$_6$) δ 9.10 (d, J=2.3 Hz, 1H), 8.42 (s, 1H), 5.22-5.20 (m, 1H), 5.00 (t, J=2.3 Hz, 1H), 4.91 (s, 1H), 4.71 (s, 1H), 3.48 (d, J=2.3 Hz, 3H), 2.28 (d, J=3.0 Hz, 3H). LC/MS (Table 2, Method B): $R_t$=3.46 min; m/z=361 [M+H]$^+$.

Example 3—Preparation of Additional Compounds

The compounds in Table 4 were prepared using procedures analogous to that described for preparation of compound I-1 from compound Int-5 and the indicated starting material.

TABLE 4

Additional Compounds

| Compound No. | Yield | Starting Material | Purification Method |
|---|---|---|---|
| I-2 | 6.7 mg, 23% | (1-methyl-1H-pyrazol-4-yl)carboxylic acid | Reverse phase HPLC (Table 3, Method 1) |
| I-3 | 23 mg, 62% | (1-methyl-1H-pyrazol-3-yl)carboxylic acid | Triturated with DMSO/H$_2$O solution |
| I-4 | 17 mg, 41% | (1-methyl-1H-imidazol-4-yl)carboxylic acid | Triturated with hot MeOH |
| I-5 | 25 mg, 51% | (1-isobutyl-1H-pyrazol-4-yl)carboxylic acid | Triturated with 10% DMSO aqueous solution |
| I-6 | 35 mg, 79% | 5-cyclopropylisoxazole-3-carboxylic acid | Triturated with hot MeOH |
| I-7 | 45 mg, 73% | 5-tert-butylthiophene-2-carboxylic acid | Reverse phase HPLC (Table 3, Method 1, non-linear gradient 40%-100% MeOH) |

TABLE 4-continued

Additional Compounds

| Compound No. | Yield | Starting Material | Purification Method |
| --- | --- | --- | --- |
| I-8 | 44 mg, 71% | 5-(trifluoromethyl)isoxazole-3-carboxylic acid | Triturated with 10% DMSO aqueous solution |
| I-9 | 13 mg, 31% | 2-methylthiazole-5-carboxylic acid | Reverse phase HPLC (Table 3, Method 2) |
| I-10 | 10 mg, 24% | 1-isopropyl-1H-pyrazole-4-carboxylic acid | Reverse phase HPLC (Table 3, Method 1) |
| I-11 | 25 mg, 52% | 1,2-dimethyl-1H-imidazole-4-carboxylic acid | Triturated with hot MeCN |
| I-12 | 29 mg, 54% | 2-methyloxazole-4-carboxylic acid | Triturated with 10% DMSO aqueous solution |
| I-13 | 25 mg, 47% | 5-methylisoxazole-3-carboxylic acid | Triturated with 10% DMSO aqueous solution |
| I-14 | 27 mg, 45% | 1-isopropyl-1H-imidazole-4-carboxylic acid HCl | Triturated with 10% DMSO aqueous solution |
| I-15 | 34 mg, 55% | 1-(trifluoromethyl)-1H-imidazole-4-carboxylic acid | Triturated with MeCN |
| I-16 | 19 mg, 30% | 1-(trifluoromethyl)-1H-pyrazole-3-carboxylic acid | Triturated with MeCN |
| I-17 | 39 mg, 32% | 1-(difluoromethyl)-1H-pyrazole-4-carboxylic acid | Reverse phase HPLC (Table 3, Method 5) |

TABLE 4-continued

Additional Compounds

| Compound No. | Yield | Starting Material | Purification Method |
|---|---|---|---|
| I-18 | 18 mg, 32% | 2,3-dimethyl-3H-imidazole-4-carboxylic acid | Reverse phase HPLC (Table 3, Method 1) |
| I-19 | 30 mg, 49% | 1-isobutyl-1H-imidazole-4-carboxylic acid HCl | Triturated with 10% DMSO aqueous solution |
| I-20 | 6.9 mg, 22% | 5-methylthiazole-2-carboxylic acid | Reverse phase HPLC (Table 3, Method 8) |
| I-21 | 40 mg, 70% | 2-cyclopropylthiazole-5-carboxylic acid | Triturated with hot MeCN |
| I-22 | 27 mg, 52% | sodium 4-methyloxazole-2-carboxylate | Triturated with hot MeCN |
| I-23 | 41 mg, 63% | 1-benzyl-1H-pyrazole-4-carboxylic acid | Reverse phase HPLC (Table 3, Method 3) |
| I-24 | 13 mg, 26% | 5,6,7,8-tetrahydroimidazo[1,2-a]pyridine-2-carboxylic acid | Reverse phase HPLC (Table 3, Method 1) |
| I-25 | 5 mg, 14% | 6,7-dihydro-5H-imidazo[2,1-c][1,4]oxazine-2-carboxylic acid | Reverse phase HPLC (Table 3, Method 4) |
| I-26 | 14 mg, 27% | 2-(trifluoromethyl)thiazole-4-carboxylic acid | Triturated with hot MeCN |
| I-27 | 5.9 mg, 12% | 1-(cyclopropylmethyl)-1H-pyrazole-4-carboxylic acid | Triturated with hot MeCN |

TABLE 4-continued

Additional Compounds

| Compound No. | Yield | Starting Material | Purification Method |
| --- | --- | --- | --- |
| I-28 | 33 mg, 65% | 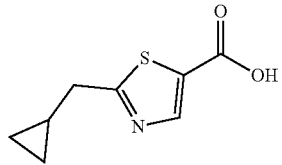 [SMILES: O=C(O)c1cnc(CC2CC2)s1] | Reverse phase HPLC (Table 3, Method 1, non-linear gradient 40%-100% MeOH) |
| I-29 | 12 mg, 23% | 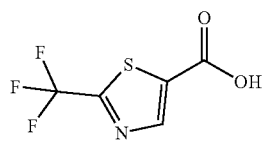 | Reverse phase HPLC (Table 3, Method 1, non-linear gradient 40%-100% MeOH) then reverse phase HPLC (Table 3, Method 4, non-linear gradient 20%-80% MeCN) |
| I-30 | 38 mg, quantitative | 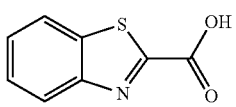 [SMILES: O=C(O)c1nc2ccccc2s1] | Triturated with hot MeCN |
| I-31 | 53 mg, 73% | 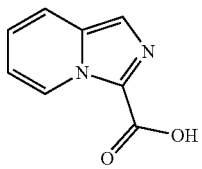 [SMILES: O=C(O)c1ncc2ccccn12] | Triturated with MeCN |
| I-32 | 53 mg, 72% | 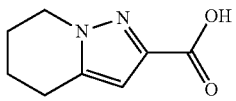 [SMILES: O=C(O)c1cc2n(n1)CCCC2] | Triturated with MeOH |
| I-33 | 26 mg, 55% | 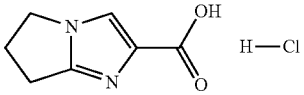 | Triturated with hot MeCN |
| I-34 | 31 mg, 50% | 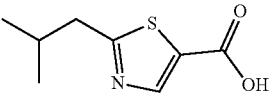 | Reverse phase HPLC (Table 3, Method 5) |
| I-35 | 21 mg, 33% | 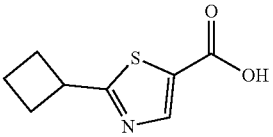 [SMILES: O=C(O)c1cnc(C2CCC2)s1] | Reverse phase HPLC (Table 3, Method 5) |
| I-36 | 16 mg, 23% | 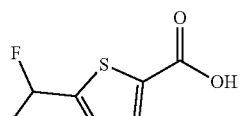 | Isolated by filtration |
| I-37 | 15 mg, 25% | 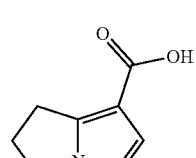 | Triturated with MeCN |

TABLE 4-continued

Additional Compounds

| Compound No. | Yield | Starting Material | Purification Method |
| --- | --- | --- | --- |
| I-38 | 25 mg, 40% | 2-(methoxymethyl)thiazole-5-carboxylic acid | Triturated with MeCN |
| I-39 | 42 mg, 70% | 2-(2,2,2-trifluoroethyl)thiazole-5-carboxylic acid | Triturated with MeCN |
| I-40 | 16 mg, 37% | 3-(trifluoromethyl)benzoic acid | Reverse phase HPLC (Table 3, Method 5) |
| I-41 | 41 mg, 65% | 4-(trifluoromethyl)benzoyl chloride | Reverse phase HPLC (Table 3, Method 4, non-linear gradient from 20% to 80% MeCN) |
| I-42 | 32 mg, 67% | 2-(trifluoromethyl)isonicotinic acid | Triturated with hot MeOH |
| I-43 | 30 mg, 65% | benzo[c][1,2,5]oxadiazole-5-carboxylic acid | Reverse phase HPLC (Table 3, Method 3) |
| I-44 | 36 mg, 75% | 6-(trifluoromethyl)nicotinic acid | Reverse phase HPLC (Table 3, Method 1) |
| I-45 | 10 mg, 20% | 5-(trifluoromethyl)picolinic acid | Reverse phase HPLC (Table 3, Method 4, non-linear gradient from 20% to 80% MeCN) |
| I-46 | 21 mg, 35% | benzo[d]thiazole-6-carboxylic acid | Reverse phase HPLC (Table 3, Method 3, non-linear gradient from 5% to 60% MeCN) |

TABLE 4-continued

Additional Compounds

| Compound No. | Yield | Starting Material | Purification Method |
|---|---|---|---|
| I-47 | 23 mg, 40% | | Reverse phase HPLC (Table 3, Method 5, non-linear gradient from 20% to 80% MeCN) |
| I-48 | 20 mg, 38% | | Reverse phase HPLC (Table 3, Method 1) |
| I-49 | 21 mg, 34% | | Triturated with hot MeCN |
| I-50 | 17 mg, 27% | | Reverse phase HPLC (Table 3, Method 1) |

Example 4—Synthesis of Compound Int-7: Lithium 2-cyclobutylbenzo[d]Thiazole-6-carboxylate The title compound was prepared according to the following procedures.

Preparation of Int-6: Ethyl 2-cyclobutylbenzo[d]thiazole-6-carboxylate

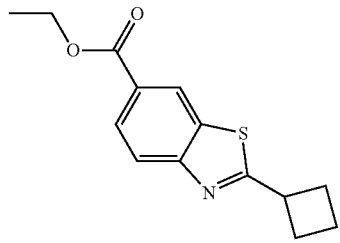 [SMILES: CCOC(=O)c1ccc2nc(C3CCC3)sc2c1]

To a suspension of ethyl 2-chloro-1,3-benzothiazole-6-carboxylate (200 mg, 0.83 mmol) and Pd(PPh$_3$)$_4$ (48 mg, 0.041 mmol) in THF (4 mL) under a nitrogen atmosphere was added 0.5 M bromo(cyclobutyl)zinc in THF (2.0 mL, 0.99 mmol). The reaction was heated to 60° C. and stirred at 60° C. for 5 h. The reaction mixture was allowed to cool to RT, quenched by the addition of distilled water and next partitioned with EtOAc. The organic layer was separated. The combined organic layer was dried (Na$_2$SO$_4$) and concentrated in vacuo. The residue was purified by flash column chromatography (cyclohexane to EtOAc, gradient elution) to afford the title compound as a white solid (96 mg, 44%). LC/MS (Table 2, Method A): R$_t$=1.69 min; m/z=262 [M+H]$^+$.

Preparation of Int-7: Lithium 2-cyclobutylbenzo[d]thiazole-6-carboxylate

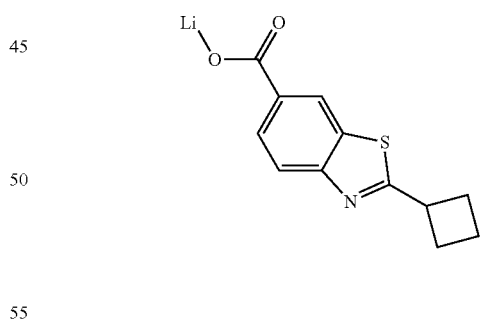

To a solution of ethyl 2-cyclobutylbenzo[d]thiazole-6-carboxylate (96 mg, 0.37 mmol) in THF (1.8 mL) was added a solution of lithium hydroxide monohydrate (77 mg, 1.8 mmol) in distilled water (0.7 mL). The reaction stirred at RT for 72 h. The reaction mixture was next concentrated in vacuo to afford the title compound as a white solid (87 mg, 99%). Material advanced to next step without characterization.

Example 5—Synthesis of Compound I-51: 3-Chloro-6-(2-cyclobutylbenzo[d]thiazole-6-carbonyl)-1,4-dimethyl-1,5,6,7-tetrahydro-2H-pyrrolo[3,4-b]pyridin-2-one

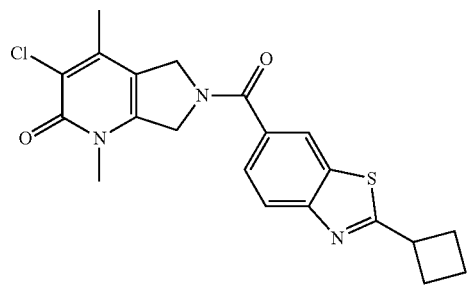 [SMILES: Cc1c2c(n(C)c(=O)c1Cl)CN(C(=O)c1ccc3nc(C4CCC4)sc3c1)C2]

To a suspension of 3-chloro-1,4-dimethyl-1,5,6,7-tetrahydro-2H-pyrrolo[3,4-b]pyridin-2-one hydrochloride (35 mg, 0.14 mmol) and lithium 2-cyclobutylbenzo[d]thiazole-6-carboxylate (40 mg, 0.17 mmol) in DMF (1.2 mL) was added HATU (96 mg, 0.25 mmol) and N,N-diisopropylethylamine (0.085 mL, 0.49 mmol). The reaction stirred at RT for 1 h. The reaction mixture was next partitioned between DCM and saturated aqueous sodium hydrogen carbonate. The organic layer was separated. The combined organic layer was washed with saturated brine, dried ($Na_2SO_4$) concentrated in vacuo. The residue was triturated with hot MeCN to afford the title compound as an off-white solid (15 mg, 26%). $^1$H NMR (400 MHz: DMSO-$d_6$) δ 8.36-8.36 (m, 1H), 8.03 (d, J=8.4 Hz, 1H), 7.71 (dd, J=1.6, 8.4 Hz, 1H), 4.95 (s, 1H), 4.92 (s, 1H), 4.77 (s, 1H), 4.70 (s, 1H), 4.06-4.02 (m, 1H), 3.48 (s, 1.5H), 3.29 (s, 1.5H), 2.48-2.36 (m, 4H), 2.27 (s, 1.5H), 2.16-2.06 (m, 2.5H), 2.01-1.97 (m, 1H). LC/MS (Table 2, Method C): $R_t$=4.01 min; m/z=413 [M+H]$^+$.

Example 6—Synthesis of Additional Compound

The following intermediate in Table 5 was prepared using an analogous reaction protocol to that described for Int-7 from ethyl 2-chloro-1,3-benzothiazole-6-carboxylate and the indicated starting material.

Example 7—Synthesis of Compound I-52: 3-Chloro-6-(2-cyclopropylbenzo[d]thiazole-6-carbonyl)-1,4-dimethyl-1,5,6,7-tetrahydro-2H-pyrrolo[3,4-b]pyridin-2-one

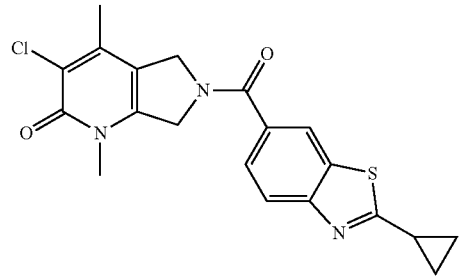 [SMILES: Cc1c2c(n(C)c(=O)c1Cl)CN(C(=O)c1ccc3nc(C4CC4)sc3c1)C2]

The title compound was prepared using an analogous reaction protocol to that described for Example 50: 3-Chloro-6-(2-cyclobutylbenzo[d]thiazole-6-carbonyl)-1,4-dimethyl-1,5,6,7-tetrahydro-2H-pyrrolo[3,4-b]pyridin-2-one, from the appropriate starting materials 3-chloro-1,4-dimethyl-1,5,6,7-tetrahydro-2H-pyrrolo[3,4-b]pyridin-2-one hydrochloride and lithium 2-cyclopropylbenzo[d]thiazole-6-carboxylate. The title compound was triturated with 10% DMSO aqueous solution to afford an off-white solid (36 mg, 41%). $^1$H NMR (400 MHz, DMSO-$d_6$) δ 8.31 (s, 1H), 7.92 (d, J=8.4 Hz, 1H), 7.67 (dd, J=1.6, 8.4 Hz, 1H), 4.95 (s, 1H), 4.91 (s, 1H), 4.76 (s, 1H), 4.71 (s, 1H), 3.47 (s, 1.5H), 3.29 (s, 1.5H), 2.60-2.54 (m, 1H), 2.26 (s, 1.5H), 2.10 (s, 1.5H), 1.30-1.24 (m, 2H), 1.19-1.14 (m, 2H). LC/MS (Table 2, Method C): $R_t$=3.60 min; m/z=399 [M+H]$^+$.

Example 8—Synthesis of Compound Int-9: 3-Chloro-1,4-dimethyl-6-(1-((3-methyloxetan-3-yl)methyl)-1H-pyrazole-4-carbonyl)-1,5,6,7-tetrahydro-2H-pyrrolo[3,4-b]pyridin-2-one

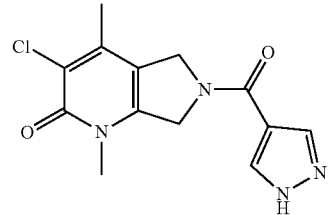 [SMILES: Cc1c2c(n(C)c(=O)c1Cl)CN(C(=O)c1cn[nH]c1)C2]

TABLE 5

Additional Compound

| Compound No. | Structure | Yield | Starting Material | LC/MS Method |
|---|---|---|---|---|
| Int-8 | Li-O-C(=O)-benzothiazole-cyclopropyl structure | 321 mg, quant. | HO-B(OH)-cyclopropyl | LC/MS (Table 2, Method F): $R_t$ = 1.41 min; m/z = 220 [M + H]$^+$ |

To a suspension of 3-chloro-1,4-dimethyl-1,5,6,7-tetrahydro-2H-pyrrolo[3,4-b]pyridin-2-one hydrochloride (150 mg, 0.64 mmol) and 4-pyrazolecarboxylic acid (79 mg, 0.71 mmol) in DCM (3 mL) was added HATU (315 mg, 0.83 mmol) and triethylamine (0.27 mL, 1.9 mmol). The reaction stirred for 2 h. The reaction mixture was filtered to afford the title compound as a tan solid (138 mg, 74%). LC/MS (Table 2, Method F): $R_t$=1.25 min; m/z=292 [M+H]$^+$.

Example 9—Synthesis of Compound I-53:
3-Chloro-1,4-dimethyl-6-(1-((3-methyloxetan-3-yl)methyl)-1H-pyrazole-4-carbonyl)-1,5,6,7-tetrahydro-2H-pyrrolo[3,4-b]pyridin-2-one

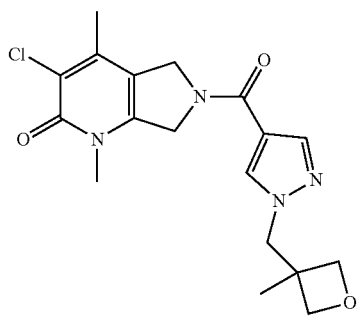 [SMILES: Cc1c2c(n(C)c(=O)c1Cl)CN(C(=O)c1cnn(CC3(C)COC3)c1)C2]

To a suspension of 3-chloro-1,4-dimethyl-6-(1H-pyrazole-4-carbonyl)-1,5,6,7-tetrahydro-2H-pyrrolo[3,4-b]pyridin-2-one (61 mg, 0.21 mmol) in DMF (1 mL) at 0° C. was added sodium hydride (60%, 13 mg, 0.31 mmol) and the reaction stirred for 15 mins. This was followed by the addition of 3-(bromomethyl)-3-methyl-oxetane (45 mg, 0.27 mmol). The reaction was allowed to warm to RT and stirred at RT for 1.25 h. The reaction mixture was quenched by the addition of distilled water (1 mL) and concentrated in vacuo. The residue was purified by reverse phase HPLC (Table 3, Method 1) to afford the title compound as a white solid (9.0 mg, 11%). $^1$H NMR (400 MHz: DMSO-d$_6$) δ 8.45 (s, 1H), 8.02 (d, J=3.0 Hz, 1H), 5.15-5.12 (m, 1H), 4.94 (s, 1H), 4.87 (s, 1H), 4.68 (s, 1H), 4.64 (d, J=6.1 Hz, 2H), 4.42 (s, 2H), 4.26 (d, J=5.9 Hz, 2H), 3.48 (d, J=6.7 Hz, 3H), 2.27 (d, J=6.8 Hz, 3H), 1.17 (s, 3H). LC/MS (Table 2, Method B): $R_t$=2.82 min; m/z=377 [M+H]$^+$.

Example 10—Synthesis of Additional Compounds

The following examples in Table 6 were prepared using an analogous reaction protocol to that described for I-53 from Int-9 and the indicated starting material.

TABLE 6

Additional Compounds

| Compound No. | Yield | Starting Material | Purification Method |
| --- | --- | --- | --- |
| I-54 | 16 mg, 32% | | Reverse phase HPLC (Table 3, Method 1) |
| I-55 | 2.6 mg, 5% | | Reverse phase HPLC (Table 3, Method 3) |
| I-56 | 18 mg, 32% | | Reverse phase HPLC (Table 3, Method 4) |
| I-57 | 16 mg, 66% | | Reverse phase HPLC (Table 3, Method 1, non-linear gradient 40% to 100% MeOH) |

Example 11—Synthesis of Compound Int-12: 3-Chloro-1,4-dimethyl-6-(5-(2,2,2-trifluoroethyl)isoxazole-3-carbonyl)-1,5,6,7-tetrahydro-2H-pyrrolo[3,4-b]pyridin-2-one The title compound was prepared according to the following procedures.

Preparation of Int-10: Ethyl 5-(bromomethyl)isoxazole-3-carboxylate

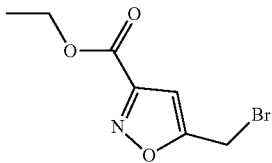

To a solution of ethyl 2-chloro-2-(hydroxyimino)acetate (5 g, 33 mmol) in diethyl ether (25 mL) at 0° C. was added 10.2 M propargyl bromide solution (4.9 mL, 50 mmol) via dropwise addition. This was followed by the addition of triethylamine (5.1 mL, 36 mmol) in diethyl ether (5 mL) via dropwise addition. The reaction was allowed to warm to RT and stirred at RT for 16 h. The reaction mixture was next partitioned between EtOAc and distilled water. The organic layer was separated. The combined organic layer was washed with saturated brine, dried (MgSO$_4$) and concentrated in vacuo. The residue was purified by flash column chromatography (cyclohexane to EtOAc, gradient elution) to afford the title compound (1.1 g, 14%). $^1$H NMR (400 MHz: CDCl$_3$) δ 6.74 (d, J=3.6 Hz, 1H), 4.50 (s, 2H), 4.49-4.42 (m, 2H), 1.42 (t, J=7.2 Hz, 3H).

Preparation of Int-11: Ethyl 5-(2,2,2-trifluoroethyl)isoxazole-3-carboxylate

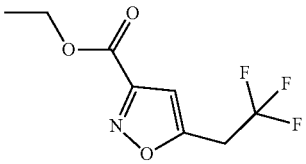

To a solution of ethyl 5-(bromomethyl)isoxazole-3-carboxylate (295 mg, 1.3 mmol) in DMF (10 mL) was added copper (I) iodide (456 mg, 2.4 mmol) and methyl 2,2-difluoro-2-(fluorosulfonyl)acetate (0.72 mL, 5.7 mmol). The reaction was heated to 100° C. and stirred at 100° C. for 16 h. The reaction mixture was next partitioned between EtOAc and distilled water. The organic layers were separated. The combined organic layer was washed with saturated brine, dried (MgSO$_4$) and concentrated in vacuo. The residue was purified by flash column chromatography (cyclohexane in EtOAc, gradient elution) to afford the title compound as a yellow oil (138 mg, 49%). LC/MS (Table 2, Method A): R$_t$=1.31 min; UV only.

Preparation of Int-12: 5-(2,2,2-Trifluoroethyl)isoxazole-3-carboxylic Acid

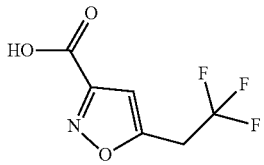 [SMILES: O=C(O)c1cc(CC(F)(F)F)on1]

A reaction vessel was charged with ethyl 5-(2,2,2-trifluoroethyl)isoxazole-3-carboxylate (65 mg, 0.29 mmol) and 6 M HCl (5.0 mL, 30 mmol). The reaction was heated to 100° C. and stirred at 100° C. for 3 h. The reaction mixture was next concentrated in vacuo and the residue azeotroped with MeCN to afford the title compound as a yellow gum (154 mg, 62%). $^1$H NMR (400 MHz: DMSO-d$_6$) δ 6.87 (s, 1H), 4.22 (q, J=10.9 Hz, 2H).

Example 12—Synthesis of Compound I-58: 3-Chloro-1,4-dimethyl-6-(5-(2,2,2-trifluoroethyl)isoxazole-3-carbonyl)-1,5,6,7-tetrahydro-2H-pyrrolo[3,4-b]pyridin-2-one

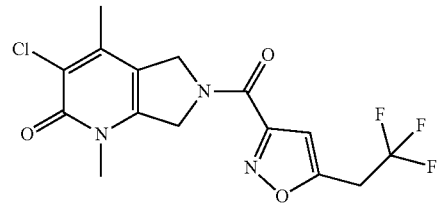 [SMILES: Cc1c2c(n(C)c(=O)c1Cl)CN(C(=O)c1cc(CC(F)(F)F)on1)C2]

To a solution of 5-(2,2,2-trifluoroethyl)isoxazole-3-carboxylic acid (65 mg, 0.33 mmol) and 3-chloro-1,4-dimethyl-1,5,6,7-tetrahydro-2H-pyrrolo[3,4-b]pyridin-2-one hydrochloride (50 mg, 0.21 mmol) in DCM (2 mL) was added triethylamine (0.089 mL, 0.64 mmol) and HATU (97 mg, 0.26 mmol). The reaction stirred at RT for 30 min. The reaction mixture was next partitioned between EtOAc and distilled water. The organic layer was separated. The combined organic layer was washed with saturated brine, dried (MgSO$_4$) and concentrated in vacuo. The residue was purified by reverse phase HPCL (Table 3, Method 4, non-linear gradient from 20% to 80% MeCN) to afford the title compound as an off-white solid (48.2 mg, 60%). $^1$H NMR (400 MHz: DMSO-d$_6$) δ 6.95 (s, 1H), 5.22 (s, 1H), 5.01-4.95 (m, 2H), 4.77-4.76 (m, 1H), 4.28 (q, J=10.9 Hz, 2H), 3.49 (s, 1.5H), 3.42 (s, 1.5H), 2.28 (s, 1.5H), 2.22 (s, 1.5H). LC/MS (Table 2, Method E): R$_t$=3.92 min; m/z=376 [M+H]$^+$.

Example 13—Synthesis of Compound Int-14: Lithium 1-(pyridin-3-ylmethyl)-1H-pyrazole-4-carboxylate The title compound was prepared according to the following procedures.

Preparation of Int-13: Ethyl 1-(pyridin-3-ylmethyl)-1H-pyrazole-4-carboxylate

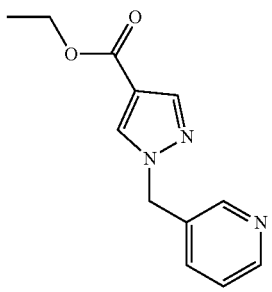 [SMILES: CCOC(=O)c1cnn(Cc2cccnc2)c1]

To a suspension of ethyl 4-pyrazolecarboxylate (150 mg, 1.1 mmol) in DMF (2 mL) at 0° C. was added sodium hydride (60%, 64 mg, 1.6 mmol) and the reaction stirred for 10 min. This was followed by the addition of 3-(bromomethyl)pyridine hydrobromide (298 mg, 1.2 mmol) and triethylamine (0.45 mL, 3.2 mmol). The reaction was allowed to warm to RT and stirred at RT for 4 h. The reaction mixture was quenched by the addition of distilled water and next partitioned with EtOAc. The organic layer separated. The combined organic layer was dried ($Na_2SO_4$) and concentrated in vacuo. The residue was purified by flash column chromatography (DCM to MeOH, gradient elution) to afford the title compound as a yellow gum (154 mg, 62%). LC/MS (Table 2, Method F): $R_t$=0.23 min; m/z=232 [M+H]$^+$.

Preparation of Int-14: Lithium 1-(pyridin-3-ylmethyl)-1H-pyrazole-4-carboxylate

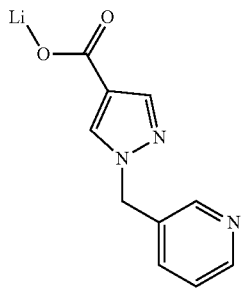

To a solution of ethyl 1-(pyridin-3-ylmethyl)-1H-pyrazole-4-carboxylate (154 mg, 0.67 mmol) in THF (5 mL) and water (1 mL) was added lithium hydroxide monohydrate (28 mg, 0.67 mmol) and the reaction stirred at RT for 16 h. A further amount of lithium hydroxide monohydrate (56 mg, 1.3 mmol) and MeOH (1 mL) were added and the reaction stirred for 2.5 h. The reaction mixture was concentrated in vacuo to afford the title compound as an off-white solid (181 mg, quantitative). LC/MS (Table 2, Method F): $R_t$=0.23 min; m/z=204 [M+H]$^+$.

Example 14—Synthesis of Compound I-59: 3-Chloro-1,4-dimethyl-6-(1-(pyridin-3-ylmethyl)-1H-pyrazole-4-carbonyl)-1,5,6,7-tetrahydro-2H-pyrrolo[3,4-b]pyridin-2-one

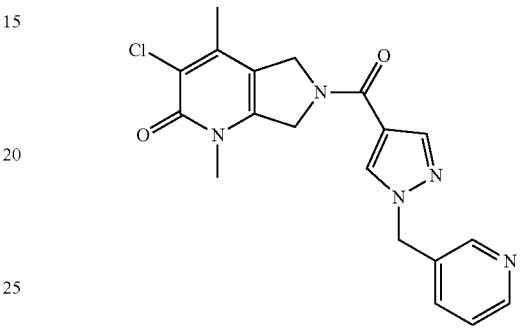

To a suspension of lithium 1-(pyridin-3-ylmethyl)-1H-pyrazole-4-carboxylate (43 mg, 0.20 mmol) in DMF (3 mL) was added HATU (84 mg, 0.22 mmol) and triethylamine (0.071 mL, 0.51 mmol). This was followed by the addition of 3-chloro-1,4-dimethyl-1,5,6,7-tetrahydro-2H-pyrrolo[3,4-b]pyridin-2-one hydrochloride (40 mg, 0.17 mmol) and the reaction stirred at RT for 18 h. The reaction mixture was next partitioned between EtOAc and distilled water. The organic layer was separated. The combined organic layer was dried ($Na_2SO_4$) concentrated in vacuo. The residue was purified by reverse phase HPLC (Table 3, Method 1) to afford the title compound as an off-white solid (5.7 mg, 9%). $^1$H NMR (400 MHz: DMSO-$d_6$) δ 8.60-8.57 (m, 2H), 8.54 (dd, J=1.6, 4.8 Hz, 1H), 8.04 (d, J=3.1 Hz, 1H), 7.73-7.70 (m, 1H), 7.41 (dd, J=5.0, 7.7 Hz, 1H), 5.47 (s, 2H), 5.17-5.15 (m, 1H), 4.96 (s, 1H), 4.87 (s, 1H), 4.68-4.67 (m, 1H), 3.48 (d, J=6.7 Hz, 3H), 2.27 (d, J=7.7 Hz, 3H). LC/MS (Table 2, Method E): $R_t$=2.77 min; m/z=384 [M+H]$^+$.

Example 15—Synthesis of Additional Compounds

The following intermediates in Table 7 were prepared using an analogous reaction protocol to that described for Int-14 from ethyl 4-pyrazolecarboxylate and the indicated starting material.

TABLE 7

Additional Compounds

| Compound No. | Structure | Yield | Starting Material | $^1$H NMR data or LC/MS Method |
|---|---|---|---|---|
| Int-15 | 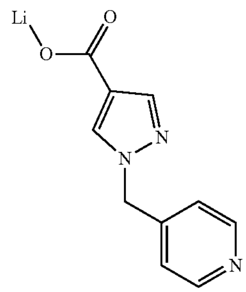 | 192 mg, quant. | | $^1$H NMR (400 MHz: DMSO-$d_6$) δ 8.49 (d, J = 4.3 Hz, 2H), 7.84-7.51 (m, 2H), 7.11 (d, J = 4.5 Hz, 2H), 5.35-5.30 (m, 2H) |
| Int-16 | 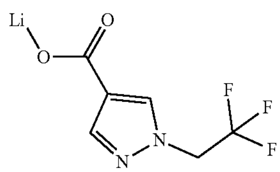 | 580 mg, 96% | | (Table 2, Method F): $R_t$ = 1.03 min; m/z = 195 [M + H]$^+$ |
| Int-17 | 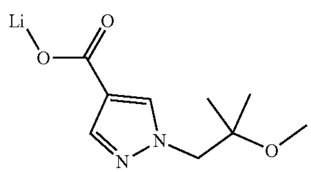 | 200 mg, quant. | | $^1$H NMR (400 MHz: DMSO-$d_6$) δ 7.57 (s, 1H), 7.41 (s, 1H), 4.03 (s, 2H), 3.17 (s, 3H), 1.04 (s, 6H) |
| Int-18 | 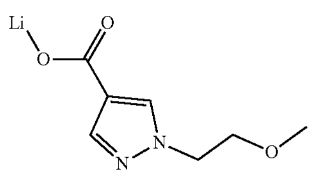 | 230 mg, quant. | | $^1$H NMR (400 MHz: DMSO-$d_6$) δ 7.67 (s, 1H), 7.45 (s, 1H), 4.17 (t, J = 5.4 Hz, 2H), 3.63 (t, J = 5.5 Hz, 2H), 3.22 (s, 3H) |

Example 16—Synthesis of Additional Compounds

The following compounds in Table 8 were prepared using an analogous reaction protocol to that described for I-12 from Int-5 and the indicated starting material.

TABLE 8

Additional Compounds

| Compound No. | Yield | Starting Material | Purification Method |
|---|---|---|---|
| I-60 | 20 mg, 23% | Int-15 | Reverse phase HPLC (Table 3, Method 1) |
| I-61 | 40 mg, 62% | Int-16 | Triturated with MeCN |
| I-62 | 16 mg, 25% | Int-17 | Reverse phase HPLC (Table 3, Method 4) |
| I-63 | 27 mg, 44% | Int-18 | Reverse phase HPLC (Table 3, Method 5, non-linear gradient 20% to 80% MeOH) |

Example 17—Synthesis of Compound Int-23: Lithium 2-((2,2-difluorocyclopropyl)methyl)thiazole-5-carboxylate The title compound was prepared according to the following procedures.

Preparation of Int-19: 2-(2,2-Difluorocyclopropyl)-N-(2,4-dimethoxybenzyl)acetamide

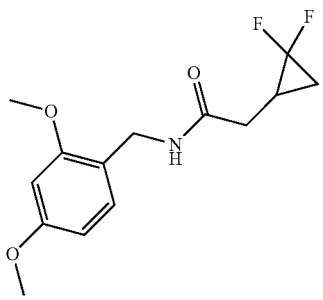 [SMILES: COc1ccc(CNC(=O)CC2CC2(F)F)c(OC)c1]

To a solution of 2-(2,2-difluorocyclopropyl)acetic acid (150 mg, 1.1 mmol), 2,4-dimethoxybenzylamine (0.20 mL, 1.3 mmol) and HATU (545 mg, 1.4 mmol) in DCM (2 mL) was added N,N-diisopropylethylamine (0.58 mL, 3.3 mmol). The reaction was stirred at RT for 2 h. The reaction mixture was next partitioned between DCM and distilled water. The organic layer was separated. The combined organic layer was dried (Na$_2$SO$_4$) and concentrated in vacuo. The residue was purified by flash column chromatography (cyclohexane in EtOAc, gradient elution) to afford the title compound as a colourless oil, crystallizing on standing, (278 mg, 88%). LC/MS (Table 2, Method F): $R_t$=1.43 min; m/z=286 [M+H]⁺.

Preparation of Int-20: 2-(2,2-Difluorocyclopropyl)-N-(2,4-dimethoxybenzyl)ethanethioamide

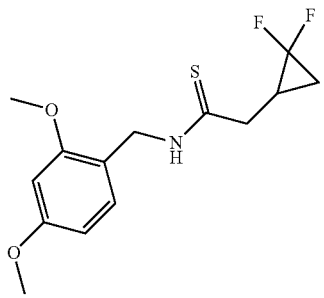

To a solution of 2-(2,2-difluorocyclopropyl)-N-(2,4-dimethoxybenzyl)acetamide (218 mg, 0.76 mmol) in toluene (5 mL) was added Lawesson reagent (185 mg, 0.46 mmol) and the reaction was next heated to 95° C. The reaction stirred at 95° C. for 1 h. The reaction mixture was concentrated in vacuo and purified directly by flash column chromatography (cyclohexane in EtOAc, gradient elution) to afford the title compound as a colourless oil (169 mg, 73%). LC/MS (Table 2, Method F): $R_t$=1.69 min; m/z=302 [M+H]⁺.

Preparation of Int-21: 2-(2,2-Difluorocyclopropyl)ethanethioamide

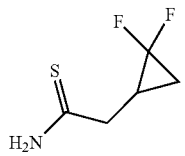

To a solution of 2-(2,2-difluorocyclopropyl)-N-(2,4-dimethoxybenzyl)ethanethioamide (75 mg, 0.25 mmol) and anisole (0.14 mL, 1.2 mmol) in DCM (4 mL) was added trifluoroacetic acid (1.0 mL, 13 mmol). The reaction stirred at RT for 18 h. The reaction mixture was next concentrated in vacuo and purified directly by flash column chromatography (cyclohexane in EtOAc, gradient elution) to afford the title compound as a yellow oil (27 mg, 72%). Material advanced to next step without characterisation.

Preparation of Int-22: Ethyl 2-((2,2-difluorocyclopropyl)methyl)thiazole-5-carboxylate

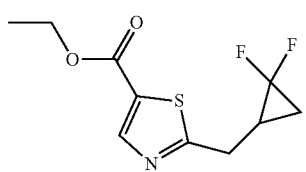 [SMILES: CCOC(=O)c1cnc(CC2CC2(F)F)s1]

A reaction vessel was charged with 2-(2,2-difluorocyclopropyl)ethanethioamide (47 mg, 0.37 mmol), ethyl 2-chloro-3-oxo-propanoate (51 mg, 0.40 mmol) and dissolved in toluene (2 mL). The reaction was next heated to 90° C. and stirred at 90° C. for 2 h. The reaction mixture was concentrated in vacuo and purified directly by flash column chromatography (cyclohexane in EtOAc, gradient elution) to afford the title compound as a yellow oil (30 mg, 39%). LC/MS (Table 2, Method F): $R_t$=1.62 min; m/z=248 [M+H]⁺.

Preparation of Int-23: Lithium 2-((2,2-difluorocyclopropyl)methyl)thiazole-5-carboxylate

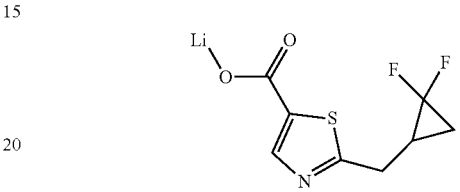

To a solution of ethyl 2-[(2,2-difluorocyclopropyl)methyl]thiazole-5-carboxylate (30 mg, 0.12 mmol) in THF (1 mL) and water (0.5 mL) was added lithium hydroxide monohydrate (5.6 mg, 0.13 mmol). The reaction stirred at RT for 2 h. The reaction mixture was next concentrated in vacuo to afford the title compound as a light yellow solid (27 mg, 99%). LC/MS (Table 2, Method F): $R_t$=1.26 min; m/z=220 [M+H]⁺.

Example 18—Synthesis of Compound I-64: 3-Chloro-6-(2-(cyclopropyl-difluoromethyl)thiazole-5-carbonyl)-1,4-dimethyl-1,5,6,7-tetrahydro-2H-pyrrolo[3,4-b]pyridin-2-one

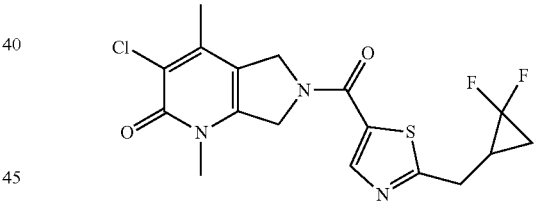

To a suspension of lithium 2-((2,2-difluorocyclopropyl)methyl)thiazole-5-carboxylate (22 mg, 0.099 mmol) and 3-chloro-1,4-dimethyl-1,5,6,7-tetrahydro-2H-pyrrolo[3,4-b]pyridin-2-one hydrochloride (19 mg, 0.082 mmol) in DMF (2 mL) was added N,N-diisopropylethylamine (0.050 mL, 0.29 mmol) and HATU (47 mg, 0.12 mmol). The reaction stirred at RT for 2 h. The reaction mixture was next concentrated in vacuo and purified directly by reverse phase HPLC (Table 3, Method 3) to afford the title compound as an off-white solid (14 mg, 44%). ¹H NMR (400 MHz: DMSO-$d_6$) δ 8.43 (d, J=2.6 Hz, 1H), 5.28 (s, 1H), 5.07 (t, J=2.3 Hz, 1H), 4.93 (s, 1H), 4.73 (s, 1H), 3.48 (d, J=4.8 Hz, 3H), 3.24-3.19 (m, 2H), 2.28 (d, J=3.4 Hz, 3H), 2.25-2.09 (m, 1H), 1.79-1.69 (m, 1H), 1.49-1.40 (m, 1H). LC/MS (Table 2, Method B): $R_t$=3.98 min; m/z=400 [M+H]⁺.

Example 19—Synthesis of Additional Compounds

The following compounds in Table 9 were prepared using an analogous reaction protocol to that described for I-16 from Int-5 and the indicated starting material.

TABLE 9

Additional Compounds

| Compound No. | Yield | Starting Material | Purification method |
|---|---|---|---|
| I-65 (unknown absolute configuration) | 3.4 mg, 10% | Int-23 | Purified by SFC purification (Table 3, Method 6) |
| I-66 (unknown absolute configuration) | 3.2 mg, 10% | Int-23 | Purified by SFC purification (Table 3, Method 6) |

Example 20—Synthesis of Compound Int-28: Lithium 2-(cyclopropyldifluoromethyl)thiazole-5-carboxylate The title compound was prepared according to the following procedures.

Preparation of Int-24: N-Methoxy-N-methylcyclopropanecarboxamide

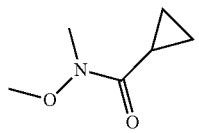

To a suspension of N,O-dimethylhydroxylamine hydrochloride (2.2 g, 22 mmol) in DCM (55 mL) at 0° C. was added triethylamine (6.1 mL, 44 mmol) via dropwise addition. This was followed by the addition of cyclopropanecarbonyl chloride (2.0 mL, 22 mmol) via dropwise addition. The reaction was allowed to warm to RT and stirred at RT for 1 h. The reaction mixture was next partitioned between DCM and saturated aqueous sodium hydrogen carbonate. The organic layer was separated. The combined organic layer was washed with 1 M HCl, saturated brine and passed through a phase separator. The filtrate was concentrated in vacuo to afford the title compound as a colourless liquid (2.6 g, 92%). $^1$H NMR (400 MHz; CDCl$_3$) δ 3.76 (s, 3H), 3.21 (s, 3H), 2.19-2.09 (m, 1H), 1.01-0.97 (m, 2H), 0.84-0.79 (m, 2H).

Preparation of Int-25: Ethyl 2-(cyclopropanecarbonyl)thiazole-5-carboxylate

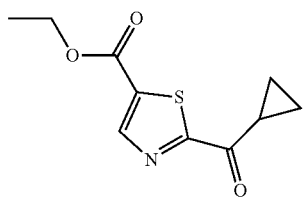

To a solution of ethyl thiazole-5-carboxylate (1.2 mL, 12 mmol) and N-methoxy-N-methyl-cyclopropanecarboxamide (1.2 mL, 12 mmol) in THF (44 mL) at −78° C. under a nitrogen atmosphere, was added a solution of 1 M lithium bis(trimethylsilyl)amide in THF (17 mL, 18 mmol) via dropwise addition. The reaction stirred at −78° C. for 2 h. The reaction mixture was quenched by the addition of saturated aqueous ammonium chloride solution, was allowed to warm to RT and next partitioned between EtOAc and distilled water. The organic layer was separated. The combined organic layer was washed with saturated brine, dried (Na$_2$SO$_4$) and concentrated in vacuo. The residue was purified by flash column chromatography (cyclohexane to EtOAc, gradient elution) to afford the title compound as a light yellow oil (692 mg, 27%). LC/MS (Table 2, Method A): R$_t$=1.46 min; m/z=226 [M+H]$^+$.

Preparation of Int-26: Ethyl 2-(2-cyclopropyl-1,3-dithiolan-2-yl)thiazole-5-carboxylate

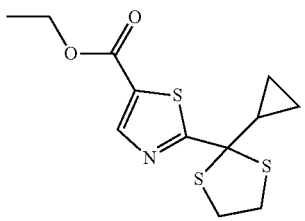 [SMILES: CCOC(=O)c1cnc(C2(C3CC3)SCCS2)s1]

To a solution of ethyl 2-(cyclopropanecarbonyl)thiazole-5-carboxylate (486 mg, 2.2 mmol) in toluene (6 mL) was added boron trifluoride diethyl etherate (0.32 mL, 2.6 mmol) and 1,2-ethanedithiol (0.54 mL, 6.5 mmol). The reaction was heated to 100° C. and stirred at 100° C. for 5 h. The reaction mixture was allowed to cool to RT and next concentrated in vacuo. The residue was purified directly by flash column chromatography (cyclohexane to EtOAc) to afford the title compound as a colourless oil (103 mg, 16%). LC/MS (Table 2, Method A): R$_t$=1.62 min; m/z=302 [M+H]$^+$.

Preparation of Int-27: Ethyl 2-(cyclopropyldifluoromethyl)thiazole-5-carboxylate

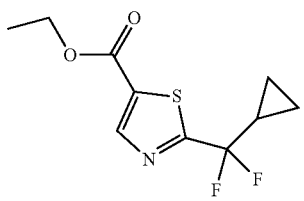 [SMILES: CCOC(=O)c1cnc(C(F)(F)C2CC2)s1]

To a suspension of N-iodosuccinimide (192 mg, 0.85 mmol) in DCM (1 mL) at −78° C. was added hydrogen fluoride pyridine (70% HF, 0.88 mL, 9.8 mmol) via dropwise addition. This was followed by the addition of a solution of ethyl 2-(2-cyclopropyl-1,3-dithiolan-2-yl)thiazole-5-carboxylate (103 mg, 0.34 mmol) in DCM (1 mL) via dropwise addition. The reaction mixture was allowed to warm to −30° C. and stirred at −30° C. for 2.5 h. The reaction mixture was quenched by the addition of saturated aqueous sodium hydrogen carbonate solution and next partitioned with DCM. The organic layer was separated. The combined organic layer was washed with saturated brine, passed through a phase separator and the filtrate was concentrated in vacuo. The residue was purified by flash column chromatography (cyclohexane in DCM) to afford the title compound as an orange oil (18 mg, 21%). LC/MS (Table 2, Method A): $R_t$=1.56 min; m/z=248 [M+H]$^+$.

Preparation of Int-28: Lithium 2-(cyclopropyldifluoromethyl)thiazole-5-carboxylate

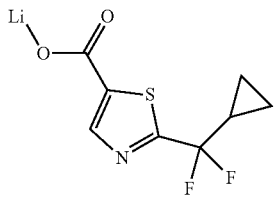

To a solution of ethyl 2-(cyclopropyldifluoromethyl)thiazole-5-carboxylate (18 mg, 0.073 mmol) in MeOH (0.75 mL) was added a solution of lithium hydroxide monohydrate (3.4 mg, 0.080 mmol) in water (0.25 mL) and the reaction stirred at RT for 3 h. The reaction mixture was next concentrated in vacuo to afford the title compound as a yellow solid (16 mg, 98%). Material advanced to next step without characterisation.

Example 21—Synthesis of Compound I-67: 3-Chloro-6-(2-(cyclopropyldifluoromethyl) thiazole-5-carbonyl)-1,4-dimethyl-1,5,6,7-tetrahydro-2H-pyrrolo[3,4-b]pyridin-2-one

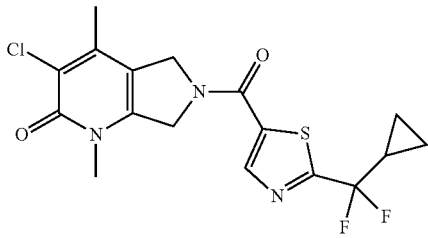 [SMILES: Cc1c2c(n(C)c(=O)c1Cl)CN(C(=O)c1cnc(C(F)(F)C3CC3)s1)C2]

To a solution of lithium 2-(cyclopropyldifluoromethyl) thiazole-5-carboxylate (16 mg, 0.071 mmol) in DMF (0.5 mL) was added HATU (32 mg, 0.085 mmol) followed by the addition of a solution of 3-chloro-1,4-dimethyl-1,5,6,7-tetrahydro-2H-pyrrolo[3,4-b]pyridin-2-one hydrochloride (18 mg, 0.078 mmol) and N,N-diisopropylethylamine (31 mL, 0.18 mmol) in DMF (0.5 mL) via dropwise addition. The reaction mixture stirred at RT for 1 h. The reaction mixture was next concentrated in vacuo and purified directly by reverse phase HPLC (Table 3, Method 3) to afford the title compound as an off-white solid (14 mg, 48%). $^1$H NMR (400 MHz: DMSO-d$_6$) δ 8.68-8.65 (m, 1H), 5.32-4.77 (m, 4H), 3.49-3.48 (m, 3H), 2.29-2.27 (m, 3H), 2.04-1.91 (m, 1H), 0.85-0.78 (m, 4H). LC/MS (Table 2, Method B): $R_t$=4.18 min; m/z=400 [M+H]$^+$.

Example 22—Synthesis of Compound Int-31: Lithium 1-methyl-5-(trifluoromethyl)-1H-pyrrole-3-carboxylate The title compound was prepared according to the following procedures.

Preparation of Int-29: Methyl 5-(trifluoromethyl)-1H-pyrrole-3-carboxylate

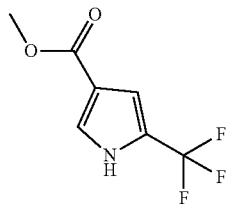

To a solution of methyl 1H-pyrrole-3-carboxylate (310 mg, 2.5 mmol) in DMF (2 mL) was added 0.5 M trifluoroiodomethane in THF (5.0 mL, 2.5 mmol) and sodium hydride (60%, 145 mg, 3.7 mmol).

The reaction stirred under a nitrogen atmosphere for 30 min. The reaction mixture was partitioned between distilled water and DCM. The organic layer was separated and concentrated in vacuo. The residue was purified by flash column chromatography (cyclohexane to diethyl ether, gradient elution) to afford the title compound as a mixture of regioisomers (3:7, 77 mg, 5%). $^1$H NMR (400 MHz, CDCl3) δ 8.94-8.93 (m, 1H), 7.53-7.53 (m, 1H), 7.05 (s, 1H), 3.86 (s, 3H).

Preparation of Int-30: Methyl 1-methyl-5-(trifluoromethyl)-1H-pyrrole-3-carboxylate

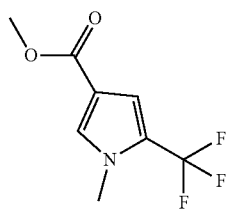

To a solution of methyl 5-(trifluoromethyl)-1H-pyrrole-3-carboxylate (75 mg, 0.39 mmol in DMF (1 mL) was added sodium hydride (12 mg, 0.51 mmol) and the reaction stirred at RT for 1 h. Iodomethane (0.24 mL, 3.9 mmol) was then added and the reaction stirred at RT for 1 h. The reaction mixture was quenched by the addition of sodium bicarbonate solution and next partitioned with EtOAc. The combined organic layer was washed with 5% LiCl solution, dried (MgSO$_4$) and concentrated in vacuo. This material was purified by flash column chromatography (cyclohexane to diethyl ether, gradient elution) to afford the title compound (12 mg, 15%). $^1$H NMR (400 MHz, CDCl$_3$) δ 7.35 (d, J=1.8 Hz, 1H), 7.01 (s, 1H), 3.83 (s, 3H), 3.77 (s, 3H).

Preparation of Int-31: Lithium 1-methyl-5-(trifluoromethyl)-1H-pyrrole-3-carboxylate

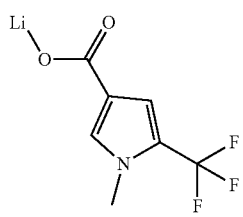

To a solution of methyl 1-methyl-5-(trifluoromethyl)pyrrole-3-carboxylate (12 mg, 0.06 mmol) in THF (0.50 mL) was added lithium hydroxide monohydrate (7.3 mg, 0.17 mmol) and distilled water (0.25 mL). The reaction stirred at RT for 5 h. The reaction mixture was concentrated in vacuo to afford the title compound as a white solid (21 mg, quantitative). Material advanced to step without characterization.

Example 23—Synthesis of Compound I-68: 3-Chloro-1,4-dimethyl-6-(1-methyl-5-(trifluoromethyl)-1H-pyrrole-3-carbonyl)-1,5,6,7-tetrahydro-2H-pyrrolo[3,4-b]pyridin-2-one

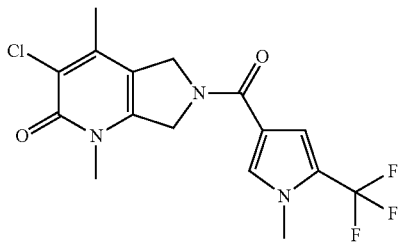 [SMILES: Cc1c2c(n(C)c(=O)c1Cl)CN(C(=O)c1cc(C(F)(F)F)n(C)c1)C2]

To a solution of lithium 1-methyl-5-(trifluoromethyl)pyrrole-3-carboxylate (11 mg, 0.057 mmol) in DMF (0.5 mL) was added HATU (33 mg, 0.086 mmol) followed by the addition of a solution of 3-chloro-1,4-dimethyl-6,7-dihydro-5H-pyrrolo[3,4-b]pyridine-2-one hydrochloride (19 mg, 0.080 mmol) and N,N-diisopropylethylamine (0.050 mL, 0.29 mmol) in DMF (0.5 mL). The reaction mixture stirred at RT for 16 h. The reaction mixture was next concentrated in vacuo and purified directly by reverse phase HPLC (Table 3, Method 5) to afford the title compound as an off-white solid (3.5 mg, 16%). $^1$H NMR (400 MHz, DMSO) δ 7.80 (d, J=2.0 Hz, 1H), 7.10 (s, 1H), 5.12 (s, 1H), 4.93 (s, 1H), 4.86 (s, 1H), 4.67 (s, 1H), 3.80 (s, 3H), 3.46 (d, J=6.6 Hz, 3H), 2.25 (d, J=7.3 Hz, 3H). (Table 2, Method B): $R_t$=3.89 min; m/z=374.2 [M+H]$^+$.

Example 24—Synthesis of Compound Int-40: 3-Chloro-1-(cyclopropylmethyl)-4-methyl-1,5,6,7-tetrahydro-2H-pyrrolo[3,4-b]pyridin-2-one hydrochloride The title compound was prepared according to the following procedures.

Preparation of Int-32: 2-Chloro-6-methoxy-4-methylnicotinonitrile

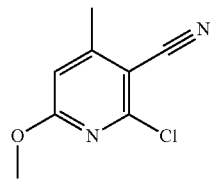

To a suspension of 2,6-dichloro-4-methylnicotinonitrile (84 g, 450 mmol) in MeOH (840 mL) at 1.5° C. under a nitrogen atmosphere was added 4.4 M sodium methoxide (108 mL, 472 mmol) via dropwise addition, over a period of 5 h. The reaction was allowed to warm to RT and stirred at RT for 16 h. The reaction mixture was allowed to cool to 3° C., slowly quenched by the addition of distilled water (100 mL) and stirred for 30 min. The reaction mixture was allowed to warm to RT, concentrated in vacuo and next partitioned between EtOAc and distilled water. The organic layer was separated. The combined organic layer was washed with saturated brine, dried (Na$_2$SO$_4$) and concentrated in vacuo. The residue was further recrystallised from MeOH to afford the title compound as a white solid and a mixture of regioisomers (5:1, 36 g, 37%). $^1$H NMR (300 MHz: CDCl$_3$) δ 6.91 (s, 0.2H), 6.61 (s, 1H), 4.05 (s, 0.6H), 3.98 (s, 3H), 2.49 (s, 3.6H).

Preparation of Int-33: Methyl 3-cyano-6-methoxy-4-methylpicolinate

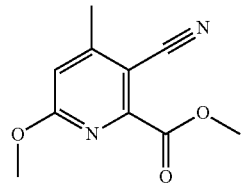

To a suspension of 2-chloro-6-methoxy-4-methylnicotinonitrile (5 g, 27 mmol) and Pd(dppf)Cl$_2$ complex with DCM (2.3 g, 2.7 mmol) in MeOH (50 mL) was added triethylamine (11 mL, 82 mmol). The reaction was purged with carbon monoxide and next heated to 70° C. The reaction stirred at 70° C. under a carbon monoxide atmosphere for 20 h. The reaction mixture was allowed to cool to RT, filtered through celite and washed with DCM. The filtrate was concentrated in vacuo and purified directly by flash column chromatography (cyclohexane to EtOAc, gradient elution) to afford the title compound as a white solid and a mixture of regioisomers (5:1, 3.9 g, 65%). $^1$H NMR (300 MHz: CDCl$_3$) δ 7.64 (s, 0.2H), 6.84 (s, 1H), 4.13 (s, 0.6H), 4.04 (s, 3H), 4.03 (s, 3H), 3.98 (s, 0.6H), 2.59 (s, 0.6H), 2.56 (s, 3H).

Preparation of Int-34: 2-Methoxy-4-methyl-5,6-dihydro-7H-pyrrolo[3,4-b]pyridin-7-one

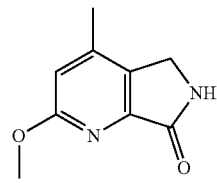

To a suspension of methyl 3-cyano-6-methoxy-4-methylpicolinate (3.9 g, 19 mmol) in EtOH (80 mL) was added Raney nickel suspended in water (5 mL). The reaction was next evacuated and placed under a hydrogen atmosphere. The reaction was heated to 40° C. and stirred at 40° C. under a hydrogen atmosphere for 36 h. The reaction mixture was allowed to cool to RT, filtered through celite and washed with DCM. The filtrate was concentrated in vacuo, filtered and washed with distilled water. The filtrate was concentrated in vacuo to afford the title compound as a white solid (1.5 g, 44%). $^1$H NMR (300 MHz: CDCl$_3$) δ 7.47 (s, 1H), 6.74 (s, 1H), 4.33 (s, 2H), 4.05 (s, 3H), 2.34 (s, 3H).

Preparation of Int-35: tert-Butyl 2-methoxy-4-methyl-5,7-dihydro-6H-pyrrolo[3,4-b]pyridine-6-carboxylate

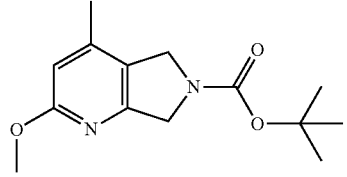 [SMILES: COc1cc(C)c2c(n1)CN(C(=O)OC(C)(C)C)C2]

To a suspension of 2-methoxy-4-methyl-5,6-dihydro-7H-pyrrolo[3,4-b]pyridin-7-one (1.5 g, 8.3 mmol) in THF (22 mL) at 0° C. was added 10 M borane dimethyl sulfide complex (4.1 mL, 41 mmol) via dropwise addition. The reaction was heated to 75° C. and stirred at 75° C. for 16 h. The reaction mixture was allowed to cool to 0° C. and quenched by the addition of MeOH (10 mL, 247 mmol) via dropwise addition followed by 6 M HCl (2.5 mL, 15 mmol) via dropwise addition. The reaction was next heated to 70° C. and stirred at 70° C. for 2 h. The reaction was allowed to cool to RT and was next basified by the addition of 2 M NaOH aqueous solution. Di-tert-butyl dicarbonate (3.6 g, 17 mmol) was added and the reaction stirred at RT for 48 h. The reaction mixture was next partitioned between EtOAc and distilled water. The organic layer was separated. The combined organic layer was washed with saturated brine, dried (Na$_2$SO$_4$) and concentrated in vacuo. The residue was purified by flash column chromatography (DCM to EtOAc, gradient elution) to afford the title compound as a white solid (760 mg, 34%). LC/MS (Table 2, Method A): R$_t$=1.53 min; m/z=265 [M+H]$^+$.

Preparation of Int-36: 4-Methyl-1,5,6,7-tetrahydro-2H-pyrrolo[3,4-b]pyridin-2-one Hydrochloride

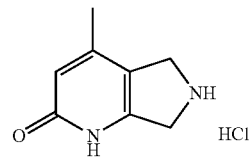

A reaction vessel was charged with tert-butyl 2-methoxy-4-methyl-5,7-dihydro-6H-pyrrolo[3,4-b]pyridine-6-carboxylate (300 mg, 1.1 mmol) and 6 M HCl in 1,4-dioxane (9.5 mL, 57 mmol). The reaction stirred at RT for 15 min and was next heated to 100° C. The reaction stirred at 100° C. for 16 h. The reaction mixture was allowed to cool to RT and next concentrated in vacuo to afford the title compound as an off-white solid (213 mg, quantitative). Material advanced to next step without characterisation.

Preparation of Int-37: tert-Butyl 4-methyl-2-oxo-1,2,5,7-tetrahydro-6H-pyrrolo[3,4-b]pyridine-6-carboxylate

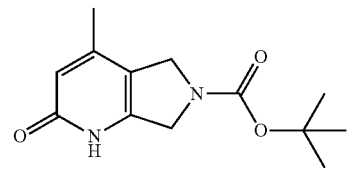 [SMILES: Cc1cc(=O)[nH]c2c1CN(C(=O)OC(C)(C)C)C2]

To a suspension of 4-methyl-1,5,6,7-tetrahydro-2H-pyrrolo[3,4-b]pyridin-2-one hydrochloride (289 mg, 1.6 mmol) in DMF (5 mL) and THF (10 mL) was added triethylamine (1.1 mL, 7.8 mmol) and di-tert-butyl dicarbonate (0.71 mL, 3.1 mmol). The reaction stirred at RT for 2 h. The reaction mixture was next concentrated in vacuo and purified directly by flash column chromatography (DCM to MeOH, gradient elution) to afford the title compound as a white solid (300 mg, 77%). LC/MS (Table 2, Method A): R$_t$=0.98 min; m/z=251 [M+H]$^+$.

Preparation of Int-38: tert-Butyl 1-(cyclopropylmethyl)-4-methyl-2-oxo-1,2,5,7-tetrahydro-6H-pyrrolo[3,4-b]pyridine-6-carboxylate

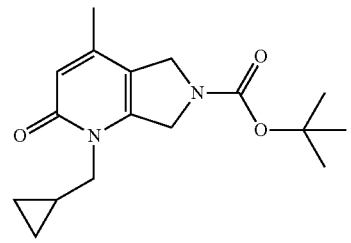 [SMILES: Cc1cc(=O)n(CC2CC2)c2c1CN(C(=O)OC(C)(C)C)C2]

To a suspension of tert-butyl 4-methyl-2-oxo-1,2,5,7-tetrahydro-6H-pyrrolo[3,4-b]pyridine-6-carboxylate (171 mg, 0.68 mmol) and potassium carbonate (283 mg, 2.1 mmol) in MeCN (0.48 mL) was added (iodomethyl)cyclopropane (0.23 mL, 2.7 mmol). The reaction was heated to 115° C. and stirred at 115° C. for 8 h. The reaction mixture was allowed to cool to RT and next partitioned between DCM and distilled water. The organic layer was separated. The combined organic layer was washed with saturated brine, dried (MgSO$_4$) and concentrated in vacuo. The residue was purified by flash column chromatography (DCM to EtOAc, gradient elution) to afford the title compound as a white solid (92 mg, 44%). $^1$H NMR (300 MHz: CDCl$_3$) δ 6.32 (s, 1H), 4.67-4.58 (m, 2H), 4.49-4.40 (m, 2H), 3.79-3.74 (m, 2H), 2.10 (s, 3H), 1.52 (s, 9H), 1.31-1.17 (m, 1H), 0.61-0.49 (m, 2H), 0.47-0.37 (m, 2H).

Preparation of Int-39: tert-Butyl 3-chloro-1-(cyclopropylmethyl)-4-methyl-2-oxo-1,2,5,7-tetrahydro-6H-pyrrolo[3,4-b]pyridine-6-carboxylate

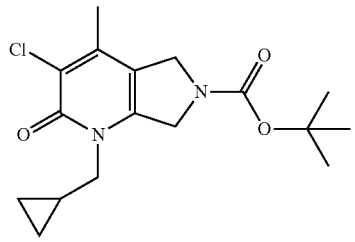 [SMILES: Cc1c2c(n(CC3CC3)c(=O)c1Cl)CN(C(=O)OC(C)(C)C)C2]

To a solution of tert-butyl 1-(cyclopropylmethyl)-4-methyl-2-oxo-1,2,5,7-tetrahydro-6H-pyrrolo[3,4-b]pyridine-6-carboxylate (92 mg, 0.76 mmol) in MeCN (1.2 mL) and DMF (0.6 mL) was added N-chlorosuccinimide (57 mg, 1.4 mmol). The reaction was heated to 55° C. and stirred at 55° C. for 1.5 h. The reaction mixture was allowed to cool to RT and next partitioned between DCM and distilled water. The organic layer was separated. The combined organic layer was washed with saturated brine, dried (Na$_2$SO$_4$) and concentrated in vacuo. The residue was purified by flash column chromatography (DCM to EtOAc, gradient elution) to afford the title compound (59 mg, 58%). LC/MS (Table 2, Method F): R$_t$=1.66 min; m/z=339 [M+H]$^+$.

Preparation of Int-40: 3-Chloro-1-(cyclopropylmethyl)-4-methyl-1,5,6,7-tetrahydro-2H-pyrrolo[3,4-b]pyridin-2-one Hydrochloride

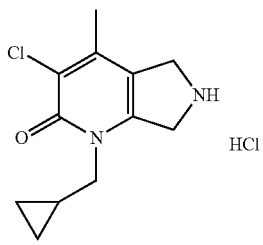 [SMILES: Cc1c2c(n(CC3CC3)c(=O)c1Cl)CNC2 ; Cl]

A reaction vessel was charged with tert-butyl 3-chloro-1-(cyclopropylmethyl)-4-methyl-2-oxo-1,2,5,7-tetrahydro-6H-pyrrolo[3,4-b]pyridine-6-carboxylate (60 mg, 0.18 mmol) and 4 M HCl in 1,4-dioxane (1.3 mL, 5.3 mmol) and the reaction stirred at RT for 2 h. The reaction mixture was next concentrated in vacuo and azeotroped with toluene to afford the title compound as an off-white solid (50 mg, quantitative). Material advanced to next step without characterisation.

Example 25—Synthesis of Compound I-69: 3-Chloro-1-(cyclopropylmethyl)-6-(2-(cyclopropylmethyl)thiazole-5-carbonyl)-4-methyl-1,5,6,7-tetrahydro-2H-pyrrolo[3,4-b]pyridin-2-one

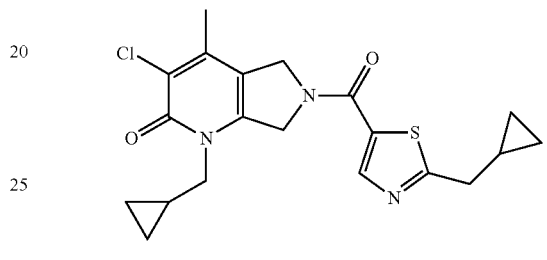

To a solution of 3-chloro-1-(cyclopropylmethyl)-4-methyl-1,5,6,7-tetrahydro-2H-pyrrolo[3,4-b]pyridin-2-one hydrochloride (26 mg, 0.095 mmol) and 2-(cyclopropylmethyl)thiazole-5-carboxylic acid (21 mg, 0.11 mmol) in DMF (1.5 mL) was added N,N-diisopropylethylamine (0.058 mL, 0.33 mmol) and HATU (65 mg, 0.17 mmol). The reaction stirred at RT for 0.5 h. The reaction mixture was next partitioned between DCM and aqueous sodium hydrogen carbonate. The organic layer was separated. The combined organic layer was washed with saturated brine, dried (Na$_2$SO$_4$) and concentrated in vacuo. The residue was purified by reverse phase HPLC (Table 3, Method 4, non-linear gradient from 20% to 80% MeCN) to afford the title compound as an off-white solid (24 mg, 61%). n$^1$H NMR (400 MHz: DMSO-d$_6$) δ 8.42 (s, 0.5H), 8.38 (s, 0.5H), 5.29-5.27 (m, 1H), 5.07-5.03 (m, 1H), 4.95 (s, 1H), 4.72 (s, 1H), 3.88 (dd, J=7.0, 15.3 Hz, 2H), 2.93 (d, J=7.0 Hz, 2H), 2.45 (d, J=7.0 Hz, 1H), 2.28 (d, J=3.4 Hz, 3H), 1.33-1.22 (m, 1H), 1.19-1.11 (m, 1H), 0.64-0.58 (m, 2H), 0.52-0.41 (m, 3H), 0.36-0.33 (m, 2H). nLC/MS (Table 2, Method B): R$_t$=4.51 min; m/z=404 [M+H]$^+$.

Example 26—Synthesis of Additional Compound

The following intermediate in Table 10 was prepared using an analogous reaction protocol to that described for Int-40 from Int-37 and the indicated starting material.

TABLE 10

Additional Compound

| Compound No. | Structure | Yield | Starting Material |
|---|---|---|---|
| Int-41 | [chlorochloromethyl-trifluoroethyl pyrrolopyridinone · HCl] | 38 mg, quantitative | F₃C-CH₂-I (2,2,2-trifluoroethyl iodide) |

Example 27—Synthesis of Additional Compounds

The following examples in Table 11 were prepared using an analogous reaction protocol to that described for 1-69 from the indicated intermediate or starting material.

TABLE 11

Additional Compounds

| Compound No. | Yield | Starting Materials | Purification Method |
|---|---|---|---|
| I-70 | 19 mg, 50% | [chloro-methyl-cyclopropylmethyl pyrrolopyridinone · HCl] and lithium 2-cyclobutylbenzo[d]thiazole-6-carboxylate | Reverse phase HPLC (Table 3, Method 4, non-linear gradient from 20% to 80% MeCN) |
| I-71 | 13 mg, 71% | [chloro-methyl-trifluoroethyl pyrrolopyridinone · HCl] and 2-(cyclopropylmethyl)thiazole-5-carboxylic acid | Flash column chromatography (DCM to EtOAc, gradient elution) |
| I-72 | 15 mg, 62% | [chloro-methyl-trifluoroethyl pyrrolopyridinone · HCl] and lithium 2-cyclopropylbenzo[d]thiazole-6-carboxylate | Flash column chromatography (DCM to EtOAc, gradient elution) |

Example 28—Synthesis of Compound Int-43: 3-Chloro-4-methoxy-1,5-dimethyl-6-(1-(trifluoromethyl)-1H-pyrazole-4-carbonyl)-1,5,6,7-tetrahydro-2H-pyrrolo[3,4-b]pyridin-2-one The title compound was prepared according to the following procedures.

Preparation of Int-42: tert-Butyl 3-chloro-4-methoxy-1,5-dimethyl-2-oxo-1,2,5,7-tetrahydro-6H-pyrrolo[3,4-b]pyridine-6-carboxylate

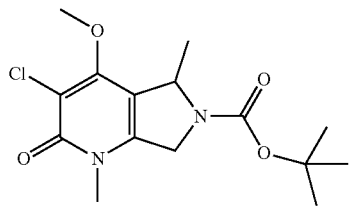 [SMILES: COc1c2c(n(C)c(=O)c1Cl)CN(C(=O)OC(C)(C)C)C2C]

To a solution of tert-butyl 4-methoxy-1,5-dimethyl-2-oxo-5,7-dihydropyrrolo[3,4-b]pyridine-6-carboxylate (164 mg, 0.56 mmol) in MeCN (2.6 mL) and DMF (1.3 mL) was added N-chlorosuccinimide (98 mg, 0.74 mmol). The reaction was allowed to warm to 50° C. and stirred at 50° C. for 20 min. The reaction mixture was allowed to cool to RT and next partitioned between distilled water and EtOAc. The organic layer was separated. The combined organic layer was washed with 5% aqueous LiCl solution, saturated brine, dried ($Na_2SO_4$), and concentrated in vacuo. The residue was purified by column chromatography (DCM to EtOAc, gradient elution) to afford the title compound as a white foam (165 mg, 90%). LC/MS (Table 2, Method A): $R_t$=1.37 min; m/z=329.1 $[M+H]^+$.

Preparation of Int-43: 3-Chloro-4-methoxy-1,5-dimethyl-1,5,6,7-tetrahydro-2H-pyrrolo[3,4-b]pyridin-2-one Hydrochloride

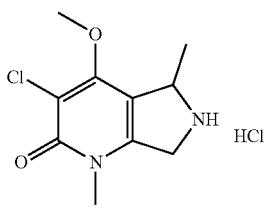

To a solution of tert-butyl 3-chloro-4-methoxy-1,5-dimethyl-2-oxo-5,7-dihydropyrrolo[3,4-b]pyridine-6-carboxylate (85 mg, 0.259 mmol) in DCM (0.3 mL) was added 4 M HCl in 1,4-dioxane (1.6 mL, 6.5 mmol) via dropwise addition and the reaction stirred at RT for 1.5 h. The reaction mixture was next concentrated in vacuo and azeotroped with MeCN to afford the title compound as a white solid (72 mg, quantitative). LC/MS (Table 2, Method A): $R_t$=0.78 min; m/z=229.0 $[M+H]^+$.

Example 29—Synthesis of Compound I-73: 3-Chloro-4-methoxy-1,5-dimethyl-6-(1-(trifluoromethyl)-1H-pyrazole-4-carbonyl)-1,5,6,7-tetrahydro-2H-pyrrolo[3,4-b]pyridin-2-one

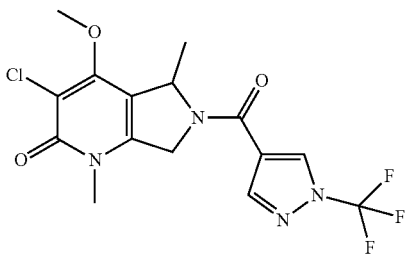 [SMILES: COc1c2c(n(C)c(=O)c1Cl)CN(C(=O)c1cnn(C(F)(F)F)c1)C2C]

To a solution of 3-chloro-4-methoxy-1,5-dimethyl-6,7-dihydro-5H-pyrrolo[3,4-b]pyridin-2-one hydrochloride (69 mg, 0.26 mmol) and 1-(trifluoromethyl)pyrazole-4-carboxylic acid (51 mg, 0.28 mmol) in DMF (1.4 mL) was added N,N-diisopropylethylamine (0.16 mL, 0.91 mmol) and HATU (108 mg, 0.28 mmol). The reaction stirred at RT for 0.5 h. The reaction mixture was purified directly by reverse phase HPLC (Table 2, Method 7) to afford the title compound as a white solid (3.6 mg, 4%). $^1$H NMR (400 MHz, DMSO-$d_6$) δ 8.31-8.27 (m, 1H), 8.10-8.05 (m, 1H), 5.58-5.36 (m, 1H), 5.01-4.96 (m, 1H), 4.85-4.74 (m, 1H), 4.18-4.09 (m, 3H), 3.54-3.49 (m, 3H), 1.60-1.40 (m, 3H). LC/MS (Table 2, Method C): $R_t$=3.77 min; m/z=391.2 $[M+H]^+$.

Example 30—Synthesis of Additional Compounds

The following compounds in Table 12 were prepared using an analogous reaction protocol to that described for I-73 from Int-43 and the indicated starting material.

TABLE 12

| | Additional Compounds | | |
|---|---|---|---|
| Compound No. | Yield | Starting Material | Purification method |
| I-74 (unknown absolute configuration) | 18 mg, 18% |  | Purified by SFC purification (Table 3, Method 7) |

TABLE 12-continued

Additional Compounds

| Compound No. | Yield | Starting Material | Purification method |
|---|---|---|---|
| I-75 (unknown absolute configuration) | 4.7 mg, 19% | 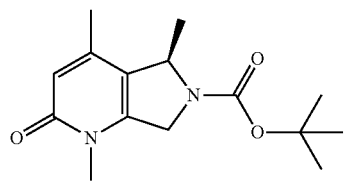 [SMILES: Cc1cc(=O)n(C)c2c1[C@@H](C)N(C(=O)OC(C)(C)C)C2] | Purified by SFC purification (Table 3, Method 7) |

Example 31—Synthesis of Compound Int-46: (R)-3-Chloro-1,4,5-trimethyl-1,5,6,7-tetrahydro-2H-pyrrolo[3,4-b]pyridin-2-one Hydrochloride The title compound was prepared according to the following procedures.

Preparation of Int-44: tert-Butyl (R)-1,4,5-trimethyl-2-oxo-1,2,5,7-tetrahydro-6H-pyrrolo[3,4-b]pyridine-6-carboxylate A reaction vessel was charged with tert-butyl-(2R)-2-methyl-4-oxo-pyrrolidine-1-carboxylate (3.5 g, 18 mmol) and 2 M methylamine in THF (44 mL, 88 mmol) and the reaction was heated to 80° C. The reaction stirred at 80° C. for 4.5 h. The reaction mixture was allowed to cool to RT and next concentrated in vacuo to afford the crude imine. In a separate reaction vessel, to a solution of 2-butynoic acid (2.1 g, 25 mmol) in DCM (84 mL) at 0° C. under a nitrogen atmosphere was added 1-chloro-N,N,2-trimethyl-1-propenylamine (3.3 mL, 25 mmol) via dropwise addition. The reaction stirred at 0° C. for 3 h. The reaction mixture solution was then added to a solution of the crude imine and triethylamine (4.7 mL, 34 mmol) in DCM (84 mL) via dropwise addition. The reaction stirred at 0° C. under a nitrogen atmosphere for 30 min. The reaction was allowed to warm to RT and stirred at RT for 6 days. The reaction mixture was quenched by the addition of saturated aqueous sodium hydrogen carbonate solution and next partitioned with DCM. The organic layer was separated, passed through a phase separator and the filtrate concentrated in vacuo. The residue was purified by flash column chromatography (DCM to EtOAc, gradient elution) to afford the title compound as an orange foam (12 g, 22%). LC/MS (Table 2, Method A): $R_t$=1.21 min; m/z=279 [M+H]$^+$.

Preparation of Int-45: tert-Butyl (R)-3-chloro-1,4,5-trimethyl-2-oxo-1,2,5,7-tetrahydro-6H-pyrrolo[3,4-b]pyridine-6-carboxylate

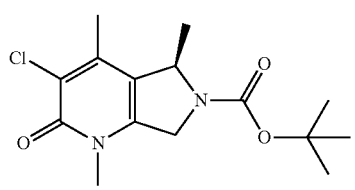 [SMILES: Cc1c2c(n(C)c(=O)c1Cl)CN(C(=O)OC(C)(C)C)[C@@H]2C]

To a solution of tert-butyl (R)-1,4,5-trimethyl-2-oxo-1,2,5,7-tetrahydro-6H-pyrrolo[3,4-b]pyridine-6-carboxylate (200 mg, 0.72 mmol) in DMF (1.7 mL) and MeCN (3.4 mL) was added N-chlorosuccinimide (124 mg, 0.93 mmol). The reaction was heated to 50° C. and stirred at 50° C. for 1 h. The reaction mixture was allowed to cool to RT and next quenched when poured into distilled water (50 mL). The reaction stirred for 30 min, was filtered and next partitioned with EtOAc. The organic layer was separated. The combined organic layer was washed with saturated brine, dried (Na$_2$SO$_4$) and concentrated in vacuo. The residue was purified by flash column chromatography (cyclohexane to EtOAc, gradient elution) to afford the title compound as a yellow solid (45 mg, 14%). LC/MS (Table 2, Method A): $R_t$=1.41 min; m/z=312 [M+H]$^+$.

Preparation of Int-46: (R)-3-Chloro-1,4,5-trimethyl-1,5,6,7-tetrahydro-2H-pyrrolo[3,4-b]pyridin-2-one Hydrochloride

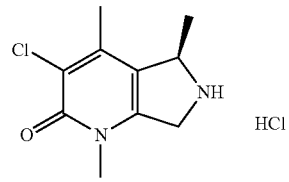

A reaction vessel was charged with tert-butyl (R)-3-chloro-1,4,5-trimethyl-2-oxo-1,2,5,7-tetrahydro-6H-pyrrolo[3,4-b]pyridine-6-carboxylate (45 mg, 0.1 mmol) and 4 M HCl in 1,4-dioxane (0.5 mL, 2 mmol) and the reaction stirred at RT for 2 h. The reaction mixture was concentrated in vacuo to afford the title compound as a red solid (33 mg, quantitative). LC/MS (Table 2, Method A): $R_t$=0.87 min; m/z=213 [M+H]$^+$.

Example 32—Synthesis of Compound I-76: (R)-3-Chloro-1,4,5-trimethyl-6-(1-(trifluoromethyl)-1H-pyrazole-4-carbonyl)-1,5,6,7-tetrahydro-2H-pyrrolo[3,4-b]pyridin-2-one

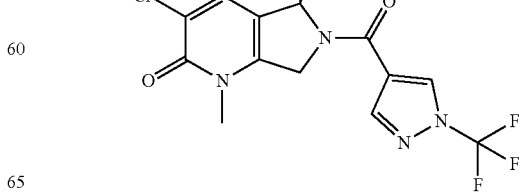

To a solution of 1-(trifluoromethyl)pyrazole-4-carboxylic acid (20 mg, 0.11 mmol) and HATU (42 mg, 0.11 mmol) in DMF (0.75 mL) was added a solution of (R)-3-chloro-1,4,5-trimethyl-1,5,6,7-tetrahydro-2H-pyrrolo[3,4-b]pyridin-2-one hydrochloride (32 mg, 0.96 mmol) and N,N-diisopropylethylamine (0.059 mL, 0.38 mmol) in DMF (0.75 mL). The reaction stirred at RT for 5 h. The reaction mixture was next concentrated in vacuo and purified directly by reverse phase HPLC (Table 3, Method 4) to afford the title compound as an off-white solid (23 mg, 65%). $^1$H NMR (400 MHz: DMSO-d$_6$) δ 9.10 (s, 0.2H), 9.05 (s, 0.8H), 8.42 (s, 0.2H), 8.37 (s, 0.8H), 5.64-5.60 (m, 0.2H), 5.44-5.39 (m, 0.8H), 5.23 (dd, J=2.8, 15.4 Hz, 0.8H), 5.04 (d, J=15.2 Hz, 0.8H), 4.93 (d, J=17.2 Hz, 0.2H), 4.81 (dd, J=2.4, 17.3 Hz, 0.2H), 3.47-3.45 (m, 3H), 2.31-2.28 (m, 3H), 1.43 (d, J=6.1 Hz, 2.4H), 1.27 (d, J=6.1 Hz, 0.6H). LC/MS (Table 2, Method B): R$_t$=3.68 min; m/z=375 [M+H]$^+$.

Example 33—Synthesis of Additional Compound

The following compound in Table 13 was prepared using an analogous reaction protocol to that described for I-76 from the indicated Int-46 and starting material.

TABLE 13

Additional Compound

| Compound No. | Yield | Starting Material | Purification Method |
|---|---|---|---|
| I-77 | 6.8 mg, 1% | 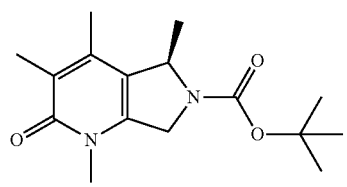 [SMILES: Cc1c2c(n(C)c(=O)c1C)CN(C(=O)OC(C)(C)C)[C@@H]2C] | Reverse phase HPLC (Table 3, Method 8) |

Example 34—Synthesis of Int-48: (R)-1,3,4,5-Tetramethyl-1,5,6,7-tetrahydro-2H-pyrrolo[3,4-b]pyridin-2-one Hydrochloride The title compound was prepared according to the following procedures.

Preparation of Int-47: tert-Butyl (R)-1,3,4,5-tetramethyl-2-oxo-1,2,5,7-tetrahydro-6H-pyrrolo[3,4-b]pyridine-6-carboxylate

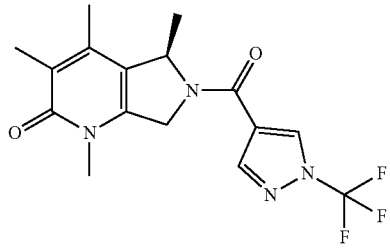

A reaction vessel was charged with tert-butyl (R)-3-chloro-1,4,5-trimethyl-2-oxo-5,7-dihydropyrrolo[3,4-b]pyridine-6-carboxylate (715 mg, 2.3 mmol), potassium carbonate (950 mg, 6.9 mmol), Pd(dppf)Cl$_2$ (170 mg, 0.23 mmol), trimethylboroxine (0.48 mL, 3.4 mmol) and solvated in 1,4-dioxane (18 mL). The reaction was evacuated, purged with argon (×3), heated to 100° C. and stirred at 100° C. for 16 h. The reaction mixture was allowed to cool to RT and trimethylboroxine (0.3 mL) was added, followed by the addition of Pd(dppf)Cl$_2$ (85 mg). The reaction was allowed to warm to 100° C. and stirred at 100° C. for 16 h. The reaction mixture was allowed to cool to RT, filtered through celite, and washed with EtOAc. The filtrate was concentrated in vacuo and the residue was purified by flash column chromatography (TBME to EtOAc/IMS (3:1), gradient elution) to afford the title compound as a brown gum (470 mg, 70%). LC/MS (Table 2, Method F): R$_t$=1.51 min; m/z=293.2 [M+H]$^+$.

Preparation of Int-48: (R)-1,3,4,5-Tetramethyl-1,5,6,7-tetrahydro-2H-pyrrolo[3,4-b]pyridin-2-one Hydrochloride

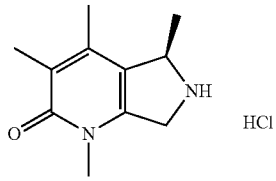

To a solution of tert-butyl (R)-1,3,4,5-tetramethyl-2-oxo-5,7-dihydropyrrolo[3,4-b]pyridine-6-carboxylate (470 mg, 1.5 mmol) in DCM (2 mL) was added 4 M HCl in 1,4-dioxane (9.0 mL, 36 mmol) via dropwise addition and the reaction stirred at RT for 1.5 h. The reaction mixture was concentrated in vacuo and azeotroped with MeCN to afford the title compound as a brown solid (395 mg, quantitative). LC/MS (Table 2, Method A): R$_t$=0.91 min; m/z=193.1 [M+H]$^+$.

Example 35—Synthesis of Compound I-78: (R)-1,3,4,5-Tetramethyl-6-(1-(trifluoromethyl)-1H-pyrazole-4-carbonyl)-1,5,6,7-tetrahydro-2H-pyrrolo[3,4-b]pyridin-2-one To a solution of (5R)-1,3,4,5-tetramethyl-6,7-dihydro-5H-pyrrolo[3,4-b]pyridin-2-one hydrochloride (330 mg, 1.4 mmol) in DMF (6 mL) was added N,N-diisopropylethylamine (0.88 mL, 5.1 mmol) followed by a solution of 1-(trifluoromethyl)pyrazole-4-carboxylic acid (286 mg, 1.6 mmol) and HATU (603 mg, 1.6 mmol) in DMF (6 mL). The reaction stirred at RT for 1 h. The reaction mixture was concentrated in vacuo and purified directly by reverse phase HPLC (Table 3, Method 8) to afford the title compound as an off-white solid (247 mg, 48%). $^1$H NMR (400 MHz: DMSO-d$_6$) δ 9.10 (s, 0.2H), 9.04 (s, 0.8H), 8.42 (s, 0.2H), 8.37 (s, 0.8H), 5.58-5.56 (m, 0.2H), 5.39-5.32 (m, 0.8H), 5.21 (d, J=15.0 Hz, 0.8H), 4.99 (d, J=14.9 Hz, 0.8H), 4.88 (d, J=16.9 Hz, 0.2H), 4.78 (d, J=16.9 Hz, 0.2H), 3.39 (d, J=4.2 Hz, 3H), 2.14 (d, J=5.9 Hz, 3H), 1.99 (s, 3H), 1.41 (d, J=6.1 Hz, 2.3H), 1.24 (d, J=6.0 Hz, 0.7H). LC/MS (Table 2, Method C): R$_t$=3.44 min; m/z=355 [M+H]$^+$.

Example 36—Synthesis of Compound Int-54: 4-Methoxy-1,5-dimethyl-1,5,6,7-tetrahydro-2H-pyrrolo[3,4-b]pyridin-2-one Hydrochloride The title compound was prepared according to the following procedures.

Preparation of Int-49: 1-(tert-Butyl) 3-ethyl 2-methyl-4-oxopyrrolidine-1,3-dicarboxylate

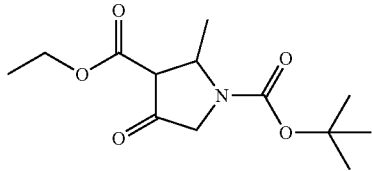 [SMILES: CCOC(=O)C1C(=O)CN(C(=O)OC(C)(C)C)C1C]

To a solution of ethyl 2-(tert-butoxycarbonylamino)acetate (13 g, 65 mmol) and ethyl trans-2-butenoate (10 mL, 84 mmol) in THF (210 mL) at 0° C. was added 1 M potassium tert-butoxide in THF (77 mL, 77 mmol) via dropwise addition over a period of 20 min. The reaction was allowed to warm to RT and stirred at RT for 16 h. The reaction mixture was quenched by the addition of 10% citric acid aqueous solution (75 mL) and next partitioned with EtOAc. The organic layer was separated. The combined organic layer was dried (Na$_2$SO$_4$) and concentrated in vacuo. The residue was purified by flash column chromatography (cyclohexane to diethyl ether, gradient elution) to afford the title compound as a light yellow oil (11 g, 65%). LC/MS (Table 2, Method A): R$_t$=1.42 min; UV only.

Preparation of Int-50: 1-(tert-Butyl) 3-ethyl 2-methyl-4-(methylamino)-2,5-dihydro-1H-pyrrole-1,3-dicarboxylate

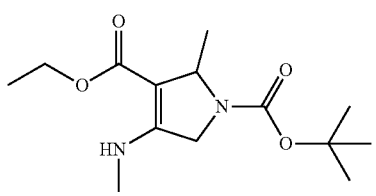 [SMILES: CCOC(=O)C1=C(NC)CN(C(=O)OC(C)(C)C)C1C]

To a solution of 1-(tert-butyl) 3-ethyl 2-methyl-4-oxopyrrolidine-1,3-dicarboxylate (5 g, 18 mmol) in acetic acid (23 mL) at 0° C. was added 2 M methylamine in THF (14 mL, 29 mmol). The reaction was allowed to warm to RT and stirred at RT for 16 h. The reaction mixture was next partitioned between DCM and saturated aqueous sodium hydrogen carbonate solution. The organic layer was separated. The combined organic layer was washed with saturated brine, passed through a phase separator and the filtrate was concentrated in vacuo to afford the title compound as an orange oil (5.2 g, 99%). LC/MS (Table 2, Method A): R$_t$=1.74 min; m/z=285 [M+H]$^+$.

Preparation of Int-51: 1-(tert-Butyl) 3-ethyl 2-methyl-4-(N-methylacetamido)-2,5-dihydro-1H-pyrrole-1,3-dicarboxylate

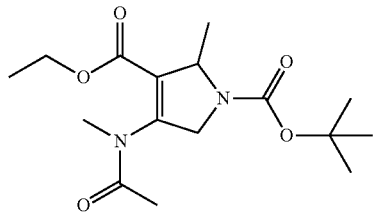 [SMILES: CCOC(=O)C1=C(N(C)C(C)=O)CN(C(=O)OC(C)(C)C)C1C]

To a solution of 1-(tert-Butyl) 3-ethyl 2-methyl-4-(methylamino)-2,5-dihydro-1H-pyrrole-1,3-dicarboxylate (6.7 g, 24 mmol) in 1,4-dioxane (80 mL) was added sodium hydride (60%, 1.9 g, 47 mmol) and the reaction stirred at RT for 15 min. Acetyl chloride (2.5 mL, 35 mmol) was then added and the reaction mixture was stirred at 40° C. for 3 h. The reaction mixture was next partitioned between distilled water and EtOAc. The organic layer was separated. The combined organic layer was dried (MgSO$_4$), concentrated in vacuo and the residue was purified by flash column chromatography (cyclohexane to EtOAc, gradient elution) to afford the title compound as an oil (4.3 g, 55%). $^1$H NMR (400 MHz, CDCl3) δ 4.97-4.77 (m, 1H), 4.45-4.09 (m, 4H), 3.09-3.04 (m, 3H), 2.07-2.03 (m, 3H), 1.50-1.43 (m, 9H), 1.32-1.24 (m, 6H).

Preparation of Int-52: tert-Butyl 4-hydroxy-1,5-dimethyl-2-oxo-1,2,5,7-tetrahydro-6H-pyrrolo[3,4-b]pyridine-6-carboxylate

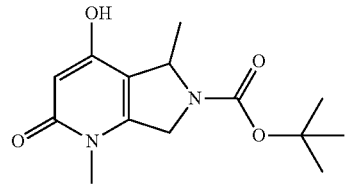 [SMILES: CC1c2c(O)cc(=O)n(C)c2CN1C(=O)OC(C)(C)C]

To a solution of 1-(tert-butyl) 3-ethyl 2-methyl-4-(N-methylacetamido)-2,5-dihydro-1H-pyrrole-1,3-dicarboxylate (2.4 g, 7.4 mmol) in THF (72 mL) under a nitrogen atmosphere was added 1 M potassium tert-butoxide in THF (15 mL, 15 mmol) and the reaction stirred at RT for 0.25 h. The reaction mixture was partitioned between distilled water and EtOAc. The aqueous phase was acidified and further partitioned with EtOAc. The organic layer was separated. The combined organic layer was dried (MgSO$_4$), concentrated in vacuo and triturated with diethyl ether to give the title compound as a white solid (1.5 g, 74%). $^1$H NMR (400

MHz, CDCl₃) δ 6.12 (s, 1H), 5.08-4.97 (m, 1H), 4.70 (d, J=15.8 Hz, 1H), 4.58-4.49 (m, 1H), 3.43 (s, 3H), 1.54-1.46 (m, 12H).

Preparation of Int-53: tert-Butyl 4-methoxy-1,5-dimethyl-2-oxo-1,2,5,7-tetrahydro-6H-pyrrolo[3,4-b]pyridine-6-carboxylate

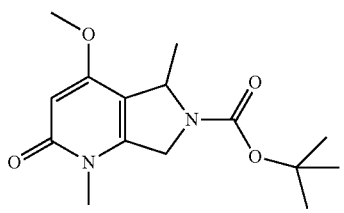 [SMILES: COc1cc(=O)n(C)c2c1C(C)N(C(=O)OC(C)(C)C)C2]

To a solution of tert-butyl 4-hydroxy-1,5-dimethyl-2-oxo-1,2,5,7-tetrahydro-6H-pyrrolo[3,4-b]pyridine-6-carboxylate (400 mg, 1.4 mmol) in DMF (13 mL) was added potassium carbonate (296 mg, 2.1 mmol) and iodomethane (0.27 mL, 4.3 mmol). The reaction stirred at RT for 1.75 h. The reaction mixture was partitioned between distilled water and EtOAc. The organic layer was separated. The combined organic layer was washed with 5% LiCl aqueous solution, saturated brine, dried (Na₂SO₄) and concentrated in vacuo. The residue was purified by flash column chromatography (DCM to MeOH, gradient elution) to afford the title compound as a white foam (186 mg, 44%). LC/MS (Table 1, Method A): $R_t$=1.27 min; m/z=295.0 [M+H]⁺.

Preparation of Int-54: 4-Methoxy-1,5-dimethyl-1,5,6,7-tetrahydro-2H-pyrrolo[3,4-b]pyridin-2-one Hydrochloride

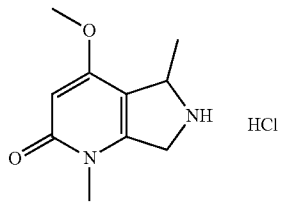

To a solution of tert-butyl 4-methoxy-1,5-dimethyl-2-oxo-1,2,5,7-tetrahydro-6H-pyrrolo[3,4-b]pyridine-6-carboxylate (20 mg, 0.068 mmol) in DCM (0.10 mL) was added 4 M HCl in 1,4-dioxane (0.42 mL, 1.7 mmol) via dropwise addition and the reaction stirred at RT for 2 h. The reaction mixture was concentrated in vacuo and azeotroped with MeCN to afford the title compound as a white solid (16 mg, quantitative). LC/MS (Table 1, Method A): $R_t$=0.64 min; m/z=195.1 [M+H]⁺.

Example 37—Synthesis of Compound I-79: 4-Methoxy-1,5-dimethyl-6-(1-(trifluoromethyl)-1H-pyrazole-4-carbonyl)-1,5,6,7-tetrahydro-2H-pyrrolo[3,4-b]pyridin-2-one

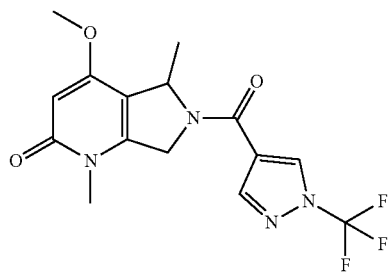 [SMILES: COc1cc(=O)n(C)c2c1C(C)N(C(=O)c1cnn(C(F)(F)F)c1)C2]

To a solution of 4-methoxy-1,5-dimethyl-6,7-dihydro-5H-pyrrolo[3,4-b]pyridin-2-one hydrochloride (16 mg, 0.068 mmol) in DMF (0.25 mL) was added N,N-diisopropylethylamine (0.041 mL, 0.24 mmol) followed by a solution of 1-(trifluoromethyl)pyrazole-4-carboxylic acid (13 mg, 0.075 mmol) and HATU (28 mg, 0.075 mmol) in DMF (0.25 mL). The reaction stirred at RT for 1 h. The reaction mixture was purified directly by reverse phase HPLC (Table 3, Method 8) to afford the title compound as a white solid (3.4 mg, 14%). ¹H NMR (400 MHz: CDCl₃) δ 8.28 (d, J=9.3 Hz, 1H), 8.09 (d, J=13.7 Hz, 1H), 5.89 (s, 1H), 5.48 (s, 0.4H), 5.34 (s, 0.6H), 4.97-4.92 (m, 1H), 4.83-4.75 (m, 1H), 3.82 (s, 3.82 (s, 3H), 3.43 (d, J=12.7 Hz, 3H), 1.53 (d, J=6.4 Hz, 1.5H, obscured by solvent peak), 1.42 (d, J=6.0 Hz, 1.5H). LC/MS (Table 2, Method C): $R_t$=3.45 min; m/z=357.3 [M+H]⁺.

Example 38—Synthesis of Additional Compounds

The following compounds in Table 14 were prepared using an analogous reaction protocol to that described for I-79 from Int-54 and the indicated starting material.

TABLE 14

Additional Compounds

| Compound No. | Yield | Starting Material | Purification method |
|---|---|---|---|
| I-80 (unknown absolute configuration) | 4 mg, 16% | | Purified by SFC purification (Table 3, Method 7) |
| I-81 (unknown absolute configuration) | 4.7 mg, 19% | | Purified by SFC purification (Table 3, Method 7) |

Example 39—Synthesis of Compound Int-58: 4-Methoxy-1,3,5-trimethyl-1,5,6,7-tetrahydro-2H-pyrrolo[3,4-b]pyridin-2-one Hydrochloride The title compound was prepared according to the following procedures.

Preparation of Int-55: 1-(tert-Butyl) 3-ethyl 2-methyl-4-(N-methylpropionamido)-2,5-dihydro-1H-pyrrole-1,3-dicarboxylate

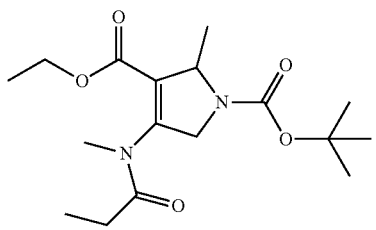 [SMILES: CCOC(=O)C1=C(N(C)C(=O)CC)CN(C(=O)OC(C)(C)C)C1C]

A reaction vessel was charged with 1-(tert-butyl) 3-ethyl 2-methyl-4-(methylamino)-2,5-dihydro-1H-pyrrole-1,3-dicarboxylate (4.9 g, 17 mmol) and solvated in propionic anhydride (17 mL, 129 mmol. The reaction was heated to 150° C. and stirred at 150° C. for 5 h. The reaction mixture was allowed to cool to RT and next concentrated in vacuo to afford the title compound as a dark red oil (6.4 g, quantitative). LC/MS (Table 2, Method A): $R_t$=1.68 min; m/z=341 [M+H]$^+$.

Preparation of Int-56: tert-Butyl 4-hydroxy-1,3,5-trimethyl-2-oxo-1,2,5,7-tetrahydro-6H-pyrrolo[3,4-b]pyridine-6-carboxylate

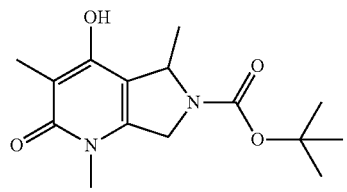 [SMILES: Cc1c(O)c2c(n(C)c1=O)CN(C(=O)OC(C)(C)C)C2C]

To a solution of 1-(tert-butyl) 3-ethyl 2-methyl-4-(N-methylpropionamido)-2,5-dihydro-1H-pyrrole-1,3-dicarboxylate (6.4 g, 19 mmol) in THF (95 mL) was added potassium tert-butoxide (11 g, 94 mmol) and the reaction stirred at RT for 10 min. The reaction mixture was allowed to cool to 0° C. and next quenched by the addition of TBME (50 mL), 5 M acetic acid in TBME (20 mL) and distilled water (30 mL). The reaction mixture was allowed to warm to RT, concentrated in vacuo and next partitioned with DCM. The organic layer was separated. The combined organic layer was washed with saturated brine, dried (Na$_2$SO$_4$) and concentrated in vacuo. The residue was purified by flash column chromatography (cyclohexane in IPA, gradient elution) to afford the title compound as an orange foam (1.34 g, 24%). LC/MS (Table 2, Method A): $R_t$=0.69 min; m/z=298 [M+H]$^+$.

Preparation of Int-57: tert-Butyl 4-methoxy-1,3,5-trimethyl-2-oxo-1,2,5,7-tetrahydro-6H-pyrrolo[3,4-b]pyridine-6-carboxylate

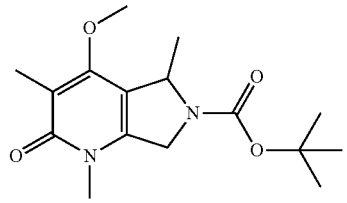 [SMILES: COc1c2c(n(C)c(=O)c1C)CN(C(=O)OC(C)(C)C)C2C]

To a suspension of tert-butyl 4-hydroxy-1,3,5-trimethyl-2-oxo-1,2,5,7-tetrahydro-6H-pyrrolo[3,4-b]pyridine-6-carboxylate (500 mg, 1.7 mmol) in THF (8 mL) was added trimethyloxonium tetrafluoroborate (502 mg, 3.4 mmol). The reaction was allowed to cool to 0° C. and sodium hydride (60%, 82 mg, 2.0 mmol) was added portionwise. The reaction stirred at 0° C. for 1.5 h. The reaction mixture was next partitioned between EtOAc and distilled water. The organic layer was separated. The combined organic layer was washed with saturated brine, dried (Na$_2$SO$_4$) and concentrated in vacuo. The residue was purified by flash column chromatography (cyclohexane in acetone, gradient elution) to afford the title compound as a brown oil (200 mg, 38%). LC/MS (Table 2, Method A): $R_t$=1.19 min; m/z=309 [M+H]$^+$.

Preparation of Int-58: 4-Methoxy-1,3,5-trimethyl-1,5,6,7-tetrahydro-2H-pyrrolo[3,4-b]pyridin-2-one Hydrochloride

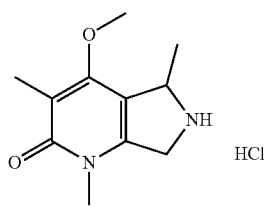

To a solution of tert-butyl 4-methoxy-1,3,5-trimethyl-2-oxo-1,2,5,7-tetrahydro-6H-pyrrolo[3,4-b]pyridine-6-carboxylate (200 mg, 0.65 mmol) in DCM (1.6 mL) was added 4 M HCl in 1,4-dioxane (1.6 mL, 6.5 mmol) and the reaction stirred at RT for 16 h. The reaction mixture was next concentrated in vacuo to afford the title compound as a dark red solid (181 mg, quantitative). LC/MS (Table 2, Method A): $R_t$=0.72 min; m/z=209 [M+H]$^+$.

Example 40—Synthesis of Compound I-82: 4-Methoxy-1,3,5-trimethyl-6-(1-(trifluoromethyl)-1H-pyrazole-4-carbonyl)-1,5,6,7-tetrahydro-2H-pyrrolo[3,4-b]pyridin-2-one As a Racemic Mixture of Stereoisomers

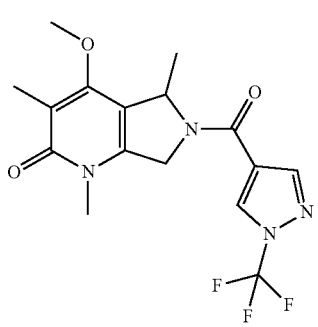 [SMILES: COc1c2c(n(C)c(=O)c1C)CN(C(=O)c1cnn(C(F)(F)F)c1)C2C]

To a solution of 1-(trifluoromethyl)pyrazole-4-carboxylic acid (81 mg, 0.45 mmol) in DMF (1.25 mL) was added HATU (171 mg, 0.45 mmol) followed by a solution of 4-methoxy-1,3,5-trimethyl-1,5,6,7-tetrahydro-2H-pyrrolo[3,4-b]pyridin-2-one hydrochloride (100 mg, 0.41 mmol) and N,N-diisopropylethylamine (0.21 mL, 1.23 mmol) in DMF (1.25 mL). The reaction stirred at RT for 1 h. The reaction mixture was next purified directly by reverse phase HPLC (Table 3, Method 2) to afford the title compound as an off-white solid (88 mg, 58%). $^1$H NMR (400 MHz: DMSO-$d_6$) δ 9.05 (s, 1H), 8.37 (s, 1H), 5.48-5.42 (m, 1H), 5.22-5.18 (m, 1H), 5.05-5.00 (m, 1H), 3.82 (s, 3H), 3.38 (s, 3H), 1.94 (s, 3H), 1.44 (d, J=5.7 Hz, 3H). LC/MS (Table 2, Method C): $R_t$=3.40 min; m/z=371 [M+H]$^+$.

Example 41—Synthesis of Additional Compounds

The following compounds in Table 15 were prepared using an analogous reaction protocol to that described for I-82 from Int-58 and the indicated starting material.

Example 42—Synthesis of Int-59: 4-Methoxy-1,3-dimethyl-1,5,6,7-tetrahydro-2H-pyrrolo[3,4-b]pyridin-2-one Hydrochloride

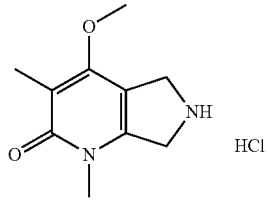

To a solution of tert-butyl 4-methoxy-1,3-dimethyl-2-oxo-5,7-dihydropyrrolo[3,4-b]pyridine-6-carboxylate (100 mg, 0.34 mmol) in DCM (0.2 mL) was added 4 M HCl in 1,4-dioxane (2.1 mL, 8.5 mmol). The reaction stirred at RT for 2 h. The reaction mixture was next concentrated in vacuo to afford the title compound as a pink solid (90 mg, quantitative). LC/MS (Table 2, Method A): $R_t$=0.72 min; m/z=195 [M+H]$^+$.

Example 43—Synthesis of Compound I-85: 4-Methoxy-1,3-dimethyl-6-(1-(2,2,2-trifluoroethyl)-1H-pyrazole-4-carbonyl)-1,5,6,7-tetrahydro-2H-pyrrolo[3,4-b]pyridin-2-one

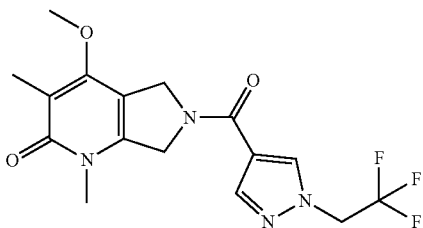 [SMILES: COc1c2c(n(C)c(=O)c1C)CN(C(=O)c1cnn(CC(F)(F)F)c1)C2]

To a solution of lithium 1-(2,2,2-trifluoroethyl)-1H-pyrazole-4-carboxylate (39 mg, 0.20 mmol) and N,N-diisopropylethylamine (0.10 mL, 0.59 mmol) in DMF (2 mL) was added HATU (96 mg, 0.25 mmol) and 4-methoxy-1,3-dimethyl-1,5,6,7-tetrahydro-2H-pyrrolo[3,4-b]pyridin-2-one hydrochloride (45 mg, 0.20 mmol). The reaction stirred

TABLE 15

Additional Compounds

| Compound No. | Yield | Starting Material | Purification method |
|---|---|---|---|
| I-83 Single stereoisomer of unknown absolute configuration | 35 mg, 23% | | Purified by SFC purification (Table 3, Method 7) |
| I-84 Single stereoisomer of unknown absolute configuration | 29 mg, 19% | | Purified by SFC purification (Table 3, Method 7) | at RT for 2 h. The reaction mixture was next partitioned between EtOAc and saturated aqueous sodium hydrogen carbonate. The organic layer was separated. The combined organic layer was washed with saturated brine, dried (Na$_2$SO$_4$) and concentrated in vacuo. The residue was purified by reverse phase HPLC (Table 3, Method 1, non-linear gradient from 40% to 100% MeOH) to afford the title compound as an off-white solid (40 mg, 55%). $^1$H NMR (400 MHz: DMSO-d$_6$) δ 8.53-8.49 (m, 1H), 8.15-8.10 (m, 1H), 5.29-5.09 (m, 4H), 4.89 (s, 1H), 4.83 (s, 1H), 3.94-3.92 (m, 3H), 3.43-3.41 (m, 3H), 1.91 (s, 3H). LC/MS (Table 2, Method E): R$_t$=3.07 min; m/z=371 [M+H]$^+$.

Example 44—Synthesis of Additional Compounds

The following compounds in Table 16 were prepared using an analogous reaction protocol to that described for I-85 from Int-59 and the indicated starting material.

TABLE 16

Additional Compounds

| Compound No. | Yield | Starting Materials | Purification method |
|---|---|---|---|
| I-86 | 16 mg, 20% | (2-(cyclopropylmethyl)thiazole-5-carboxylic acid) | Flash column chromatography (DCM to MeOH, gradient elution) |
| I-87 | 41 mg, 53% | (1-(trifluoromethyl)-1H-pyrazole-4-carboxylic acid) | Reverse phase HPLC (Table 3, Method 3) |

Example 45—Synthesis of Compound Int-61: 4-Ethoxy-1,3-dimethyl-1,5,6,7-tetrahydro-2H-pyrrolo[3,4-b]pyridin-2-one Hydrochloride The title compound was prepared according to the following procedures.

Preparation of Int-60: tert-Butyl 4-ethoxy-1,3-dimethyl-2-oxo-1,2,5,7-tetrahydro-6H-pyrrolo[3,4-b]pyridine-6-carboxylate

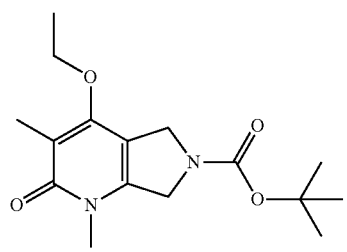 [SMILES: CCOc1c2c(n(C)c(=O)c1C)CN(C(=O)OC(C)(C)C)C2]

To a suspension of sodium hydride (60%, 80 mg, 2.0 mmol) in THF (10 mL) at 0° C. was added tert-butyl 4-hydroxy-1,3-dimethyl-2-oxo-5,7-dihydropyrrolo[3,4-b] pyridine-6-carboxylate (280 mg, 1.0 mmol) and the reaction stirred at 0° C. for 15 min. The reaction was allowed to warm to RT and triethyloxonium tetrafluoroborate (380 mg, 2.0 mmol) was added. The reaction stirred at RT for 1 h. The reaction mixture was next partitioned between EtOAc and distilled water. The organic layer was separated. The combined organic layer was washed with saturated brine, dried (Na$_2$SO$_4$) and concentrated in vacuo. The residue was purified by flash column chromatography (DCM in MeOH, gradient elution) followed by flash column chromatography (EtOAc in IMS, gradient elution) to afford the title compound as a colourless oil (74 mg, 18%). $^1$H NMR (400 MHz: CDCl$_3$) δ 4.66-4.53 (m, 4H), 4.09-3.96 (m, 2H), 3.49-3.42 (m, 3H), 2.06 (d, J=5.9 Hz, 3H), 1.52 (s, 9H), 1.41-1.32 (m, 3H).

Preparation of Int-61: 4-Ethoxy-1,3-dimethyl-1,5,6,7-tetrahydro-2H-pyrrolo[3,4-b]pyridin-2-one Hydrochloride To a solution of tert-butyl 4-ethoxy-1,3-dimethyl-2-oxo-1,2,5,7-tetrahydro-6H-pyrrolo[3,4-b]pyridine-6-carboxylate (70 mg, 0.23 mmol) in DCM (0.5 mL) was added 4 M HCl in 1,4-dioxane (1.4 mL, 5.7 mmol) and the reaction stirred at RT for 1.5 h. The reaction mixture was next concentrated in vacuo and azeotroped with MeCN to afford the title compound as a brown solid (54 mg, 57%). LC/MS (Table 2, Method A): R$_t$=1.33 min; m/z=209 [M+H]$^+$.

Example 46—Synthesis of Compound I-88: 4-Ethoxy-1,3-dimethyl-6-(1-(trifluoromethyl)-1H-pyrazole-4-carbonyl)-1,5,6,7-tetrahydro-2H-pyrrolo[3,4-b]pyridin-2-one

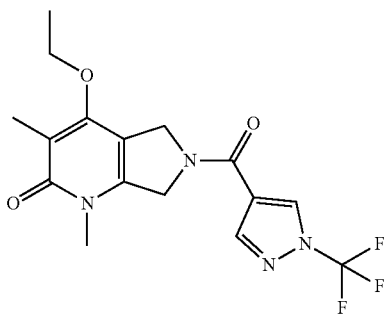 [SMILES: CCOc1c2c(n(C)c(=O)c1C)CN(C(=O)c1cnn(C(F)(F)F)c1)C2]

To a solution of 1-(trifluoromethyl)pyrazole-4-carboxylic acid (30 mg, 0.17 mmol) and N,N-diisopropylethylamine (0.068 mL, 0.39 mmol) in DMF (2 mL) was added HATU (74 mg, 0.20 mmol) and 4-ethoxy-1,3-dimethyl-1,5,6,7-tetrahydro-2H-pyrrolo[3,4-b]pyridin-2-one hydrochloride (54 mg, 0.13 mmol). The reaction stirred at RT for 1.25 h. The reaction mixture was next partitioned between EtOAc and saturated aqueous sodium hydrogen carbonate solution. The organic layer was separated. The combined organic layer was washed with saturated brine, dried ($Na_2SO_4$) and concentrated in vacuo. The residue was purified by reverse phase HPLC (Table 3, Method 4) to afford the title compound as an off-white solid (21 mg, 42%). $^1$H NMR (400 MHz: DMSO-$d_6$) δ 9.10-9.08 (m, 1H), 8.41 (s, 1H), 5.16-5.11 (m, 2H), 4.88-4.82 (m, 2H), 4.18-4.10 (m, 2H), 3.41-3.40 (m, 3H), 1.93 (s, 3H), 1.35-1.29 (m, 3H). LC/MS (Table 2, Method E): $R_t$=3.49 min; m/z=371 [M+H]$^+$.

Example 47—Synthesis of Compound Int-63: 4-(Difluoromethoxy)-1,3-dimethyl-1,5,6,7-tetrahydro-2H-pyrrolo[3,4-b]pyridin-2-one hydrochloride The title compound was prepared according to the following procedures.

Preparation of Int-62: tert-Butyl 4-(difluoromethoxy)-1,3-dimethyl-2-oxo-1,2,5,7-tetrahydro-6H-pyrrolo[3,4-b]pyridine-6-carboxylate

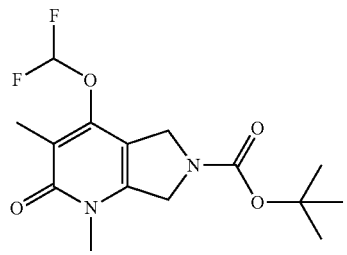 [SMILES: Cc1c(OC(F)F)c2c(n(C)c1=O)CN(C(=O)OC(C)(C)C)C2]

To a suspension of tert-butyl 4-hydroxy-1,3-dimethyl-2-oxo-5,7-dihydropyrrolo[3,4-b]pyridine-6-carboxylate (100 mg, 0.18 mmol) in DMF (0.9 mL) was added cesium carbonate (116 mg, 0.36 mmol) and the reaction was next heated to 100° C. Methyl chlorodifluoroacetate (0.038 mL, 0.36 mmol) was added and the reaction stirred at 100° C. for 2.5 h. The reaction mixture was next partitioned between EtOAc and distilled water. The organic layer was separated. The combined organic layer was washed with saturated brine, dried ($Na_2SO_4$) and concentrated in vacuo. The residue was purified by reverse phase HPLC (Table 3, Method 8) to afford the title compound as a white solid (130 mg, quantitative). LC/MS (Table 2, Method A): $R_t$=1.79 min; m/z=331 [M+H]$^+$.

Preparation of Int-63: 4-(Difluoromethoxy)-1,3-dimethyl-1,5,6,7-tetrahydro-2H-pyrrolo[3,4-b]pyridin-2-one Hydrochloride

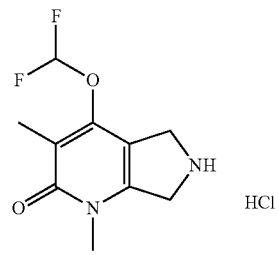 [SMILES: Cc1c(OC(F)F)c2c(n(C)c1=O)CNC2 ; Cl]

To a solution of tert-butyl 4-(difluoromethoxy)-1,3-dimethyl-2-oxo-1,2,5,7-tetrahydro-6H-pyrrolo[3,4-b]pyridine-6-carboxylate (70 mg, 0.21 mmol) in DCM (0.5 mL) was added 4 M HCl in 1,4-dioxane (1.3 mL, 5.3 mmol). The reaction stirred at RT for 1 h. The reaction mixture was next concentrated in vacuo and azeotroped with MeCN to afford the title compound as a brown solid (59 mg, 99%). LC/MS (Table 2, Method A): $R_t$=1.38 min; m/z=231 [M+H]$^+$.

Example 48—Synthesis of Compound I-89: 4-(Difluoromethoxy)-1,3-dimethyl-6-(1-(trifluoromethyl)-1H-pyrazole-4-carbonyl)-1,5,6,7-tetrahydro-2H-pyrrolo[3,4-b]pyridin-2-one

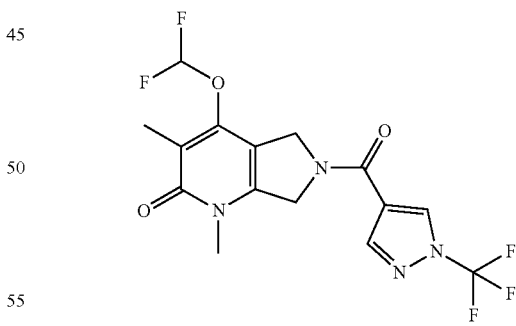

To a solution of 4-(difluoromethoxy)-1,3-dimethyl-1,5,6,7-tetrahydro-2H-pyrrolo[3,4-b]pyridin-2-one hydrochloride (56 mg, 0.21 mmol) and N,N-diisopropylethylamine (0.013 mL, 0.74 mmol) in DMF (0.75 mL) was added a solution of 1-(trifluoromethyl)pyrazole-4-carboxylic acid (44 mg, 0.24 mmol) and HATU (92 mg, 0.24 mmol) in DMF (0.75 mL). The reaction stirred at RT for 30 min. The reaction mixture concentrated in vacuo and purified directly by reverse phase HPLC (Table 3, Method 4) to afford the title compound as an off-white solid (69 mg, 83%). $^1$H NMR (400 MHz:

DMSO-$d_6$) δ 9.11-9.07 (m, 1H), 8.43-8.37 (m, 1H), 7.38-6.96 (m, 1H), 5.24-5.22 (m, 1H), 5.01 (t, J=2.4 Hz, 1H), 4.94 (s, 1H), 4.72 (s, 1H), 3.46 (s, 3H), 1.99 (s, 3H). LC/MS (Table 2, Method B): $R_t$=3.67 min; m/z=393 [M+H]$^+$.

Example 49—Synthesis of Compound Int-64: 1,3-Dimethyl-4-(methylthio)-1,5,6,7-tetrahydro-2H-pyrrolo[3,4-b]pyridin-2-one Hydrochloride

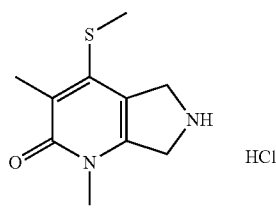

A reaction vessel was charged with tert-butyl 1,3-dimethyl-4-methylsulfanyl-2-oxo-5,7-dihydropyrrolo[3,4-b]pyridine-6-carboxylate (330 mg, 1.1 mmol) and 4 M HCl in 1,4-dioxane (5.3 mL, 21 mmol). The reaction stirred at RT for 2 h. The reaction mixture was next concentrated in vacuo and azeotroped with toluene to afford the title compound as a pink solid (264 mg, quantitative). LC/MS (Table 2, Method A): $R_t$=0.79 min; m/z=211 [M+H]$^+$.

Example 50—Synthesis of Compound I-90: 1,3-Dimethyl-4-(methylthio)-6-(1-(trifluoromethyl)-1H-pyrazole-4-carbonyl)-1,5,6,7-tetrahydro-2H-pyrrolo[3,4-b]pyridin-2-one

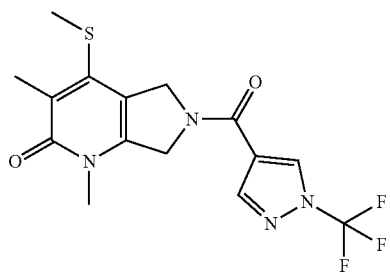 [SMILES: CSc1c2c(n(C)c(=O)c1C)CN(C(=O)c1cnn(C(F)(F)F)c1)C2]

To a solution of 1-(trifluoromethyl)pyrazole-4-carboxylic acid (44 mg, 0.24 mmol) in DMF (1 mL) was added HATU (100 mg, 0.26 mmol), triethylamine (0.085 mL, 0.61 mmol) and 1,3-dimethyl-4-(methylthio)-1,5,6,7-tetrahydro-2H-pyrrolo[3,4-b]pyridin-2-one hydrochloride (50 mg, 0.20 mmol). The reaction stirred at RT for 2 h. The reaction mixture was next partitioned between DCM and saturated aqueous sodium hydrogen carbonate. The organic layer was separated and concentrated in vacuo. The residue was purified directly by reverse phase HPLC (Table 3, Method 4, non-linear gradient from 20% to 80% MeCN) to afford the title compound as an off-white solid (46 mg, 61%). $^1$H NMR (400 MHz: DMSO-$d_6$) δ 9.09 (d, J=4.0 Hz, 1H), 8.40 (td, J=0.7, 11.3 Hz, 1H), 5.19-5.18 (m, 1H), 5.06 (t, J=2.4 Hz, 1H), 4.90 (s, 1H), 4.77 (s, 1H), 3.43 (d, J=1.4 Hz, 3H), 2.45 (s, 3H), 2.21 (d, J=5.4 Hz, 3H). LC/MS (Table 2, Method B): $R_t$=3.91 min; m/z=373 [M+H]$^+$.

Example 51—Synthesis of Additional Compound

The following compound in Table 17 was prepared using an analogous reaction protocol to that described for I-90 from Int-64 and the indicated starting material.

TABLE 17

| Additional Compound | | | |
|---|---|---|---|
| Compound No. | Yield | Starting Material | Purification method |
| I-91 | 59 mg, 78% | 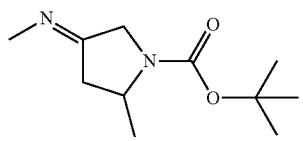 | Triturated with 10% DMSO aqueous solution |

Example 52—Synthesis of Compound Int-68: 1,4,5-Trimethyl-1,5,6,7-tetrahydro-2H-pyrrolo[3,4-b]pyridin-2-one Hydrochloride The title compound was prepared according to the following procedures.

Preparation of Int-65: tert-Butyl (E)-2-methyl-4-(methylimino)pyrrolidine-1-carboxylate A reaction vessel was charged with tert-butyl 2-methyl-4-oxo-pyrrolidine-1-carboxylate (5 g, 25 mmol) and dissolved in 2 M methylamine in THF (63 mL, 125 mmol). The reaction was heated to 80° C. and stirred at 80° C. for 18 h. The reaction mixture was concentrated in vacuo to afford the title compound as a yellow oil (5.3 g, quantitative). Material advanced to next step without characterization.

Preparation of Int-66: tert-Butyl 2-methyl-4-(N-methylbut-2-ynamido)-2,5-dihydro-1H-pyrrole-1-carboxylate

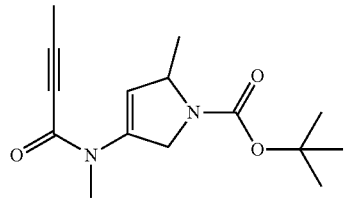 [SMILES: CC#CC(=O)N(C)C1=CC(C)N(C(=O)OC(C)(C)C)C1]

To a solution of but-2-ynoyl chloride (2.6 g, 25 mmol) in DCM (60 mL) at 0° C. under a nitrogen atmosphere was added tert-butyl (E)-2-methyl-4-(methylimino)pyrrolidine-1-carboxylate (5.3 g, 25 mmol) and triethylamine (6.9 mL, 50 mmol) via dropwise addition. The reaction stirred at 0° C. for 30 min. The reaction was allowed to warm to RT and stirred at RT for 5.5 days. The reaction mixture was next partitioned between saturated aqueous sodium hydrogen carbonate, passed through a phase separator and the filtrate was concentrated in vacuo. The residue was purified by flash column chromatography (DCM to MeOH, gradient elution) followed by reverse phase HPLC (Table 3, Method 2, non-linear gradient from 10% to 90% MeCN) to afford the title compound as a white solid (976 mg, 14%). LC/MS (Table 2, Method A): $R_t$=1.20 min; m/z=279 [M+H]$^+$.

Preparation of Int-67: tert-Butyl 1,4,5-trimethyl-2-oxo-1,2,5,7-tetrahydro-6H-pyrrolo[3,4-b]pyridine-6-carboxylate

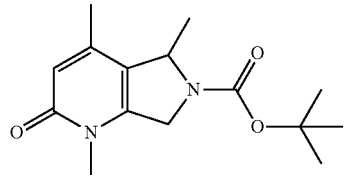 [SMILES: Cc1cc(=O)n(C)c2c1C(C)N(C(=O)OC(C)(C)C)C2]

To a solution of tert-butyl 2-methyl-4-(N-methylbut-2-ynamido)-2,5-dihydro-1H-pyrrole-1-carboxylate (976 mg, 3.5 mmol) in DCM (35 mL) was added silver tetrafluoroborate (34 mg, 0.18 mmol) and chloro(triphenylphosphine)gold (87 mg, 0.18 mmol). The reaction stirred at RT for 16 h. The reaction was heated to reflux and stirred at reflux for 27.5 h. The reaction mixture was next concentrated in vacuo and purified directly by flash column chromatography (DCM to MeOH, gradient elution) to afford the title compound as a brown gum (750 mg, 77%). LC/MS (Table 2, Method A): $R_t$=1.20 min; m/z=279 [M+H]$^+$.

Preparation of Int-68: 1,4,5-Trimethyl-1,5,6,7-tetrahydro-2H-pyrrolo[3,4-b]pyridin-2-one Hydrochloride

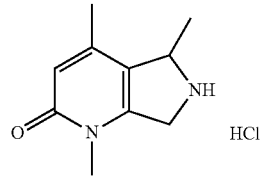

A reaction vessel was charged with tert-butyl 1,4,5-trimethyl-2-oxo-1,2,5,7-tetrahydro-6H-pyrrolo[3,4-b]pyridine-6-carboxylate (0.049 mL, 0.37 mmol) and 4 M HCl in 1,4-dioxane (5.0 mL, 20 mmol). The reaction stirred at RT for 1 h. The reaction mixture was next concentrated in vacuo to afford the title compound as a beige solid (80 mg, quantitative). LC/MS (Table 2, Method A): $R_t$=0.56 min; m/z=179 [M+H]$^+$.

Example 53—Synthesis of Compound I-92: 1,4,5-Trimethyl-6-(1-(trifluoromethyl)-1H-pyrazole-4-carbonyl)-1,5,6,7-tetrahydro-2H-pyrrolo[3,4-b]pyridin-2-one

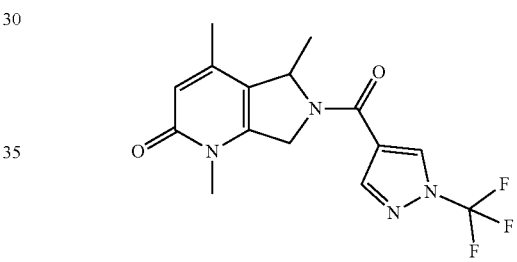

To a solution of 1,4,5-trimethyl-1,5,6,7-tetrahydro-2H-pyrrolo[3,4-b]pyridin-2-one hydrochloride (80 mg, 0.37 mmol) and 1-(trifluoromethyl)pyrazole-4-carboxylic acid (81 mg, 0.45 mmol) in DMF (2 mL) was added N,N-diisopropylethylamine (0.23 mL, 1.3 mmol) and HATU (213 mg, 0.56 mmol). The reaction stirred at RT for 2 h. The reaction mixture was next partitioned between DCM and saturated aqueous sodium hydrogen carbonate. The organic layer was separated. The combined organic layer was washed with saturated brine, dried (Na$_2$SO$_4$) and concentrated in vacuo. The residue was purified by SFC purification (Table 3, Method 9) to afford the title compound of unknown absolute configuration-stereoisomer 1, as an off-white solid (10 mg, 8%). $^1$H NMR (300 MHz: DMSO-d$_6$) δ 9.10 (s, 0.2H), 9.06 (s, 0.8H), 8.43 (s, 0.2H), 8.38 (s, 0.8H), 6.21 (s, 1H), 5.60-5.57 (m, 0.2H), 5.38-5.32 (m, 0.8H), 5.23 (dd, J=2.6, 15.3 Hz, 0.8H), 5.02 (d, J=15.3 Hz, 0.8H), 4.90 (d, J=17.3 Hz, 0.2H), 4.83-4.78 (m, 0.2H), 3.37 (d, J=5.1 Hz, 3H), 2.18 (s, 3H), 1.44 (d, J=6.0 Hz, 2.4H), 1.26 (d, J=6.1 Hz, 0.6H). LC/MS (Table 2, Method B): $R_t$=3.23 min; m/z=341 [M+H]$^+$.

Example 54—Synthesis of Additional Compounds

The following compounds in Table 18 were prepared using an analogous reaction protocol to that described for 1-92 from Int-68 and the indicated starting material.

TABLE 18

| Compound No. | Yield | Starting Material | Purification method |
|---|---|---|---|
| I-93 unknown absolute configuration | 3.5 mg, 3% | 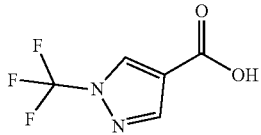 | Purified by SFC purification (Table 3, Method 9) |
| I-94 unknown absolute configuration | 22 mg, 19% | 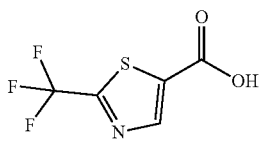 [SMILES: O=C(O)c1cnc(C(F)(F)F)s1] | SFC purification (Table 3, Method 10) |
| I-95 unknown absolute configuration | 17 mg, 14% | 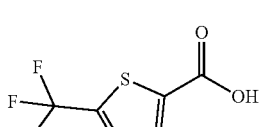 | SFC purification (Table 3, Method 10) |
| I-96 unknown absolute configuration | 21 mg, 19% | 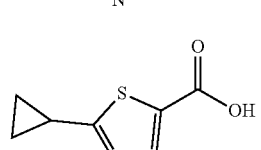 | SFC purification (Table 3, Method 11) |
| I-97 unknown absolute configuration | 23 mg, 21% | 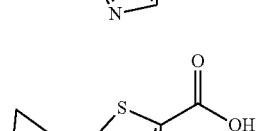 | SFC purification (Table 3, Method 11) |
| I-98 unknown absolute configuration | 41 mg, 29% | Int-8 | SFC purification (Table 3, Method 13) |
| I-99 unknown absolute configuration | 30 mg, 21% | Int-8 | SFC purification (Table 3, Method 13) |
| I-100 unknown absolute configuration | 15 mg, 11% | 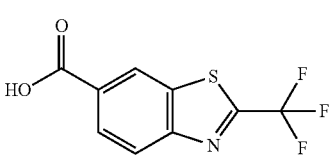 [SMILES: O=C(O)c1ccc2nc(C(F)(F)F)sc2c1] | SFC purification (Table 3, Method 13, non-linear gradient from 15% to 85% MeOH) |
| I-101 unknown absolute configuration | 17 mg, 12% | 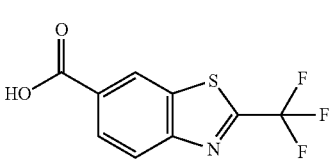 [SMILES: O=C(O)c1ccc2nc(C(F)(F)F)sc2c1] | SFC purification (Table 3, Method 13, non-linear gradient from 15% to 85% MeOH) |
| I-102 unknown absolute configuration | 24 mg, 33% | Int-8 | SFC purification (Table 3, Method 4) |
| I-103 (unknown absolute configuration) | 18 mg, 26% | Int-8 | SFC purification (Table 3, Method 5) |

Example 55—Synthesis of Compound Int-69: 1,4-Dimethyl-1,5,6,7-tetrahydro-2H-pyrrolo[3,4-b]pyridin-2-one Hydrochloride

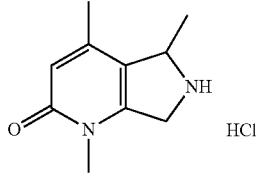

A reaction vessel was charged with tert-butyl 1,4-dimethyl-2-oxo-1,2,5,7-tetrahydro-6H-pyrrolo[3,4-b]pyridine-6-carboxylate (606 mg, 2.3 mmol) and at 0° C. 4 M HCl in 1,4-dioxane (14 mL, 57 mmol) was added. The reaction was allowed to warm to RT and stirred at RT for 1.5 h. The reaction mixture was concentrated in vacuo and azeotroped with toluene to afford the title compound as an off-white solid (540 mg, quantitative). $^1$H NMR (400 MHz: DMSO-$d_6$) δ 0.35-10.35 (m, 2H), 6.23 (s, 1H), 4.58 (s, 2H), 4.34 (t, J=5.3 Hz, 2H), 3.34 (s, 3H), 2.11 (s, 3H). LC/MS (Table 2, Method A): $R_t$=0.39 min; m/z=165 [M+H]$^+$.

Example 56—Synthesis of Compound I-104: 1,4-Dimethyl-6-(1-methyl-1H-pyrazole-4-carbonyl)-1,5,6,7-tetrahydro-2H-pyrrolo[3,4-b]pyridin-2-one

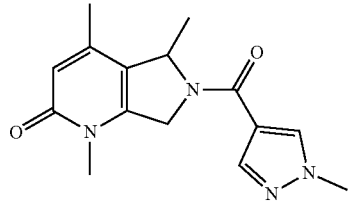 [SMILES: Cc1cc(=O)n(C)c2c1C(C)N(C(=O)c1cnn(C)c1)C2]

To a solution of 1,4-dimethyl-1,5,6,7-tetrahydro-2H-pyrrolo[3,4-b]pyridin-2-one hydrochloride (40 mg, 0.17 mmol), 1-methyl-1H-pyrazole-4-carboxylic acid (26 mg, 0.20 mmol) and HATU (116 mg, 0.31 mmol) in DCM (1.5 mL) was added N,N-diisopropylethylamine (0.10 mL, 0.59 mmol). The reaction stirred at RT for 1.5 h. The reaction mixture was concentrated in vacuo and was purified directly by reverse phase HPLC (Table 3, Method 5, non-linear gradient from 20% to 80% MeOH) to afford the title compound as an off-white solid (35 mg, 75%). $^1$H NMR (400 MHz: DMSO-$d_6$) δ 8.36 (d, J=8.3 Hz, 1H), 7.95 (d, J=6.3 Hz, 1H), 6.20 (s, 1H), 5.11-5.08 (m, 1H), 4.88-4.82 (m, 2H), 4.60 (s, 1H), 3.92 (s, 3H), 3.39 (d, J=6.9 Hz, 3H), 2.15 (d, J=5.0 Hz, 3H). LC/MS (Table 2, Method E): $R_t$=2.2 min; m/z=273 [M+H]$^+$.

Example 57—Synthesis of Compound Int-74: 1,4,7-Trimethyl-1,5,6,7-tetrahydro-2H-pyrrolo[3,4-b]pyridin-2-one Hydrochloride The title compound was prepared according to the following procedures.

Preparation of Int-70: 2-Acetyl-6-methoxy-4-methylnicotinonitrile

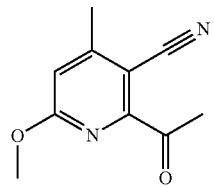

A reaction vessel was charged with 2-chloro-6-methoxy-4-methylnicotinonitrile (1.3 g, 7.2 mmol), PdCl$_2$(PPh$_3$)$_2$ (354 mg, 0.51 mmol), tributyl(1-ethoxyvinyl)tin (2.9 mL, 8.7 mmol) and toluene (11 mL). The reaction was evacuated, purged with argon (×3) and next heated to 115° C. The reaction stirred at 115° C. for 2 h under a nitrogen atmosphere. The reaction mixture was allowed to cool to 0° C. and quenched by the addition of 6 M HCl (2.5 mL) via dropwise addition. The reaction was allowed to cool to RT and stirred at RT 20 min. The reaction mixture was allowed to cool to 0° C. and next basified by the addition of 6 M NaOH aqueous solution. The reaction was allowed to cool to RT, stirred at RT 30 min, filtered through celite and washed with EtOAc. The filtrate was partitioned between EtOAc and distilled water. The organic layer was separated. The combined organic layer was washed with saturated brine, dried (Na$_2$SO$_4$) and concentrated in vacuo. The residue was purified by flash column chromatography (cyclohexane to EtOAc, gradient elution) to afford the title compound as a white solid (918 mg, 67%). LC/MS (Table 2, Method A): $R_t$=1.26 min; m/z=191 [M+H]$^+$.

Preparation of Int-71: 2-Methoxy-4,7-dimethyl-6,7-dihydro-5H-pyrrolo[3,4-b]pyridine

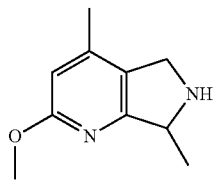

To a suspension of 2-acetyl-6-methoxy-4-methylnicotinonitrile (800 mg, 4.2 mmol) in EtOH (24 mL) was added Raney nickel suspended in water (0.25 g, 4.2 mmol). The reaction was next evacuated and placed under a hydrogen atmosphere. The reaction was heated to 40° C. and stirred at 40° C. under a hydrogen atmosphere for 16 h. The reaction mixture was allowed to cool to RT, filtered through celite and washed with distilled water. The filtrate was concentrated in vacuo to afford the title compound as a pink oil (420 mg, 44%). LC/MS (Table 2, Method A): $R_t$=0.98 min; m/z=179 [M+H]$^+$.

Preparation of Int-72: tert-Butyl 2-methoxy-1,4,7-trimethyl-1,2,5,7-tetrahydro-6H-pyrrolo[3,4-b]pyridine-6-carboxylate

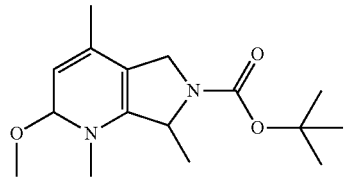 [SMILES: COC1C=C(C)C2=C(C(C)N(C(=O)OC(C)(C)C)C2)N1C]

To a solution of 2-methoxy-4,7-dimethyl-6,7-dihydro-5H-pyrrolo[3,4-b]pyridine (420 mg, 2.4 mmol) in 1,4-dioxane (6 mL) and distilled water (6 mL) was added sodium hydrogen carbonate (396 mg, 4.7 mmol) and di-tert-butyl dicarbonate (617 mg, 2.8 mmol). The reaction stirred at RT for 16 h. The reaction mixture was next partitioned between EtOAc and distilled water. The organic layer was separated. The combined organic layer was washed with saturated brine, dried ($Na_2SO_4$) and concentrated in vacuo. The residue was purified by flash column chromatography (cyclohexane to EtOAc, gradient elution) to afford the title compound as a yellow oil (350 mg, 77%). LC/MS (Table 2, Method A): $R_t$=1.67 min; m/z=279 [M+H]$^+$.

Preparation of Int-73: tert-Butyl 1,4,7-trimethyl-2-oxo-1,2,5,7-tetrahydro-6H-pyrrolo[3,4-b]pyridine-6-carboxylate

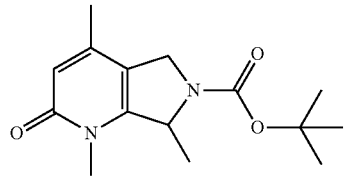 [SMILES: Cc1cc(=O)n(C)c2c1CN(C(=O)OC(C)(C)C)C2C]

A reaction vessel was charged with tert-butyl 2-methoxy-1,4,7-trimethyl-1,2,5,7-tetrahydro-6H-pyrrolo[3,4-b]pyridine-6-carboxylate (335 mg, 1.2 mmol), potassium acetate (354 mg, 3.6 mmol) and solvated in MeCN (7 mL) under a nitrogen atmosphere. This was followed by the addition of iodomethane (0.75 mL, 12 mmol) and the reaction was next heated to 80° C. The reaction stirred at 80° C. for 16 h. The reaction mixture was allowed to cool to RT, filtered through celite and washed with EtOAc. The filtrate was concentrated in vacuo. The residue was purified by flash column chromatography (DCM to MeOH, gradient elution) followed by reverse phase HPLC (Table 3, Method 8, non-linear gradient from 0% to 95% MeCN) to afford the title compound as a white solid (198 mg, 59%). LC/MS (Table 2, Method A): $R_t$=1.20 min; m/z=279 [M+H]$^+$.

Preparation of Int-74: 1,4,7-Trimethyl-1,5,6,7-tetrahydro-2H-pyrrolo[3,4-b]pyridin-2-one Hydrochloride

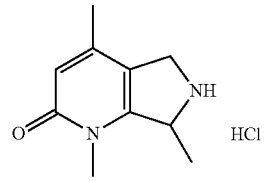

To a solution of tert-butyl 1,4,7-trimethyl-2-oxo-1,2,5,7-tetrahydro-6H-pyrrolo[3,4-b]pyridine-6-carboxylate (195 mg, 0.70 mmol) in 1,4-dioxane (2 mL) was added 4 M HCl in 1,4-dioxane (3.5 mL, 14 mmol) and the reaction stirred at RT for 2 h. The reaction mixture was next concentrated in vacuo to afford the title compound as a white solid (210 mg, quantitative). Material advanced to next step without characterisation.

Example 58—Synthesis of Compound I-107: 1,4,7-Trimethyl-6-(1-methyl-1H-pyrazole-4-carbonyl)-1,5,6,7-tetrahydro-2H-pyrrolo[3,4-b]pyridin-2-one

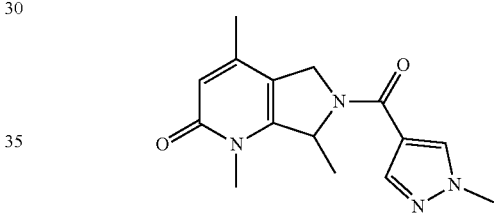

To a solution of 1-methyl-1H-pyrazole-4-carboxylic acid (68 mg, 0.54 mmol) in DMF (1 mL) was added HATU (279 mg, 0.73 mmol) followed by a solution of 1,4,7-trimethyl-1,5,6,7-tetrahydro-2H-pyrrolo[3,4-b]pyridin-2-one hydrochloride (105 mg, 0.49 mmol) and N,N-diisopropylethylamine (0.30 mL, 1.7 mmol) in DMF (2.5 mL). The reaction stirred at RT for 16 h. The reaction mixture was purified directly by reverse phase HPLC (Table 3, Method 8, non-linear gradient from 5% to 50% MeCN) to afford the title compound as an off-white solid (74 mg, 53%). $^1$H NMR (400 MHz: DMSO-d$_6$) δ 8.34 (s, 0.2H), 8.29 (s, 0.8H), 7.97 (s, 0.2H), 7.89 (s, 0.8H), 6.19 (s, 1H), 5.66-5.64 (m, 0.2H), 5.54-5.48 (m, 0.8H), 4.90 (dd, J=3.0, 12.7 Hz, 0.8H), 4.72 (d, J=12.6 Hz, 0.8H), 4.64 (d, J=12.7 Hz, 0.2H), 4.47 (d, J=16.3 Hz, 0.2H), 3.90 (s, 3H), 3.40 (d, J=13.9 Hz, 3H), 2.13 (s, 3H), 1.46 (d, J=6.2 Hz, 2.5H), 1.39 (d, J=7.0 Hz, 0.5H). LC/MS (Table 2, Method C): $R_t$=2.22 min; m/z=287 [M+H]$^+$.

Example 59—Synthesis of Additional Compounds

The following compounds in Table 19 were prepared using an analogous reaction protocol to that described for I-105 from Int-74 and the indicated starting material.

TABLE 19

Additional Compounds

| Compound No. | Yield | Starting Material | Purification method |
|---|---|---|---|
| I-106 (unknown absolute configuration) | 22 mg, 16% | 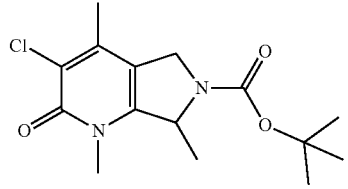 [SMILES: Cc1c2c(n(C)c(=O)c1Cl)C(C)N(C(=O)OC(C)(C)C)C2] | Purified by SFC purification (Table 3, Method 12) |
| I-107 (unknown absolute configuration) | 22 mg, 15% | 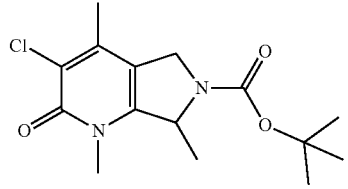 [SMILES: Cc1c2c(n(C)c(=O)c1Cl)C(C)N(C(=O)OC(C)(C)C)C2] | Purified by SFC purification (Table 3, Method 12) |

Example 60—Synthesis of Compound Int-76: 3-Chloro-1,4,7-trimethyl-1,5,6,7-tetrahydro-2H-pyrrolo[3,4-b]pyridin-2-one Hydrochloride The title compound was prepared according to the following procedures.

Preparation of Int-75: tert-Butyl 3-chloro-1,4,7-trimethyl-2-oxo-1,2,5,7-tetrahydro-6H-pyrrolo[3,4-b]pyridine-6-carboxylate To a solution of tert-butyl 1,4,7-trimethyl-2-oxo-5,7-dihydropyrrolo[3,4-b]pyridine-6-carboxylate (0.40 g, 1.4 mmol) in MeCN (6.7 mL) and DMF (3.3 mL) was added N-chlorosuccinimide (0.25 g, 1.9 mmol). The reaction was allowed to warm to 50° C. and stirred at 50° C. for 20 min. The reaction mixture was allowed to cool to RT and next partitioned between distilled water and EtOAc. The organic layer was separated. The combined organic layer was washed with 5% LiCl solution, saturated brine, dried (Na$_2$SO$_4$), and concentrated in vacuo. The residue was purified by flash column chromatography (cyclohexane to IPA, gradient elution) to afford the title compound as a yellow oil (355 mg, 79%). LC/MS (Table 2, Method A): R$_t$=1.50 min; m/z=313 [M+H]$^+$.

Preparation of Int-76: 3-Chloro-1,4,7-trimethyl-1,5,6,7-tetrahydro-2H-pyrrolo[3,4-b]pyridin-2-one Hydrochloride

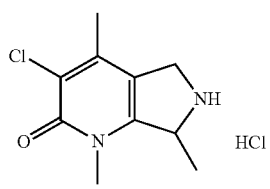

To a solution of tert-butyl 3-chloro-1,4,7-trimethyl-2-oxo-5,7-dihydropyrrolo[3,4-b]pyridine-6-carboxylate (355 mg, 1.1 mmol) in DCM (5 mL) was added 4 M HCl in 1,4-dioxane (5.7 mL, 23 mmol) and the reaction stirred at RT for 4 days. The reaction mixture was filtered, washed with DCM and concentrated in vacuo to afford the title compound as a purple solid (246 mg, 87%). LC/MS (Table 2, Method A): R$_t$=0.77 min; m/z=213 [M+H]$^+$.

Example 61—Synthesis of Compound I-108: 3-Chloro-1,4,7-trimethyl-6-(1-(trifluoromethyl)-1H-pyrazole-4-carbonyl)-1,5,6,7-tetrahydro-2H-pyrrolo[3,4-b]pyridin-2-one

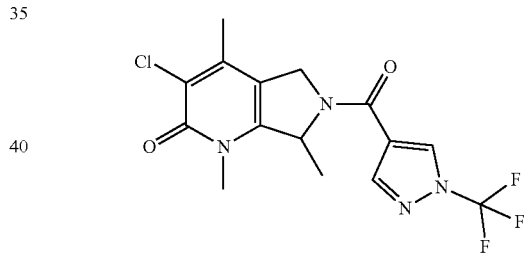

To a solution of 1-(trifluoromethyl)pyrazole-4-carboxylic acid (95 mg, 0.53 mmol) in DMF (1.5 mL) was added HATU (201 mg, 0.53 mmol) followed by a solution of 3-chloro-1,4,7-trimethyl-6,7-dihydro-5H-pyrrolo[3,4-b]pyridin-2-one; hydrochloride (120 mg, 0.48 mmol) and N,N-diisopropylethylamine (0.29 mL, 1.7 mmol) in DMF (1.5 mL). The reaction stirred at RT for 16 h. The reaction mixture was purified directly by reverse phase HPLC (Table 3, Method 8, non-linear gradient from 5% to 98% MeCN) followed by SFC purification (Table 3, Method 7) to afford the title compound of unknown absolute configuration-stereoisomer 1, as an off-white solid (49 mg, 27%). $^1$H NMR (400 MHz: DMSO-d$_6$) δ 9.04 (s, 1H), 8.37 (s, 1H), 5.61-5.53 (m, 1H), 5.03 (dd, J=4.2, 12.6 Hz, 1H), 4.84 (d, J=12.1 Hz, 1H), 3.48 (s, 3H), 2.25 (s, 3H), 1.50 (d, J=5.3 Hz, 3H). LC/MS (Table 2, Method B): R$_t$=3.75 min; m/z=375.2 [M+H]$^+$.

Example 62—Synthesis of Additional Compound

The following compound in Table 20 was prepared using an analogous reaction protocol to that described for I-108 from Int-76 and the indicated starting material.

147

TABLE 20

Additional Compound

| Compound No. | Yield | StartingMaterial | Purification method |
|---|---|---|---|
| I-109 unknown absolute configuration-stereoisomer | 49 mg, 27% | 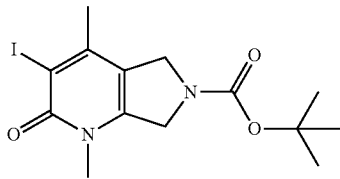 [SMILES: Cc1c2c(n(C)c(=O)c1I)CN(C(=O)OC(C)(C)C)C2] | Purified by SFC purification (Table 3, Method 7) |

Example 63—Synthesis of Int-79: 1,4-Dimethyl-3-(trifluoromethyl)-1,5,6,7-tetrahydro-2H-pyrrolo[3,4-b]pyridin-2-one Hydrochloride The title compound was prepared according to the following procedures.

Preparation of Int-77: tert-Butyl 3-iodo-1,4-dimethyl-2-oxo-1,2,5,7-tetrahydro-6H-pyrrolo[3,4-b]pyridine-6-carboxylate

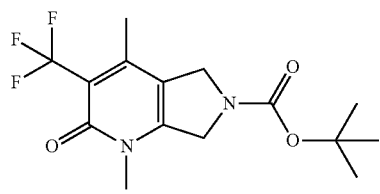 [SMILES: Cc1c2c(n(C)c(=O)c1C(F)(F)F)CN(C(=O)OC(C)(C)C)C2]

To a solution of tert-butyl 1,4-dimethyl-2-oxo-1,2,5,7-tetrahydro-6H-pyrrolo[3,4-b]pyridine-6-carboxylate (200 mg, 0.76) in DMF (2 mL) and MeCN (4 mL) was added N-iodosuccinimide (238 mg, 1.1 mmol) and the reaction was heated to 50° C. The reaction stirred at 50° C. for 1 h. The reaction mixture was next partitioned between EtOAc and distilled water. The organic layer was separated. The combined organic layer was washed with saturated brine, dried ($Na_2SO_4$) and concentrated in vacuo. The residue was purified by flash column chromatography (cyclohexane to EtOAc, gradient elution) to afford the title compound as a yellow oil (268 mg, 72%). LC/MS (Table 2, Method F): $R_t$=1.36 min; m/z=391 $[M+H]^+$.

Preparation of Int-78: tert-Butyl 1,4-dimethyl-2-oxo-3-(trifluoromethyl)-1,2,5,7-tetrahydro-6H-pyrrolo[3,4-b]pyridine-6-carboxylate

148

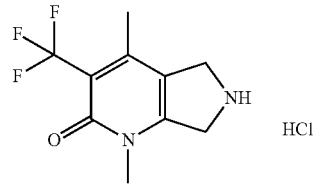 [SMILES: Cc1c2c(n(C)c(=O)c1C(F)(F)F)CNC2 ; Cl]

To a solution of tert-butyl 3-iodo-1,4-dimethyl-2-oxo-1,2,5,7-tetrahydro-6H-pyrrolo[3,4-b]pyridine-6-carboxylate (268 mg, 0.69 mmol) and copper(I) iodide (157 mg, 0.82 mmol) in DMF (6.7 mL) was added methyl 2,2-difluoro-2-(fluorosulfonyl)acetate (0.10 mL, 0.82 mmol) and the reaction was heated to 75° C. The reaction stirred at 75° C. for 26 h. The reaction mixture was allowed to cool to RT and was next partitioned between EtOAc and distilled water. The organic layer was separated. The combined organic layer was washed with saturated brine, dried ($Na_2SO_4$) and concentrated in vacuo. The residue was purified by flash column chromatography (cyclohexane to EtOAc, gradient elution) to afford the title compound as a pale yellow solid (112 mg, 49%). LC/MS (Table 2, Method F): $R_t$=1.37 min; m/z=333 $[M+H]^+$.

Preparation of Int-79: 1,4-Dimethyl-3-(trifluoromethyl)-1,5,6,7-tetrahydro-2H-pyrrolo[3,4-b]pyridin-2-one Hydrochloride

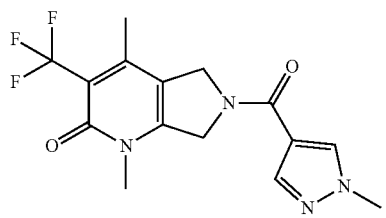 [SMILES: Cc1c2c(n(C)c(=O)c1C(F)(F)F)CN(C(=O)c1cnn(C)c1)C2]

A reaction vessel was charged with tert-butyl 1,4-dimethyl-2-oxo-3-(trifluoromethyl)-1,2,5,7-tetrahydro-6H-pyrrolo[3,4-b]pyridine-6-carboxylate (112 mg, 0.34 mmol) at 0° C. and 4 M HCl in 1,4-dioxane (2.1 mL, 8.4 mmol) was added. The reaction was allowed to warm to RT and stirred at RT for 18 h. The reaction mixture was next concentrated in vacuo and azeotroped with toluene to afford the title compound as a beige solid (85 mg, 93%). LC/MS (Table 2, Method A): $R_t$=0.82 min; m/z=233 $[M+H]^+$.

Example 64—Synthesis of Compound I-110: 1,4-Dimethyl-6-(1-methyl-1H-pyrazole-4-carbonyl)-3-(trifluoromethyl)-1,5,6,7-tetrahydro-2H-pyrrolo[3,4-b]pyridin-2-one To a solution of 1,4-dimethyl-3-(trifluoromethyl)-1,5,6,7-tetrahydro-2H-pyrrolo[3,4-b]pyridin-2-one hydrochloride (40 mg, 0.15 mmol), 1-methyl-TH-pyrazole-4-carboxylic acid (23 mg, 0.18 mmol) and HATU (102 mg, 0.27 mmol) in DCM (1 mL) was added N,N-diisopropylethylamine (0.091 mL, 0.52 mmol). The reaction stirred at RT for 1 h. The reaction mixture was next partitioned between EtOAc and distilled water. The organic layer was separated. The combined organic layer was washed with saturated brine, dried ($Na_2SO_4$) and concentrated in vacuo. The residue was purified by reverse phase HPLC (Table 3, Method 1) to afford the title compound as an off-white solid (25 mg, 48%). $^1$H NMR (300 MHz: DMSO-$d_6$) δ 8.42 (s, 1H), 8.00 (s, 1H), 5.22 (s, 1H), 4.99-4.95 (m, 2H), 4.72 (s, 1H), 3.96 (s, 3H), 3.48 (d, J=9.1 Hz, 3H), 2.39-2.33 (m, 3H). LC/MS (Table 2, Method B): $R_t$=3.07 min; m/z=341 [M+H]$^+$.

Example 65—Synthesis of Compound Int-81: 1,3,4-Trimethyl-1,5,6,7-tetrahydro-2H-pyrrolo[3,4-b]pyridin-2-one Hydrochloride The title compound was prepared according to the following procedures.

Preparation of Int-80: tert-Butyl 1,3,4-trimethyl-2-oxo-1,2,5,7-tetrahydro-6H-pyrrolo[3,4-b]pyridine-6-carboxylate

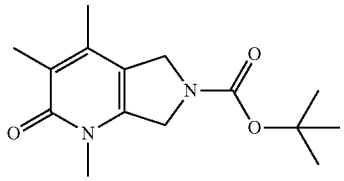 [SMILES: Cc1c2c(n(C)c(=O)c1C)CN(C(=O)OC(C)(C)C)C2]

A reaction vessel was charged with tert-butyl 3-chloro-1,4-dimethyl-2-oxo-1,2,5,7-tetrahydro-6H-pyrrolo[3,4-b]pyridine-6-carboxylate (4.6 g, 15 mmol), potassium carbonate (6.4 g, 46 mmol), trimethylboroxine (3.2 mL, 23 mmol), Pd(dppf)Cl$_2$ (1.2 g, 1.6 mmol) and solvated in 1,4-dioxane (120 mL). The reaction was evacuated, purged with argon (×3) and next heated to 100° C. The reaction stirred at 100° C. for 18 h under a nitrogen atmosphere. The reaction mixture was allowed to cool to RT, filtered through celite and washed with EtOAc. The filtrate was concentrated in vacuo and purified by flash column chromatography (TBME to EtOAc:IMS 3:1, gradient elution) to afford the title compound as a pale yellow solid (3.5 g, 80%). LC/MS (Table 2, Method F): $R_t$=1.45 min; m/z=279 [M+H]$^+$.

Preparation of Int-81: 1,3,4-Trimethyl-1,5,6,7-tetrahydro-2H-pyrrolo[3,4-b]pyridin-2-one Hydrochloride

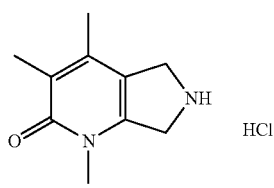

To a solution of tert-butyl 1,3,4-trimethyl-2-oxo-1,2,5,7-tetrahydro-6H-pyrrolo[3,4-b]pyridine-6-carboxylate (3.5 g, 13 mmol) in DCM (50 mL) was added 4 M HCl in 1,4-dioxane (60 mL, 240 mmol) and the reaction stirred at RT for 2 h. The reaction mixture was concentrated in vacuo and then triturated with diethyl ether to afford the title compound as a pink solid (2.5 g, 91%). LC/MS (Table 2, Method A): $R_t$=0.72 min; m/z=179 [M+H]$^+$.

Example 66—Synthesis of Compound I-111: 6-(2-Cyclopropylbenzo[d]thiazole-6-carbonyl)-1,3,4-trimethyl-1,5,6,7-tetrahydro-2H-pyrrolo[3,4-b]pyridin-2-one

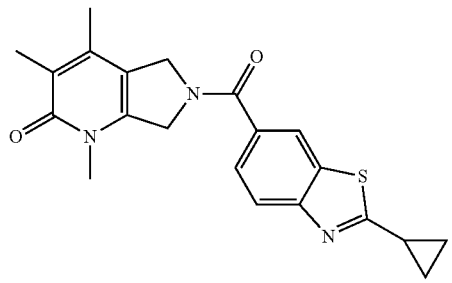 [SMILES: Cc1c2c(n(C)c(=O)c1C)CN(C(=O)c1ccc3nc(C4CC4)sc3c1)C2]

To a solution of lithium 2-cyclopropylbenzo[d]thiazole-6-carboxylate (33 mg, 0.15 mmol), N,N-diisopropylethylamine (0.073 mL, 0.42 mmol) and HATU (69 mg, 0.18 mmol) in DMF (1.5 mL) was added 1,3,4-trimethyl-1,5,6,7-tetrahydro-2H-pyrrolo[3,4-b]pyridin-2-one hydrochloride (30 mg, 0.14 mmol). The reaction stirred at RT for 2.5 h. The reaction mixture was next partitioned between DCM and saturated aqueous sodium hydrogen carbonate. The organic layer was separated. The combined organic layer was washed with saturated brine, dried ($Na_2SO_4$) and concentrated in vacuo. The residue was purified by reverse phase HPLC (Table 3, Method 4) to afford the title compound as an off-white solid (21 mg, 39%). $^1$H NMR (400 MHz: DMSO-$d_6$) δ 8.32 (dd, J=1.4, 3.5 Hz, 1H), 7.94-7.92 (m, 1H), 7.69 (dd, J=1.8, 8.4 Hz, 1H), 4.95-4.89 (m, 2H), 4.75-4.66 (m, 2H), 3.43 (s, 1.5H), 3.24 (s, 1.5H), 2.62-2.55 (m, 1H), 2.14-2.13 (m, 1.5H), 2.01-1.96 (m, 4.5H), 1.32-1.26 (m, 2H), 1.25-1.16 (m, 2H). LC/MS (Table 1, Method B): $R_t$=3.67 min; m/z=380 [M+H]$^+$.

Example 67—Synthesis of Additional Compound

The following compound in Table 21 was prepared using an analogous reaction protocol to that described for I-111 from Int-81 and the indicated starting material.

TABLE 21

Additional Compound

| Compound No. | Starting Material | Purification method |
|---|---|---|
| I-112 | ![structure] | Reverse phase HPLC (Table 3, Method 4) |

Example 68—Synthesis of Compound Int-83: 3-Fluoro-1,4-dimethyl-6-(1-(trifluoromethyl)-1H-pyrazole-4-carbonyl)-1,5,6,7-tetrahydro-2H-pyrrolo[3,4-b]pyridin-2-one The title compound was prepared according to the following procedures.

Preparation of Int-82: tert-Butyl 3-fluoro-1,4-dimethyl-2-oxo-1,2,5,7-tetrahydro-6H-pyrrolo[3,4-b]pyridine-6-carboxylate

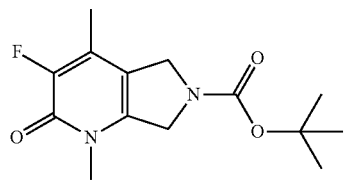 [SMILES: Cc1c2c(n(C)c(=O)c1F)CN(C(=O)OC(C)(C)C)C2]

To a solution of tert-butyl (Z)-3-(methylimino)pyrrolidine-1-carboxylate (5.4 g, 27 mmol) in toluene (22 mL) was added ethyl 2-fluoroacetoacetate (3.9 mL, 31 mmol) and triethylamine (7.6 mL, 55 mmol). The reaction was evacuated, purged with argon (×3) and heated to 110° C. The reaction stirred at 110° C. for 17 h. The reaction mixture was allowed to cool to RT and next concentrated in vacuo. The residue was purified directly by flash column chromatography (DCM to MeCN, gradient elution) to afford the title compound as a pale yellow solid (713 mg, 9%). LC/MS (Table 2, Method A): $R_t$=1.33 min; m/z=283 [M+H]$^+$.

Preparation of Int-83: 3-Fluoro-1,4-dimethyl-1,5,6,7-tetrahydro-2H-pyrrolo[3,4-b]pyridin-2-one Hydrochloride

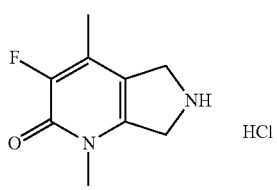

To a solution of tert-butyl 3-fluoro-1,4-dimethyl-2-oxo-1,2,5,7-tetrahydro-6H-pyrrolo[3,4-b]pyridine-6-carboxylate (710 mg, 2.5 mmol) in DCM (0.5 mL) was added 4 M HCl in 1,4-dioxane (16 mL, 63 mmol) and the reaction stirred at RT for 1 h. The reaction mixture was concentrated in vacuo and azeotroped with MeCN to afford the title compound as a white solid (578 mg, quantitative). LC/MS (Table 2, Method B): $R_t$=0.53 min; m/z=183 [M+H]$^+$.

Example 69—Synthesis of Compound I-113: 3-Fluoro-1,4-dimethyl-6-(1-(trifluoromethyl)-1H-pyrazole-4-carbonyl)-1,5,6,7-tetrahydro-2H-pyrrolo[3,4-b]pyridin-2-one

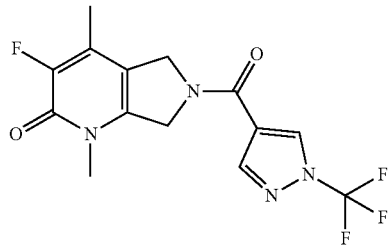 [SMILES: Cc1c2c(n(C)c(=O)c1F)CN(C(=O)c1cnn(C(F)(F)F)c1)C2]

To a solution of 1-(trifluoromethyl)pyrazole-4-carboxylic acid (36 mg, 0.20 mmol) in DMF (0.75 mL) was added HATU (77 mg, 0.20 mmol) followed by a solution of 3-fluoro-1,4-dimethyl-6,7-dihydro-5H-pyrrolo[3,4-b]pyridin-2-one; hydrochloride (40 mg, 0.18 mmol) and N,N-diisopropylethylamine (0.11 mL, 0.64 mmol) in DMF (0.75 mL). The reaction stirred at RT for 1 h. The reaction mixture was concentrated in vacuo and purified directly by reverse phase HPLC (Table 3, Method 5) to afford the title compound as an off-white solid (30 mg, 46%). $^1$H NMR (400 MHz; DMSO-$d_6$) δ 9.09-9.05 (m, 1H), 8.39 (s, 1H), 5.16-4.95 (m, 2H), 4.86-4.66 (m, 2H), 3.46-3.43 (m, 3H), 2.15-2.13 (m, 3H). LC/MS (Table 1, Method E): $R_t$=3.09 min; m/z=345.2 [M+H]$^+$.

Example 70—Synthesis of Compound Int-86: (R)-3-Fluoro-1,4,5-trimethyl-1,5,6,7-tetrahydro-2H-pyrrolo[3,4-b]pyridin-2-one hydrochloride The title compound was prepared according to the following procedures.

Preparation of Int-84: tert-Butyl (R,Z)-2-methyl-4-(methylimino)pyrrolidine-1-carboxylate

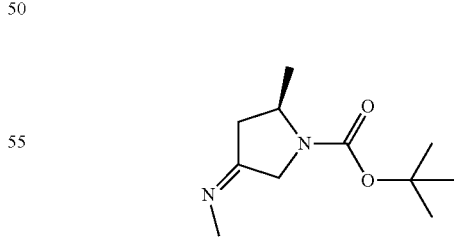

A reaction vessel was charged with tert-butyl (2R)-2-methyl-4-oxo-pyrrolidine-1-carboxylate (220 mg, 1.1 mmol) and solvated in 2 M methylamine in THF (1.1 mL, 2.2 mmol). The reaction stirred at RT for 16 h. The reaction mixture was concentrated in vacuo to give the title compound as a yellow oil (240 mg, quantitative). Material advanced to next step without characterisation.

Preparation of Int-85: tert-Butyl (R)-3-fluoro-1,4,5-trimethyl-2-oxo-1,2,5,7-tetrahydro-6H-pyrrolo[3,4-b]pyridine-6-carboxylate

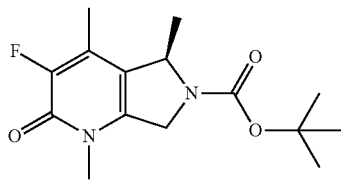

To a solution of tert-butyl (4E)-2-methyl-4-methyliminopyrrolidine-1-carboxylate (0.23 g, 1.1 mmol) in toluene (1.4 mL) was added triethylamine (301 uL, 2.2 mmol) and ethyl 2-fluoroacetoacetate (0.16 mL, 1.24 mmol). The reaction was allowed to warm to 120° C. and stirred at 120° C. for 16 h. The reaction mixture was allowed to cool to RT and next partitioned between EtOAc and saturated sodium hydrogen carbonate. The organic layer was separated. The combined organic layer was washed with saturated brine, dried ($Na_2SO_4$), and concentrated in vacuo. The residue was purified by flash column chromatography (DCM to EtOAc, gradient elution) to afford the title compound as a yellow solid (37 mg, 12%). LC/MS (Table 1, Method F): $R_t$=1.42 min; m/z=297.2 [M+H]$^+$.

Preparation of Int-86: (R)-3-Fluoro-1,4,5-trimethyl-1,5,6,7-tetrahydro-2H-pyrrolo[3,4-b]pyridin-2-one Hydrochloride

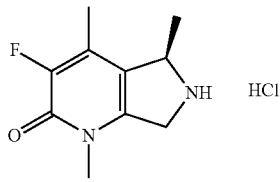

To a solution of tert-butyl (5R)-3-fluoro-1,4,5-trimethyl-2-oxo-5,7-dihydropyrrolo[3,4-b]pyridine-6-carboxylate (17 mg, 0.057 mmol) in DCM (0.2 mL) was added 4 M HCl in 1,4-dioxane (0.36 mL, 1.4 mmol) and the reaction stirred at RT for 2 h. The reaction mixture was concentrated in vacuo and azeotroped with MeCN to afford the title compound as a brown solid (14 mg, quantitative). LC/MS (Table 2, Method A): $R_t$=0.68 min; m/z=197.1 [M+H]$^+$.

Example 71—Synthesis of Compound I-114: (R)-3-Fluoro-1,4,5-trimethyl-6-(1-(trifluoromethyl)-1H-pyrazole-4-carbonyl)-1,5,6,7-tetrahydro-2H-pyrrolo[3,4-b]pyridin-2-one

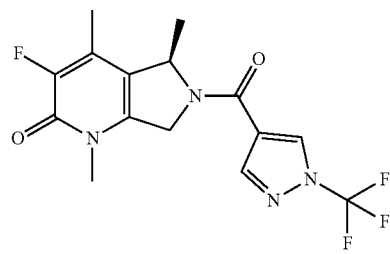 [SMILES: Cc1c2c(n(C)c(=O)c1F)CN(C(=O)c1cnn(C(F)(F)F)c1)[C@@H]2C]

To a solution of (5R)-3-fluoro-1,4,5-trimethyl-6,7-dihydro-5H-pyrrolo[3,4-b]pyridin-2-one hydrochloride (16 mg, 0.067 mmol) in DMF (0.5 mL) was added N,N-diisopropylethylamine (0.041 mL, 0.24 mmol) followed by a solution of 1-(trifluoromethyl)pyrazole-4-carboxylic acid (13 mg, 0.074 mmol) and HATU (28 mg, 0.074 mmol) in DMF (0.5 mL). The reaction stirred at RT for 1 h. The reaction mixture was purified directly by reverse phase HPLC (Table 3, Method 8) to afford the title compound as an off-white solid (13 mg, 54%). $^1$H NMR (400 MHz: CDCl$_3$) δ 8.33-8.28 (m, 1H), 8.09-8.07 (m, 1H), 5.54-5.51 (m, 0.7H), 5.31-5.29 (m, 0.3H), 4.99-4.96 (m, 1H), 4.83-4.78 (m, 1H), 3.56-3.50 (m, 3H), 2.20 (s, 3H), 1.56-1.54 (m, 2H), 1.45 (d, J=5.9 Hz, 1H). LC/MS (Table 2, Method D): $R_t$=3.26 min; m/z=359.6 [M+H]$^+$.

Example 72—Compound Characterization

Physical characterization data for exemplary compounds is provided in Table 22 below.

TABLE 22

Compound NMR and LC/MS Data

| Compound No. | $^1$H NMR data | LC/MS Method |
|---|---|---|
| I-2 | $^1$H NMR (400 MHz: DMSO-d$_6$) δ 8.38 (s, 1H), 7.96 (d, J = 2.0 Hz, 1H), 5.12 (s, 1H), 4.93-4.85 (m, 2H), 4.67 (s, 1H), 3.92 (s, 3H), 3.48 (d, J = 8.8 Hz, 3H), 2.27 (d, J = 8.9 Hz, 3H) | (Table 2, Method B): $R_t$ = 2.59 min; m/z = 307 [M + H]$^+$ |
| I-3 | $^1$H NMR (400 MHz: DMSO-d$_6$) δ 7.74 (d, J = 2.1 Hz, 1H), 6.70 (d, J = 1.9 Hz, 1H), 5.23-5.23 (m, 1H), 5.04 (s, 1H), 4.87 (s, 1H), 4.69-4.69 (m, 1H), 3.94 (s, 3H), 3.45 (s, 3H), 2.23-2.23 (s, 3H) | (Table 2, Method C): $R_t$ = 2.68 min; m/z = 307 [M + H]$^+$ |
| I-4 | $^1$H NMR (400 MHz: DMSO-d$_6$) δ 7.80 (s, 1H), 7.74 (d, J = 4.7 Hz, 1H), 5.34 (dd, J = 2.4, 2.4 Hz, 1H), 5.15 (dd, J = 2.5, 2.5 Hz, 1H), 4.86 (dd, J = 2.5, 2.5 Hz, 1H), 4.67 (s, 1H), 3.72 (s, 3H), 3.44 (d, J = 11.4 Hz, 3H), 2.24 (d, J = 9.6 Hz, 3H) | (Table 2, Method C): $R_t$ = 1.99 min; m/z = 307 [M + H]$^+$ |
| I-5 | $^1$H NMR (400 MHz: DMSO-d$_6$) δ 8.37 (s, 1H), 7.97 (d, J = 2.8 Hz, 1H), 5.12 (s, 1H), 4.92 (dd, J = 2.6, 2.6 Hz, 1H), 4.84 (s, 1H), 4.65 (s, 1H), 3.98 (d, J = 7.3 Hz, 2H), 3.47 (d, J = 8.5 Hz, 3H), 2.26 (d, J = 8.7 Hz, 3H), 2.20-2.12 (m, 1H), 0.86 (d, J = 6.7 Hz, 6H) | (Table 2, Method C): $R_t$ = 3.24 min; m/z = 349 [M + H]$^+$ |

TABLE 22-continued

Compound NMR and LC/MS Data

| Compound No. | $^1$H NMR data | LC/MS Method |
|---|---|---|
| I-6 | $^1$H NMR (400 MHz: DMSO-$d_6$) δ 6.59 (d, J = 1.9 Hz, 1H), 5.16 (s, 1H), 4.96-4.91 (m, 2H), 4.72 (dd, J-2.2, 2.2 Hz, 1H), 3.46 (s, 1.5H), 3.40 (s, 1.5H), 2.26-2.19 (m, 4H), 1.15-1.10 (m, 2H), 0.99-0.94 (m, 2H) | (Table 2, Method C): $R_t$ = 3.65 min; m/z = 334 [M + H]$^+$ |
| I-7 | $^1$H NMR (400 MHz: DMSO-$d_6$) δ 7.67 (d, J = 4.0 Hz, 1H), 7.03 (d, J = 4.0 Hz, 1H), 5.27-5.22 (m, 1H), 5.04 (s, 1H), 4.92 (s, 1H), 4.71 (s, 1H), 3.47 (s, 3H), 2.27 (s, 3H), 1.39 (s, 9H) | (Table 2, Method B): $R_t$ = 4.50 min; m/z = 365 [M + H]$^+$ |
| I-8 | $^1$H NMR (400 MHz: DMSO-$d_6$) δ 7.89 (s, 1H), 5.20 (s, 1H), 4.99 (dd, J = 1.5 Hz, 2H), 4.78 (s, 1H), 3.47 (s, 1.5H), 3.40 (s, 1.5H), 2.27 (s, 1.5H), 2.20 (s, 1.5H) | (Table 2, Method D): $R_t$ = 3.96 min; m/z = 362 [M + H]$^+$ |
| I-9 | $^1$H NMR (400 MHz: DMSO-$d_6$) δ 8.33 (d, J = 3.1 Hz, 1H), 5.23 (s, 1H), 5.02 (dd, J = 2.3, 2.3 Hz, 1H), 4.90 (dd, J = 2.3, 2.3 Hz, 1H), 4.70 (s, 1H), 3.46 (d, J = 5.0 Hz, 3H), 2.70 (s, 3H), 2.25 (d, J = 3.6 Hz, 3H) | (Table 2, Method C): $R_t$ = 2.76 min; m/z = 324 [M + H]$^+$ |
| I-10 | $^1$H NMR (400 MHz: DMSO-$d_6$) δ 8.38 (s, 1H), 7.99 (d, J = 2.0 Hz, 1H), 5.15 (s, 1H), 4.96 (s, 1H), 4.87 (t, J = 2.4 Hz, 1H), 4.68 (s, 1H), 4.65-4.55 (m, 1H), 3.48 (d, J = 9.3 Hz, 3H), 2.28 (d, J = 9.5 Hz, 3H), 1.47 (d, J = 6.8 Hz, 6H) | (Table 2, Method B): $R_t$ = 3.13 min; m/z = 335 [M + H]$^+$ |
| I-11 | $^1$H NMR (400 MHz: DMSO-$d_6$) δ 7.72 (s, 1H), 5.32 (s, 1H), 5.13 (s, 1H), 4.85 (s, 1H), 4.65 (s, 1H), 3.61 (s, 3H), 3.44 (d, J = 9.6 Hz, 3H), 2.33 (s, 3H), 2.24 (d, J = 5.9 Hz, 3H) | (Table 2, Method C): $R_t$ = 1.83 min; m/z = 321 [M + H]$^+$ |
| I-12 | $^1$H NMR (400 MHz: DMSO-$d_6$) δ 8.63 (s, 1H), 5.23 (s, 1H), 5.04 (t, J = 2.4, 1H), 4.88 (t, J = 2.3 Hz, 1H), 4.69 (t, J = 2.3 Hz, 1H), 3.44 (d, J = 12.3 Hz, 3H), 2.53-2.48 (m, 3H, three protons obscured by solvent peak), 2.24 (d, J = 8.9 Hz, 3H) | (Table 2, Method C): $R_t$ = 2.70 min; m/z = 308 [M + H]$^+$ |
| I-13 | $^1$H NMR (400 MHz: CDCl$_3$) δ 6.51 (d, J = 8.7 Hz, 1H), 5.23 (t, J = 2.0 Hz, 1H), 5.11 (t, J = 2.2 Hz, 1H), 4.92 (t, J = 2.2 Hz, 1H), 4.82 (t, J = 2.1 Hz, 1H), 3.56 (d, J = 5.9 Hz, 3H), 2.51 (s, 3H), 2.29 (d, J = 8.9 Hz, 3H) | (Table 2, Method C): $R_t$ = 3.16 min; m/z = 308 [M + H]$^+$ |
| I-14 | $^1$H NMR (400 MHz: DMSO-$d_6$) δ 7.95 (s, 1H), 7.88 (d, J = 4.2 Hz, 1H), 5.36 (t, J = 2.5 Hz, 1H), 5.17 (t, J = 2.5 Hz, 1H), 4.87 (s, 1H), 4.67 (s, 1H), 4.53-4.46 (m, 1H), 3.44 (d, J = 12.4 Hz, 3H), 2.24 (d, J = 10.1 Hz, 3H), 1.43 (d, J = 6.7 Hz, 6H) | (Table 2, Method C): $R_t$ = 2.40 min; m/z = 335 [M + H]$^+$ |
| I-15 | $^1$H NMR (400 MHz: CDCl$_3$) δ 8.01 (dd, J = 1.4, 6.1 Hz, 1H), 7.88 (dd, J = 1.3, 4.0 Hz, 1H), 5.38 (t, J = 2.2 Hz, 1H), 5.25 (t, J = 2.3 Hz, 1H), 4.94 (t, J = 2.3 Hz, 1H), 4.83 (t, J = 2.3, 2.3 Hz, 1H), 3.57 (d, J = 2.7 Hz, 3H), 2.30 (s, 3H) | (Table 2, Method C): $R_t$ = 3.15 min; m/z = 361.5 [M + H]$^+$ |
| I-16 | $^1$H NMR (400 MHz: CDCl$_3$) δ 7.89 (t, J = 2.4 Hz, 1H), 7.09 (dd, J = 2.5, 9.8 Hz, 1H), 5.31 (t, J = 2.1 Hz, 1H), 5.17 (t, J = 2.2 Hz, 1H), 4.94 (t, J = 2.4 Hz, 1H), 4.84 (t, J = 2.1 Hz, 1H), 3.56 (d, J = 6.4 Hz, 3H), 2.30 (d, J = 9.2 Hz, 3H) | (Table 2, Method C): $R_t$ = 3.86 min; m/z = 361.2 [M + H]$^+$ |
| I-17 | $^1$H NMR (400 MHZ, DMSO-$d_6$) δ 8.87 (d, J = 3.0 Hz, 1H), 8.27 (s, 1H), 7.88 (t, J = 58.9 Hz, 1H), 5.22-4.64 (m, 4H), 3.47 (d, J = 3.8 Hz, 3H), 2.26 (d, J = 4.0 Hz, 3H) | (Table 2, Method B): $R_t$ = 3.06 min; m/z = 343.2 [M + H]$^+$ |
| I-18 | $^1$H NMR (400 MHz: DMSO-$d_6$) δ 7.57 (s, 1H), 5.12 (s, 1H), 4.90 (d, J = 4.1 Hz, 2H), 4.71 (s, 1H), 3.70 (s, 3H), 3.45 (d, J = 12.0 Hz, 3H), 2.36 (s, 3H), 2.25 (d, J = 11.7 Hz, 3H) | (Table 2, Method B): $R_t$ = 1.90 min; m/z = 321 [M + H]$^+$ |
| I-19 | $^1$H NMR (400 MHz: DMSO-$d_6$) δ 7.85 (s, 1H), 7.78 (d, J = 4.9 Hz, 1H), 5.37 (t, J = 2.4 Hz, 1H), 5.17 (t, J = 2.5 Hz, 1H), 4.87 (t, J = 2.5 Hz, 1H), 4.68 (t, J = 2.5 Hz, 1H), 3.85 (d, J = 7.1 Hz, 2H), 3.45 (d, J = 10.6 Hz, 3H), 2.24 (d, J = 8.9 Hz, 3H), 2.08-2.00 (m, 1H), 0.84 (d, J = 6.7 Hz, 6H) | (Table 2, Method B): $R_t$ = 2.88 min; m/z = 349 [M + H]$^+$ |
| I-20 | $^1$H NMR (400 MHz: CDCl$_3$) δ 7.62 (d, J = 6.2 Hz, 1H), 5.40 (t, J = 2.4 Hz, 1H), 5.27 (t, J = 2.1 Hz, 1H), 4.94 (t, J = 2.2 Hz, 1H), 4.84 (t, J = 2.0 Hz, 1H), 3.58 (d, J = 6.6 Hz, 3H), 2.56 (s, 3H), 2.31 (d, J = 2.7 Hz, 3H) | (Table 2, Method C): $R_t$ = 3.43 min; m/z = 324 [M + H]$^+$ |
| I-21 | $^1$H NMR (400 MHz: DMSO-$d_6$) δ 8.27 (d, J = 2.4 Hz, 1H), 5.22-5.20 (m, 1H), 5.01 (t, J = 2.3 Hz, 1H), 4.89 (s, 1H), 4.69 (s, 1H), 3.46 (d, J = 4.3 Hz, 3H), 2.25 (d, J = 3.2 Hz, 3H), 2.07 (s, 1H), 1.22-1.16 (m, 2H), 1.07-1.01 (m, 2H) | (Table 2, Method C): $R_t$ = 3.23 min; m/z = 350 [M + H]$^+$ |
| I-22 | $^1$H NMR (400 MHz: DMSO-$d_6$) δ 8.08-8.08 (m, 1H), 5.33 (s, 1H), 5.14 (t, J = 2.1 Hz, 1H), 4.93 (t, J = 2.1 Hz, 1H), 4.73 (t, J = 2.1 Hz, 1H), 3.45 (d, J = 11.6 Hz, 3H), 2.26-2.22 (m, 6H) | (Table 2, Method C): $R_t$ = 2.90 min; m/z = 308 [M + H]$^+$ |
| I-23 | $^1$H NMR (400 MHz: DMSO-$d_6$) δ 8.55 (s, 1H), 8.02 (d, J = 2.9 Hz, 1H), 7.40-7.28 (m, 5H), 5.42 (s, 2H), 5.15 (s, 1H), 4.95 (t, J = 2.4 Hz, 1H), 4.87 (t, J = 2.4 Hz, 1H), 4.67 (s, 1H), 3.48 (d, J = 7.0 Hz, 3H), 2.27 (d, J = 7.7 Hz, 3H) | (Table 2, Method B): $R_t$ = 3.56 min; m/z = 383 [M + H]$^+$ |
| I-24 | $^1$H NMR (400 MHz: DMSO-$d_6$) δ 7.69 (s, 1H), 5.33 (s, 1H), 5.15 (s, 1H), 4.88 (t, J = 2.4 Hz, 1H), 4.68 (t, J = 2.6 Hz, 1H), 4.02 (t, J = 5.6 Hz, 2H), 3.45 (d, J = 12.0 Hz, 3H), 2.80 (t, J = 6.1 Hz, 2H), 2.25 (d, J = 7.7 Hz, 3H), 1.94-1.87 (m, 4H) | (Table 2, Method B): $R_t$ = 1.98 min; m/z = 347 [M + H]$^+$ |
| I-25 | $^1$H NMR (400 MHz: DMSO-$d_6$) δ 7.83 (s, 1H), 5.32 (s, 1H), 5.13 (t, J = 2.4 Hz, 1H), 4.89 (s, 1H), 4.81 (s, 2H), 4.69 (s, 1H), 4.14-4.02 (m, 4H), 3.45 (d, J = 16.1 Hz, 3H), 2.25 (d, J = 11.5 Hz, 3H) | (Table 2, Method B): $R_t$ = 2.27 min; m/z = 349 [M + H]$^+$ |

TABLE 22-continued

Compound NMR and LC/MS Data

| Compound No. | ¹H NMR data | LC/MS Method |
|---|---|---|
| I-26 | ¹H NMR (300 MHz: DMSO-$d_6$) δ 8.81 (s, 1H), 5.25-5.23 (m, 1H), 5.05-4.95 (m, 2H), 4.77 (s, 1H), 3.47 (s, 1.5H), 3.38 (s, 1.5H), 2.27 (s, 1.5H), 2.18 (s, 1.5H) | (Table 2, Method C): $R_t$ = 3.79 min; m/z = 378 [M + H]⁺ |
| I-27 | ¹H NMR (300 MHz: CDCl₃) δ 8.09 (s, 1H), 7.84 (d, J = 7.9 Hz, 1H), 5.01 (s, 1H), 4.92 (s, 2H), 4.81 (s, 1H), 4.04 (d, J = 7.2 Hz, 2H), 3.56 (s, 3H), 2.29 (s, 3H), 1.37-1.26 (m, 1H), 0.75-0.67 (m, 2H), 0.46-0.39 (m, 2H) | (Table 2, Method C): $R_t$ = 3.03 min; m/z = 347 [M + H]⁺ |
| I-28 | ¹H NMR (400 MHz: DMSO-$d_6$) δ 8.39 (d, J = 2.5 Hz, 1H), 5.28-5.25 (m, 1H), 5.06 (t, J = 2.3 Hz, 1H), 4.93 (t, J = 2.3 Hz, 1H), 4.73 (s, 1H), 3.48 (d, J = 4.6 Hz, 3H), 2.93 (d, J = 7.2 Hz, 2H), 2.27 (d, J = 3.6 Hz, 3H), 1.20-1.11 (m, 1H), 0.64-0.58 (m, 2H), 0.37-0.32 (m, 2H) | (Table 2, Method E): $R_t$ = 3.59 min; m/z = 364 [M + H]⁺ |
| I-29 | ¹H NMR (400 MHz: DMSO-$d_6$) δ 8.80 (s, 1H), 5.31 (s, 1H), 5.12 (s, 1H), 4.98 (s, 1H), 4.77 (s, 1H), 3.48 (s, 3H), 2.28 (s, 3H) | (Table 2, Method B): $R_t$ = 4.02 min; m/z = 378 [M + H]⁺ |
| I-30 | 1H NMR (400 MHz: DMSO-$d_6$) δ 8.24 (d, J = 8.1 Hz, 2H), 7.66-7.59 (m, 2H), 5.54 (s, 1H), 5.35 (s, 1H), 5.02 (s, 1H), 4.82 (s, 1H), 3.49 (s, 3H), 2.28 (s, 3H) | (Table 2, Method D): $R_t$ = 4.08 min; m/z = 360 [M + H]⁺ |
| I-31 | ¹H NMR (400 MHz: DMSO-$d_6$) δ 9.46 (dd, J = 4.9, 6.9 Hz, 1H), 7.83 (d, J = 8.9 Hz, 1H), 7.74 (s, 1H), 7.18-7.13 (m, 1H), 7.02 (t, J = 6.9 Hz, 1H), 5.48 (s, 1H), 5.29 (t, J = 2.4 Hz, 1H), 4.99 (s, 1H), 4.79 (s, 1H), 3.48 (d, J = 9.8 Hz, 3H), 2.26 (d, J = 8.7 Hz, 3H) | (Table 2, Method C): $R_t$ = 3.58 min; m/z = 343 [M + H]⁺ |
| I-32 | ¹H NMR (400 MHz: DMSO-$d_6$) δ 6.48 (s, 1H), 5.24 (t, J = 2.3 Hz, 1H), 5.05 (s, 1H), 4.88 (s, 1H), 4.68 (t, J = 2.5 Hz, 1H), 4.18-4.08 (m, 2H), 3.44 (d, J = 16.2 Hz, 3H), 2.79 (t, J = 6.3 Hz, 2H), 2.23 (d, J = 13.1 Hz, 3H), 2.03-1.97 (m, 2H), 1.85-1.78 (m, 2H | (Table 2, Method C): $R_t$ = 3.21 min; m/z = 347 [M + H]⁺ |
| I-33 | ¹H NMR (300 MHz, DMSO) δ 7.74 (s, 1H), 5.33 (t, J = 2.5 Hz, 1H), 5.14 (s, 1H), 4.86 (t, J = 2.7 Hz, 1H), 4.67 (t, J = 2.4 Hz, 1H), 4.01 (t, J = 7.1 Hz, 2H), 3.44 (d, J = 7.2 Hz, 3H), 2.80 (t, J = 7.5 Hz, 2H), 2.59-2.52 (m, 2H), 2.24 (d, J = 4.9 Hz, 3H) | (Table 2, Method D): $R_t$ = 2.52 min; m/z = 333 [M + H]⁺ |
| I-34 | ¹H NMR (400 MHz: DMSO-$d_6$) δ 8.39 (d, J = 3.0 Hz, 1H), 5.28-5.25 (m, 1H), 5.06 (s, 1H), 4.92 (s, 1H), 4.72 (s, 1H), 3.48 (d, J = 5.9 Hz, 3H), 2.91 (d, J = 7.2 Hz, 2H), 2.27 (d, J = 4.4 Hz, 3H), 2.13-2.05 (m, 1H), 0.97 (d, J = 6.7 Hz, 6H) | (Table 2, Method B): $R_t$ = 4.04 min; m/z = 366 [M + H]⁺ |
| I-35 | ¹H NMR (400 MHz: DMSO-$d_6$) δ 8.39 (d, J = 2.1 Hz, 1H), 5.26 (s, 1H), 5.05 (s, 1H), 4.93 (s, 1H), 4.73 (s, 1H), 3.95-3.91 (m, 1H), 3.48 (d, J = 4.3 Hz, 3H), 2.48-2.41 (m, 2H), 2.35-2.26 (m, 5H), 2.04-2.00 (m, 1H), 1.98-1.90 (m, 1H) | (Table 2, Method B): $R_t$ = 3.87 min; m/z = 364 [M + H]⁺ |
| I-36 | ¹H NMR (400 MHz: DMSO-$d_6$) δ 8.68-8.67 (m, 1H), 7.41 (t, J = 53.4 Hz, 1H), 5.30-5.27 (m, 1H), 5.08 (s, 1H), 4.95 (s, 1H), 4.75-4.75 (m, 1H), 3.47 (d, J = 2.2 Hz, 3H), 2.26 (s, 3H)d | (Table 2, Method C): $R_t$ = 3.26 min; m/z = 360 [M + H]⁺ |
| I-37 | ¹H NMR (400 MHz: DMSO-$d_6$) δ 8.03 (s, 1H), 5.13 (s, 1H), 4.93 (s, 1H), 4.84 (s, 1H), 4.65 (s, 1H), 4.11 (t, J = 7.2 Hz, 2H), 3.45 (d, J = 6.8 Hz, 3H), 3.00 (t, J = 7.3 Hz, 2H), 2.61-2.56 (m, 2H), 2.26 (d, J = 5.4 Hz, 3H) | (Table 2, Method D): $R_t$ = 2.57 min; m/z = 333 [M + H]⁺ |
| I-38 | ¹H NMR (400 MHz: DMSO-$d_6$) δ 8.44 (d, J = 2.9 Hz, 1H), 5.26-5.25 (m, 1H), 5.04 (s, 1H), 4.92 (s, 1H), 4.75 (s, 2H), 4.73-4.70 (m, 1H), 3.46 (d, J = 3.8 Hz, 3H), 3.44 (s, 3H), 2.26 (d, J = 2.6 Hz, 3H) | (Table 2, Method C): $R_t$ = 2.89 min; m/z = 354 [M + H]⁺ |
| I-39 | ¹H NMR (400 MHz: DMSO-$d_6$) δ 8.44 (d, J = 3.8 Hz, 1H), 5.24 (s, 1H), 5.05 (s, 1H), 4.94 (t, J = 2.3 Hz, 1H), 4.74 (s, 1H), 4.41-4.31 (m, 2H), 3.47 (s, 1.5H), 3.38 (s, 1.5H), 2.26 (s, 1.5H), 2.17 (s, 1.5H) | (Table 2, Method C): $R_t$ = 3.63 min; m/z = 392 [M + H]⁺ |
| I-40 | ¹H NMR (400 MHz: DMSO-$d_6$) δ 7.98-7.91 (m, 3H), 7.76 (t, J = 8.1 Hz, 1H), 4.96 (t, J = 2.2 Hz, 1H), 4.91 (s, 1H), 4.77 (s, 1H), 4.68 (t, J = 2.3 Hz, 1H), 3.50 (s, 1.5H), 3.32 (s, 1.5H), 2.28 (s, 1.5H), 2.12 (s, 1.5H) | (Table 2, Method B): $R_t$ = 4.14 min; m/z = 371 [M + H]⁺ |
| I-41 | ¹H NMR (400 MHz: DMSO-$d_6$) δ 7.89 (d, J = 8.4 Hz, 2H), 7.84 (d, J = 8.4 Hz, 2H), 4.96 (t, J = 2.4 Hz, 1H), 4.89-4.88 (m, 1H), 4.77-4.75 (m, 1H), 4.66 (t, J = 2.4 Hz, 1H), 3.49 (s, 1.5H), 3.32 (s, 1.5H), 2.28 (s, 1.5H), 2.12 (s, 1.5H) | (Table 2, Method E): $R_t$ = 4.11 min; m/z = 371 [M + H]⁺ |
| I-42 | ¹H NMR (400 MHz: DMSO-$d_6$) δ 8.94 (d, J = 4.9 Hz, 1H), 8.05-8.05 (m, 1H), 7.94 (t, J = 4.3 Hz, 1H), 4.94 (t, J = 2.3 Hz, 1H), 4.88-4.86 (m, 1H), 4.74 (s, 1H), 4.65 (t, J-2.3 Hz, 1H), 3.48 (s, 1.5H), 3.30 (s, 1.5H), 2.27 (s, 1.5H), 2.11 (s, 1.5H) | (Table 2, Method C): $R_t$ = 3.40 min; m/z = 372 [M + H]⁺ |
| I-43 | ¹H NMR (400 MHz: DMSO-$d_6$) δ 8.42 (d, J = 5.4 Hz, 1H), 8.20 (d, J = 9.5 Hz, 1H), 7.70 (d, J = 9.3 Hz, 1H), 4.99 (d, J = 6.7 Hz, 2H), 4.80-4.78 (m, 2H), 3.50 (s, 1.5H), 3.32 (s, 1.5H), 2.29 (s, 1.5H), 2.13-2.09 (m, 1.5H) | (Table 2, Method B): $R_t$ = 3.62 min; m/z = 345 [M + H]⁺ |
| I-44 | ¹H NMR (400 MHz: DMSO-$d_6$) δ 9.01 (s, 1H), 8.38-8.33 (m, 1H), 8.07 (d, J = 8.2 Hz, 1H), 4.98 (t, J = 2.3 Hz, 1H), 4.94 (s, 1H), 4.79 (s, 1H), 4.73 (t, J = 2.0 Hz, 1H) , 3.50 (s, 1.5H), 3.32 (s, 1.5H), 2.29 (s, 1.5H), 2.13 (s, 1.5H) | (Table 2, Method B): $R_t$ = 3.69 min; m/z = 372 [M + H]⁺ |

TABLE 22-continued

Compound NMR and LC/MS Data

| Compound No. | $^1$H NMR data | LC/MS Method |
|---|---|---|
| I-45 | $^1$H NMR (400 MHz: DMSO-d$_6$) δ 9.12 (s, 1H), 8.46-8.43 (m, 1H), 8.08 (t, J = 7.9 Hz, 1H), 5.18 (s, 1H), 5.01 (s, 1H), 4.95 (s, 1H), 4.81 (t, J = 2.2 Hz, 1H), 3.50 (s, 1.5H), 3.37 (s, 1.5H), 2.29 (s, 1.5H), 2.17 (s, 1.5H) | (Table 2, Method B): R$_t$ = 3.95 min; m/z = 372 [M + H]$^+$ |
| I-46 | $^1$H NMR (400 MHz: DMSO-d$_6$) δ 9.55 (s, 1H), 8.50 (d, J = 2.0 Hz, 1H), 8.20 (d, J = 8.4 Hz, 1H), 7.78 (dd, J = 1.8, 8.4 Hz, 1H), 5.00 (s, 1H), 4.95 (s, 1H), 4.80 (s, 1H), 4.75 (s, 1H), 3.50 (s, 1.5H), 3.31 (s, 1.5H), 2.29 (s, 1.5H), 2.12 (s, 1.5H) | (Table 2, Method B): R$_t$ = 3.07 min; m/z = 360 [M + H]$^+$ |
| I-47 | $^1$H NMR (400 MHz: DMSO-d$_6$) δ 8.80 (d, J = 5.0 Hz, 1H), 8.47 (s, 1H), 7.65 (d, J = 9.4 Hz, 1H), 7.45 (s, 1H), 6.97 (dd, J = 1.3, 9.3 Hz, 1H), 5.05-4.74 (m, 4H), 3.49 (s, 1.5H), 3.43-3.33 (m, 1.5H, one and a half protons obscured by solvent peak), 2.28 (s, 1.5H), 2.17 (s, 1.5H) | (Table 2, Method E): R$_t$ = 2.68 min; m/z = 343 [M + H]$^+$ |
| I-48 | $^1$H NMR (400 MHz: DMSO-d$_6$) δ 9.17-9.13 (m, 2H), 8.45-8.43 (m, 1H), 4.97 (d, J = 2.3 Hz, 2H), 4.77 (d, J = 13.9 Hz, 2H), 3.50 (s, 1.5H), 3.33 (s, 1.5H), 2.29 (s, 1.5H), 2.13 (s, 1.5H) | (Table 2, Method E): R$_t$ = 3.41 min; m/z = 372 [M + H]$^+$ |
| I-49 | $^1$H NMR (300 MHz: DMSO-d$_6$) δ 8.66-8.64 (m, 1H), 8.37 (d, J = 8.5 Hz, 1H), 7.92 (dd, J = 1.7, 8.5 Hz, 1H), 4.99 (s, 1H), 4.91 (s, 1H), 4.79 (s, 1H), 4.70 (s, 1H), 3.49 (s, 1.5H), 3.29 (s, 1.5H), 2.28 (s, 1.5H), 2.09 (s, 1.5H) | (Table 2, Method C): R$_t$ = 4.11 min; m/z = 427 [M + H]$^+$ |
| I-50 | $^1$H NMR (400 MHz: DMSO-d$_6$) δ 7.57-7.53 (m, 2H), 7.44 (d, J = 7.7 Hz, 1H), 5.07 (s, 4H), 4.94 (s, 1H), 4.89 (s, 1H), 4.75 (s, 1H), 4.68 (t, J = 2.5 Hz, 1H), 3.49 (s, 1.5H), 3.33 (s, 1.5H), 2.28 (s, 1.5H), 2.13 (s, 1.5H) | (Table 2, Method B): R$_t$ = 3.05 min; m/z = 345 [M + H]$^+$ |
| I-54 | $^1$H NMR (400 MHz: DMSO-d$_6$) δ 8.45 (s, 1H), 8.00 (d, J = 2.8 Hz, 1H), 5.12 (s, 1H), 4.93 (t, J = 2.5 Hz, 1H), 4.86 (t, J = 2.5 Hz, 1H), 4.69-4.64 (m, 3H), 4.50 (d, J = 7.2 Hz, 2H), 4.45 (t, J = 6.1 Hz, 2H), 3.50-3.42 (m, 4H), 2.27 (d, J = 8.9 Hz, 3H) | (Table 2, Method B): R$_t$ = 2.62 min; m/z = 363 [M + H]$^+$ |
| I-55 | $^1$H NMR (400 MHz: DMSO-d$_6$) δ 8.40 (s, 1H), 7.98 (d, J = 2.6 Hz, 1H), 5.13 (s, 1H), 4.94 (t, J = 2.6 Hz, 1H), 4.86 (s, 1H), 4.68 (s, 1H), 4.10 (d, J = 7.5 Hz, 2H), 3.48 (d, J = 8.9 Hz, 3H), 2.47-2.34 (m, 1H), 2.28 (d, J = 9.2 Hz, 3H), 1.66-1.51 (m, 6H), 1.32-1.24 (m, 2H) | (Table 2, Method B): R$_t$ = 3.84 min; m/z = 375 [M + H]$^+$ |
| I-56 | $^1$H NMR (400 MHz: DMSO-d$_6$) δ 8.45 (s, 1H), 8.00 (d, J = 2.6 Hz, 1H), 5.13 (s, 1H), 4.94 (t, J = 2.6 Hz, 1H), 4.87 (t, J = 2.5 Hz, 1H), 4.67 (s, 1H), 4.19 (d, J = 7.5 Hz, 2H), 3.82-3.75 (m, 1H), 3.70-3.62 (m, 2H), 3.53-3.50 (m, 1H), 3.48 (d, J = 8.9 Hz, 3H), 2.81-2.68 (m, 1H), 2.28 (d, J = 9.3 Hz, 3H), 1.99-1.89 (m, 1H), 1.68-1.58 (m, 1H) | (Table 2, Method C): R$_t$ = 2.79 min; m/z = 377 [M + H]$^+$ |
| I-60 | $^1$H NMR (400 MHz: DMSO-d$_6$) δ 8.61 (s, 1H), 8.57-8.55 (m, 2H), 8.08 (d, J = 3.0 Hz, 1H), 7.20-7.18 (m, 2H), 5.50 (s, 2H), 5.16 (s, 1H), 4.97 (s, 1H), 4.90-4.86 (m, 1H), 4.69 (s, 1H), 3.48 (d, J = 4.3 Hz, 3H), 2.28 (d, J = 5.1 Hz, 3H) | (Table 2, Method B): R$_t$ = 2.20 min; m/z = 384 [M + H]$^+$ |
| I-61 | $^1$H NMR (400 MHz: DMSO-d$_6$) δ 8.51-8.50 (m, 1H), 8.13 (d, J = 4.2 Hz, 1H), 5.26-5.12 (m, 3H), 4.94 (s, 1H), 4.88-4.85 (m, 1H), 4.69-4.65 (m, 1H), 3.48-3.45 (m, 3H), 2.27-2.24 (m, 3H) | (Table 2, Method C): R$_t$ = 3.08 min; m/z = 475 [M + H]$^+$ |
| I-62 | $^1$H NMR (400 MHz: DMSO-d$_6$) δ 8.21 (s, 1H), 7.96 (d, J = 3.3 Hz, 1H), 5.12 (s, 1H), 4.93 (s, 1H), 4.85 (s, 1H), 4.68-4.64 (m, 1H), 4.19 (s, 2H), 3.46 (d, J = 4.5 Hz, 3H), 3.19 (s, 3H), 2.26 (d, J = 4.3 Hz, 3H), 1.10 (s, 6H) | (Table 2, Method B): R$_t$ = 3.11 min; m/z = 379 [M + H]$^+$ |
| I-63 | $^1$H NMR (400 MHz: DMSO-d$_6$) δ 8.34 (s, 1H), 7.98 (d, J = 2.5 Hz, 1H), 5.11 (s, 1H), 4.92 (t, J = 2.7 Hz, 1H), 4.85 (t, J = 2.5 Hz, 1H), 4.66 (s, 1H), 4.32 (t, J = 5.3 Hz, 2H), 3.73 (t, J = 5.3 Hz, 2H), 3.46 (d, J = 7.8 Hz, 3H), 3.24 (s, 3H), 2.26 (d, J = 8.1 Hz, 3H | (Table 2, Method E): R$_t$ = 2.63 min; m/z = 351 [M + H]$^+$ |
| I-65 | $^1$H NMR (400 MHz: DMSO-d$_6$) δ 8.43 (d, J = 2.5 Hz, 1H), 5.27 (s, 1H), 5.07 (t, J = 2.3 Hz, 1H), 4.93 (s, 1H), 4.73 (s, 1H), 3.48 (d, J = 4.6 Hz, 3H), 3.24-3.20 (m, 2H), 2.27 (d, J = 3.3 Hz, 3H), 2.24-2.12 (m, 1H), 1.79-1.69 (m, 1H), 1.49-1.40 (m, 1H) | (Table 2, Method E): R$_t$ = 3.62 min; m/z = 400 [M + H]$^+$ |
| I-66 | $^1$H NMR (400 MHz: DMSO-d$_6$) δ 8.43 (d, J = 2.5 Hz, 1H), 5.28 (s, 1H), 5.07 (s, 1H), 4.93 (s, 1H), 4.73 (s, 1H), 3.48 (d, J = 5.4 Hz, 3H), 3.25-3.20 (m, 2H), 2.27 (d, J = 3.4 Hz, 3H), 2.24-2.12 (m, 1H), 1.79-1.69 (m, 1H), 1.49-1.40 (m, 1H) | (Table 2, Method E): R$_t$ = 3.62 min; m/z = 400 [M + H]$^+$ |
| I-70 | $^1$H NMR (400 MHz: DMSO-d$_6$) δ 8.39 (d, J = 4.1 Hz, 1H), 8.05 (d, J = 8.4 Hz, 1H), 7.76-7.72 (m, 1H), 5.02-4.97 (m, 2H), 4.77 (s, 1H), 4.72 (s, 1H), 4.08-4.00 (m, 1H), 3.88 (d, J = 7.0 Hz, 1H), 3.71 (d, J = 5.5 Hz, 1H), 2.48-2.38 (m, 3H), 2.29 (s, 1H), 2.13-2.09 (m, 3H), 2.00 (t, J = 8.6 Hz, 1H), 1.31-1.25 (m, 1H), 1.15-1.07 (m,1H), 0.55-0.49 (m, 1H), 0.46-0.40 (m, 2H), 0.33-0.30 (m, 1H) | (Table 2, Method B): R$_t$ = 5.00 min; m/z = 454 [M + H]$^+$ |
| I-71 | $^1$H NMR (400 MHz: DMSO-d$_6$) δ 8.42 (s, 0.5H), 8.36 (s, 0.5H), 5.18 (s, 1H), 5.07-4.90 (m, 4H), 4.72 (s, 1H), 2.91 (d, J = 7.1 Hz, 2H), 2.29 (d, J = 2.3 Hz, 3H), 1.24-1.09 (m, 1H), 0.62-0.56 (m, 2H), 0.33 (q, J = 4.9 Hz, 2H) | (Table 2, Method B): R$_t$ = 4.25 min; m/z = 431 [M + H]$^+$ |

TABLE 22-continued

Compound NMR and LC/MS Data

| Compound No. | $^1$H NMR data | LC/MS Method |
|---|---|---|
| I-72 | $^1$H NMR (400 MHz: DMSO-$d_6$) δ 8.29 (d, J = 16.9 Hz, 1H), 7.93 (d, J = 8.4 Hz, 1H), 7.71-7.65 (m, 1H), 5.01-4.94 (m, 2H), 4.88-4.71 (m, 4H), 2.61-2.54 (m, 1H), 2.31 (s, 1H), 2.14 (s, 2H), 1.30-1.26 (m, 2H), 1.19-1.17 (m, 2H) | (Table 2, Method B): $R_t$ = 4.32 min; m/z = 467 [M + H]$^+$ |
| I-74 | $^1$H NMR (400 MHz: DMSO-$d_6$) δ d 9.05 (s, 1H), 8.37 (s, 1H), 5.51-5.44 (m, 1H), 5.23 (dd, J = 2.8, 15.4 Hz, 1H), 5.06 (d, J = 15.4 Hz, 1H), 4.00 (s, 3H), 3.44 (s, 3H), 1.44 (d, J = 6.1 Hz, 2.5H), 1.26 (d, J = 4.9 Hz, 0.5H) | (Table 2, Method E): $R_t$ = 3.52 min; m/z = 391.2 [M + H]$^+$ |
| I-75 | $^1$H NMR (400 MHz: DMSO-$d_6$) δ d 9.05 (s, 1H), 8.37 (s, 1H), 5.51-5.44 (m, 1H), 5.23 (dd, J = 2.8, 15.4 Hz, 1H), 5.06 (d, J = 15.4 Hz, 1H), 4.00 (s, 3H), 3.44 (s, 3H), 1.44 (d, J = 6.1 Hz, 2.5H), 1.26 (d, J = 4.9 Hz, 0.5H) | (Table 2, Method B): $R_t$ = 3.70 min; m/z = 392.1 [M + H]$^+$ |
| I-77 | $^1$H NMR (400 MHz: DMSO-$d_6$) δ 8.87 (s, 0.2H), 8.83 (s, 0.8H), 8.29 (s, 0.2H), 8.24 (s, 0.8H), 7.87 (t, J = 57.2 Hz, 1H), 5.63-5.60 (m, 0.2H), 5.42-5.38 (m, 0.8H), 5.22 (dd, J = 2.6, 15.2 Hz, 0.8H), 5.03 (d, J = 15.2 Hz, 0.8H), 4.93 (d, J = 17.2 Hz, 0.2H), 4.81-4.81 (m, 0.2H), 3.46 (s, 3H), 2.31-2.27 (m, 3H), 1.42 (d, J = 6.1 Hz, 2.3H), 1.29 (d, J = 5.9 Hz, 0.7H) | (Table 2, Method C): $R_t$ = 3.08 min; m/z = 357 [M + H]$^+$ |
| I-80 | $^1$H NMR (400 MHz: DMSO-$d_6$) δ 9.03 (s, 1H), 8.35 (s, 1H), 5.81 (s, 1H), 5.25-5.18 (m, 2H), 5.00 (d, J = 14.9 Hz, 1H), 3.80-3.78 (m, 3H), 3.43-3.37 (m, 3H, three protons obscured by solvent peak), 1.42 (d, J = 6.1 Hz, 2.5H), 1.20 (d, J = 6.1 Hz, 0.5H) | (Table 2, Method E): $R_t$ = 3.20 min; m/z = 357.3 [M + H]$^+$ |
| I-81 | $^1$H NMR (400 MHz: DMSO-$d_6$) δ 9.03 (s, 1H), 8.35 (s, 1H), 5.82 (s, 1H), 5.25-5.18 (m, 2H), 5.00 (d, J = 14.9 Hz, 1H), 3.80-3.78 (m, 3H), 3.43-3.37 (m, 3H, three protons obscured by solvent peak), 1.42 (d, J = 6.1 Hz, 2.5H), 1.20 (d, J = 6.1 Hz, 0.5H) | (Table 2, Method E): $R_t$ = 3.20 min; m/z = 357.3 [M + H]$^+$ |
| I-83 | $^1$H NMR (400 MHz: DMSO-$d_6$) δ 9.04 (s, 1H), 8.36 (s, 1H), 5.48-5.41 (m, 1H), 5.20 (dd, J = 2.3, 15.2 Hz, 1H), 5.02 (d, J = 14.9 Hz, 1H), 3.82 (s, 3H), 3.38 (s, 3H), 1.94 (s, 3H), 1.43 (d, J = 6.1 Hz, 3H) | (Table 2, Method E): $R_t$ = 3.41 min; m/z = 371 [M + H]$^+$ |
| I-84 | $^1$H NMR (400 MHz: DMSO-$d_6$) δ 9.04 (s, 1H), 8.36 (s, 1H), 5.48-5.42 (m, 1H), 5.20 (dd, J = 2.1, 15.0 Hz, 1H), 5.02 (d, J = 14.9 Hz, 1H), 3.82 (s, 3H), 3.38 (s, 3H), 1.94 (s, 3H), 1.43 (d, J = 6.1 Hz, 3H) | (Table 2, Method B): $R_t$ = 3.46 min; m/z = 371 [M + H]$^+$ |
| I-86 | $^1$H NMR (400 MHz: DMSO-$d_6$) δ 8.37 (s, 0.5H), 8.34 (s, 0.5H), 5.27 (s, 1H), 5.19 (s, 1H), 4.93 (s, 1H), 4.86 (s, 1H), 3.91 (d, J = 4.9 Hz, 3H), 3.39 (d, J = 3.4 Hz, 3H), 2.91 (d, J = 7.1 Hz, 2H), 1.90 (s, 3H), 1.25-1.09 (m, 1H), 0.62-0.56 (m, 2H), 0.35-0.30 (m, 2H) | (Table 2, Method D): $R_t$ = 3.34 min; m/z = 359 [M + H]$^+$ |
| I-87 | $^1$H NMR (400 MHz: DMSO-$d_6$) δ 9.10 (d, J = 4.0 Hz, 1H), 8.41-8.41 (m, 1H), 5.21 (s, 1H), 5.15 (s, 1H), 4.91 (s, 1H), 4.87 (s, 1H), 3.92 (d, J = 4.0 Hz, 3H), 3.41 (s, 3H), 1.91 (s, 3H) | (Table 2, Method B): $R_t$ = 3.44 min; m/z = 357 [M + H] + |
| I-91 | $^1$H NMR (400 MHz: CDCl$_3$) δ 8.21 (s, 1H), 5.04 (s, 2H), 4.95 (s, 2H), 3.51 (s, 3H), 3.02 (d, J = 7.2 Hz, 2H), 2.40 (d, J = 7.7 Hz, 3H), 2.37 (s, 3H), 1.25-1.18 (m, 1H), 0.75-0.69 (m, 2H), 0.41-0.36 (m, 2H) | (Table 2, Method D): $R_t$ = 3.74 min; m/z = 375 [M + H]$^+$ |
| I-93 | $^1$H NMR (400 MHz: DMSO-$d_6$) δ 9.11 (s, 0.2H), 9.06 (s, 0.8H), 8.43 (s, 0.2H), 8.38 (s, 0.8H), 6.20 (s, 1H), 5.61-5.56 (m, 0.2H), 5.38-5.32 (m, 0.8H), 5.23 (dd, J = 2.7, 15.4 Hz, 0.8H), 5.02 (d, J = 15.3 Hz, 0.8H), 4.91 (d, J = 19.0 Hz, 0.2H), 4.80 (d, J = 18.2 Hz, 0.2H), 3.38 (d, J = 5.3 Hz, 3H), 2.18 (s, 3H), 1.44 (d, J = 6.1 Hz, 2.4H), 1.26 (d, J = 6.1 Hz, 0.6H) | (Table 2, Method B): $R_t$ = 3.22 min; m/z = 341 [M + H]$^+$ |
| I-94 | $^1$H NMR (400 MHz: DMSO-$d_6$) δ 8.82-8.75 (m, 1H), 6.23 (s, 1H), 5.43-5.37 (m, 1H), 5.34 (dd, J = 2.5, 15.1 Hz, 1H), 5.16 (d, J = 14.7 Hz, 1H), 3.39-3.37 (m, 3H), 2.19 (d, J = 1.0 Hz, 3H), 1.48-1.33 (m, 3H) | (Table 2, Method E): $R_t$ = 3.71 min; m/z = 358 [M + H]$^+$ |
| I-95 | $^1$H NMR (400 MHz: DMSO-$d_6$) δ 8.82-8.74 (m, 1H), 6.22 (s, 1H), 5.43-5.37 (m, 1H), 5.34 (dd, J = 2.4, 15.1 Hz, 1H), 5.16 (d, J = 15.5 Hz, 1H), 3.40-3.37 (m, 3H), 2.19 (d, J = 0.9 Hz, 3H), 1.48-1.34 (m, 3H) | (Table 2, Method E): $R_t$ = 3.71 min; m/z = 358 [M + H]$^+$ |
| I-96 | $^1$H NMR (400 MHz: DMSO-$d_6$) δ 8.23 (s, 1H), 6.20 (s, 1H), 5.35 (dd, J = 2.6, 6.0 Hz, 1H), 5.26 (dd, J = 2.4, 14.9 Hz, 1H), 5.08 (d, J = 15.1 Hz, 1H), 3.37 (s, 3H), 2.49-2.45 (m, 1H), 2.18 (s, 3H), 1.42 (d, J = 6.0 Hz, 3H), 1.20 (dd, J = 3.1, 8.3 Hz, 2H), 1.10-1.04 (m, 2H) | (Table 2, Method B): $R_t$ = 3.21 min; m/z = 330 [M + H]$^+$ |
| I-97 | $^1$H NMR (400 MHz: DMSO-$d_6$) δ 8.23 (s, 1H), 6.20 (s, 1H), 5.38-5.34 (m, 1H), 5.25 (dd, J = 2.4, 15.1 Hz, 1H), 5.08 (d, J = 15.3 Hz, 1H), 3.40-3.36 (m, 3H), 2.49-2.45 (m, 1H), 2.18 (s, 3H), 1.42 (d, J = 6.0 Hz, 3H), 1.20 (dd, J = 3.2, 8.2 Hz, 2H), 1.10-1.02 (m, 2H) | (Table 2, Method B): $R_t$ = 3.21 min; m/z = 330 [M + H]$^+$ |
| I-98 | $^1$H NMR (400 MHz: DMSO-$d_6$) δ 8.29 (d, J = 1.7 Hz, 1H), 7.96-7.91 (m, 1H), 7.69-7.62 (m, 1H), 6.18 (s, 1H), 5.49-5.39 (m, 0.7H), 5.28-5.20 (m, 0.3H), 5.09 (dd, J = 15.6, 2.4 Hz, | (Table 2, Method E): $R_t$ = 3.47 min; m/z = 380 [M + H]$^+$ |

TABLE 22-continued

Compound NMR and LC/MS Data

| Compound No. | ¹H NMR data | LC/MS Method |
|---|---|---|
| | 0.7H), 4.93 (d, J = 16.8 Hz, 0.3H), 4.85 (d, J = 17.5 Hz, 0.3H), 4.61 (d, J = 15.6 Hz, 0.7H), 3.40 (s, 1H), 3.19 (s, 2H), 2.62-2.54 (m, 1H), 2.19 (s, 2H), 2.06 (s, 1H), 1.49 (d, J = 6.1 Hz, 2H), 1.32-1.24 (m, 2H), 1.2-1.15 (m, 2H), 1.02 (d, J = 6.6 Hz, 1H) | |
| I-99 | ¹H NMR (400 MHz: DMSO-d₆) δ 8.29 (1H, d, J = 1.7 Hz), 7.96-7.91 (1H, m), 7.69-7.62 (1H, m), 6.18 (1H, s), 5.49-5.39 (0.7H, m), 5.28-5.20 (0.3H, m), 5.09 (0.7H, dd, J = 15.6, 2.4 Hz), 4.93 (0.3H, d, J = 16.8 Hz), 4.85 (0,3H, d, J = 17.5 Hz), 4.61 (0.7H, d, J = 15.6 Hz), 3.40 (1H, s), 3.19 (2H, s), 2.62-2.54 (1H, m), 2.19 (2H, s), 2.06 (1H, s), 1.49 (2H, d, J = 6.1 Hz), 1.32-1.24 (2H, m), 1.21-1.15 (2H, m), 1.02 (1H, d, J = 6.6 Hz) | (Table 2, Method B): $R_t$ = 3.53 min; m/z = 380 [M + H]⁺ |
| I-100 | ¹H NMR (400 MHz: DMSO-d₆) δ 8.64 (s, 1H), 8.41-8.37 (m, 1H), 7.91 (dd, J = 1.5, 8.5 Hz, 1H), 6.20 (s, 1H), 5.48-5.43 (m, 0.7H), 5.23-5.21 (m, 0.3H), 5.09-4.87 (m, 1.3H), 4.62 (d, J = 15.3 Hz, 0.7H), 3.42 (s, 0.9H), 3.19 (s, 2.1H), 2.21 (s, 2.1H), 2.06 (s, 0.9H), 1.52 (d, J = 6.1 Hz, 2.1H), 1.03 (d, J = 6.0 Hz, 0.9H) | (Table 2, Method B): $R_t$ = 4.05 min; m/z = 408 [M + H]⁺ |
| I-101 | ¹H NMR (400 MHz: DMSO-d₆) δ 8.64 (s, 1H), 8.41-8.37 (m, 1H), 7.91 (dd, J = 1.5, 8.5 Hz, 1H), 6.20 (s, 1H), 5.48-5.43 (m, 0.7H), 5.22 (dd, J = 2.3, 6.1 Hz, 0.3H), 5.09-4.87 (m, 1.4H), 4.62 (d, J = 15.6 Hz, 0.6H), 3.41 (s, 0.8H), 3.19 (s, 2.2H), 2.21 (s, 2.2H), 2.06 (s, 0.8H), 1.52 (d, J = 6.1 Hz, 2.2H), 1.03 (d, J = 6.1 Hz, 0.8H). | (Table 2, Method B): $R_t$ = 4.05 min; m/z = 408 [M + H]⁺ |
| I-102 | ¹H NMR (400 MHz: DMSO-d₆) δ 8.30 (d, J = 1.0 Hz, 1H), 7.93 (d, J = 8.5 Hz, 1H), 7.67 (dd, J = 1.5, 8.0 Hz, 1H), 6.18 (s, 1H), 5.46-5.40 (m, 0.7H), 5.26-5.23 (m, 0.3H), 5.10 (dd, J = 2.1, 15.8 Hz, 0.7H), 4.95-4.84 (m, 0.6H), 4.62 (d, J = 15.1 Hz, 0.7H), 3.41 (s, 0.9H), 3.20 (s, 2.1H), 2.63-2.55 (m, 1H), 2.19 (s, 2.1H), 2.07 (s, 0.9H), 1.48 (d, J = 6.7 Hz, 2.1H), 1.32-1.27 (m, 2H), 1.20-1.16 (m, 2H), 1.02 (d, J = 7.5 Hz, 0.9H) | (Table 2, Method E): $R_t$ = 3.48 min; m/z = 380 [M + H]⁺ |
| I-103 | ¹H NMR (400 MHz: DMSO-d₆) δ 8.30 (d, J = 1.3 Hz, 1H), 7.93 (d, J = 8.4 Hz, 1H), 7.69-7.64 (m, 1H), 6.19 (s, 1H), 5.47-5.40 (m, 0.7H), 5.24 (d, J = 4.9 Hz, 0.3H), 5.10 (dd, J = 2.5, 15.4 Hz, 0.7H), 4.96-4.84 (m, 0.6H), 4.61 (d, J = 15.4 Hz, 0.7H), 3.41-3.38 (m, 0.8H), 3.20 (s, 2.2H), 2.62-2.55 (m, 1H), 2.19 (s, 2.2H), 2.07 (s, 0.8H), 1.49 (d, J = 6.1 Hz, 2.2H), 1.32-1.26 (m, 2H), 1.21-1.15 (m, 2H), 1.02 (d, J = 6.0 Hz, 0.8H) | (Table 2, Method B): $R_t$ = 3.54 min; m/z = 380 [M + H]⁺ |
| I-106 | ¹H NMR (400 MHz: DMSO-d₆) δ 8.35 (s, 0.2H), 8.30 (s, 0.8H), 7.99 (s, 0.2H), 7.91 (s, 0.8H), 6.21 (s, 1H), 5.68-5.64 (m, 0.2H), 5.56-5.50 (m, 0.8H), 4.92 (dd, J = 2.9, 12.6 Hz, 0.8H), 4.73 (d, J = 12.5 Hz, 0.8H), 4.67 (d, J = 13.8 Hz, 0.2H), 4.49 (dd, J = 2.1, 15.8 Hz, 0.2H), 3.91 (s, 3H), 3.43 (s, 0.5H), 3.39 (s, 2.5H), 2.15 (s, 3H), 1.48 (d, J = 6.3 Hz, 2.5H), 1.41 (d, J = 6.2 Hz, 0.5H) | (Table 2, Method B): $R_t$ = 2.31 min; m/z = 287 [M + H]⁺ |
| I-107 | ¹H NMR (400 MHz: DMSO-d₆) δ 8.35 (s, 0.2H), 8.30 (s, 0.8H), 7.99 (s, 0.2H), 7.91 (s, 0.8H), 6.21 (s, 1H), 5.67-5.65 (m, 0.2H), 5.55-5.49 (m, 0.8H), 4.91 (dd, J = 3.1, 12.6 Hz, 0.8H), 4.73 (d, J = 12.7 Hz, 0.8H), 4.67 (d, J = 14.3 Hz, 0.2H), 4.48 (d, J = 14.3 Hz, 0.2H), 3.91 (s, 3H), 3.42 (d, J = 14.3 Hz, 3H), 2.14 (s, 3H), 1.48 (d, J = 6.1 Hz, 2.5H), 1.40 (d, J = 7.2 Hz, 0.5H) | (Table 2, Method B): $R_t$ = 2.31 min; m/z = 287 [M + H]⁺ |
| I-109 | ¹H NMR (400 MHz: DMSO-d₆) δ 9.04 (s, 1H), 8.37 (s, 1H), 5.61-5.54 (m, 1H), 5.03 (dd, J = 4.2, 12.6 Hz, 1H), 4.84 (d, J = 12.1 Hz, 1H), 3.48 (s, 3H), 2.25 (s, 3H), 1.50 (d, J = 5.3 Hz, 3H) | (Table 2, Method B): $R_t$ = 3.75 min; m/z = 375.2 [M + H]⁺ |
| I-112 | ¹H NMR (400 MHz: DMSO-d₆) δ 9.07 (s, 1H), 8.39 (s, 1H), 5.16-4.91 (m, 2H), 4.87-4.64 (m, 2H), 3.40-3.39 (m, 3H), 2.12-2.10 (m, 3H), 1.99 (s, 3H) | (Table 2, Method B): $R_t$ = 3.39 min; m/z = 341.2 [M + H]⁺ |

Example 73—Muscarinic Acetylcholine Receptor Activation

Exemplary compounds were tested for ability to activate the muscarinic acetylcholine receptor. Experimental procedures and results are provided below.

Part I—Experimental Procedures for Human and Rat M4 PAM pERK Assay

Chinese hamster ovary (CHO) cells expressing either hM4 or rM4 receptors were frozen in assay ready vials ($5\times10^6$ cells/vial) after bulking-up in culture. The day before an assay, vial(s) were thawed and cells seeded in 384 well white proxiplates at 1000/well for hM4 cells and at 2000/well for rM4 cells, in 10 μL of growth media (Hams/F12 with glutamax and 10% FCS) and incubated overnight at 37° C./5% $CO_2$.

On the following morning, the growth media was removed by 'flicking out' over a bin, patting the inverted plate onto tissue, and then replacing with 10 μL of wash media (Hams/F12 with glutamax and 8 mM HEPES, NB: serum free). Then, the wash media was removed in the same way and replaced with 8 μL/well of the serum free media. Plates were then re-incubated for a further 4 hours at 37° C./5% $CO_2$.

Compounds for testing were solubilized to 10 mM in DMSO and compound addition plates, consisting of ten-point concentration response curves (CRC) in duplicate points (10 μM top concentration, 12 log dilution series), were prepared by acoustic dispensing and the compound management group.

After the 4-hour incubation in serum free media, a 4 μL aliquot of the 3× compound solution containing an $EC_{20}$ of acetylcholine (10 nM final concentration) was added to the cell plate using a 384 well plate to plate transfer. Then, the plate lid was replaced, and the cells incubated for 5 mins at 37° C./5% $CO_2$. Following this final incubation, all cellular processes were stopped by the addition of 4 μL/well of lysis and blocking buffer and plates were incubated for 30 minutes at RT on an orbital shaker (gentle setting). Then, a final addition of 4 μL/well of antibody detection mix, containing both the Europium-Cryptate (donor) and d2 (acceptor) tagged detection components, was added followed by a further 2-hour incubation at RT, and then the plate was read using a TR-FRET (time resolved fluorescence resonance energy transfer) based protocol.

Part II—Experimental Procedures for M4 GTPγS PAM Assay

The M4 GTPγS PAM method was used. Membranes were prepared for GTPgS binding assays from CHO-K1 cells stably expressing human M4 receptor. Briefly, cells were grown in 5-layer cell culture flasks. Cells were washed with 50 mL of PBS and then dissociated with 0.05% trypsin. Dissociated cells were then collected by centrifugation at 650×g for 8 minutes at 4° C. Pellets were washed again in PBS by centrifugation and resuspended in 30 mL of 20 mM HEPES, 10 mM EDTA, pH 7.4. After sitting on ice for 30 min, membranes were collected by centrifugation at 50000×g for 15' at 4° C., resuspended in 30 mL of 20 mM HEPES, 0.1 mM EDTA, pH 7.4 and collected again by centrifugation. Pellets were then washed twice by centrifugation in 30 mL of 20 mM HEPES, pH 7.4, and stored at −80° C. until the day of the assay. On the day of the assay, pellets were thawed on ice and resuspended in 1 mL of 20 mM HEPES, pH 7.4, 10 mM $MgCl_2$, 100 mM NaCl using dounce homogenization. Membrane protein concentration is determined by BCA protein assay (Promega, Madison, WI) according to Promega guidelines.

On the day of the assay, serial dilutions of test PAM compounds were brought up in assay buffer (20 mM HEPES, 10 mM $MgCl_2$, 100 mM NaCl) at 4× final assay concentration. 25 ml/well of membrane homogenates (containing 5 mg of membrane protein) were prepared in assay buffer supplemented with GDP at 4× final assay concentration (final assay concentration of GDP is 5 uM for M2 and 0.1 uM for M4) and dispensed into 96 well polypropylene, U-bottom Greiner plates. 25 ml of vehicle or test PAM compound at 4× of final assay concentration diluted in the assay buffer were added to membrane and plates are incubated for 10-15 minutes at room temperature with gentle shaking. Then, 25 mL of EC20 acetylcholine in assay buffer at 4× final assay concentration was added to assay plates (EC20 final assay concentrations was 40 nM for human M4).

Plates were then incubated, with shaking, for an additional 10-15 minutes. 25 mL of 0.4 nM $^{35}$S-GTP (Perkin Elmer, Waltham, MA) in assay buffer was added to assay mixtures. The binding reaction is left on the shaker for 1 hour at room temperature. Membranes in assay reactions were then transferred to GF/C filter plates (Unifilter, Perkin Elmer) and washed three times using a FilterMate Harvester (Perkin Elmer) with cold assay buffer containing no GDP. Filter plates were then dried at 40° C. overnight followed by the addition of 20 mL/well of Beta Plate Scintillation liquid. Plates are top and bottom sealed before being read on TopCount scintillation counter (Perkin Elmer, Waltham, MA).

Part III—Results

Results are presented below in Table 23. Compounds having an activity designated as "A" had an $EC_{50}$<100 nM; compounds having an activity designated as "B" had an $EC_{50}$ in the range of 100 nM to 500 nM; compounds having an activity designated as "C" had an $EC_{50}$ of from greater than 500 nM to 2000 nM; and compounds having an activity designated as "D" had an $EC_{50}$>2000 nM. N/A indicates that no data were available.

TABLE 23

| Compound No. | Human M4 PAM pERK $EC_{50}$ | Rat M4 PAM pERK $EC_{50}$ | Human M4 PAM GTPγS $EC_{50}$ |
|---|---|---|---|
| I-1 | A | C | B |
| I-2 | A | D | N/A |
| I-3 | C | D | D |
| I-4 | C | D | N/A |
| I-5 | C | D | N/A |
| I-6 | B | D | D |
| I-7 | C | D | N/A |
| I-8 | A | D | D |
| I-9 | A | C | C |
| I-10 | B | D | N/A |
| I-11 | D | N/A | D |
| I-12 | B | D | D |
| I-14 | C | D | D |
| I-15 | B | D | N/A |
| I-16 | B | D | N/A |
| I-17 | A | C | D |
| I-18 | C | D | D |
| I-19 | C | D | D |
| I-21 | A | C | B |
| I-22 | B | D | C |
| I-23 | B | C | N/A |
| I-24 | C | D | D |

TABLE 23-continued

| Compound No. | Human M4 PAM pERK $EC_{50}$ | Rat M4 PAM pERK $EC_{50}$ | Human M4 PAM GTPγS $EC_{50}$ |
|---|---|---|---|
| I-25 | C | D | N/A |
| I-26 | B | D | D |
| I-27 | C | D | N/A |
| I-28 | A | C | B |
| I-29 | A | C | C |
| I-31 | D | D | N/A |
| I-32 | B | D | C |
| I-33 | B | D | N/A |
| I-34 | B | C | N/A |
| I-35 | B | D | N/A |
| I-36 | A | C | C |
| I-37 | D | D | N/A |
| I-38 | B | D | N/A |
| I-39 | C | D | N/A |
| I-40 | C | D | D |
| I-41 | B | C | B |
| I-42 | C | D | D |
| I-43 | B | C | N/A |
| I-44 | B | C | A |
| I-45 | B | D | D |
| I-46 | A | C | N/A |
| I-47 | A | C | N/A |
| I-48 | D | N/A | D |
| I-49 | B | C | C |
| I-50 | B | B | N/A |
| I-51 | A | B | N/A |
| I-52 | B | B | C |
| I-53 | D | D | N/A |
| I-54 | B | D | N/A |
| I-55 | B | D | N/A |
| I-56 | D | D | N/A |
| I-57 | D | D | N/A |
| I-58 | C | D | N/A |
| I-59 | C | D | N/A |
| I-60 | B | D | N/A |
| I-61 | C | D | N/A |
| I-62 | D | D | C |
| I-63 | D | D | D |
| I-64 | A | C | N/A |
| I-65 | A | C | N/A |
| I-66 | A | D | C |
| I-67 | A | C | B |
| I-68 | A | B | N/A |
| I-69 | B | D | N/A |
| I-70 | B | B | N/A |
| I-71 | C | D | D |
| I-72 | B | B | B |
| I-73 | B | C | B |
| I-74 | A | C | C |
| I-75 | D | D | D |
| I-76 | A | B | A |
| I-77 | A | B | N/A |
| I-78 | A | B | N/A |
| I-79 | C | D | C |
| I-80 | B | D | D |
| I-81 | D | D | D |
| I-82 | B | C | B |
| I-83 | A | C | B |
| I-84 | C | D | D |
| I-85 | C | D | N/A |
| I-86 | B | D | N/A |
| I-87 | A | D | B |
| I-88 | A | D | N/A |
| I-89 | B | D | C |
| I-90 | B | D | C |
| I-91 | B | D | N/A |
| I-92 | D | D | D |
| I-93 | A | D | N/A |
| I-94 | D | D | D |
| I-95 | B | D | C |
| I-96 | D | D | D |
| I-97 | B | D | D |
| I-98 | D | D | D |
| I-99 | B | C | C |
| I-100 | D | D | D |
| I-101 | B | D | N/A |
| I-102 | D | D | D |
| I-103 | B | C | D |
| I-104 | B | D | N/A |
| I-105 | D | N/A | D |
| I-106 | D | N/A | D |
| I-107 | D | D | D |
| I-108 | C | D | D |
| I-109 | C | D | D |
| I-110 | B | D | N/A |
| I-111 | D | B | N/A |
| I-112 | A | D | B |
| I-113 | A | D | C |
| I-114 | A | B | N/A |

Example 74—Ability of Compounds to Impact Behavior Activity of Rats

Exemplary compounds were tested for ability to impact the behavior of rats pre-treated with amphetamine. Experimental procedures and results are provided below.

Part I—Experimental Procedures

Animals: Adult male, Sprague Dawley rats (Envigo, Indianapolis, IN, USA) were housed in a colony maintained at 23° C. with 12 hour light/dark cycles (lights on at 0600 hour). All animals weighed 290-330 g at the beginning of the study and were equally divided into 5 groups (n=8 per group) and received one of the treatment conditions listed below. Animal protocols were approved by an Animal Care and Use Committee.

Behavioral Procedures: Studies were conducted in MedAssociates open field chambers (27.3 cm×27.3 cm×20.3 cm, MedAssociates, St. Albans, VT) in which movement was automatically tracked and recorded by 16 beam arrays. Administration pretreatment of the test article was determined to coincide with Tmax at the time of the amphetamine-evoked session with optimal route of administration. All groups were subcutaneously treated with 0.5 mg/kg amphetamine (AMP). The test article (i.e., test compound) was tested in three dose groups with a half-log increase between doses. Risperidone (0.55 mg/kg, 30 minutes, subcutaneous administration) was used as a positive control and was administered to group 5. To determine the role of test article on AMP-evoked hyperlocomotion, rats were placed in the open area and allowed to habituate for 30 min before being subcutaneously dosed with 0.5 mg/kg AMP. Locomotor data (distance traveled) was recorded as 5-minute bins throughout the 90-minute session. The dose of AMP was chosen based on the selective increase in locomotor behavior relative to stereotypes. The dose of risperidone was chosen that produced reliable effects and served as a positive control.

Statistical Analysis: Spontaneous locomotion (prior to AMP administration) was calculated as the total distance traveled during the first 30 minutes of the experimental session. AMP-evoked responses were calculated as the total distance traveled during the last 60 minutes of the experimental session which commenced immediately after AMP administration. Locomotor data were analyzed by a one-way ANOVA. When there was a significant overall ANOVA, post hoc comparisons were made by Dunnett's test with statistical significance determined as $p<0.05$.

Part II—Results

Rats that received one of the following test compounds at the specified dose displayed a reduction in amphetamine-evoked hyperlocomotion activity, which indicates beneficial effect of the test compound on the rat:

| Compound No. | Dose Amount of Compound |
|---|---|
| I-1 | 32 mg/kg |
| I-76 | 3.2 mg/kg |
| I-87 | 32 mg/kg |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:
1. A compound represented by Formula I:

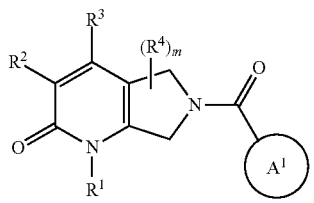

(I)

or a pharmaceutically acceptable salt thereof;
wherein:
$R^1$ is $C_{1-6}$ alkyl, $C_{1-6}$ haloalkyl, $C_{3-6}$ cycloalkyl,-($C_{1-6}$ alkylene)-($C_{3-6}$ cycloalkyl), or hydrogen;
$R^2$ is halo, $C_{1-4}$ alkyl, $C_{1-4}$ haloalkyl, or hydrogen;
$R^3$ is $C_{1-4}$ alkyl, $C_{1-4}$ haloalkyl, $C_{1-4}$ alkoxyl,-S-($C_{1-4}$ alkyl), or halo;
$R^4$ represents independently for each occurrence $C_{1-4}$ alkyl, $C_{1-4}$ haloalkyl, or halo;
$R^5$ represents independently for each occurrence $C_{1-6}$ alkyl, halo, $C_{1-6}$ haloalkyl, $C_{3-6}$ cycloalkyl, hydroxyl, $C_{1-6}$ alkoxyl,-($C_{1-6}$ alkylene)-($C_{1-6}$ alkoxyl),-($C_{1-6}$ alkylene)-($C_{3-6}$ cycloalkyl),-($C_{1-6}$ haloalkylene)-($C_{3-6}$ cycloalkyl), or —($C_{1-6}$ alkylene)-($C_{3-6}$ halocycloalkyl); or two occurrences of $R^5$ are taken together with their intervening atoms to form a 4-7 membered ring containing 1 or 2 heteroatoms independently selected from the group consisting of oxygen, nitrogen, and sulfur;
$R^6$ is (i) —($C_{0-4}$ alkylene)-(3-7 membered saturated or unsaturated heterocyclyl containing 1, 2, or 3 heteroatoms independently selected from the group consisting of nitrogen, oxygen, and sulfur), (ii)-($C_{0-4}$ alkylene)-(5-6 membered heteroaryl containing 1, 2, or 3 heteroatoms independently selected from the group consisting of nitrogen, oxygen, and sulfur), or (iii)-($C_{0-4}$ alkylene)-phenyl, wherein the heterocyclyl, heteroaryl, and phenyl are substituted with 0, 1, 2, or 3 occurrences of $R^7$,
$R^7$ represents independently for each occurrence $C_{1-6}$ alkyl, halo, $C_{1-6}$ haloalkyl, $C_{3-6}$ cycloalkyl, hydroxyl, or $C_{1-6}$ alkoxyl;
$A^1$ is a 5-6 membered monocyclic heteroaryl containing 1, 2, or 3 heteroatoms independently selected from the group consisting of nitrogen, oxygen, and sulfur, an 8-10 membered bicyclic heteroaryl containing 1, 2, or 3 heteroatoms independently selected from the group consisting of nitrogen, oxygen, and sulfur, or phenyl, wherein the monocyclic heteroaryl, bicyclic heteroaryl, and phenyl are substituted with n occurrences of $R^5$ and t occurrences of $R^6$;
m is 0, 1, 2, or 3;
n is 0, 1, or 2; and
t is 0 or 1.

2. The compound of claim 1, wherein the compound is a compound of Formula I.

3. The compound of claim 1, wherein the compound is a compound of Formula Ia or a pharmaceutically acceptable salt thereof:

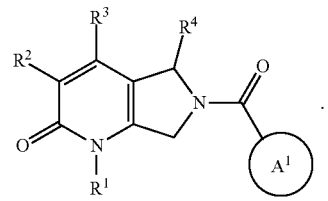

Ia

4. The compound of claim 3, or a pharmaceutically acceptable salt thereof, wherein $A^1$ is a 5 membered monocyclic heteroaryl containing 1 or 2 heteroatoms independently selected from the group consisting of nitrogen and oxygen, wherein the 5 membered monocyclic heteroaryl is substituted with n occurrences of $R^5$ and t occurrences of $R^6$.

5. The compound of claim 3, or a pharmaceutically acceptable salt thereof, wherein $A^1$ is pyrazolyl, imidazolyl, oxazolyl, isoxazolyl, thiazolyl, pyrrolyl, thiophenyl, or pyridinyl, each of which is substituted with n occurrences of $R^5$ and t occurrences of $R^6$.

6. The compound of claim 3, wherein $A^1$ is pyrazolyl substituted with n occurrences of $R^5$ and t occurrences of $R^6$.

7. The compound of claim 1, wherein the compound is a compound of Formula Ib, Ic, Id, or Ie, or a pharmaceutically acceptable salt thereof:

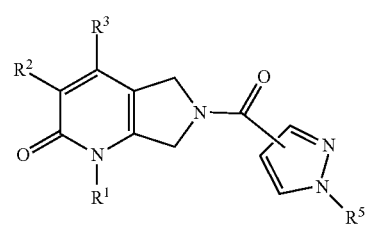

Ib

-continued

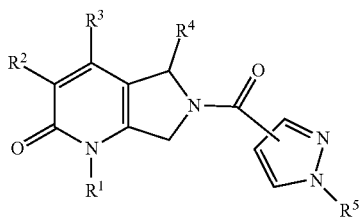
Ic

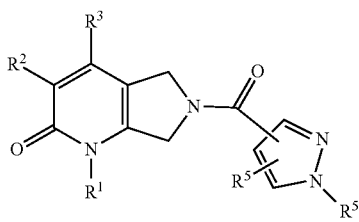
Id

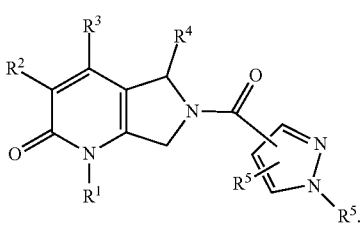
Ie

8. The compound of claim 1, wherein the compound is a compound of Formula If or Ig, or a pharmaceutically acceptable salt thereof:

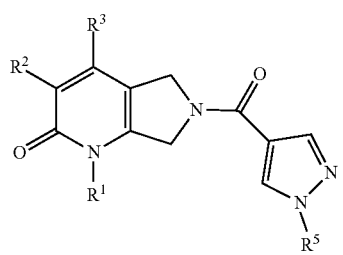
If

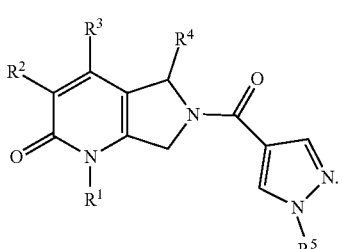
Ig

9. The compound of claim 8, or a pharmaceutically acceptable salt thereof, wherein $R^1$ is methyl.
10. The compound of claim 8, or a pharmaceutically acceptable salt thereof, wherein $R^2$ is chloro or fluoro.
11. The compound of claim 8, or a pharmaceutically acceptable salt thereof, wherein $R^3$ is methyl.
12. The compound of claim 8, or a pharmaceutically acceptable salt thereof, wherein $R^4$ is methyl.
13. The compound of claim 8, or a pharmaceutically acceptable salt thereof, wherein $R^5$ is $C_{1-6}$ haloalkyl.
14. The compound of claim 8, or a pharmaceutically acceptable salt thereof, wherein $R^5$ is —$CF_3$.

15. A compound selected from the group consisting of:

| Compound No. | Structure |
|---|---|
| I-1 | 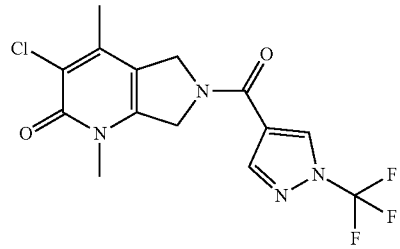 [SMILES: Cc1c2c(n(C)c(=O)c1Cl)CN(C(=O)c1cnn(C(F)(F)F)c1)C2] |
| I-2 | 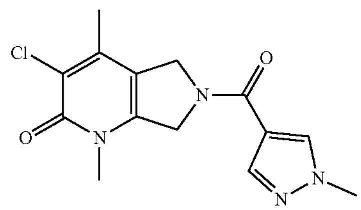 [SMILES: Cc1c2c(n(C)c(=O)c1Cl)CN(C(=O)c1cnn(C)c1)C2] |
| I-3 | 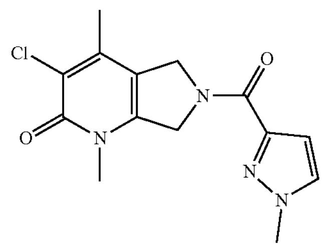 [SMILES: Cc1c2c(n(C)c(=O)c1Cl)CN(C(=O)c1ccn(C)n1)C2] |
| I-4 | 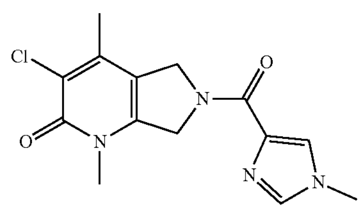 [SMILES: Cc1c2c(n(C)c(=O)c1Cl)CN(C(=O)c1cn(C)cn1)C2] |
| I-5 | 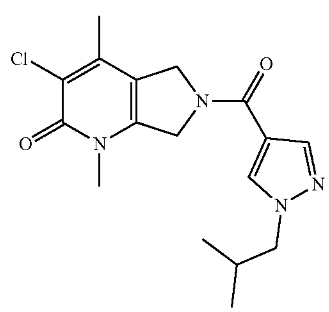 [SMILES: Cc1c2c(n(C)c(=O)c1Cl)CN(C(=O)c1cnn(CC(C)C)c1)C2] |
| I-6 | 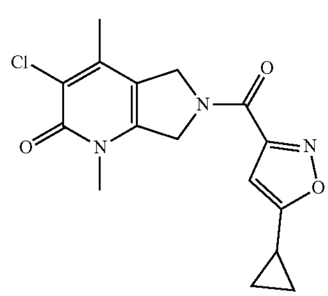 [SMILES: Cc1c2c(n(C)c(=O)c1Cl)CN(C(=O)c1cc(C3CC3)on1)C2] |

-continued

| Compound No. | Structure |
|---|---|
| I-7 | 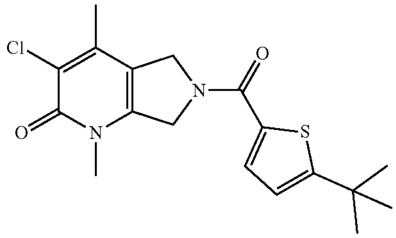 [SMILES: Cc1c2c(n(C)c(=O)c1Cl)CN(C(=O)c1ccc(C(C)(C)C)s1)C2] |
| I-8 | 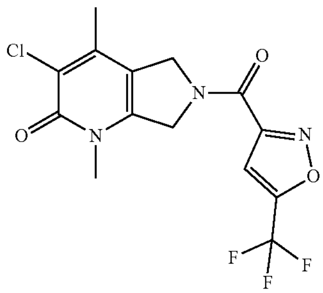 [SMILES: Cc1c2c(n(C)c(=O)c1Cl)CN(C(=O)c1cc(C(F)(F)F)on1)C2] |
| I-9 | 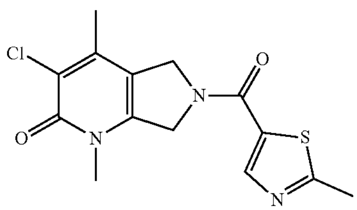 [SMILES: Cc1ncc(C(=O)N2Cc3c(C)c(Cl)c(=O)n(C)c3C2)s1] |
| I-10 | 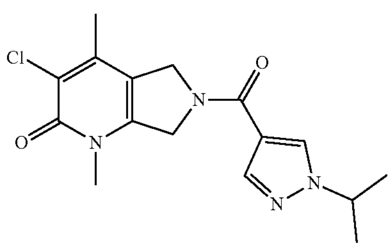 [SMILES: Cc1c2c(n(C)c(=O)c1Cl)CN(C(=O)c1cnn(C(C)C)c1)C2] |
| I-11 | 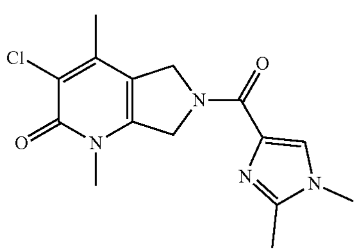 [SMILES: Cc1c2c(n(C)c(=O)c1Cl)CN(C(=O)c1cn(C)c(C)n1)C2] |
| I-12 | 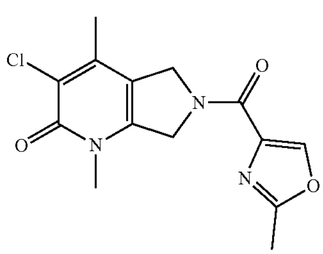 [SMILES: Cc1nc(C(=O)N2Cc3c(C)c(Cl)c(=O)n(C)c3C2)co1] |

-continued

| Compound No. | Structure |
|---|---|
| I-13 | 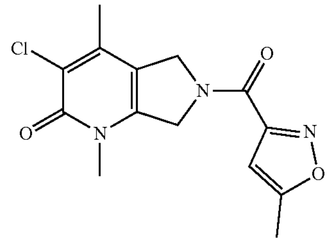 [SMILES: Cc1cc(C(=O)N2Cc3c(C)c(Cl)c(=O)n(C)c3C2)no1] |
| I-14 | 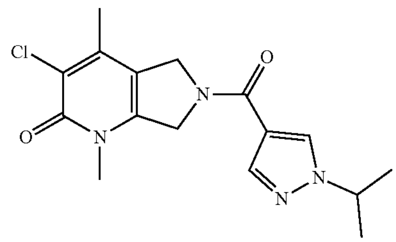 [SMILES: Cc1c2c(n(C)c(=O)c1Cl)CN(C(=O)c1cnn(C(C)C)c1)C2] |
| I-15 | 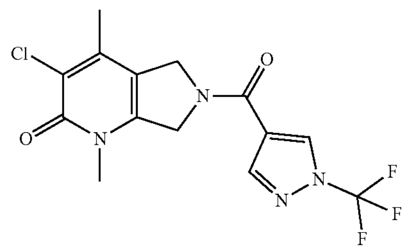 [SMILES: Cc1c2c(n(C)c(=O)c1Cl)CN(C(=O)c1cnn(C(F)(F)F)c1)C2] |
| I-16 | 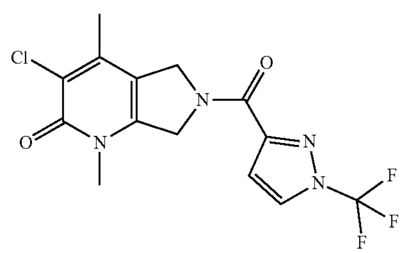 [SMILES: Cc1c2c(n(C)c(=O)c1Cl)CN(C(=O)c1ccn(C(F)(F)F)n1)C2] |
| I-17 | 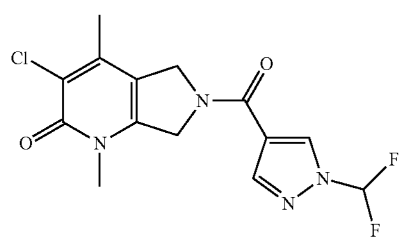 [SMILES: Cc1c2c(n(C)c(=O)c1Cl)CN(C(=O)c1cnn(C(F)F)c1)C2] |
| I-18 | 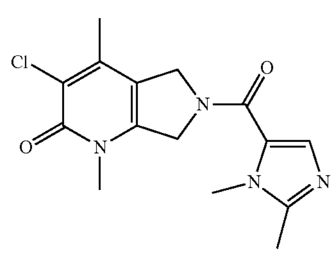 [SMILES: Cc1c2c(n(C)c(=O)c1Cl)CN(C(=O)c1cnc(C)n1C)C2] |

-continued

| Compound No. | Structure |
|---|---|
| I-19 | 3-chloro-4,N-dimethyl pyrrolopyridinone carbonyl-(1-isobutyl-imidazol-4-yl) |
| I-20 | 3-chloro-4,N-dimethyl pyrrolopyridinone carbonyl-(5-methylthiazol-2-yl) |
| I-21 | 3-chloro-4,N-dimethyl pyrrolopyridinone carbonyl-(2-cyclopropylthiazol-5-yl) |
| I-22 | 3-chloro-4,N-dimethyl pyrrolopyridinone carbonyl-(4-methyloxazol-2-yl) |
| I-23 | 3-chloro-4,N-dimethyl pyrrolopyridinone carbonyl-(1-benzylpyrazol-4-yl) |
| I-24 | 3-chloro-4,N-dimethyl pyrrolopyridinone carbonyl-(5,6,7,8-tetrahydroimidazo[1,2-a]pyridin-2-yl) |
| I-25 | 3-chloro-4,N-dimethyl pyrrolopyridinone carbonyl-(6,7-dihydro-5H-imidazo[2,1-b][1,3]oxazin-2-yl) |
| I-26 | 3-chloro-4,N-dimethyl pyrrolopyridinone carbonyl-(2-trifluoromethylthiazol-4-yl) |
| I-27 | 3-chloro-4,N-dimethyl pyrrolopyridinone carbonyl-(1-cyclopropylmethyl-pyrazol-4-yl) |
| I-28 | 3-chloro-4,N-dimethyl pyrrolopyridinone carbonyl-(2-cyclopropylmethyl-thiazol-5-yl) |
| I-29 | 3-chloro-4,N-dimethyl pyrrolopyridinone carbonyl-(2-trifluoromethylthiazol-5-yl) |
| I-30 | 3-chloro-4,N-dimethyl pyrrolopyridinone carbonyl-(benzothiazol-2-yl) |

| Compound No. | Structure |
|---|---|
| I-31 | 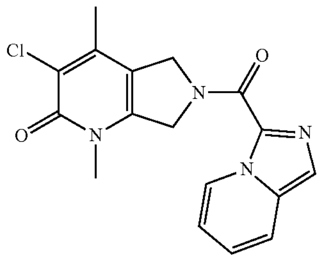 [SMILES: Cc1c2c(n(C)c(=O)c1Cl)CN(C(=O)c1ncc3ccccn13)C2] |
| I-32 | 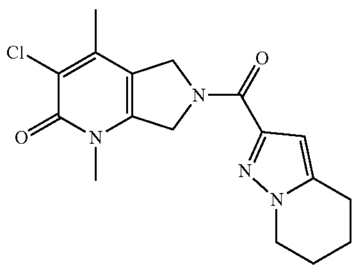 [SMILES: Cc1c2c(n(C)c(=O)c1Cl)CN(C(=O)c1cc3n(n1)CCCC3)C2] |
| I-33 | 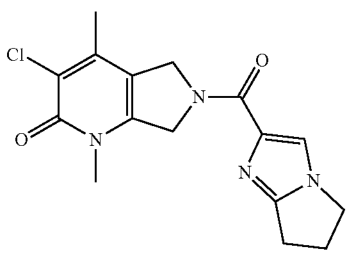 [SMILES: Cc1c2c(n(C)c(=O)c1Cl)CN(C(=O)c1cn3c(n1)CCC3)C2] |
| I-34 | 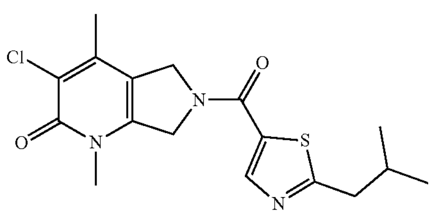 [SMILES: Cc1c2c(n(C)c(=O)c1Cl)CN(C(=O)c1cnc(CC(C)C)s1)C2] |
| I-35 | 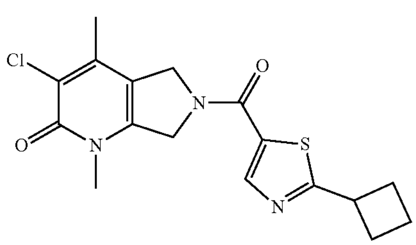 [SMILES: Cc1c2c(n(C)c(=O)c1Cl)CN(C(=O)c1cnc(C3CCC3)s1)C2] |
| I-36 | 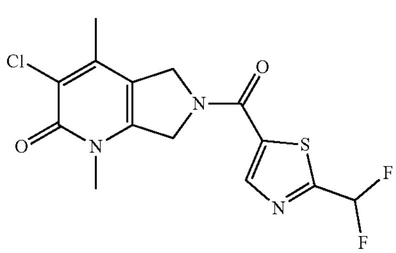 [SMILES: Cc1c2c(n(C)c(=O)c1Cl)CN(C(=O)c1cnc(C(F)F)s1)C2] |
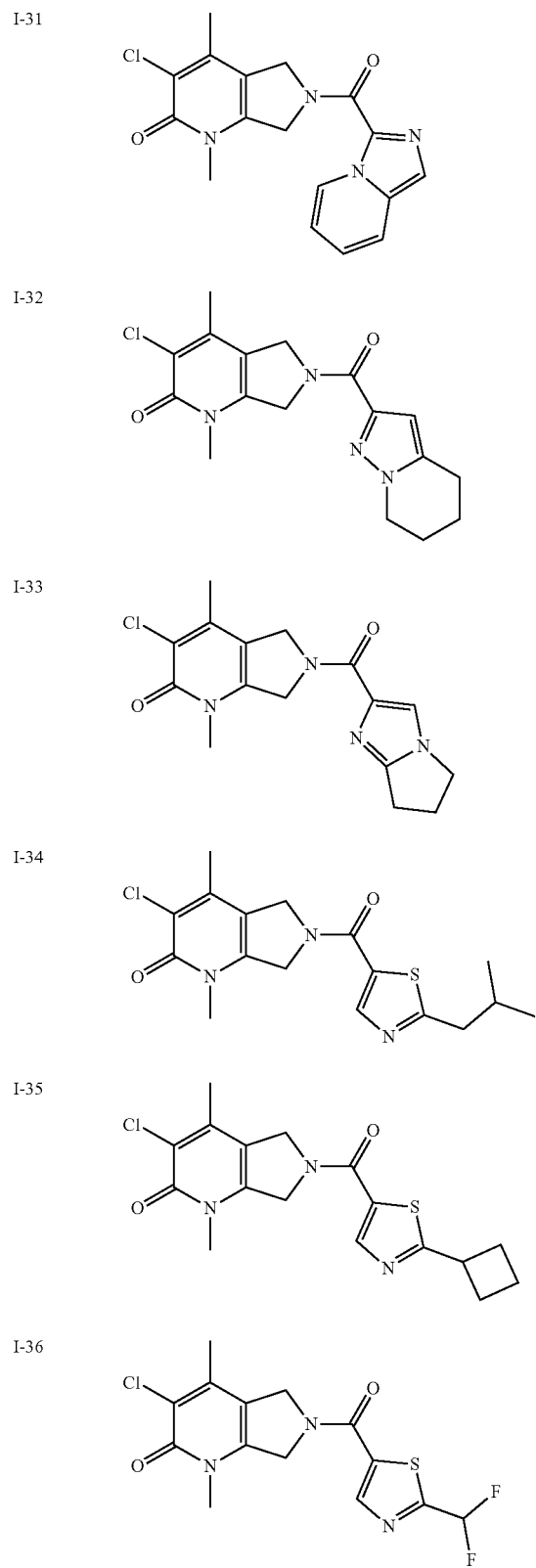
| Compound No. | Structure |
|---|---|
| I-37 | 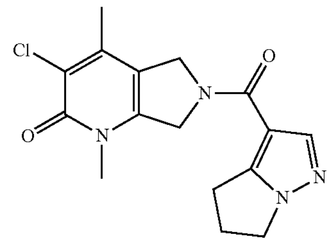 [SMILES: Cc1c2c(n(C)c(=O)c1Cl)CN(C(=O)c1cnn3c1CCC3)C2] |
| I-38 | 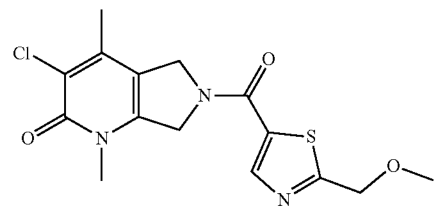 [SMILES: COCc1ncc(C(=O)N2Cc3c(C)c(Cl)c(=O)n(C)c3C2)s1] |
| I-39 | 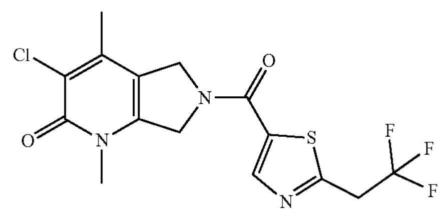 [SMILES: Cc1c2c(n(C)c(=O)c1Cl)CN(C(=O)c1cnc(CC(F)(F)F)s1)C2] |
| I-40 | 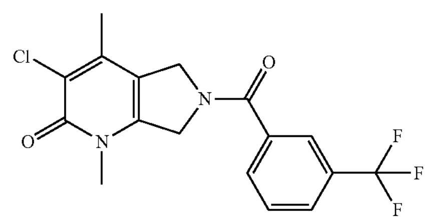 |
| I-41 | 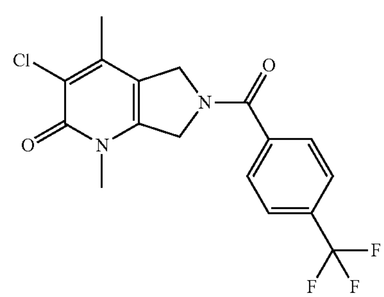 [SMILES: Cc1c2c(n(C)c(=O)c1Cl)CN(C(=O)c1ccc(C(F)(F)F)cc1)C2] |
| I-42 | 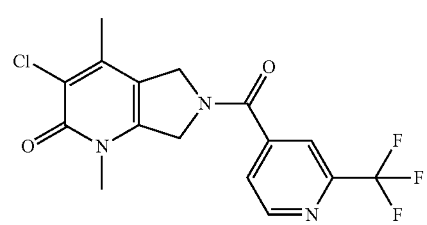 [SMILES: Cc1c2c(n(C)c(=O)c1Cl)CN(C(=O)c1ccnc(C(F)(F)F)c1)C2] |
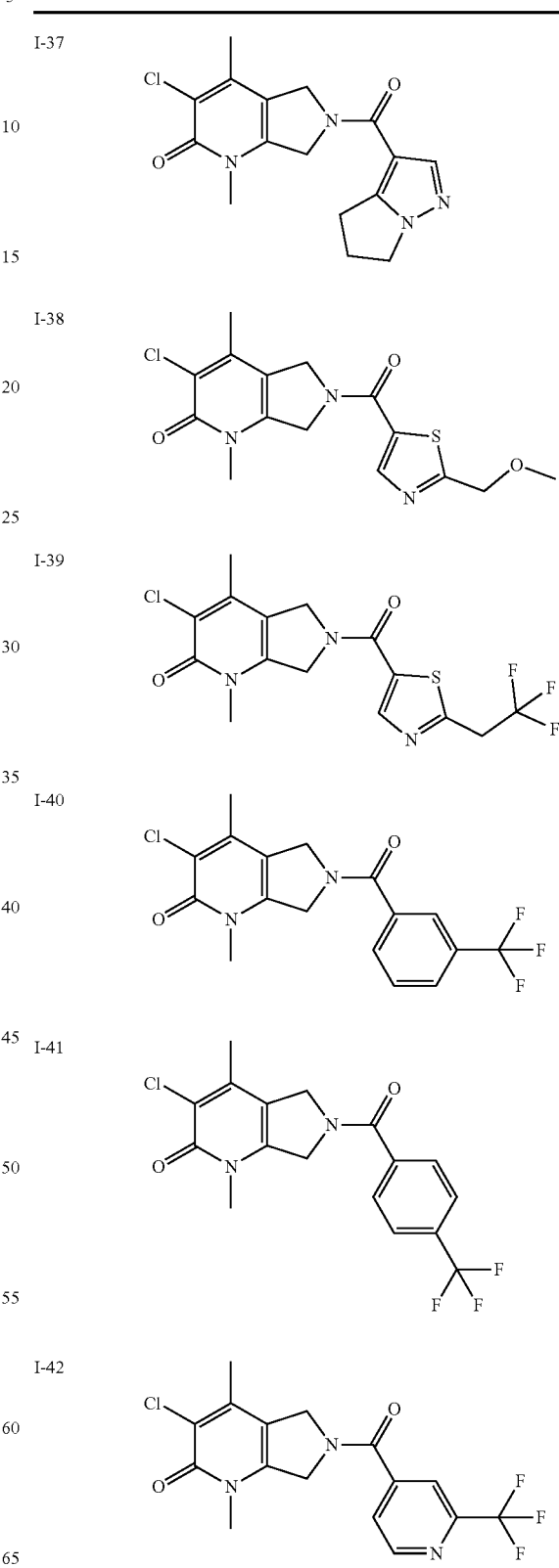

| Compound No. | Structure |
|---|---|
| I-43 | 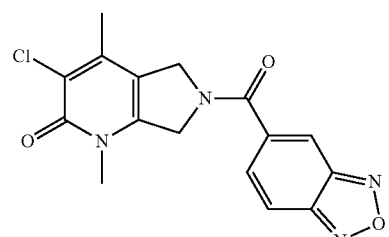 |
| I-44 | 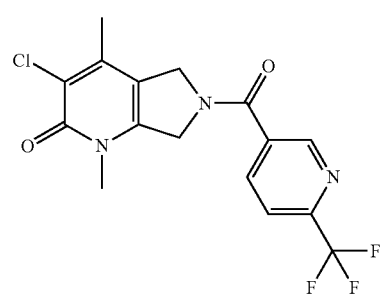 [SMILES: Cc1c2c(n(C)c(=O)c1Cl)CN(C(=O)c1ccc(C(F)(F)F)nc1)C2] |
| I-45 | 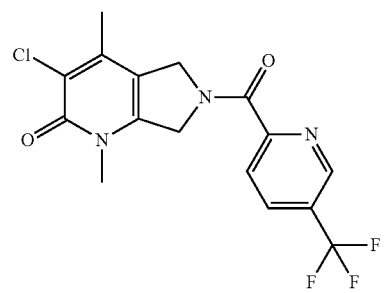 [SMILES: Cc1c2c(n(C)c(=O)c1Cl)CN(C(=O)c1ccc(C(F)(F)F)cn1)C2] |
| I-46 | 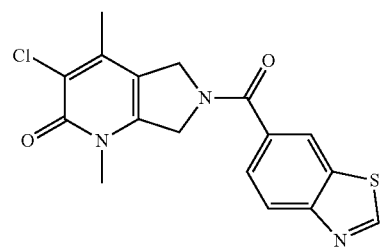 [SMILES: Cc1c2c(n(C)c(=O)c1Cl)CN(C(=O)c1ccc3ncsc3c1)C2] |
| I-47 | 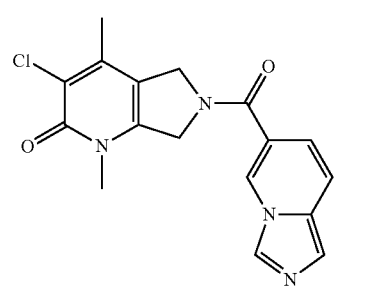 [SMILES: Cc1c2c(n(C)c(=O)c1Cl)CN(C(=O)c1ccc3cncn3c1)C2] |
| I-48 | 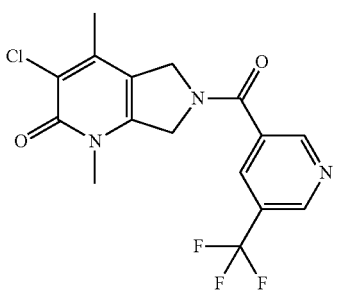 [SMILES: Cc1c2c(n(C)c(=O)c1Cl)CN(C(=O)c1cncc(C(F)(F)F)c1)C2] |
| I-49 | 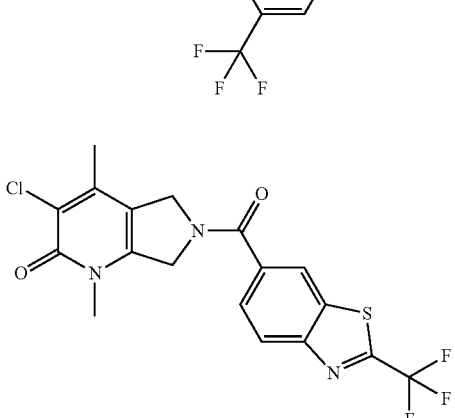 |
| I-50 | 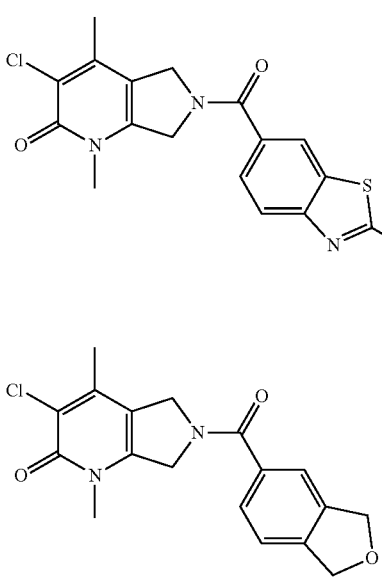 |
| I-51 | 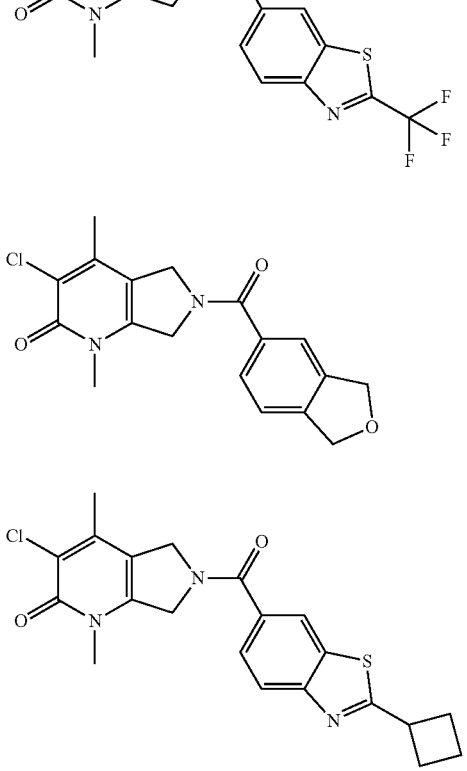 |
| I-52 | 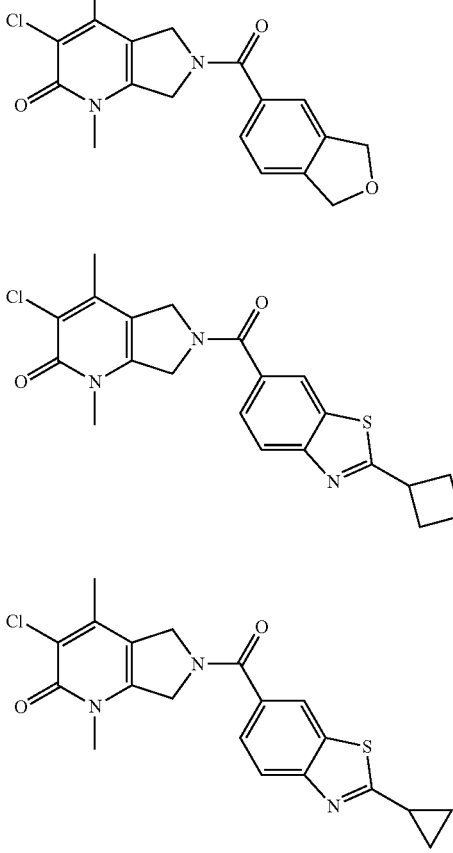 |

-continued
| Compound No. | Structure |
|---|---|
| I-53 | 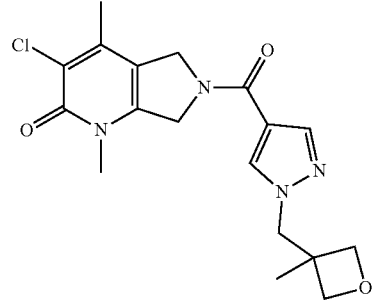 [SMILES: Cc1c2c(n(C)c(=O)c1Cl)CN(C(=O)c1cnn(CC3(C)COC3)c1)C2] |
| I-54 | 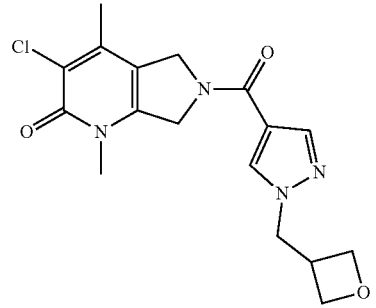 [SMILES: Cc1c2c(n(C)c(=O)c1Cl)CN(C(=O)c1cnn(CC3COC3)c1)C2] |
| I-55 | 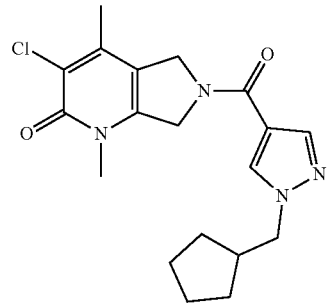 [SMILES: Cc1c2c(n(C)c(=O)c1Cl)CN(C(=O)c1cnn(CC3CCCC3)c1)C2] |
| I-56 | 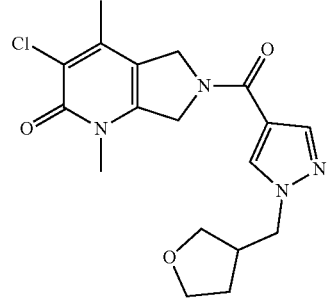 [SMILES: Cc1c2c(n(C)c(=O)c1Cl)CN(C(=O)c1cnn(CC3CCOC3)c1)C2] |
-continued
| Compound No. | Structure |
|---|---|
| I-57 | 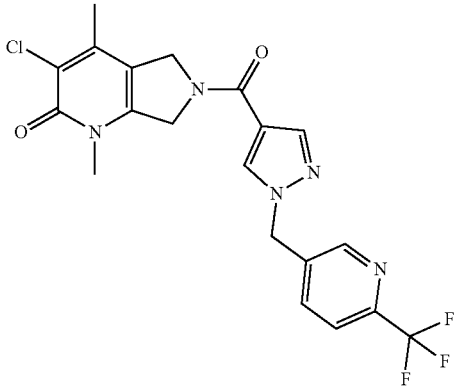 [SMILES: Cc1c2c(n(C)c(=O)c1Cl)CN(C(=O)c1cnn(Cc3ccc(C(F)(F)F)nc3)c1)C2] |
| I-58 | 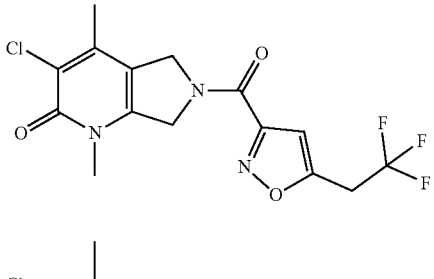 |
| I-59 | 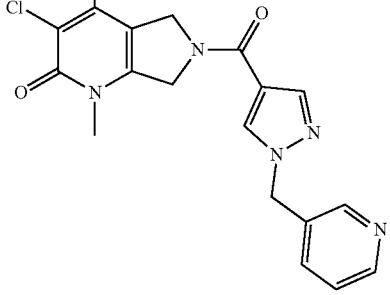 |
| I-60 | 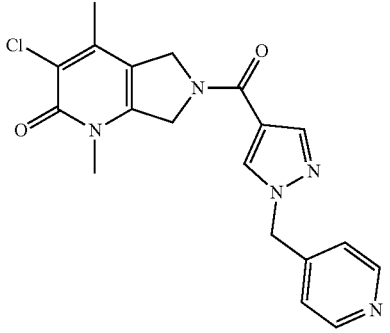 [SMILES: Cc1c2c(n(C)c(=O)c1Cl)CN(C(=O)c1cnn(Cc3ccncc3)c1)C2] |
| I-61 | 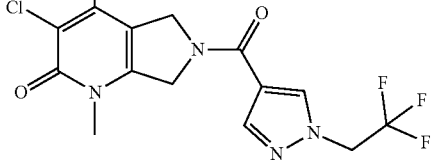 |

-continued
| Compound No. | Structure |
|---|---|
| I-62 | 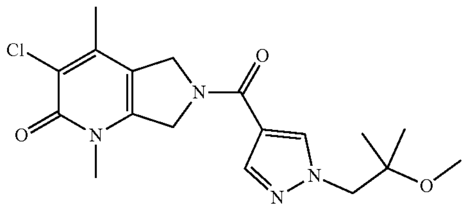 [SMILES: COC(C)(C)Cn1cc(C(=O)N2Cc3c(C)c(Cl)c(=O)n(C)c3C2)cn1] |
| I-63 | 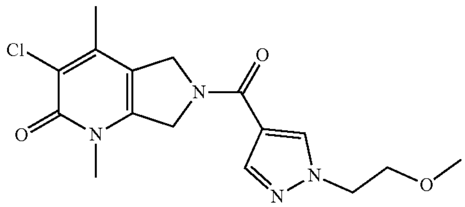 [SMILES: COCCn1cc(C(=O)N2Cc3c(C)c(Cl)c(=O)n(C)c3C2)cn1] |
| I-64 | 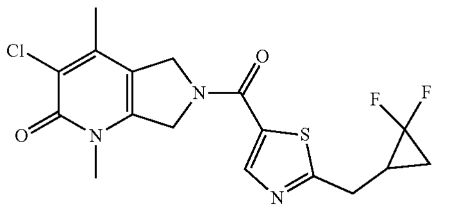 [SMILES: Cc1c2c(n(C)c(=O)c1Cl)CN(C(=O)c1cnc(CC3CC3(F)F)s1)C2] |
| I-65 | 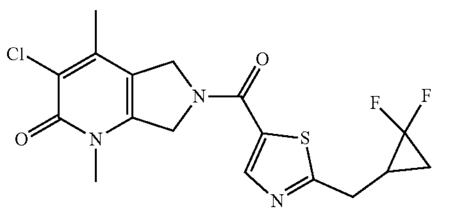 [SMILES: Cc1c2c(n(C)c(=O)c1Cl)CN(C(=O)c1cnc(CC3CC3(F)F)s1)C2] |
| I-66 | 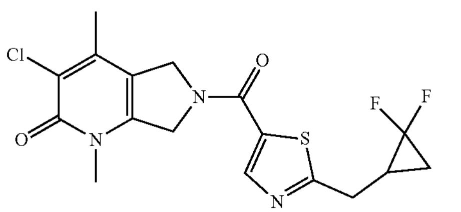 [SMILES: Cc1c2c(n(C)c(=O)c1Cl)CN(C(=O)c1cnc(CC3CC3(F)F)s1)C2] |
| I-67 | 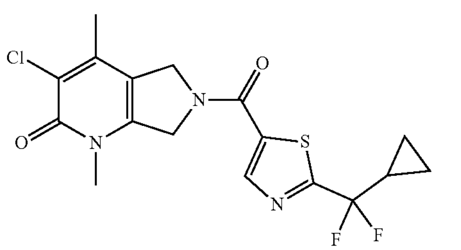 [SMILES: Cc1c2c(n(C)c(=O)c1Cl)CN(C(=O)c1cnc(C(F)(F)C3CC3)s1)C2] |
| I-68 | 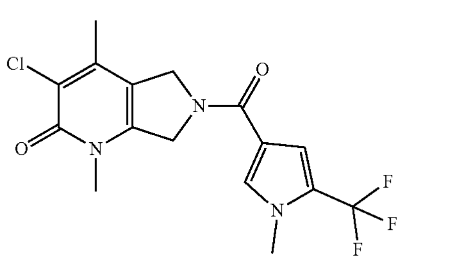 [SMILES: Cc1c2c(n(C)c(=O)c1Cl)CN(C(=O)c1cc(C(F)(F)F)n(C)c1)C2] |
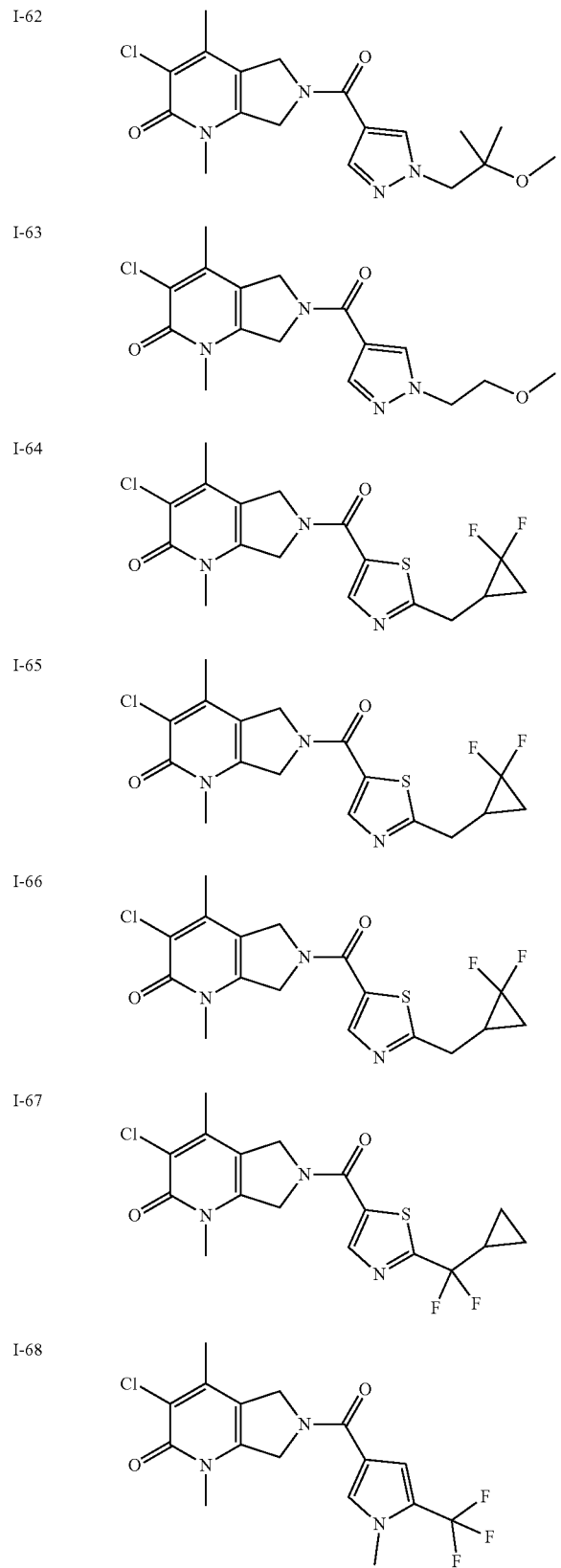
-continued
| Compound No. | Structure |
|---|---|
| I-69 | 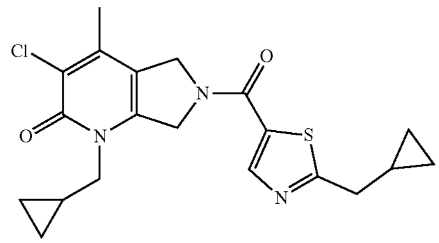 [SMILES: Cc1c2c(n(CC3CC3)c(=O)c1Cl)CN(C(=O)c1cnc(CC3CC3)s1)C2] |
| I-70 | 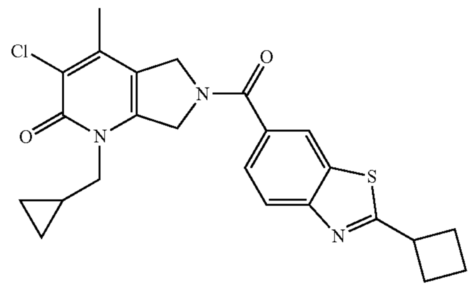 [SMILES: Cc1c2c(n(CC3CC3)c(=O)c1Cl)CN(C(=O)c1ccc3nc(C4CCC4)sc3c1)C2] |
| I-71 | 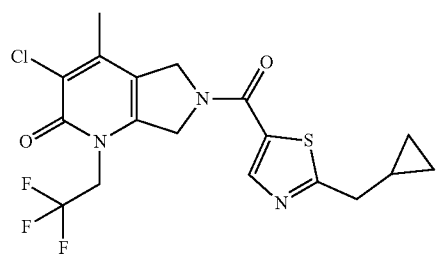 [SMILES: Cc1c2c(n(CC(F)(F)F)c(=O)c1Cl)CN(C(=O)c1cnc(CC3CC3)s1)C2] |
| I-72 | 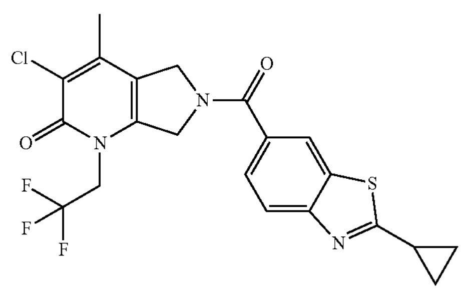 [SMILES: Cc1c2c(n(CC(F)(F)F)c(=O)c1Cl)CN(C(=O)c1ccc3nc(C4CC4)sc3c1)C2] |
| I-73 | 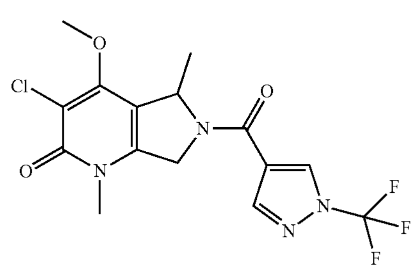 [SMILES: COc1c2c(n(C)c(=O)c1Cl)CN(C(=O)c1cnn(C(F)(F)F)c1)C2C] |
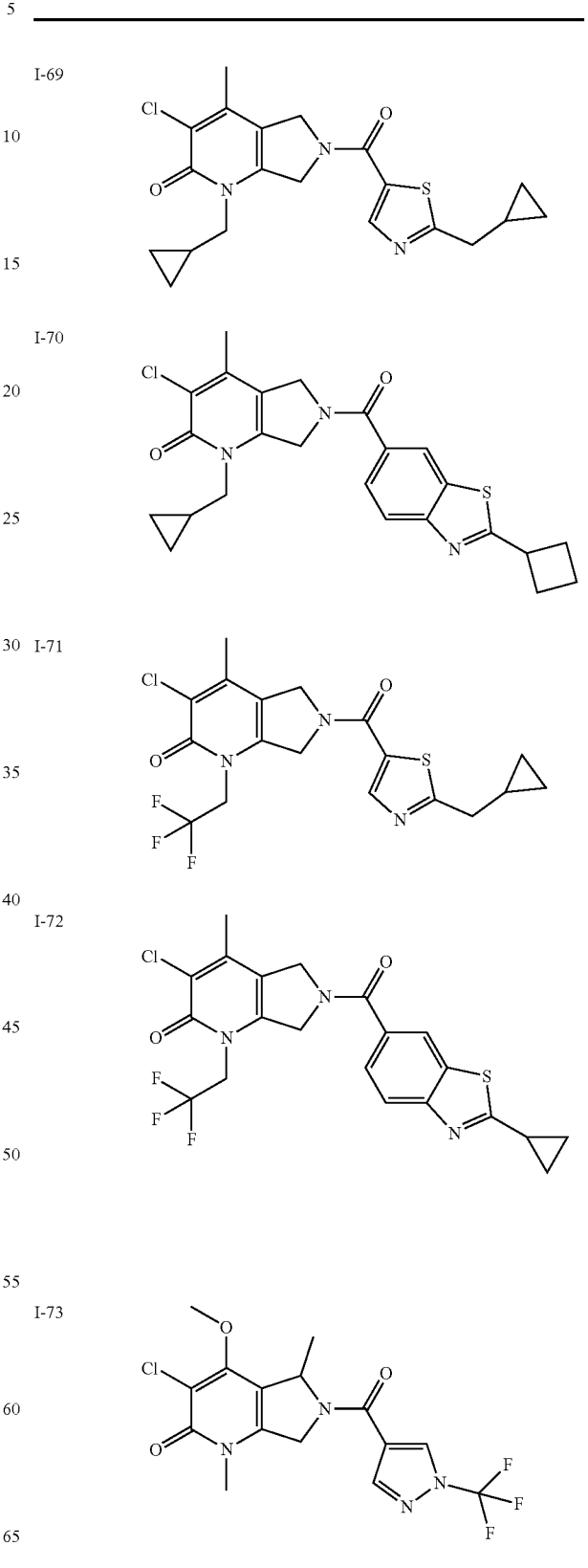

| Compound No. | Structure |
|---|---|
| I-74 | 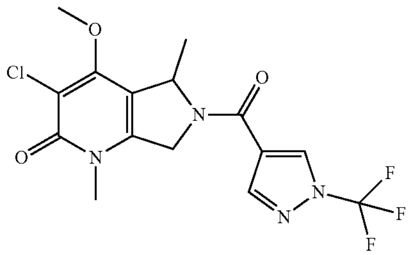 [SMILES: COc1c2c(n(C)c(=O)c1Cl)CN(C(=O)c1cnn(C(F)(F)F)c1)C2C] |
| I-75 | 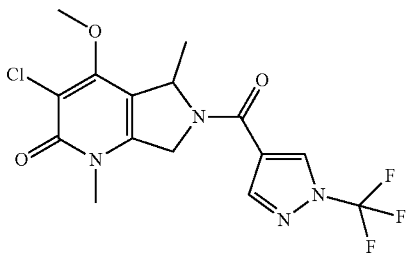 [SMILES: COc1c2c(n(C)c(=O)c1Cl)CN(C(=O)c1cnn(C(F)(F)F)c1)C2C] |
| I-76 | 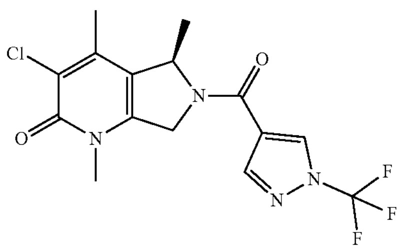 [SMILES: Cc1c2c(n(C)c(=O)c1Cl)CN(C(=O)c1cnn(C(F)(F)F)c1)[C@@H]2C] |
| I-77 | 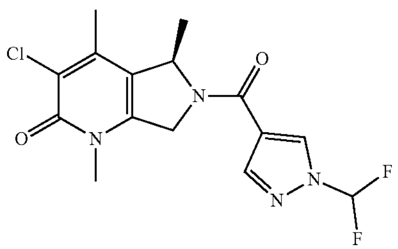 [SMILES: Cc1c2c(n(C)c(=O)c1Cl)CN(C(=O)c1cnn(C(F)F)c1)[C@@H]2C] |
| I-78 | 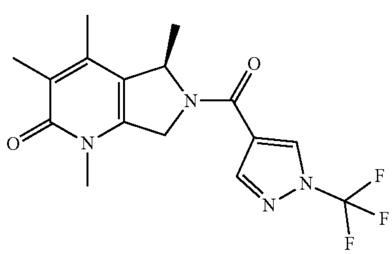 [SMILES: Cc1c2c(n(C)c(=O)c1C)CN(C(=O)c1cnn(C(F)(F)F)c1)[C@@H]2C] |
| I-79 | 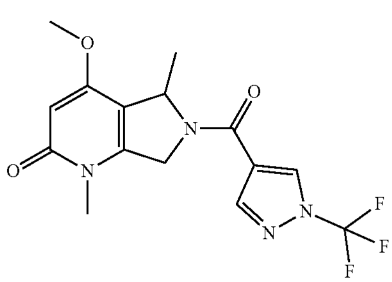 [SMILES: COc1cc(=O)n(C)c2c1C(C)N(C(=O)c1cnn(C(F)(F)F)c1)C2] |

| Compound No. | Structure |
|---|---|
| I-80 | 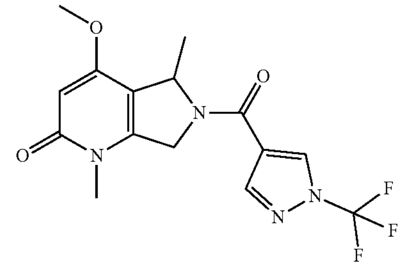 [SMILES: COc1cc(=O)n(C)c2c1C(C)N(C(=O)c1cnn(C(F)(F)F)c1)C2] |
| I-81 | 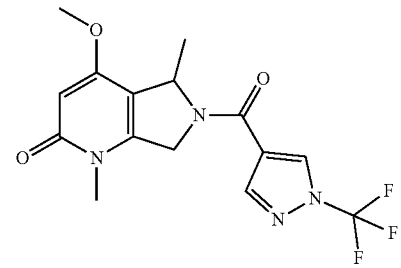 [SMILES: COc1cc(=O)n(C)c2c1C(C)N(C(=O)c1cnn(C(F)(F)F)c1)C2] |
| I-82 | 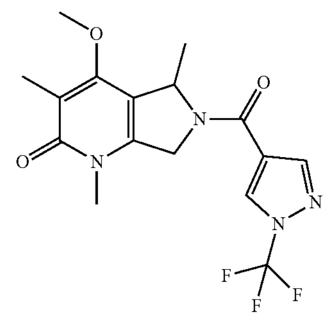 [SMILES: COc1c2c(n(C)c(=O)c1C)CN(C(=O)c1cnn(C(F)(F)F)c1)C2C] |
| I-83 | Stereoisomer 1 |
| I-84 | Stereoisomer 2 |

-continued

| Compound No. | Structure |
|---|---|
| I-85 | 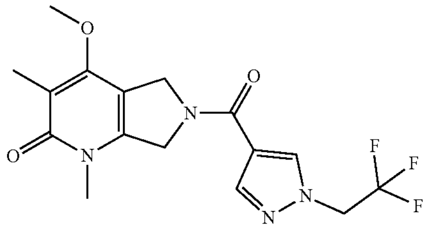 [SMILES: COc1c2c(n(C)c(=O)c1C)CN(C(=O)c1cnn(CC(F)(F)F)c1)C2] |
| I-86 | 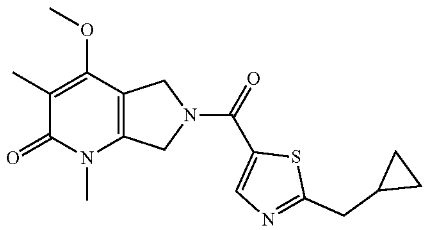 |
| I-87 | 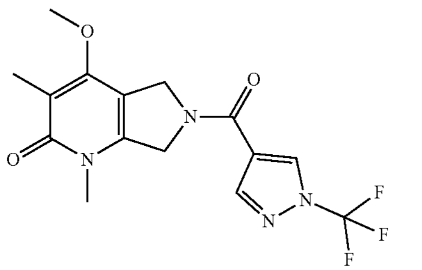 |
| I-88 | 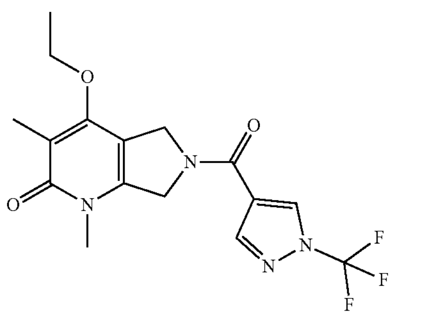 [SMILES: CCOc1c2c(n(C)c(=O)c1C)CN(C(=O)c1cnn(C(F)(F)F)c1)C2] |
| I-89 | 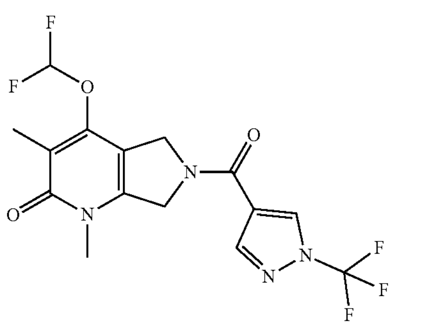 [SMILES: Cc1c(OC(F)F)c2c(n(C)c1=O)CN(C(=O)c1cnn(C(F)(F)F)c1)C2] |

-continued

| Compound No. | Structure |
|---|---|
| I-90 | 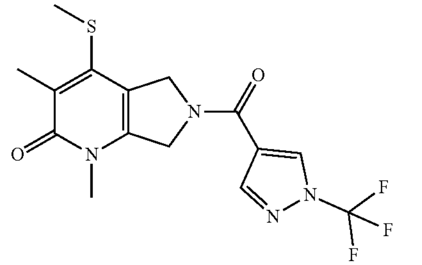 |
| I-91 | 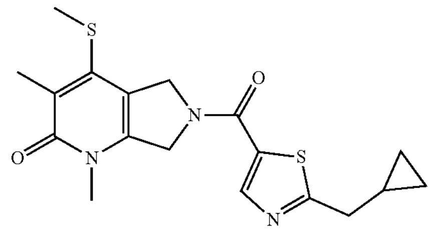 [SMILES: CSc1c2c(n(C)c(=O)c1C)CN(C(=O)c1cnc(CC3CC3)s1)C2] |
| I-92 | 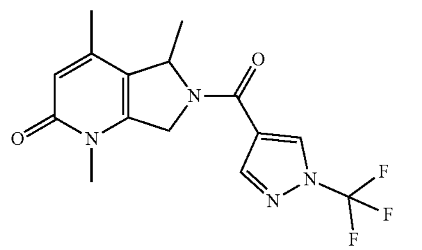 [SMILES: Cc1cc(=O)n(C)c2c1C(C)N(C(=O)c1cnn(C(F)(F)F)c1)C2] |
| I-93 | 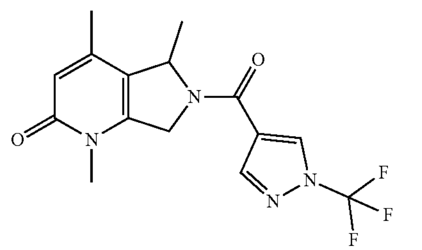 [SMILES: Cc1cc(=O)n(C)c2c1C(C)N(C(=O)c1cnn(C(F)(F)F)c1)C2] |
| I-94 | 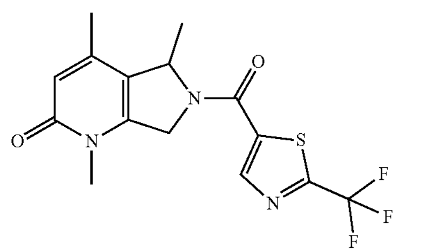 [SMILES: Cc1cc(=O)n(C)c2c1C(C)N(C(=O)c1cnc(C(F)(F)F)s1)C2] |
| I-95 | 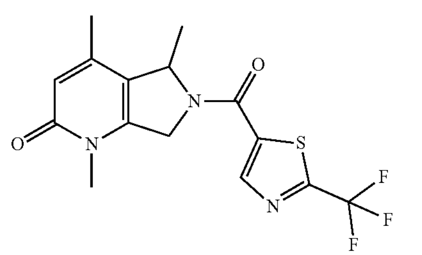 [SMILES: Cc1cc(=O)n(C)c2c1C(C)N(C(=O)c1cnc(C(F)(F)F)s1)C2] |

| Compound No. | Structure |
|---|---|
| I-96 | 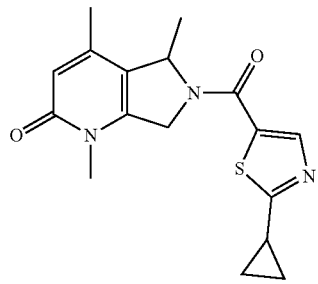 [SMILES: Cc1cc(=O)n(C)c2c1C(C)N(C(=O)c1cnc(C3CC3)s1)C2] |
| I-97 | 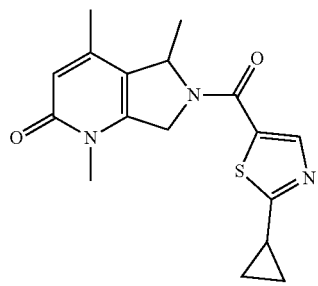 [SMILES: Cc1cc(=O)n(C)c2c1C(C)N(C(=O)c1cnc(C3CC3)s1)C2] |
| I-98 | 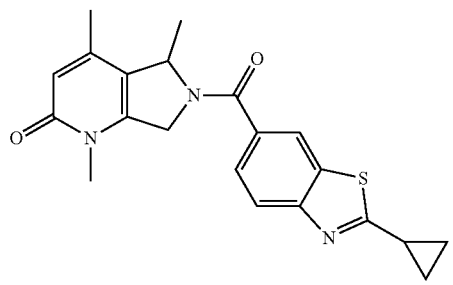 |
| I-99 | 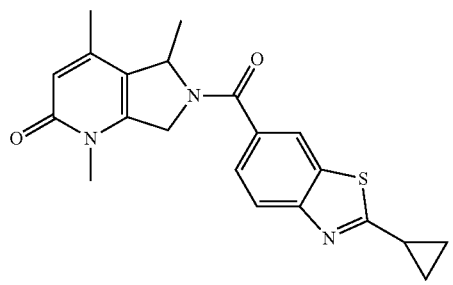 |
| I-100 | 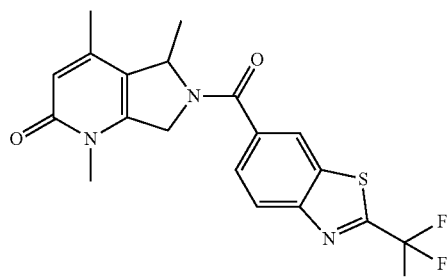 |
| Compound No. | Structure |
|---|---|
| I-101 | 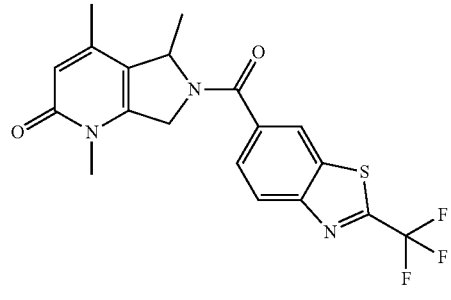 [SMILES: Cc1cc(=O)n(C)c2c1C(C)N(C(=O)c1ccc3nc(C(F)(F)F)sc3c1)C2] |
| I-102 | 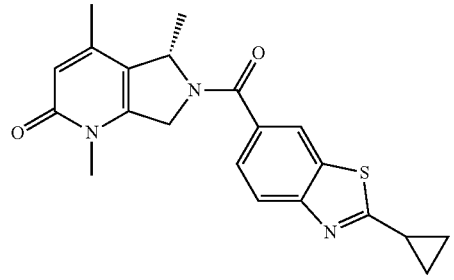 |
| I-103 | 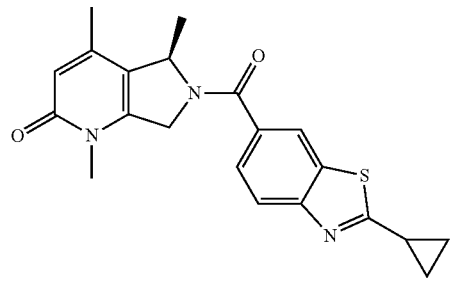 [SMILES: Cc1cc(=O)n(C)c2c1[C@@H](C)N(C(=O)c1ccc3nc(C4CC4)sc3c1)C2] |
| I-104 | 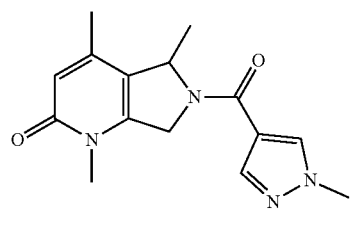 [SMILES: Cc1cc(=O)n(C)c2c1C(C)N(C(=O)c1cnn(C)c1)C2] |
| I-105 | 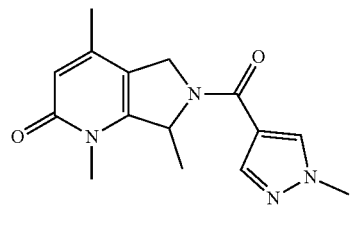 [SMILES: Cc1cc(=O)n(C)c2c1CN(C(=O)c1cnn(C)c1)C2C] |
| I-106 | 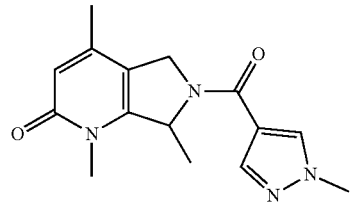 [SMILES: Cc1cc(=O)n(C)c2c1CN(C(=O)c1cnn(C)c1)C2C] |

| Compound No. | Structure |
|---|---|
| I-107 | 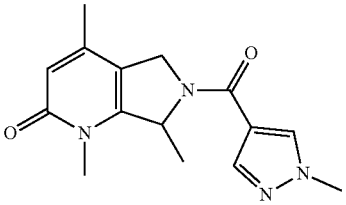 [SMILES: Cc1cc(=O)n(C)c2c1CN(C(=O)c1cnn(C)c1)C2C] |
| I-108 | 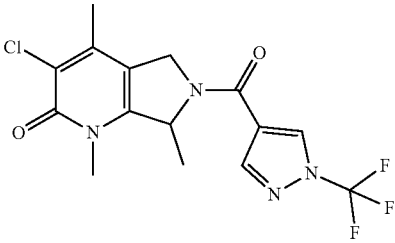 [SMILES: Cc1c2c(n(C)c(=O)c1Cl)C(C)N(C(=O)c1cnn(C(F)(F)F)c1)C2] |
| I-109 | 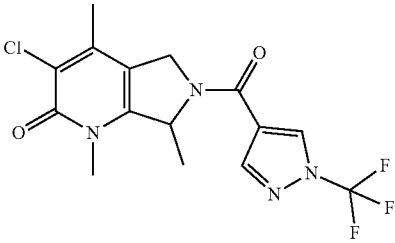 [SMILES: Cc1c2c(n(C)c(=O)c1Cl)C(C)N(C(=O)c1cnn(C(F)(F)F)c1)C2] |
| I-110 | 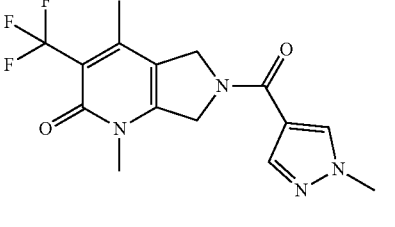 |
| I-111 | 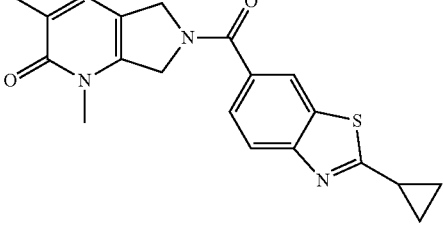 |
| I-112 | 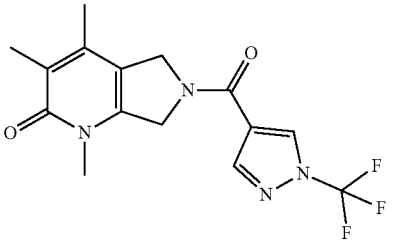 [SMILES: Cc1c2c(n(C)c(=O)c1C)CN(C(=O)c1cnn(C(F)(F)F)c1)C2] |
| Compound No. | Structure |
|---|---|
| I-113 | 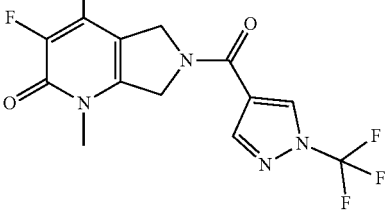 |
| I-114 | 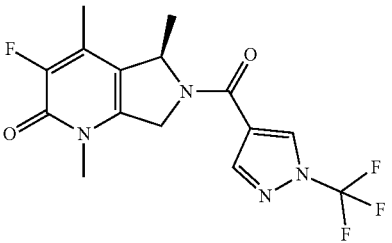 [SMILES: Cc1c2c(n(C)c(=O)c1F)CN(C(=O)c1cnn(C(F)(F)F)c1)[C@@H]2C] |
| I-115 | 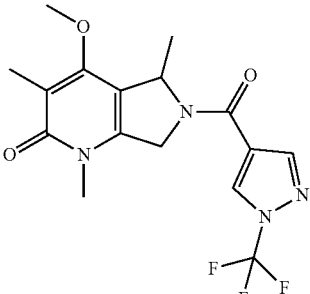 |
and a pharmaceutically acceptable salt of any of the foregoing.
16. The compound of claim 15, wherein the compound is selected from the group consisting of:
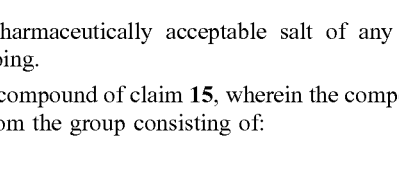
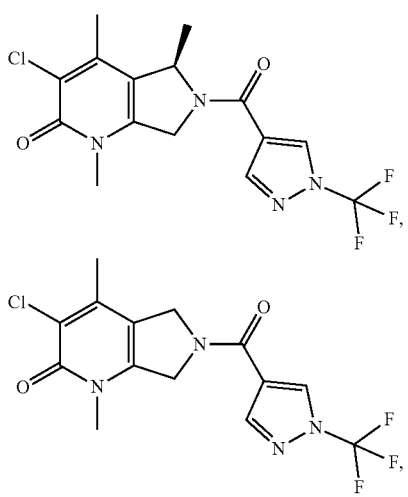

193
-continued
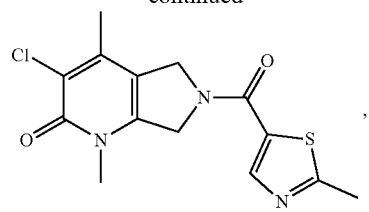
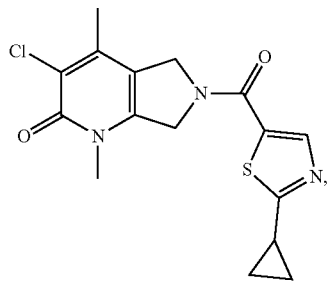
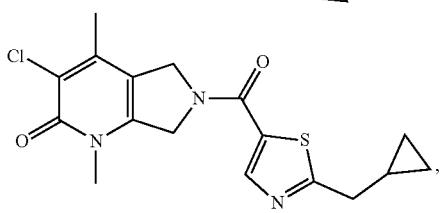
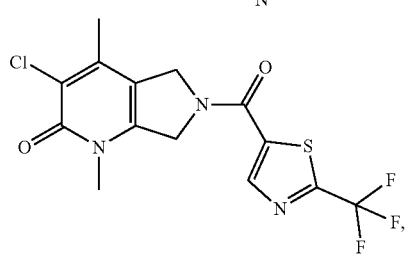
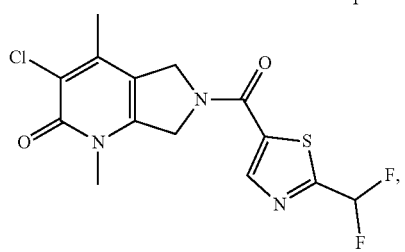
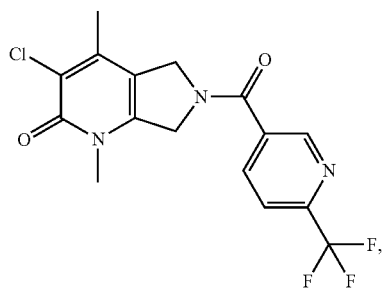
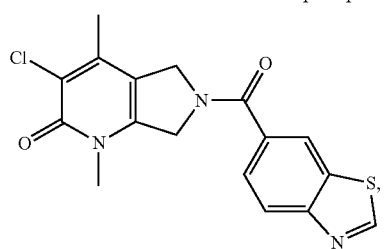
194
-continued
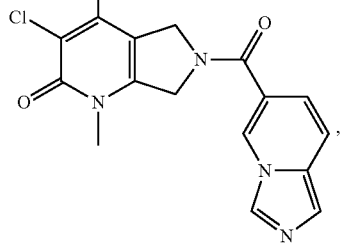
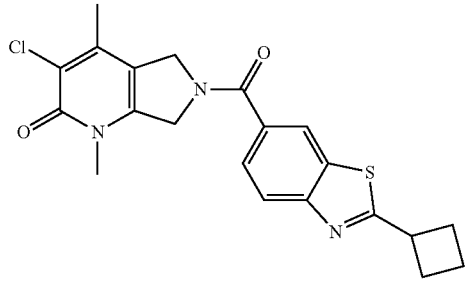
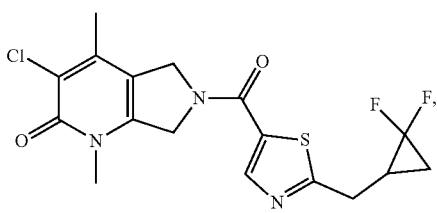
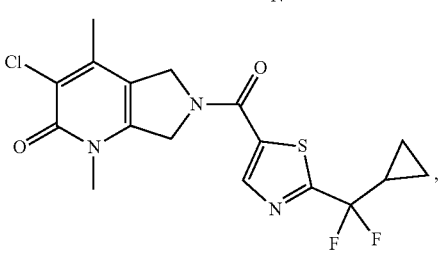
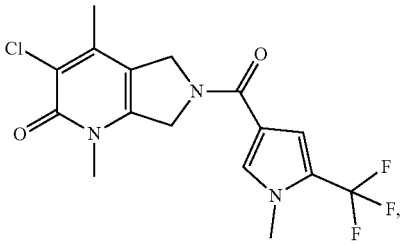
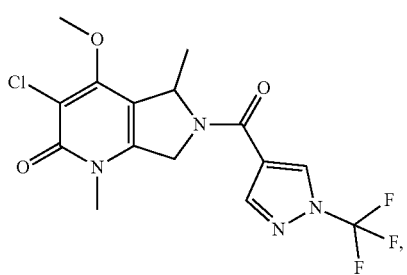

-continued
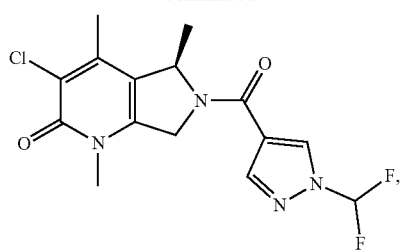
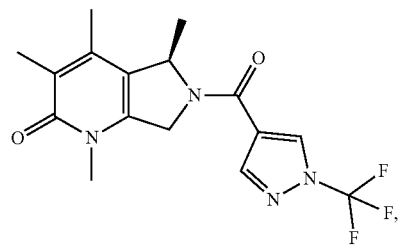
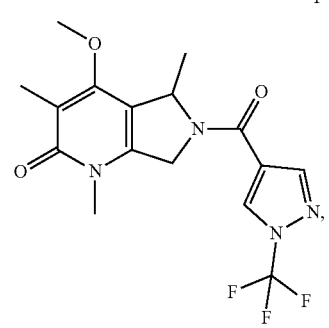
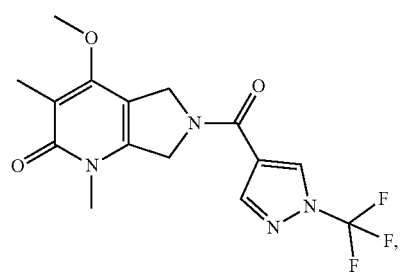
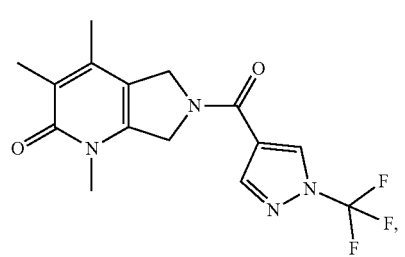
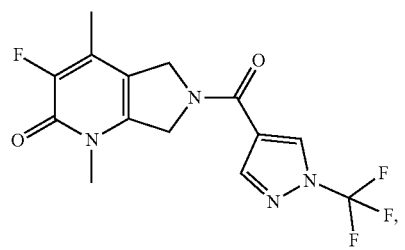
-continued
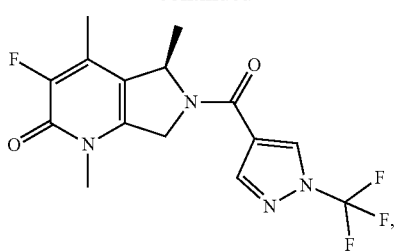
and a pharmaceutically acceptable salt of any of the foregoing.
17. A compound having a structure:
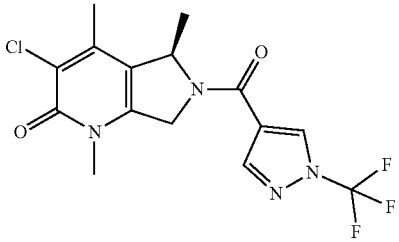 [SMILES: Cc1c2c(n(C)c(=O)c1Cl)CN(C(=O)c1cnn(C(F)(F)F)c1)[C@@H]2C]
or a pharmaceutically acceptable salt thereof.
18. The compound of claim 17, wherein the compound is
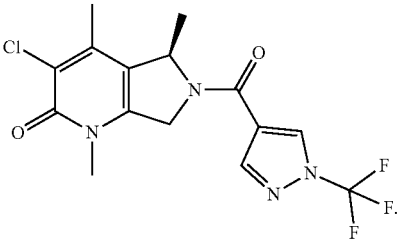 [SMILES: Cc1c2c(n(C)c(=O)c1Cl)CN(C(=O)c1cnn(C(F)(F)F)c1)[C@@H]2C]
19. A compound having a structure:
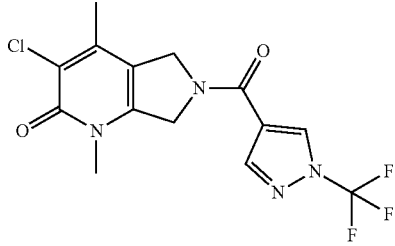 [SMILES: Cc1c2c(n(C)c(=O)c1Cl)CN(C(=O)c1cnn(C(F)(F)F)c1)C2]
or a pharmaceutically acceptable salt thereof.

20. The compound of claim 19, wherein the compound is

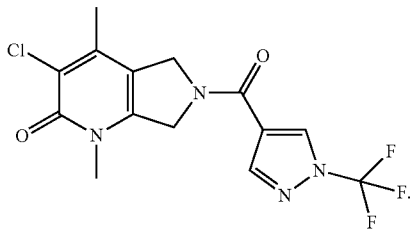 [SMILES: Cc1c2c(n(C)c(=O)c1Cl)CN(C(=O)c1cnn(C(F)(F)F)c1)C2]

21. A compound having a structure:

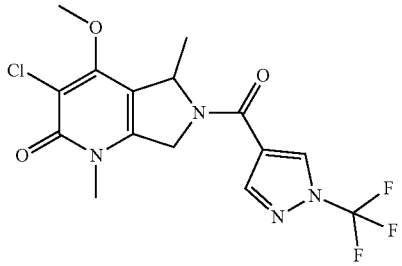 [SMILES: COc1c2c(n(C)c(=O)c1Cl)CN(C(=O)c1cnn(C(F)(F)F)c1)C2C]

or a pharmaceutically acceptable salt thereof.

22. The compound of claim 21, wherein the compound is

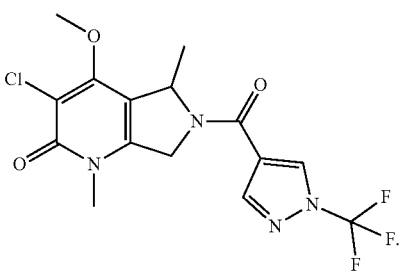 [SMILES: COc1c2c(n(C)c(=O)c1Cl)CN(C(=O)c1cnn(C(F)(F)F)c1)C2C]

23. A pharmaceutical composition comprising a compound of claim 1, or a pharmaceutically acceptable salt thereof, and a pharmaceutically acceptable carrier.

24. A method of treating a disorder selected from the group consisting of a neurologic disorder, a movement disorder, a mood disorder, a cognitive disorder, an attention disorder, and an addictive disorder comprising administering a therapeutically effective amount of a compound of claim 1, or a pharmaceutically acceptable salt thereof, to a subject in need thereof.

25. A method of treating schizophrenia comprising administering a therapeutically effective amount of a compound of claim 1, or a pharmaceutically acceptable salt thereof, to a subject in need thereof.

26. A method of treating a muscarinic acetylcholine receptor mediated disorder in a subject in need thereof, comprising administering to the subject a therapeutically effective amount of an orthosteric agonist of a muscarinic acetylcholine receptor and a compound of claim 1, or a pharmaceutically acceptable salt thereof.

27. A process for preparing a compound of Formula C, or a pharmaceutically acceptable salt thereof, comprising:
coupling Compound A to a compound of Formula B to produce a compound of Formula C:

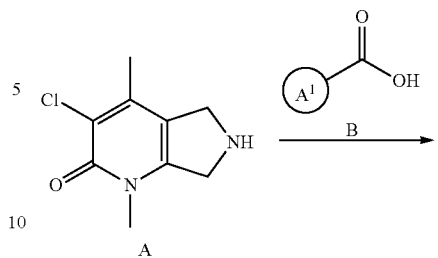

wherein $A^1$ is an optionally substituted 5-6 membered monocyclic heteroaryl, an 8-10 membered bicyclic heteroaryl, or phenyl.

28. The pharmaceutical composition of claim 23, wherein the compound is

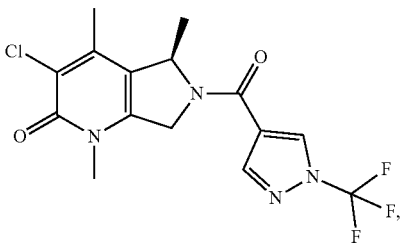 [SMILES: Cc1c2c(n(C)c(=O)c1Cl)CN(C(=O)c1cnn(C(F)(F)F)c1)[C@@H]2C]

or a pharmaceutically acceptable salt thereof.

29. The pharmaceutical composition of claim 23, wherein the compound is

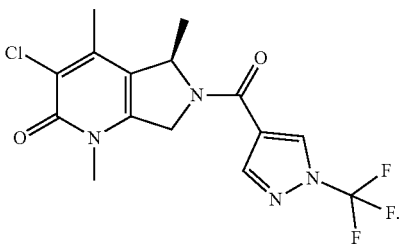 [SMILES: Cc1c2c(n(C)c(=O)c1Cl)CN(C(=O)c1cnn(C(F)(F)F)c1)[C@@H]2C]

30. The pharmaceutical composition of claim 23, wherein the compound is

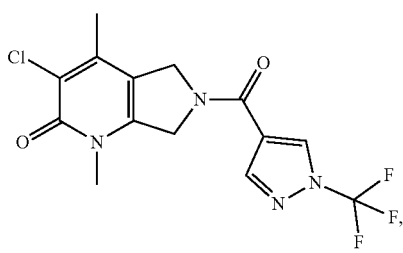 [SMILES: Cc1c2c(n(C)c(=O)c1Cl)CN(C(=O)c1cnn(C(F)(F)F)c1)C2]

or a pharmaceutically acceptable salt thereof.

31. The pharmaceutical composition of claim 23, wherein the compound is

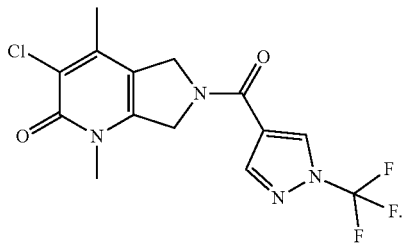 [SMILES: Cc1c2c(n(C)c(=O)c1Cl)CN(C(=O)c1cnn(C(F)(F)F)c1)C2]

32. The pharmaceutical composition of claim 23, wherein the compound is

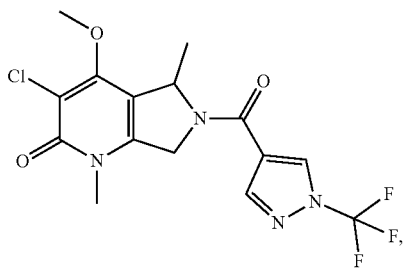 [SMILES: COc1c2c(n(C)c(=O)c1Cl)CN(C(=O)c1cnn(C(F)(F)F)c1)C2C]

or a pharmaceutically acceptable salt thereof.

33. The pharmaceutical composition of claim 23, wherein the compound is

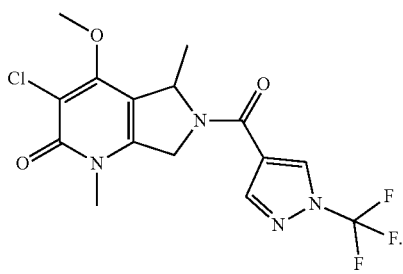 [SMILES: COc1c2c(n(C)c(=O)c1Cl)CN(C(=O)c1cnn(C(F)(F)F)c1)C2C]

34. The method of claim 25, wherein the compound is

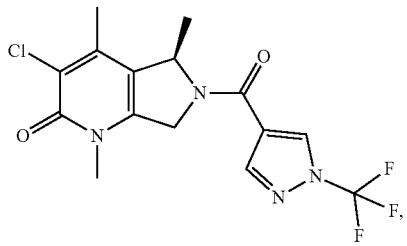 [SMILES: Cc1c2c(n(C)c(=O)c1Cl)CN(C(=O)c1cnn(C(F)(F)F)c1)[C@@H]2C]

or a pharmaceutically acceptable salt thereof.

35. The method of claim 25, wherein the compound is

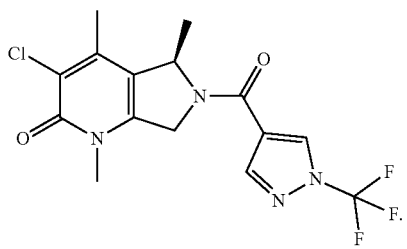 [SMILES: Cc1c2c(n(C)c(=O)c1Cl)CN(C(=O)c1cnn(C(F)(F)F)c1)[C@@H]2C]

36. The method of claim 25, wherein the compound is

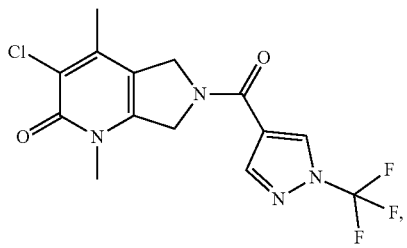 [SMILES: Cc1c2c(n(C)c(=O)c1Cl)CN(C(=O)c1cnn(C(F)(F)F)c1)C2]

or a pharmaceutically acceptable salt thereof.

37. The method of claim 25, wherein the compound is

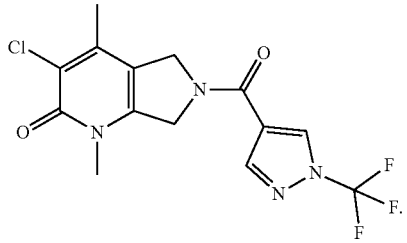 [SMILES: Cc1c2c(n(C)c(=O)c1Cl)CN(C(=O)c1cnn(C(F)(F)F)c1)C2]

38. The method of claim 25, wherein the compound is

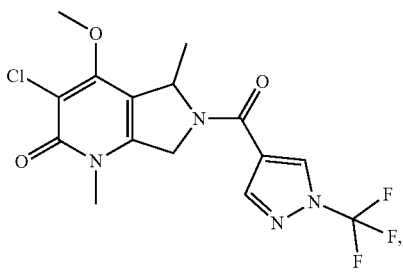 [SMILES: COc1c2c(n(C)c(=O)c1Cl)CN(C(=O)c1cnn(C(F)(F)F)c1)C2C]

or a pharmaceutically acceptable salt thereof.

39. The method of claim 25, wherein the compound is

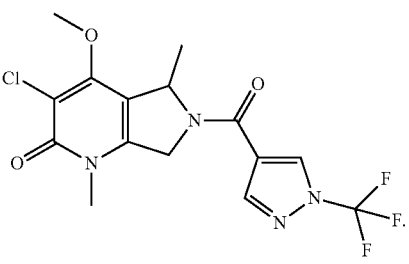 [SMILES: COc1c2c(n(C)c(=O)c1Cl)CN(C(=O)c1cnn(C(F)(F)F)c1)C2C]

40. The method of claim 26, wherein the orthosteric agonist is an orthosteric agonist of muscarinic acetylcholine receptor subtype M1 and/or M4.

41. The method of claim 40, wherein the compound is a compound of Formula If or Ig, or a pharmaceutically acceptable salt thereof:

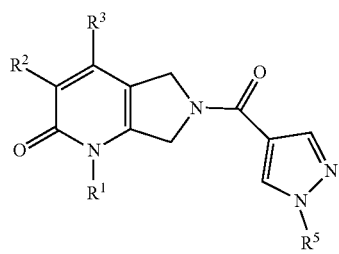

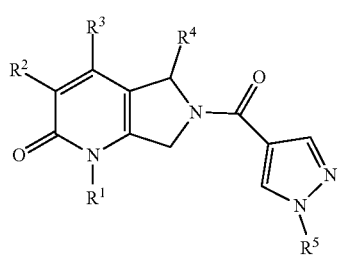

wherein $R^5$ is —$CF_3$, and wherein the muscarinic acetylcholine receptor mediated disorder is selected from the group consisting of schizophrenia, Alzheimer's Disease, bipolar disorder, autism, and major depressive disorder.

42. The method of claim 26, wherein the orthosteric agonist is xanomeline or a pharmaceutically acceptable salt thereof.

43. The method of claim 26, wherein the orthosteric agonist is xanomeline or a pharmaceutically acceptable salt thereof, and wherein the muscarinic acetylcholine receptor mediated disorder is schizophrenia or Alzheimer's Disease.

44. The method of claim 43, wherein the compound is

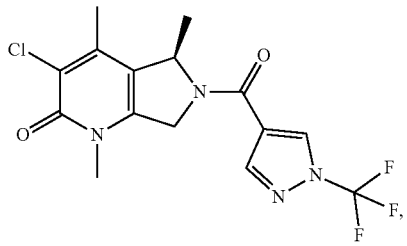 [SMILES: Cc1c2c(n(C)c(=O)c1Cl)CN(C(=O)c1cnn(C(F)(F)F)c1)[C@@H]2C]

or a pharmaceutically acceptable salt thereof.

45. The method of claim 43, wherein the compound is

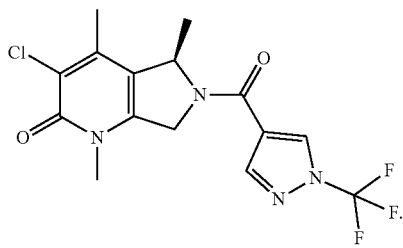 [SMILES: Cc1c2c(n(C)c(=O)c1Cl)CN(C(=O)c1cnn(C(F)(F)F)c1)[C@@H]2C]

46. The method of claim 43, wherein the compound is

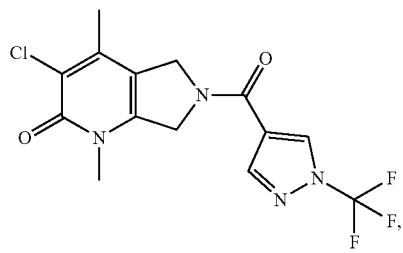 [SMILES: Cc1c2c(n(C)c(=O)c1Cl)CN(C(=O)c1cnn(C(F)(F)F)c1)C2]

or a pharmaceutically acceptable salt thereof.

47. The method of claim 43, wherein the compound is

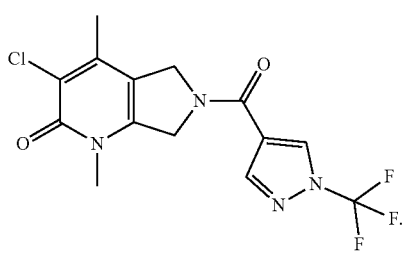 [SMILES: Cc1c2c(n(C)c(=O)c1Cl)CN(C(=O)c1cnn(C(F)(F)F)c1)C2]

48. The method of claim 43, wherein the compound is
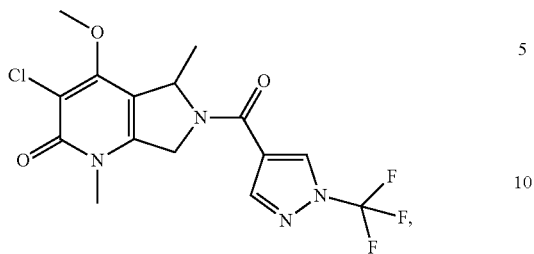
or a pharmaceutically acceptable salt thereof.
49. The method of claim 43, wherein the compound is
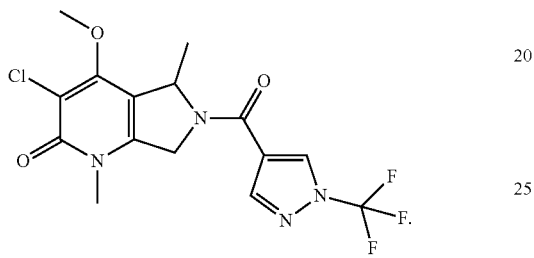
50. The process of claim 27, wherein the coupling of Compound A and the compound of Formula B is HATU-mediated acid amine coupling.
* * * * *

UNITED STATES PATENT AND TRADEMARK OFFICE
CERTIFICATE OF CORRECTION

PATENT NO. : 12,421,242 B2
APPLICATION NO. : 18/740233
DATED : September 23, 2025
INVENTOR(S) : Kevin Matthew Gardinier et al.

It is certified that error appears in the above-identified patent and that said Letters Patent is hereby corrected as shown below:

In the Claims

In Column 169, Line 48, Claim 1, delete "cycloalkyl,-($C_{1-6}$" and insert --cycloalkyl, -($C_{1-6}$--.

In Column 169, Line 51, Claim 1, delete "alkoxyl,-S-($C_{1-4}$" and insert --alkoxyl, -S-($C_{1-4}$--.

In Column 169, Line 57, Claim 1, delete "alkoxyl,-($C_{1-6}$" and insert --alkoxyl, -($C_{1-6}$--.

In Column 169, Line 57, Claim 1, delete "alkoxyl),-($C_{1-6}$" and insert --alkoxyl), -($C_{1-6}$--.

In Column 169, Line 58, Claim 1, delete "cycloalkyl),-($C_{1-6}$ haloalkylene)" and insert --cycloalkyl), -($C_{1-6}$ haloalkylene)--.

In Column 169, Line 67, Claim 1, delete "(ii)-($C_{0-4}$ alkylene)-" and insert --(ii) -($C_{0-4}$ alkylene)- --.

In Column 170, Line 3, Claim 1, delete "(iii)-($C_{0-4}$" and insert --(iii) -($C_{0-4}$--.

In Column 170, Line 6, Claim 1, delete "$R^7$," and insert --$R^7$;--.

In Column 170, Line 10, Claim 1, delete "$^A1$" and insert --$A^1$--.

In Column 174, Lines 15-25, Claim 15, delete " 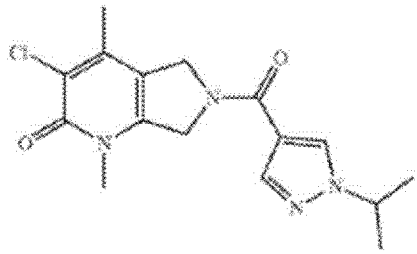 " and insert

Signed and Sealed this
Third Day of February, 2026

John A. Squires
*Director of the United States Patent and Trademark Office*

CERTIFICATE OF CORRECTION (continued)
U.S. Pat. No. 12,421,242 B2

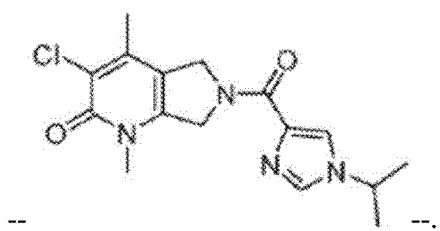
--                              --.

In Column 174, Lines 26-35, Claim 15, delete " 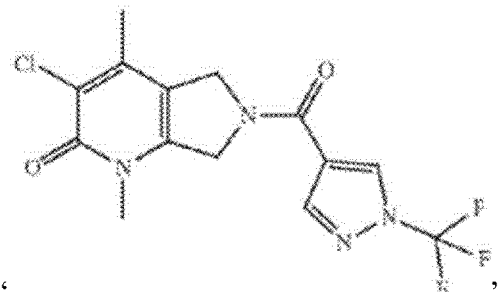 " and insert

--                              --.

In Column 190, Lines 41-48, Claim 15, delete " 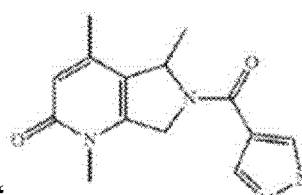 " and insert

--                              --.